(12) United States Patent
Saus et al.

(10) Patent No.: US 7,326,768 B2
(45) Date of Patent: Feb. 5, 2008

(54) GOODPASTURE ANTIGEN-BINDING PROTEIN ISOFORMS AND PROTEIN MISFOLDED-MEDIATED DISORDERS

(76) Inventors: Juan Saus, Conde de Altea 8, 7a, Valencia (ES) 46005; Fernando Revert, Luis Vives, 43 Moncada, Valencia (ES) 46113; Francisco Revert-Ros, Dr. Sanchis Sivera, 27-6a, Valcencia (ES) 46008

(*) Notice: Subject to any disclaimer, the term of this patent is extended or adjusted under 35 U.S.C. 154(b) by 278 days.

(21) Appl. No.: 10/772,656

(22) Filed: Feb. 5, 2004

(65) Prior Publication Data

US 2004/0175758 A1   Sep. 9, 2004

Related U.S. Application Data

(60) Provisional application No. 60/445,043, filed on Feb. 5, 2003, provisional application No. 60/445,004, filed on Feb. 5, 2003, provisional application No. 60/445,003, filed on Feb. 5, 2003.

(51) Int. Cl.
  *C07K 5/10* (2006.01)
(52) U.S. Cl. .................................................. 530/300
(58) Field of Classification Search .................. None
  See application file for complete search history.

(56) References Cited

U.S. PATENT DOCUMENTS

| 6,506,559 B1 | 1/2003 | Fire et al. |
| 6,579,969 B1 | 6/2003 | Saus |

FOREIGN PATENT DOCUMENTS

| EP | 1 347 046 | 9/2003 |
| WO | WO 00/50607 | 8/2000 |
| WO | WO 00/58473 | 10/2000 |
| WO | WO 01/54733 | 8/2001 |
| WO | WO 02/061430 | 8/2002 |
| WO | WO 02/097044 | 12/2002 |
| WO | WO 03/048193 | 6/2003 |

OTHER PUBLICATIONS

Feldmann et al, Nature 435:612-619, 2005.*
Fox et al, Nephrol Nursing J 28:305-310, 2001.*
Gura, Science, 1997, 278:1041-1042.*
Johnson and Tracey, 'Peptide and Protein Drug Delivery', In: Encyclopedia of Controlled Drug Delivery, vol. 2, 1999, pp. 816-833.*
Brown, Expert Opin Drug Deliv 2:29-42, 2005.*
Torchilin et al Drug Discovery Today:8:259-266, 2003.*
Tatusova, et al., (1999), FEMS Microbiol. Lett. "BLAST 2 sequences, a new tool form comparing protein and nucleotide sequences", vol. 174, pp. 247-250.

(Continued)

*Primary Examiner*—Misook Yu
*Assistant Examiner*—Mark Halvorson
(74) *Attorney, Agent, or Firm*—McDonnell Boehnen Hulbert & Berghoff LLP

(57) ABSTRACT

The present invention provides novel isoforms of the Goodpasture antigen binding protein (GPBP), and related reagents, and also provides methods for isolating and detecting such novel GPBP isoforms. The invention further provides methods identifying compounds to treat one or more of an autoimmune condition and a protein deposit-mediated disorder, as well as novel compounds and methods for treating such conditions and/or disorders.

10 Claims, 14 Drawing Sheets

OTHER PUBLICATIONS

Jones, et al., (1986), Nature, "Replacing the complementarity-determining regions in a human antibody with those from a mouse", vol. 321, pp. 522-525.

Morrison, et al., (1984), Proc. Natl. Acad. Sci., U.S.A., "Chimeric human antibody molecules: Mouse antigen-binding domains with human constant region domains", vol. 81, pp. 6851-6855.

Morrison and Oi, (1988), Adv. Immunol., "Genetically engineered antibody molecules", vol. 44, pp. 65-92.

Verhoeyen, et al., (1988), Science, "Reshaping human antibodies: grafting an antilysozyme activity", vol. 239, pp. 1534-1536.

Padlan, (1991), Molec. Immun., "A possible procedure for reducing the immunogenicity of antibody variable domains while preserving their ligand-binding properties", vol. 28, pp. 489-498.

Padlan, (1994), Molec. Immunol., "Anatomy of the antibody molecule", vol. 31(3), pp. 169-217.

Kettleborough, C.A., et al., (1991), Protein Eng., "humanization of a mouse monoclonal antibody by CDR-grafting: the importance of framework residues on loop conformation", vol. 4(7), pp. 773-783.

Pham, C.T., & T.J. Ley, (1999), Proc. Natl Acad Sci USA, "Dipeptidyl peptidase I is required for the processing and activation of granzymes A and B in vivo", vol. 96(15), pp. 8627-8632.

Chapman, H.A., (1998), Curr Opin Immunol, "Endosomal proteolysis and MHC class II function", vol. 10(1), pp. 93-102.

Demotz, S., et al., (1989), J. Immunol, "Processing of tetanus toxin by human antigen-presenting cells", vol. 143(12), pp. 3881-3886.

Turk, V., et al., (2001), EMBO J, "Lysosomal cysteine proteases: facts and opportunities", vol. 20(17, pp. 4629-4633.

Prusiner, S.B., (1998),Proc Natl Acad Sci USA, "Prions", vol. 95(23), pp. 13363-13383.

Raya, A., et al., (1999), J. Biol. Chem., "Characterization of a novel type of serine/threonin kinase that specifically phosphorylates the human goodpasture antigen", vol. 274, pp. 12642-12649.

Aniento, F., et al., (1993), J. Biol. Chem., "Uptake and degradation of glyceraldehydes-3-phosphate dehydrogenase by rat liver lysosomes", vol. 268, pp. 10463-10470.

Raya, A., et al., (2000), J. Biol. Chem., "Goodpasture antigen-binding protein, the kinase that phosphorylates the goodpasture antigen, is an alternatively spliced variant implicated in autoimmune pathogenesis", vol. 275, pp. 40392-40399.

Miñana MD, et al., (1998), Neuropharmacology, "Nicotine prevents glutamate-induced proteolysis of the microtubule-associated protein MAP-2 and glutamate neurotoxicity in primary cultures of cerebellar neurons", vol. 37, pp. 847-857.

Supattapone, S., et al., (2001), J. Virol, "Branched polyamines cure prion-infected neuroblastoma cells", vol. 75, pp. 3453-3461.

Prusiner, S.B, (2001), N England J Med, "Shattuck Lecture-Neurodegenerative Diseases and Prions", vol. 344, pp. 1516-1526.

Kaneko, K., et al., (1997), Proc. Natl. Acad. Sci. USA, "Evidence for protein X binding to a discontinuous epitope on the cellular prion protein during scrapie prion propagation", vol. 94, pp. 10069-10074.

Ma, J. and Lindquist, (2002), Science, "Conversion of PrP to a self-perpetuating $PrP^{sc}$-like conformation in the cytosol", vol. 298, pp. 1785-1788.

Nixon, et al., (2000), Neurochem Res, "The endosomal-lysosomal system of neurons in alzheimer's disease pathogenesis: a review", vol. 25, pp. 1161-1172.

Andrea, M.R., et al., (2001), Histopathology, "Evidence that neurons accumulating amyloid can undergo lysis to form amyloid plaques in alzheimer's disease", vol. 38, pp. 120-134.

Eichberg, J., & Iyer, (1996), Neurochem Res, "Phosphorylation of myelin proteins: recent advances", vol. 21, pp. 527-535.

* cited by examiner

A

```
  n4'                                    Δ102
  →RRCEWTRDSAAGFSLPFFSLFLPYLKLASRGLSSGGSAGR
           Δ174                                Δ246
  NAGVTATAAAADGWKGRLPSPLVLLPRSARCQARRRRGGR
                                    pep-2
                Δ315                           Δ369
  TSSLLLLPPTPERALFASPSPDPSPRGLGASSGAAEGAGA

GLLLGCRASM
```

B

In vitro

C

Ex vivo

A

B

SEQUENCE LISTING

<160> NUMBER OF SEQ ID NOS: 103

<210> SEQ ID NO 1
<211> LENGTH: 2389
<212> TYPE: DNA
<213> ORGANISM: Homo sapiens
<220> FEATURE:
<221> NAME/KEY: CDS
<222> LOCATION: (409)..(2283)
<223> OTHER INFORMATION:

<400> SEQUENCE: 1

```
gcaggaagat ggcggcggta gcggaggtgt gagtggacgc gggactcagc ggccggattt      60
tctcttccct tcttttccct tttccttccc tatttgaaat tggcatcgag ggggctaagt     120
tcgggtggca gcgccgggcg caacgcaggg gtcacggcga cggcggcggc ggctgacggc     180
tggaagggta ggcttccttc accgctcgtc ctccttcctc gctccgctcg gtgtcaggcg     240
cggcggcggc gcggcgggcg gacttcgtcc ctcctcctgc tccccccac accggagcgg      300 gcactcttcg cttcgccatc ccccgaccct tcaccccgag gactgggcgc ctcctccggc     360
gcagctgagg gagcgggggc cggtctcctg ctcggttgtc gagcctcc atg tcg gat      417
                                                      Met Ser Asp
                                                       1 aat cag agc tgg aac tcg tcg ggc tcg gag gag gat cca gag acg gag      465
Asn Gln Ser Trp Asn Ser Ser Gly Ser Glu Glu Asp Pro Glu Thr Glu
  5                  10                  15 tct ggg ccg cct gtg gag cgc tgc ggg gtc ctc agt aag tgg aca aac      513
```

```
Ser Gly Pro Pro Val Glu Arg Cys Gly Val Leu Ser Lys Trp Thr Asn
 20              25                  30                  35 tac att cat ggg tgg cag gat cgt tgg gta gtt ttg aaa aat aat gct         561
Tyr Ile His Gly Trp Gln Asp Arg Trp Val Val Leu Lys Asn Asn Ala
             40                  45                  50 ctg agt tac tac aaa tct gaa gat gaa aca gag tat ggc tgc aga gga         609
Leu Ser Tyr Tyr Lys Ser Glu Asp Glu Thr Glu Tyr Gly Cys Arg Gly
         55                  60                  65 tcc atc tgt ctt agc aag gct gtc atc aca cct cac gat ttt gat gaa         657
Ser Ile Cys Leu Ser Lys Ala Val Ile Thr Pro His Asp Phe Asp Glu
     70                  75                  80 tgt cga ttt gat att agt gta aat gat agt gtt tgg tat ctt cgt gct         705
Cys Arg Phe Asp Ile Ser Val Asn Asp Ser Val Trp Tyr Leu Arg Ala
 85                  90                  95 cag gat cca gat cat aga cag caa tgg ata gat gcc att gaa cag cac         753
Gln Asp Pro Asp His Arg Gln Gln Trp Ile Asp Ala Ile Glu Gln His
100                 105                 110                 115 aag act gaa tct gga tat gga tct gaa tcc agc ttg cgt cga cat ggc         801
Lys Thr Glu Ser Gly Tyr Gly Ser Glu Ser Ser Leu Arg Arg His Gly
                120                 125                 130 tca atg gtg tcc ctg gtg tct gga gca agt ggc tac tct gca aca tcc         849
Ser Met Val Ser Leu Val Ser Gly Ala Ser Gly Tyr Ser Ala Thr Ser
            135                 140                 145 acc tct tca ttc aag aaa ggc cac agt tta cgt gag aag ttg gct gaa         897
Thr Ser Ser Phe Lys Lys Gly His Ser Leu Arg Glu Lys Leu Ala Glu
        150                 155                 160 atg gaa aca ttt aga gac atc tta tgt aga caa gtt gac acg cta cag         945
Met Glu Thr Phe Arg Asp Ile Leu Cys Arg Gln Val Asp Thr Leu Gln
165                 170                 175 aag tac ttt gat gcc tgt gct gat gct gtc tct aag gat gaa ctt caa         993
Lys Tyr Phe Asp Ala Cys Ala Asp Ala Val Ser Lys Asp Glu Leu Gln
180                 185                 190                 195 agg gat aaa gtg gta gaa gat gat gaa gat gac ttt cct aca acg cgt        1041
Arg Asp Lys Val Val Glu Asp Asp Glu Asp Asp Phe Pro Thr Thr Arg
                200                 205                 210 tct gat ggt gac ttc ttg cat agt acc aac ggc aat aaa gaa aag tta        1089
Ser Asp Gly Asp Phe Leu His Ser Thr Asn Gly Asn Lys Glu Lys Leu
            215                 220                 225 ttt cca cat gtg aca cca aaa gga att aat ggt ata gac ttt aaa ggg        1137
Phe Pro His Val Thr Pro Lys Gly Ile Asn Gly Ile Asp Phe Lys Gly
        230                 235                 240 gaa gcg ata act ttt aaa gca act act gct gga atc ctt gca aca ctt        1185
Glu Ala Ile Thr Phe Lys Ala Thr Thr Ala Gly Ile Leu Ala Thr Leu
245                 250                 255 tct cat tgt att gaa cta atg gtt aaa cgt gag gac agc tgg cag aag        1233
Ser His Cys Ile Glu Leu Met Val Lys Arg Glu Asp Ser Trp Gln Lys
260                 265                 270                 275 aga ctg gat aag gaa act gag aag aaa aga aga aca gag gaa gca tat        1281
Arg Leu Asp Lys Glu Thr Glu Lys Lys Arg Arg Thr Glu Glu Ala Tyr
                280                 285                 290 aaa aat gca atg aca gaa ctt aag aaa aaa tcc cac ttt gga gga cca        1329
Lys Asn Ala Met Thr Glu Leu Lys Lys Lys Ser His Phe Gly Gly Pro
            295                 300                 305 gat tat gaa gaa ggc cct aac agt ctg att aat gaa gaa gag ttc ttt        1377
Asp Tyr Glu Glu Gly Pro Asn Ser Leu Ile Asn Glu Glu Glu Phe Phe
        310                 315                 320 gat gct gtt gaa gct gct ctt gac aga caa gat aaa ata gaa gaa cag        1425
Asp Ala Val Glu Ala Ala Leu Asp Arg Gln Asp Lys Ile Glu Glu Gln
325                 330                 335
```

-continued

| | | |
|---|---|---|
| tca cag agt gaa aag gtg aga tta cat tgg cct aca tcc ttg ccc tct<br>Ser Gln Ser Glu Lys Val Arg Leu His Trp Pro Thr Ser Leu Pro Ser<br>340                          345                    350                    355 | 1473 |
| gga gat gcc ttt tct tct gtg ggg aca cat aga ttt gtc caa aag ccc<br>Gly Asp Ala Phe Ser Ser Val Gly Thr His Arg Phe Val Gln Lys Pro<br>                    360                    365                    370 | 1521 |
| tat agt cgc tct tcc tcc atg tct tcc att gat cta gtc agt gcc tct<br>Tyr Ser Arg Ser Ser Ser Met Ser Ser Ile Asp Leu Val Ser Ala Ser<br>375                          380                    385 | 1569 |
| gat gat gtt cac aga ttc agc tcc cag gtt gaa gag atg gtg cag aac<br>Asp Asp Val His Arg Phe Ser Ser Gln Val Glu Glu Met Val Gln Asn<br>                    390                    395                    400 | 1617 |
| cac atg act tac tca tta cag gat gta ggc gga gat gcc aat tgg cag<br>His Met Thr Tyr Ser Leu Gln Asp Val Gly Gly Asp Ala Asn Trp Gln<br>405                          410                    415 | 1665 |
| ttg gtt gta gaa gaa gga gaa atg aag gta tac aga aga gaa gta gaa<br>Leu Val Val Glu Glu Gly Glu Met Lys Val Tyr Arg Arg Glu Val Glu<br>420                          425                    430                    435 | 1713 |
| gaa aat ggg att gtt ctg gat cct tta aaa gct acc cat gca gtt aaa<br>Glu Asn Gly Ile Val Leu Asp Pro Leu Lys Ala Thr His Ala Val Lys<br>                    440                    445                    450 | 1761 |
| ggc gtc aca gga cat gaa gtc tgc aat tat ttc tgg aat gtt gac gtt<br>Gly Val Thr Gly His Glu Val Cys Asn Tyr Phe Trp Asn Val Asp Val<br>455                          460                    465 | 1809 |
| cgc aat gac tgg gaa aca act ata gaa aac ttt cat gtg gtg gaa aca<br>Arg Asn Asp Trp Glu Thr Thr Ile Glu Asn Phe His Val Val Glu Thr<br>                    470                    475                    480 | 1857 |
| tta gct gat aat gca atc atc att tat caa aca cac aag agg gtg tgg<br>Leu Ala Asp Asn Ala Ile Ile Ile Tyr Gln Thr His Lys Arg Val Trp<br>485                          490                    495 | 1905 |
| cct gct tct cag cga gac gta tta tat ctt tct gtc att cga aag ata<br>Pro Ala Ser Gln Arg Asp Val Leu Tyr Leu Ser Val Ile Arg Lys Ile<br>500                          505                    510                    515 | 1953 |
| cca gcc ttg act gaa aat gac cct gaa act tgg ata gtt tgt aat ttt<br>Pro Ala Leu Thr Glu Asn Asp Pro Glu Thr Trp Ile Val Cys Asn Phe<br>                    520                    525                    530 | 2001 |
| tct gtg gat cat gac agt gct cct cta aac aac cga tgt gtc cgt gcc<br>Ser Val Asp His Asp Ser Ala Pro Leu Asn Asn Arg Cys Val Arg Ala<br>535                          540                    545 | 2049 |
| aaa ata aat gtt gct atg att tgt caa acc ttg gta agc cca cca gag<br>Lys Ile Asn Val Ala Met Ile Cys Gln Thr Leu Val Ser Pro Pro Glu<br>                    550                    555                    560 | 2097 |
| gga aac cag gaa att agc agg gac aac att cta tgc aag att aca tat<br>Gly Asn Gln Glu Ile Ser Arg Asp Asn Ile Leu Cys Lys Ile Thr Tyr<br>565                          570                    575 | 2145 |
| gta gct aat gtg aac cct gga gga tgg gca cca gcc tca gtg tta agg<br>Val Ala Asn Val Asn Pro Gly Gly Trp Ala Pro Ala Ser Val Leu Arg<br>580                          585                    590                    595 | 2193 |
| gca gtg gca aag cga gag tat cct aaa ttt cta aaa cgt ttt act tct<br>Ala Val Ala Lys Arg Glu Tyr Pro Lys Phe Leu Lys Arg Phe Thr Ser<br>                    600                    605                    610 | 2241 |
| tac gtc caa gaa aaa act gca gga aag cct att ttg ttc tag<br>Tyr Val Gln Glu Lys Thr Ala Gly Lys Pro Ile Leu Phe<br>615                          620 | 2283 |
| tattaacagg tactagaaga tatgttttat cttttttttaa ctttatttga ctaatatgac | 2343 |
| tgtcaatact aaaatttagt tgttgaaagt atttactatg tttttt | 2389 |

<210> SEQ ID NO 2
<211> LENGTH: 624

```
<212> TYPE: PRT
<213> ORGANISM: Homo sapiens

<400> SEQUENCE: 2

Met Ser Asp Asn Gln Ser Trp Asn Ser Gly Ser Glu Asp Pro
1               5                   10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
                35                  40                  45

Asn Asn Ala Leu Ser Tyr Tyr Lys Ser Glu Asp Glu Thr Glu Tyr Gly
    50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
                100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205

Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Ala Phe Ser Ser Val Gly Thr His Arg Phe Val
    355                 360                 365

Gln Lys Pro Tyr Ser Arg Ser Ser Met Ser Ser Ile Asp Leu Val
        370                 375                 380

Ser Ala Ser Asp Asp Val His Arg Phe Ser Ser Gln Val Glu Glu Met
385                 390                 395                 400
```

```
Val Gln Asn His Met Thr Tyr Ser Leu Gln Asp Val Gly Gly Asp Ala
                405                 410                 415

Asn Trp Gln Leu Val Val Glu Glu Gly Glu Met Lys Val Tyr Arg Arg
            420                 425                 430

Glu Val Glu Glu Asn Gly Ile Val Leu Asp Pro Leu Lys Ala Thr His
        435                 440                 445

Ala Val Lys Gly Val Thr Gly His Glu Val Cys Asn Tyr Phe Trp Asn
    450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Ile Tyr Gln Thr His Lys
                485                 490                 495

Arg Val Trp Pro Ala Ser Gln Arg Asp Val Leu Tyr Leu Ser Val Ile
            500                 505                 510

Arg Lys Ile Pro Ala Leu Thr Glu Asn Asp Pro Glu Thr Trp Ile Val
        515                 520                 525

Cys Asn Phe Ser Val Asp His Asp Ser Ala Pro Leu Asn Asn Arg Cys
    530                 535                 540

Val Arg Ala Lys Ile Asn Val Ala Met Ile Cys Gln Thr Leu Val Ser
545                 550                 555                 560

Pro Pro Glu Gly Asn Gln Glu Ile Ser Arg Asp Asn Ile Leu Cys Lys
                565                 570                 575

Ile Thr Tyr Val Ala Asn Val Asn Pro Gly Gly Trp Ala Pro Ala Ser
            580                 585                 590

Val Leu Arg Ala Val Ala Lys Arg Glu Tyr Pro Lys Phe Leu Lys Arg
        595                 600                 605

Phe Thr Ser Tyr Val Gln Glu Lys Thr Ala Gly Lys Pro Ile Leu Phe
    610                 615                 620

<210> SEQ ID NO 3
<211> LENGTH: 2311
<212> TYPE: DNA
<213> ORGANISM: Homo sapiens
<220> FEATURE:
<221> NAME/KEY: CDS
<222> LOCATION: (409)..(2205)
<223> OTHER INFORMATION:

<400> SEQUENCE: 3
gcaggaagat ggcggcggta gcggaggtgt gagtggacgc gggactcagc ggccggattt      60
tctcttccct tctttttccct tttccttccc tatttgaaat tggcatcgag ggggctaagt    120
tcgggtggca cgccgggcg caacgcaggg gtcacggcga cggcggcggc ggctgacggc      180 tggaaggta ggcttccttc accgctcgtc ctccttcctc gctccgctcg tgtcaggcg       240 cggcggcggc gcggcgggcg gacttcgtcc ctcctcctgc tcccccccac accgagcgg      300 gcactcttcg cttcgccatc ccccgaccct tcaccccgag gactgggcgc tcctccggc      360 gcagctgagg gagcggggc cggtctcctg ctcggttgtc gagcctcc atg tcg gat      417
                                                   Met Ser Asp
                                                     1 aat cag agc tgg aac tcg tcg ggc tcg gag gag gat cca gag acg gag      465
Asn Gln Ser Trp Asn Ser Ser Gly Ser Glu Glu Asp Pro Glu Thr Glu
        5                  10                 15 tct ggg ccg cct gtg gag cgc tgc ggg gtc ctc agt aag tgg aca aac      513
Ser Gly Pro Pro Val Glu Arg Cys Gly Val Leu Ser Lys Trp Thr Asn
20                  25                  30                 35
```

-continued

```
tac att cat ggg tgg cag gat cgt tgg gta gtt ttg aaa aat aat gct       561
Tyr Ile His Gly Trp Gln Asp Arg Trp Val Val Leu Lys Asn Asn Ala
            40                  45                  50 ctg agt tac tac aaa tct gaa gat gaa aca gag tat ggc tgc aga gga       609
Leu Ser Tyr Tyr Lys Ser Glu Asp Glu Thr Glu Tyr Gly Cys Arg Gly
        55                  60                  65 tcc atc tgt ctt agc aag gct gtc atc aca cct cac gat ttt gat gaa       657
Ser Ile Cys Leu Ser Lys Ala Val Ile Thr Pro His Asp Phe Asp Glu
    70                  75                  80 tgt cga ttt gat att agt gta aat gat agt gtt tgg tat ctt cgt gct       705
Cys Arg Phe Asp Ile Ser Val Asn Asp Ser Val Trp Tyr Leu Arg Ala
85                  90                  95 cag gat cca gat cat aga cag caa tgg ata gat gcc att gaa cag cac       753
Gln Asp Pro Asp His Arg Gln Gln Trp Ile Asp Ala Ile Glu Gln His
100                 105                 110                 115 aag act gaa tct gga tat gga tct gaa tcc agc ttg cgt cga cat ggc       801
Lys Thr Glu Ser Gly Tyr Gly Ser Glu Ser Ser Leu Arg Arg His Gly
                120                 125                 130 tca atg gtg tcc ctg gtg tct gga gca agt ggc tac tct gca aca tcc       849
Ser Met Val Ser Leu Val Ser Gly Ala Ser Gly Tyr Ser Ala Thr Ser
            135                 140                 145 acc tct tca ttc aag aaa ggc cac agt tta cgt gag aag ttg gct gaa       897
Thr Ser Ser Phe Lys Lys Gly His Ser Leu Arg Glu Lys Leu Ala Glu
        150                 155                 160 atg gaa aca ttt aga gac atc tta tgt aga caa gtt gac acg cta cag       945
Met Glu Thr Phe Arg Asp Ile Leu Cys Arg Gln Val Asp Thr Leu Gln
    165                 170                 175 aag tac ttt gat gcc tgt gct gat gct gtc tct aag gat gaa ctt caa       993
Lys Tyr Phe Asp Ala Cys Ala Asp Ala Val Ser Lys Asp Glu Leu Gln
180                 185                 190                 195 agg gat aaa gtg gta gaa gat gat gaa gat gac ttt cct aca acg cgt      1041
Arg Asp Lys Val Val Glu Asp Asp Glu Asp Asp Phe Pro Thr Thr Arg
                200                 205                 210 tct gat ggt gac ttc ttg cat agt acc aac ggc aat aaa gaa aag tta      1089
Ser Asp Gly Asp Phe Leu His Ser Thr Asn Gly Asn Lys Glu Lys Leu
            215                 220                 225 ttt cca cat gtg aca cca aaa gga att aat ggt ata gac ttt aaa ggg      1137
Phe Pro His Val Thr Pro Lys Gly Ile Asn Gly Ile Asp Phe Lys Gly
        230                 235                 240 gaa gcg ata act ttt aaa gca act act gct gga atc ctt gca aca ctt      1185
Glu Ala Ile Thr Phe Lys Ala Thr Thr Ala Gly Ile Leu Ala Thr Leu
    245                 250                 255 tct cat tgt att gaa cta atg gtt aaa cgt gag gac agc tgg cag aag      1233
Ser His Cys Ile Glu Leu Met Val Lys Arg Glu Asp Ser Trp Gln Lys
260                 265                 270                 275 aga ctg gat aag gaa act gag aag aaa aga aga aca gag gaa gca tat      1281
Arg Leu Asp Lys Glu Thr Glu Lys Lys Arg Arg Thr Glu Glu Ala Tyr
                280                 285                 290 aaa aat gca atg aca gaa ctt aag aaa aaa tcc cac ttt gga gga cca      1329
Lys Asn Ala Met Thr Glu Leu Lys Lys Lys Ser His Phe Gly Gly Pro
            295                 300                 305 gat tat gaa gaa ggc cct aac agt ctg att aat gaa gaa gag ttc ttt      1377
Asp Tyr Glu Glu Gly Pro Asn Ser Leu Ile Asn Glu Glu Glu Phe Phe
        310                 315                 320 gat gct gtt gaa gct gct ctt gac aga caa gat aaa ata gaa gaa cag      1425
Asp Ala Val Glu Ala Ala Leu Asp Arg Gln Asp Lys Ile Glu Glu Gln
    325                 330                 335 tca cag agt gaa aag gtg aga tta cat tgg cct aca tcc ttg ccc tct      1473
Ser Gln Ser Glu Lys Val Arg Leu His Trp Pro Thr Ser Leu Pro Ser
340                 345                 350                 355
```

```
gga gat gcc ttt tct tct gtg ggg aca cat aga ttt gtc caa aag gtt    1521
Gly Asp Ala Phe Ser Ser Val Gly Thr His Arg Phe Val Gln Lys Val
                360                 365                 370 gaa gag atg gtg cag aac cac atg act tac tca tta cag gat gta ggc    1569
Glu Glu Met Val Gln Asn His Met Thr Tyr Ser Leu Gln Asp Val Gly
            375                 380                 385 gga gat gcc aat tgg cag ttg gtt gta gaa gaa gga gaa atg aag gta    1617
Gly Asp Ala Asn Trp Gln Leu Val Val Glu Glu Gly Glu Met Lys Val
        390                 395                 400 tac aga aga gaa gta gaa gaa aat ggg att gtt ctg gat cct tta aaa    1665
Tyr Arg Arg Glu Val Glu Glu Asn Gly Ile Val Leu Asp Pro Leu Lys
405                 410                 415 gct acc cat gca gtt aaa ggc gtc aca gga cat gaa gtc tgc aat tat    1713
Ala Thr His Ala Val Lys Gly Val Thr Gly His Glu Val Cys Asn Tyr
420                 425                 430                 435 ttc tgg aat gtt gac gtt cgc aat gac tgg gaa aca act ata gaa aac    1761
Phe Trp Asn Val Asp Val Arg Asn Asp Trp Glu Thr Thr Ile Glu Asn
                440                 445                 450 ttt cat gtg gtg gaa aca tta gct gat aat gca atc atc att tat caa    1809
Phe His Val Val Glu Thr Leu Ala Asp Asn Ala Ile Ile Ile Tyr Gln
            455                 460                 465 aca cac aag agg gtg tgg cct gct tct cag cga gac gta tta tat ctt    1857
Thr His Lys Arg Val Trp Pro Ala Ser Gln Arg Asp Val Leu Tyr Leu
        470                 475                 480 tct gtc att cga aag ata cca gcc ttg act gaa aat gac cct gaa act    1905
Ser Val Ile Arg Lys Ile Pro Ala Leu Thr Glu Asn Asp Pro Glu Thr
485                 490                 495 tgg ata gtt tgt aat ttt tct gtg gat cat gac agt gct cct cta aac    1953
Trp Ile Val Cys Asn Phe Ser Val Asp His Asp Ser Ala Pro Leu Asn
500                 505                 510                 515 aac cga tgt gtc cgt gcc aaa ata aat gtt gct atg att tgt caa acc    2001
Asn Arg Cys Val Arg Ala Lys Ile Asn Val Ala Met Ile Cys Gln Thr
                520                 525                 530 ttg gta agc cca cca gag gga aac cag gaa att agc agg gac aac att    2049
Leu Val Ser Pro Pro Glu Gly Asn Gln Glu Ile Ser Arg Asp Asn Ile
            535                 540                 545 cta tgc aag att aca tat gta gct aat gtg aac cct gga gga tgg gca    2097
Leu Cys Lys Ile Thr Tyr Val Ala Asn Val Asn Pro Gly Gly Trp Ala
        550                 555                 560 cca gcc tca gtg tta agg gca gtg gca aag cga gag tat cct aaa ttt    2145
Pro Ala Ser Val Leu Arg Ala Val Ala Lys Arg Glu Tyr Pro Lys Phe
565                 570                 575 cta aaa cgt ttt act tct tac gtc caa gaa aaa act gca gga aag cct    2193
Leu Lys Arg Phe Thr Ser Tyr Val Gln Glu Lys Thr Ala Gly Lys Pro
580                 585                 590                 595 att ttg ttc tag tattaacagg tactagaaga tatgttttat cttttttttaa       2245
Ile Leu Phe ctttatttga ctaatatgac tgtcaatact aaaatttagt tgttgaaagt atttactatg  2305
tttttt                                                             2311

<210> SEQ ID NO 4
<211> LENGTH: 598
<212> TYPE: PRT
<213> ORGANISM: Homo sapiens

<400> SEQUENCE: 4

Met Ser Asp Asn Gln Ser Trp Asn Ser Ser Gly Ser Glu Glu Asp Pro
1               5                   10                  15
```

```
Glu Thr Glu Ser Gly Pro Pro Val Glu Arg Cys Gly Val Leu Ser Lys
             20              25              30

Trp Thr Asn Tyr Ile His Gly Trp Gln Asp Arg Trp Val Val Leu Lys
             35              40              45

Asn Asn Ala Leu Ser Tyr Tyr Lys Ser Glu Asp Glu Thr Glu Tyr Gly
 50              55              60

Cys Arg Gly Ser Ile Cys Leu Ser Lys Ala Val Ile Thr Pro His Asp
 65              70              75              80

Phe Asp Glu Cys Arg Phe Asp Ile Ser Val Asn Asp Ser Val Trp Tyr
             85              90              95

Leu Arg Ala Gln Asp Pro Asp His Arg Gln Gln Trp Ile Asp Ala Ile
            100             105             110

Glu Gln His Lys Thr Glu Ser Gly Tyr Gly Ser Glu Ser Ser Leu Arg
            115             120             125

Arg His Gly Ser Met Val Ser Leu Val Ser Gly Ala Ser Gly Tyr Ser
    130             135             140

Ala Thr Ser Thr Ser Ser Phe Lys Lys Gly His Ser Leu Arg Glu Lys
145             150             155             160

Leu Ala Glu Met Glu Thr Phe Arg Asp Ile Leu Cys Arg Gln Val Asp
            165             170             175

Thr Leu Gln Lys Tyr Phe Asp Ala Cys Ala Asp Ala Val Ser Lys Asp
            180             185             190

Glu Leu Gln Arg Asp Lys Val Val Glu Asp Asp Glu Asp Asp Phe Pro
            195             200             205

Thr Thr Arg Ser Asp Gly Asp Phe Leu His Ser Thr Asn Gly Asn Lys
    210             215             220

Glu Lys Leu Phe Pro His Val Thr Pro Lys Gly Ile Asn Gly Ile Asp
225             230             235             240

Phe Lys Gly Glu Ala Ile Thr Phe Lys Ala Thr Thr Ala Gly Ile Leu
            245             250             255

Ala Thr Leu Ser His Cys Ile Glu Leu Met Val Lys Arg Glu Asp Ser
            260             265             270

Trp Gln Lys Arg Leu Asp Lys Glu Thr Glu Lys Lys Arg Arg Thr Glu
            275             280             285

Glu Ala Tyr Lys Asn Ala Met Thr Glu Leu Lys Lys Lys Ser His Phe
            290             295             300

Gly Gly Pro Asp Tyr Glu Glu Gly Pro Asn Ser Leu Ile Asn Glu Glu
305             310             315             320

Glu Phe Phe Asp Ala Val Glu Ala Ala Leu Asp Arg Gln Asp Lys Ile
            325             330             335

Glu Glu Gln Ser Gln Ser Glu Lys Val Arg Leu His Trp Pro Thr Ser
            340             345             350

Leu Pro Ser Gly Asp Ala Phe Ser Ser Val Gly Thr His Arg Phe Val
            355             360             365

Gln Lys Val Glu Glu Met Val Gln Asn His Met Thr Tyr Ser Leu Gln
            370             375             380

Asp Val Gly Gly Asp Ala Asn Trp Gln Leu Val Glu Glu Gly Glu
385             390             395             400

Met Lys Val Tyr Arg Arg Glu Val Glu Asn Gly Ile Val Leu Asp
                405             410             415

Pro Leu Lys Ala Thr His Ala Val Lys Gly Val Thr Gly His Glu Val
            420             425             430

Cys Asn Tyr Phe Trp Asn Val Asp Val Arg Asn Asp Trp Glu Thr Thr
```

```
                  435                 440                 445
Ile Glu Asn Phe His Val Val Glu Thr Leu Ala Asp Asn Ala Ile Ile
    450                 455                 460

Ile Tyr Gln Thr His Lys Arg Val Trp Pro Ala Ser Gln Arg Asp Val
465                 470                 475                 480

Leu Tyr Leu Ser Val Ile Arg Lys Ile Pro Ala Leu Thr Glu Asn Asp
                485                 490                 495

Pro Glu Thr Trp Ile Val Cys Asn Phe Ser Val Asp His Asp Ser Ala
            500                 505                 510

Pro Leu Asn Asn Arg Cys Val Arg Ala Lys Ile Asn Val Ala Met Ile
        515                 520                 525

Cys Gln Thr Leu Val Ser Pro Pro Glu Gly Asn Gln Glu Ile Ser Arg
    530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
            580                 585                 590

Gly Lys Pro Ile Leu Phe
        595

<210> SEQ ID NO 5
<211> LENGTH: 2389
<212> TYPE: DNA
<213> ORGANISM: Homo sapiens
<220> FEATURE:
<221> NAME/KEY: CDS
<222> LOCATION: (100 )..(2283)
<223> OTHER INFORMATION:

<400> SEQUENCE: 5
gcaggaagat ggcggcggta gcggaggtgt gagtggacgc gggactcagc ggccggattt    60
tctcttccct tcttttccct tttccttccc tatttgaaa ttg gca tcg agg ggg     114
                                            Leu Ala Ser Arg Gly
                                              1               5 cta agt tcg ggt ggc agc gcc ggg cgc aac gca ggg gtc acg gcg acg    162
Leu Ser Ser Gly Gly Ser Ala Gly Arg Asn Ala Gly Val Thr Ala Thr
             10                  15                  20 gcg gcg gcg gct gac ggc tgg aag ggt agg ctt cct tca ccg ctc gtc    210
Ala Ala Ala Ala Asp Gly Trp Lys Gly Arg Leu Pro Ser Pro Leu Val
         25                  30                  35 ctc ctt cct cgc tcc gct cgg tgt cag gcg cgg cgg cgc ggc ggg        258
Leu Leu Pro Arg Ser Ala Arg Cys Gln Ala Arg Arg Arg Gly Gly
     40                  45                  50 cgg act tcg tcc ctc ctc ctg ctc ccc ccc aca ccg gag cgg gca ctc    306
Arg Thr Ser Ser Leu Leu Leu Leu Pro Pro Thr Pro Glu Arg Ala Leu
 55                  60                  65 ttc gct tcg cca tcc ccc gac cct tca ccc cga gga ctg ggc gcc tcc    354
Phe Ala Ser Pro Ser Pro Asp Pro Ser Pro Arg Gly Leu Gly Ala Ser
 70                  75                  80                  85 tcc ggc gca gct gag gga gcg ggg gcc ggt ctc ctg ctc ggt tgt cga    402
Ser Gly Ala Ala Glu Gly Ala Gly Ala Gly Leu Leu Leu Gly Cys Arg
                 90                  95                 100 gcc tcc atg tcg gat aat cag agc tgg aac tcg tcg ggc tcg gag gag    450
Ala Ser Met Ser Asp Asn Gln Ser Trp Asn Ser Ser Gly Ser Glu Glu
            105                 110                 115 gat cca gag acg gag tct ggg ccg cct gtg gag cgc tgc ggg gtc ctc    498
```

```
                    Asp Pro Glu Thr Glu Ser Gly Pro Val Glu Arg Cys Gly Val Leu
                        120                 125                 130 agt aag tgg aca aac tac att cat ggg tgg cag gat cgt tgg gta gtt        546
Ser Lys Trp Thr Asn Tyr Ile His Gly Trp Gln Asp Arg Trp Val Val
        135                 140                 145 ttg aaa aat aat gct ctg agt tac tac aaa tct gaa gat gaa aca gag        594
Leu Lys Asn Asn Ala Leu Ser Tyr Tyr Lys Ser Glu Asp Glu Thr Glu
150                 155                 160                 165 tat ggc tgc aga gga tcc atc tgt ctt agc aag gct gtc atc aca cct        642
Tyr Gly Cys Arg Gly Ser Ile Cys Leu Ser Lys Ala Val Ile Thr Pro
                170                 175                 180 cac gat ttt gat gaa tgt cga ttt gat att agt gta aat gat agt gtt        690
His Asp Phe Asp Glu Cys Arg Phe Asp Ile Ser Val Asn Asp Ser Val
        185                 190                 195 tgg tat ctt cgt gct cag gat cca gat cat aga cag caa tgg ata gat        738
Trp Tyr Leu Arg Ala Gln Asp Pro Asp His Arg Gln Gln Trp Ile Asp
            200                 205                 210 gcc att gaa cag cac aag act gaa tct gga tat gga tct gaa tcc agc        786
Ala Ile Glu Gln His Lys Thr Glu Ser Gly Tyr Gly Ser Glu Ser Ser
215                 220                 225 ttg cgt cga cat ggc tca atg gtg tcc ctg gtg tct gga gca agt ggc        834
Leu Arg Arg His Gly Ser Met Val Ser Leu Val Ser Gly Ala Ser Gly
230                 235                 240                 245 tac tct gca aca tcc acc tct tca ttc aag aaa ggc cac agt tta cgt        882
Tyr Ser Ala Thr Ser Thr Ser Ser Phe Lys Lys Gly His Ser Leu Arg
                250                 255                 260 gag aag ttg gct gaa atg gaa aca ttt aga gac atc tta tgt aga caa        930
Glu Lys Leu Ala Glu Met Glu Thr Phe Arg Asp Ile Leu Cys Arg Gln
        265                 270                 275 gtt gac acg cta cag aag tac ttt gat gcc tgt gct gat gct gtc tct        978
Val Asp Thr Leu Gln Lys Tyr Phe Asp Ala Cys Ala Asp Ala Val Ser
            280                 285                 290 aag gat gaa ctt caa agg gat aaa gtg gta gaa gat gat gaa gat gac       1026
Lys Asp Glu Leu Gln Arg Asp Lys Val Val Glu Asp Asp Glu Asp Asp
295                 300                 305 ttt cct aca acg cgt tct gat ggt gac ttc ttg cat agt acc aac ggc       1074
Phe Pro Thr Thr Arg Ser Asp Gly Asp Phe Leu His Ser Thr Asn Gly
310                 315                 320                 325 aat aaa gaa aag tta ttt cca cat gtg aca cca aaa gga att aat ggt       1122
Asn Lys Glu Lys Leu Phe Pro His Val Thr Pro Lys Gly Ile Asn Gly
                330                 335                 340 ata gac ttt aaa ggg gaa gcg ata act ttt aaa gca act act gct gga       1170
Ile Asp Phe Lys Gly Glu Ala Ile Thr Phe Lys Ala Thr Thr Ala Gly
        345                 350                 355 atc ctt gca aca ctt tct cat tgt att gaa cta atg gtt aaa cgt gag       1218
Ile Leu Ala Thr Leu Ser His Cys Ile Glu Leu Met Val Lys Arg Glu
            360                 365                 370 gac agc tgg cag aag aga ctg gat aag gaa act gag aag aaa aga aga       1266
Asp Ser Trp Gln Lys Arg Leu Asp Lys Glu Thr Glu Lys Lys Arg Arg
375                 380                 385 aca gag gaa gca tat aaa aat gca atg aca gaa ctt aag aaa aaa tcc       1314
Thr Glu Glu Ala Tyr Lys Asn Ala Met Thr Glu Leu Lys Lys Lys Ser
390                 395                 400                 405 cac ttt gga gga cca gat tat gaa gaa ggc cct aac agt ctg att aat       1362
His Phe Gly Gly Pro Asp Tyr Glu Glu Gly Pro Asn Ser Leu Ile Asn
                410                 415                 420 gaa gaa gag ttc ttt gat gct gtt gaa gct gct ctt gac aga caa gat       1410
Glu Glu Glu Phe Phe Asp Ala Val Glu Ala Ala Leu Asp Arg Gln Asp
        425                 430                 435
```

```
aaa ata gaa gaa cag tca cag agt gaa aag gtg aga tta cat tgg cct      1458
Lys Ile Glu Glu Gln Ser Gln Ser Glu Lys Val Arg Leu His Trp Pro
        440                 445                 450 aca tcc ttg ccc tct gga gat gcc ttt tct tct gtg ggg aca cat aga      1506
Thr Ser Leu Pro Ser Gly Asp Ala Phe Ser Ser Val Gly Thr His Arg
455                 460                 465 ttt gtc caa aag ccc tat agt cgc tct tcc tcc atg tct tcc att gat      1554
Phe Val Gln Lys Pro Tyr Ser Arg Ser Ser Ser Met Ser Ser Ile Asp
470                 475                 480                 485 cta gtc agt gcc tct gat gat gtt cac aga ttc agc tcc cag gtt gaa      1602
Leu Val Ser Ala Ser Asp Asp Val His Arg Phe Ser Ser Gln Val Glu
                490                 495                 500 gag atg gtg cag aac cac atg act tac tca tta cag gat gta ggc gga      1650
Glu Met Val Gln Asn His Met Thr Tyr Ser Leu Gln Asp Val Gly Gly
            505                 510                 515 gat gcc aat tgg cag ttg gtt gta gaa gaa gga gaa atg aag gta tac      1698
Asp Ala Asn Trp Gln Leu Val Val Glu Glu Gly Glu Met Lys Val Tyr
        520                 525                 530 aga aga gaa gta gaa gaa aat ggg att gtt ctg gat cct tta aaa gct      1746
Arg Arg Glu Val Glu Glu Asn Gly Ile Val Leu Asp Pro Leu Lys Ala
535                 540                 545 acc cat gca gtt aaa ggc gtc aca gga cat gaa gtc tgc aat tat ttc      1794
Thr His Ala Val Lys Gly Val Thr Gly His Glu Val Cys Asn Tyr Phe
550                 555                 560                 565 tgg aat gtt gac gtt cgc aat gac tgg gaa aca act ata gaa aac ttt      1842
Trp Asn Val Asp Val Arg Asn Asp Trp Glu Thr Thr Ile Glu Asn Phe
                570                 575                 580 cat gtg gtg gaa aca tta gct gat aat gca atc atc att tat caa aca      1890
His Val Val Glu Thr Leu Ala Asp Asn Ala Ile Ile Ile Tyr Gln Thr
            585                 590                 595 cac aag agg gtg tgg cct gct tct cag cga gac gta tta tat ctt tct      1938
His Lys Arg Val Trp Pro Ala Ser Gln Arg Asp Val Leu Tyr Leu Ser
        600                 605                 610 gtc att cga aag ata cca gcc ttg act gaa aat gac cct gaa act tgg      1986
Val Ile Arg Lys Ile Pro Ala Leu Thr Glu Asn Asp Pro Glu Thr Trp
615                 620                 625 ata gtt tgt aat ttt tct gtg gat cat gac agt gct cct cta aac aac      2034
Ile Val Cys Asn Phe Ser Val Asp His Asp Ser Ala Pro Leu Asn Asn
630                 635                 640                 645 cga tgt gtc cgt gcc aaa ata aat gtt gct atg att tgt caa acc ttg      2082
Arg Cys Val Arg Ala Lys Ile Asn Val Ala Met Ile Cys Gln Thr Leu
                650                 655                 660 gta agc cca cca gag gga aac cag gaa att agc agg gac aac att cta      2130
Val Ser Pro Pro Glu Gly Asn Gln Glu Ile Ser Arg Asp Asn Ile Leu
            665                 670                 675 tgc aag att aca tat gta gct aat gtg aac cct gga gga tgg gca cca      2178
Cys Lys Ile Thr Tyr Val Ala Asn Val Asn Pro Gly Gly Trp Ala Pro
        680                 685                 690 gcc tca gtg tta agg gca gtg gca aag cga gag tat cct aaa ttt cta      2226
Ala Ser Val Leu Arg Ala Val Ala Lys Arg Glu Tyr Pro Lys Phe Leu
695                 700                 705 aaa cgt ttt act tct tac gtc caa gaa aaa act gca gga aag cct att      2274
Lys Arg Phe Thr Ser Tyr Val Gln Glu Lys Thr Ala Gly Lys Pro Ile
710                 715                 720                 725 ttg ttc tag tattaacagg tactagaaga tatgttttat cttttttaa               2323
Leu Phe ctttatttga ctaatatgac tgtcaatact aaaatttagt tgttgaaagt atttactatg   2383
tttttt                                                               2389
```

```
<210> SEQ ID NO 6
<211> LENGTH: 727
<212> TYPE: PRT
<213> ORGANISM: Homo sapiens

<400> SEQUENCE: 6
```

| | | | | | | | | | | | | | | |
|---|---|---|---|---|---|---|---|---|---|---|---|---|---|---|
| Leu | Ala | Ser | Arg | Gly | Leu | Ser | Ser | Gly | Gly | Ser | Ala | Gly | Arg | Asn | Ala |
| 1 | | | | 5 | | | | | 10 | | | | | 15 | |

| Gly | Val | Thr | Ala | Thr | Ala | Ala | Ala | Asp | Gly | Trp | Lys | Gly | Arg | Leu |
|---|---|---|---|---|---|---|---|---|---|---|---|---|---|---|
| | | | 20 | | | | | 25 | | | | | 30 | |

| Pro | Ser | Pro | Leu | Val | Leu | Leu | Pro | Arg | Ser | Ala | Arg | Cys | Gln | Ala | Arg |
|---|---|---|---|---|---|---|---|---|---|---|---|---|---|---|---|
| | | 35 | | | | | 40 | | | | | 45 | | | |

Arg Arg Arg Gly Gly Arg Thr Ser Ser Leu Leu Leu Leu Pro Pro Thr
         50                  55                  60

Pro Glu Arg Ala Leu Phe Ala Ser Pro Ser Pro Asp Pro Ser Pro Arg
 65                  70                  75                  80

Gly Leu Gly Ala Ser Ser Gly Ala Ala Glu Gly Ala Gly Ala Gly Leu
                 85                  90                  95

Leu Leu Gly Cys Arg Ala Ser Met Ser Asp Asn Gln Ser Trp Asn Ser
                100                 105                 110

Ser Gly Ser Glu Glu Asp Pro Glu Thr Glu Ser Gly Pro Pro Val Glu
            115                 120                 125

Arg Cys Gly Val Leu Ser Lys Trp Thr Asn Tyr Ile His Gly Trp Gln
        130                 135                 140

Asp Arg Trp Val Val Leu Lys Asn Asn Ala Leu Ser Tyr Tyr Lys Ser
145                 150                 155                 160

Glu Asp Glu Thr Glu Tyr Gly Cys Arg Gly Ser Ile Cys Leu Ser Lys
                165                 170                 175

Ala Val Ile Thr Pro His Asp Phe Asp Glu Cys Arg Phe Asp Ile Ser
                180                 185                 190

Val Asn Asp Ser Val Trp Tyr Leu Arg Ala Gln Asp Pro Asp His Arg
            195                 200                 205

Gln Gln Trp Ile Asp Ala Ile Glu Gln His Lys Thr Glu Ser Gly Tyr
        210                 215                 220

Gly Ser Glu Ser Ser Leu Arg Arg His Gly Ser Met Val Ser Leu Val
225                 230                 235                 240

Ser Gly Ala Ser Gly Tyr Ser Ala Thr Ser Thr Ser Ser Phe Lys Lys
                245                 250                 255

Gly His Ser Leu Arg Glu Lys Leu Ala Glu Met Glu Thr Phe Arg Asp
                260                 265                 270

Ile Leu Cys Arg Gln Val Asp Thr Leu Gln Lys Tyr Phe Asp Ala Cys
            275                 280                 285

Ala Asp Ala Val Ser Lys Asp Glu Leu Gln Arg Asp Lys Val Val Glu
        290                 295                 300

Asp Asp Glu Asp Asp Phe Pro Thr Thr Arg Ser Asp Gly Asp Phe Leu
305                 310                 315                 320

His Ser Thr Asn Gly Asn Lys Glu Lys Leu Phe Pro His Val Thr Pro
                325                 330                 335

Lys Gly Ile Asn Gly Ile Asp Phe Lys Gly Glu Ala Ile Thr Phe Lys
                340                 345                 350

Ala Thr Thr Ala Gly Ile Leu Ala Thr Leu Ser His Cys Ile Glu Leu
            355                 360                 365

Met Val Lys Arg Glu Asp Ser Trp Gln Lys Arg Leu Asp Lys Glu Thr
        370                 375                 380

```
Glu Lys Lys Arg Arg Thr Glu Glu Ala Tyr Lys Asn Ala Met Thr Glu
385                 390                 395                 400

Leu Lys Lys Lys Ser His Phe Gly Gly Pro Asp Tyr Glu Glu Gly Pro
            405                 410                 415

Asn Ser Leu Ile Asn Glu Glu Phe Phe Asp Ala Val Glu Ala Ala
                420                 425                 430

Leu Asp Arg Gln Asp Lys Ile Glu Glu Gln Ser Gln Ser Glu Lys Val
        435                 440                 445

Arg Leu His Trp Pro Thr Ser Leu Pro Ser Gly Asp Ala Phe Ser Ser
450                 455                 460

Val Gly Thr His Arg Phe Val Gln Lys Pro Tyr Ser Arg Ser Ser Ser
465                 470                 475                 480

Met Ser Ser Ile Asp Leu Val Ser Ala Ser Asp Val His Arg Phe
                485                 490                 495

Ser Ser Gln Val Glu Glu Met Val Gln Asn His Met Thr Tyr Ser Leu
        500                 505                 510

Gln Asp Val Gly Gly Asp Ala Asn Trp Gln Leu Val Glu Glu Gly
        515                 520                 525

Glu Met Lys Val Tyr Arg Arg Glu Val Glu Glu Asn Gly Ile Val Leu
530                 535                 540

Asp Pro Leu Lys Ala Thr His Ala Val Lys Gly Val Thr Gly His Glu
545                 550                 555                 560

Val Cys Asn Tyr Phe Trp Asn Val Asp Val Arg Asn Asp Trp Glu Thr
                565                 570                 575

Thr Ile Glu Asn Phe His Val Val Glu Thr Leu Ala Asp Asn Ala Ile
                580                 585                 590

Ile Ile Tyr Gln Thr His Lys Arg Val Trp Pro Ala Ser Gln Arg Asp
        595                 600                 605

Val Leu Tyr Leu Ser Val Ile Arg Lys Ile Pro Ala Leu Thr Glu Asn
610                 615                 620

Asp Pro Glu Thr Trp Ile Val Cys Asn Phe Ser Val Asp His Asp Ser
625                 630                 635                 640

Ala Pro Leu Asn Asn Arg Cys Val Arg Ala Lys Ile Asn Val Ala Met
                645                 650                 655

Ile Cys Gln Thr Leu Val Ser Pro Pro Glu Gly Asn Gln Glu Ile Ser
        660                 665                 670

Arg Asp Asn Ile Leu Cys Lys Ile Thr Tyr Val Ala Asn Val Asn Pro
        675                 680                 685

Gly Gly Trp Ala Pro Ala Ser Val Leu Arg Ala Val Ala Lys Arg Glu
690                 695                 700

Tyr Pro Lys Phe Leu Lys Arg Phe Thr Ser Tyr Val Gln Glu Lys Thr
705                 710                 715                 720

Ala Gly Lys Pro Ile Leu Phe
                725

<210> SEQ ID NO 7
<211> LENGTH: 2311
<212> TYPE: DNA
<213> ORGANISM: Homo sapiens
<220> FEATURE:
<221> NAME/KEY: CDS
<222> LOCATION: (100)..(2205)
<223> OTHER INFORMATION:

<400> SEQUENCE: 7
```

-continued

```
gcaggaagat ggcggcggta gcggaggtgt gagtggacgc gggactcagc ggccggattt      60
tctcttccct tcttttccct tttccttccc tatttgaaa ttg gca tcg agg ggg       114
                                             Leu Ala Ser Arg Gly
                                              1               5 cta agt tcg ggt ggc agc gcc ggg cgc aac gca ggg gtc acg gcg acg       162
Leu Ser Ser Gly Gly Ser Ala Gly Arg Asn Ala Gly Val Thr Ala Thr
            10                  15                  20 gcg gcg gcg gct gac ggc tgg aag ggt agg ctt cct tca ccg ctc gtc       210
Ala Ala Ala Ala Asp Gly Trp Lys Gly Arg Leu Pro Ser Pro Leu Val
        25                  30                  35 ctc ctt cct cgc tcc gct cgg tgt cag gcg cgg cgg cgg cgc ggc ggg       258
Leu Leu Pro Arg Ser Ala Arg Cys Gln Ala Arg Arg Arg Arg Gly Gly
    40                  45                  50 cgg act tcg tcc ctc ctc ctg ctc ccc ccc aca ccg gag cgg gca ctc       306
Arg Thr Ser Ser Leu Leu Leu Leu Pro Pro Thr Pro Glu Arg Ala Leu
55                  60                  65 ttc gct tcg cca tcc ccc gac cct tca ccc cga gga ctg ggc gcc tcc       354
Phe Ala Ser Pro Ser Pro Asp Pro Ser Pro Arg Gly Leu Gly Ala Ser
70                  75                  80                  85 tcc ggc gca gct gag gga gcg ggg gcc ggt ctc ctg ctc ggt tgt cga       402
Ser Gly Ala Ala Glu Gly Ala Gly Ala Gly Leu Leu Leu Gly Cys Arg
            90                  95                 100 gcc tcc atg tcg gat aat cag agc tgg aac tcg tcg ggc tcg gag gag       450
Ala Ser Met Ser Asp Asn Gln Ser Trp Asn Ser Ser Gly Ser Glu Glu
        105                 110                 115 gat cca gag acg gag tct ggg ccg cct gtg gag cgc tgc ggg gtc ctc       498
Asp Pro Glu Thr Glu Ser Gly Pro Pro Val Glu Arg Cys Gly Val Leu
    120                 125                 130 agt aag tgg aca aac tac att cat ggg tgg cag gat cgt tgg gta gtt       546
Ser Lys Trp Thr Asn Tyr Ile His Gly Trp Gln Asp Arg Trp Val Val
135                 140                 145 ttg aaa aat aat gct ctg agt tac tac aaa tct gaa gat gaa aca gag       594
Leu Lys Asn Asn Ala Leu Ser Tyr Tyr Lys Ser Glu Asp Glu Thr Glu
150                 155                 160                 165 tat ggc tgc aga gga tcc atc tgt ctt agc aag gct gtc atc aca cct       642
Tyr Gly Cys Arg Gly Ser Ile Cys Leu Ser Lys Ala Val Ile Thr Pro
            170                 175                 180 cac gat ttt gat gaa tgt cga ttt gat att agt gta aat gat agt gtt       690
His Asp Phe Asp Glu Cys Arg Phe Asp Ile Ser Val Asn Asp Ser Val
        185                 190                 195 tgg tat ctt cgt gct cag gat cca gat cat aga cag caa tgg ata gat       738
Trp Tyr Leu Arg Ala Gln Asp Pro Asp His Arg Gln Gln Trp Ile Asp
    200                 205                 210 gcc att gaa cag cac aag act gaa tct gga tat gga tct gaa tcc agc       786
Ala Ile Glu Gln His Lys Thr Glu Ser Gly Tyr Gly Ser Glu Ser Ser
215                 220                 225 ttg cgt cga cat ggc tca atg gtg tcc ctg gtg tct gga gca agt ggc       834
Leu Arg Arg His Gly Ser Met Val Ser Leu Val Ser Gly Ala Ser Gly
230                 235                 240                 245 tac tct gca aca tcc acc tct tca ttc aag aaa ggc cac agt tta cgt       882
Tyr Ser Ala Thr Ser Thr Ser Ser Phe Lys Lys Gly His Ser Leu Arg
            250                 255                 260 gag aag ttg gct gaa atg gaa aca ttt aga gac atc tta tgt aga caa       930
Glu Lys Leu Ala Glu Met Glu Thr Phe Arg Asp Ile Leu Cys Arg Gln
        265                 270                 275 gtt gac acg cta cag aag tac ttt gat gcc tgt gct gat gct gtc tct       978
Val Asp Thr Leu Gln Lys Tyr Phe Asp Ala Cys Ala Asp Ala Val Ser
    280                 285                 290 aag gat gaa ctt caa agg gat aaa gtg gta gaa gat gat gaa gat gac      1026
```

```
                Lys Asp Glu Leu Gln Arg Asp Lys Val Val Glu Asp Glu Asp Asp
                    295                 300                 305 ttt cct aca acg cgt tct gat ggt gac ttc ttg cat agt acc aac ggc      1074
Phe Pro Thr Thr Arg Ser Asp Gly Asp Phe Leu His Ser Thr Asn Gly
310                 315                 320                 325 aat aaa gaa aag tta ttt cca cat gtg aca cca aaa gga att aat ggt      1122
Asn Lys Glu Lys Leu Phe Pro His Val Thr Pro Lys Gly Ile Asn Gly
                330                 335                 340 ata gac ttt aaa ggg gaa gcg ata act ttt aaa gca act act gct gga      1170
Ile Asp Phe Lys Gly Glu Ala Ile Thr Phe Lys Ala Thr Thr Ala Gly
            345                 350                 355 atc ctt gca aca ctt tct cat tgt att gaa cta atg gtt aaa cgt gag      1218
Ile Leu Ala Thr Leu Ser His Cys Ile Glu Leu Met Val Lys Arg Glu
        360                 365                 370 gac agc tgg cag aag aga ctg gat aag gaa act gag aag aaa aga aga      1266
Asp Ser Trp Gln Lys Arg Leu Asp Lys Glu Thr Glu Lys Lys Arg Arg
    375                 380                 385 aca gag gaa gca tat aaa aat gca atg aca gaa ctt aag aaa aaa tcc      1314
Thr Glu Glu Ala Tyr Lys Asn Ala Met Thr Glu Leu Lys Lys Lys Ser
390                 395                 400                 405 cac ttt gga gga cca gat tat gaa gaa ggc cct aac agt ctg att aat      1362
His Phe Gly Gly Pro Asp Tyr Glu Glu Gly Pro Asn Ser Leu Ile Asn
                410                 415                 420 gaa gaa gag ttc ttt gat gct gtt gaa gct gct ctt gac aga caa gat      1410
Glu Glu Glu Phe Phe Asp Ala Val Glu Ala Ala Leu Asp Arg Gln Asp
            425                 430                 435 aaa ata gaa gaa cag tca cag agt gaa aag gtg aga tta cat tgg cct      1458
Lys Ile Glu Glu Gln Ser Gln Ser Glu Lys Val Arg Leu His Trp Pro
        440                 445                 450 aca tcc ttg ccc tct gga gat gcc ttt tct tct gtg ggg aca cat aga      1506
Thr Ser Leu Pro Ser Gly Asp Ala Phe Ser Ser Val Gly Thr His Arg
    455                 460                 465 ttt gtc caa aag gtt gaa gag atg gtg cag aac cac atg act tac tca      1554
Phe Val Gln Lys Val Glu Glu Met Val Gln Asn His Met Thr Tyr Ser
470                 475                 480                 485 tta cag gat gta ggc gga gat gcc aat tgg cag ttg gtt gta gaa gaa      1602
Leu Gln Asp Val Gly Gly Asp Ala Asn Trp Gln Leu Val Val Glu Glu
                490                 495                 500 gga gaa atg aag gta tac aga aga gaa gta gaa gaa aat ggg att gtt      1650
Gly Glu Met Lys Val Tyr Arg Arg Glu Val Glu Glu Asn Gly Ile Val
            505                 510                 515 ctg gat cct tta aaa gct acc cat gca gtt aaa ggc gtc aca gga cat      1698
Leu Asp Pro Leu Lys Ala Thr His Ala Val Lys Gly Val Thr Gly His
        520                 525                 530 gaa gtc tgc aat tat ttc tgg aat gtt gac gtt cgc aat gac tgg gaa      1746
Glu Val Cys Asn Tyr Phe Trp Asn Val Asp Val Arg Asn Asp Trp Glu
    535                 540                 545 aca act ata gaa aac ttt cat gtg gtg gaa aca tta gct gat aat gca      1794
Thr Thr Ile Glu Asn Phe His Val Val Glu Thr Leu Ala Asp Asn Ala
550                 555                 560                 565 atc atc att tat caa aca cac aag agg gtg tgg cct gct tct cag cga      1842
Ile Ile Ile Tyr Gln Thr His Lys Arg Val Trp Pro Ala Ser Gln Arg
                570                 575                 580 gac gta tta tat ctt tct gtc att cga aag ata cca gcc ttg act gaa      1890
Asp Val Leu Tyr Leu Ser Val Ile Arg Lys Ile Pro Ala Leu Thr Glu
            585                 590                 595 aat gac cct gaa act tgg ata gtt tgt aat ttt tct gtg gat cat gac      1938
Asn Asp Pro Glu Thr Trp Ile Val Cys Asn Phe Ser Val Asp His Asp
        600                 605                 610
```

-continued

```
agt gct cct cta aac aac cga tgt gtc cgt gcc aaa ata aat gtt gct      1986
Ser Ala Pro Leu Asn Asn Arg Cys Val Arg Ala Lys Ile Asn Val Ala
    615                 620                 625 atg att tgt caa acc ttg gta agc cca cca gag gga aac cag gaa att      2034
Met Ile Cys Gln Thr Leu Val Ser Pro Pro Glu Gly Asn Gln Glu Ile
630                 635                 640                 645 agc agg gac aac att cta tgc aag att aca tat gta gct aat gtg aac      2082
Ser Arg Asp Asn Ile Leu Cys Lys Ile Thr Tyr Val Ala Asn Val Asn
                650                 655                 660 cct gga gga tgg gca cca gcc tca gtg tta agg gca gtg gca aag cga      2130
Pro Gly Gly Trp Ala Pro Ala Ser Val Leu Arg Ala Val Ala Lys Arg
            665                 670                 675 gag tat cct aaa ttt cta aaa cgt ttt act tct tac gtc caa gaa aaa      2178
Glu Tyr Pro Lys Phe Leu Lys Arg Phe Thr Ser Tyr Val Gln Glu Lys
        680                 685                 690 act gca gga aag cct att ttg ttc tag tattaacagg tactagaaga            2225
Thr Ala Gly Lys Pro Ile Leu Phe
    695                 700 tatgttttat ctttttttaa ctttatttga ctaatatgac tgtcaatact aaaatttagt    2285
tgttgaaagt atttactatg tttttt                                         2311

<210> SEQ ID NO 8
<211> LENGTH: 701
<212> TYPE: PRT
<213> ORGANISM: Homo sapiens

<400> SEQUENCE: 8

Leu Ala Ser Arg Gly Leu Ser Ser Gly Gly Ser Ala Gly Arg Asn Ala
1               5                   10                  15

Gly Val Thr Ala Thr Ala Ala Ala Asp Gly Trp Lys Gly Arg Leu
            20                  25                  30

Pro Ser Pro Leu Val Leu Leu Pro Arg Ser Ala Arg Cys Gln Ala Arg
            35                  40                  45

Arg Arg Arg Gly Gly Arg Thr Ser Leu Leu Leu Pro Pro Thr
    50                  55                  60

Pro Glu Arg Ala Leu Phe Ala Ser Pro Ser Asp Pro Ser Pro Arg
65              70                  75                  80

Gly Leu Gly Ala Ser Gly Ala Ala Glu Gly Ala Gly Ala Gly Leu
                85                  90                  95

Leu Leu Gly Cys Arg Ala Ser Met Ser Asp Asn Gln Ser Trp Asn Ser
            100                 105                 110

Ser Gly Ser Glu Glu Asp Pro Glu Thr Glu Ser Gly Pro Pro Val Glu
        115                 120                 125

Arg Cys Gly Val Leu Ser Lys Trp Thr Asn Tyr Ile His Gly Trp Gln
    130                 135                 140

Asp Arg Trp Val Val Leu Lys Asn Asn Ala Leu Ser Tyr Tyr Lys Ser
145                 150                 155                 160

Glu Asp Glu Thr Glu Tyr Gly Cys Arg Gly Ser Ile Cys Leu Ser Lys
                165                 170                 175

Ala Val Ile Thr Pro His Asp Phe Glu Cys Arg Phe Asp Ile Ser
            180                 185                 190

Val Asn Asp Ser Val Trp Tyr Leu Arg Ala Gln Asp Pro Asp His Arg
        195                 200                 205

Gln Gln Trp Ile Asp Ala Ile Glu Gln His Lys Thr Glu Ser Gly Tyr
    210                 215                 220

Gly Ser Glu Ser Ser Leu Arg Arg His Gly Ser Met Val Ser Leu Val
```

-continued

```
                225                 230                 235                 240
Ser Gly Ala Ser Gly Tyr Ser Ala Thr Ser Thr Ser Ser Phe Lys Lys
                245                 250                 255

Gly His Ser Leu Arg Glu Lys Leu Ala Glu Met Glu Thr Phe Arg Asp
            260                 265                 270

Ile Leu Cys Arg Gln Val Asp Thr Leu Gln Lys Tyr Phe Asp Ala Cys
            275                 280                 285

Ala Asp Ala Val Ser Lys Asp Glu Leu Gln Arg Asp Lys Val Val Glu
        290                 295                 300

Asp Asp Glu Asp Asp Phe Pro Thr Thr Arg Ser Asp Gly Asp Phe Leu
305                 310                 315                 320

His Ser Thr Asn Gly Asn Lys Glu Lys Leu Phe Pro His Val Thr Pro
                325                 330                 335

Lys Gly Ile Asn Gly Ile Asp Phe Lys Gly Glu Ala Ile Thr Phe Lys
                340                 345                 350

Ala Thr Thr Ala Gly Ile Leu Ala Thr Leu Ser His Cys Ile Glu Leu
            355                 360                 365

Met Val Lys Arg Glu Asp Ser Trp Gln Lys Arg Leu Asp Lys Glu Thr
        370                 375                 380

Glu Lys Lys Arg Arg Thr Glu Glu Ala Tyr Lys Asn Ala Met Thr Glu
385                 390                 395                 400

Leu Lys Lys Lys Ser His Phe Gly Gly Pro Asp Tyr Glu Glu Gly Pro
                405                 410                 415

Asn Ser Leu Ile Asn Glu Glu Phe Phe Asp Ala Val Glu Ala Ala
                420                 425                 430

Leu Asp Arg Gln Asp Lys Ile Glu Glu Gln Ser Gln Ser Glu Lys Val
            435                 440                 445

Arg Leu His Trp Pro Thr Ser Leu Pro Ser Gly Asp Ala Phe Ser Ser
        450                 455                 460

Val Gly Thr His Arg Phe Val Gln Lys Val Glu Met Val Gln Asn
465                 470                 475                 480

His Met Thr Tyr Ser Leu Gln Asp Val Gly Gly Asp Ala Asn Trp Gln
                485                 490                 495

Leu Val Val Glu Glu Gly Glu Met Lys Val Tyr Arg Arg Glu Val Glu
                500                 505                 510

Glu Asn Gly Ile Val Leu Asp Pro Leu Lys Ala Thr His Ala Val Lys
            515                 520                 525

Gly Val Thr Gly His Glu Val Cys Asn Tyr Phe Trp Asn Val Asp Val
        530                 535                 540

Arg Asn Asp Trp Glu Thr Thr Ile Glu Asn Phe His Val Val Glu Thr
545                 550                 555                 560

Leu Ala Asp Asn Ala Ile Ile Tyr Gln Thr His Lys Arg Val Trp
                565                 570                 575

Pro Ala Ser Gln Arg Asp Val Leu Tyr Leu Ser Val Ile Arg Lys Ile
            580                 585                 590

Pro Ala Leu Thr Glu Asn Asp Pro Glu Thr Trp Ile Val Cys Asn Phe
        595                 600                 605

Ser Val Asp His Asp Ser Ala Pro Leu Asn Asn Arg Cys Val Arg Ala
        610                 615                 620

Lys Ile Asn Val Ala Met Ile Cys Gln Thr Leu Val Ser Pro Pro Glu
625                 630                 635                 640

Gly Asn Gln Glu Ile Ser Arg Asp Asn Ile Leu Cys Lys Ile Thr Tyr
                645                 650                 655
```

-continued

```
Val Ala Asn Val Asn Pro Gly Gly Trp Ala Pro Ala Ser Val Leu Arg
        660                 665                 670

Ala Val Ala Lys Arg Glu Tyr Pro Lys Phe Leu Lys Arg Phe Thr Ser
        675                 680                 685

Tyr Val Gln Glu Lys Thr Ala Gly Lys Pro Ile Leu Phe
        690                 695                 700

<210> SEQ ID NO 9
<211> LENGTH: 1914
<212> TYPE: DNA
<213> ORGANISM: Artificial
<220> FEATURE:
<223> OTHER INFORMATION: Derived sequence
<220> FEATURE:
<221> NAME/KEY: CDS
<222> LOCATION: (1)..(1914)
<223> OTHER INFORMATION:

<400> SEQUENCE: 9 gga gcg ggg gcc ggt ctc ctg ctc ggt tgt cga gcc tcc atg tcg gat     48
Gly Ala Gly Ala Gly Leu Leu Leu Gly Cys Arg Ala Ser Met Ser Asp
1               5                   10                  15 aat cag agc tgg aac tcg tcg ggc tcg gag gag gat cca gag acg gag     96
Asn Gln Ser Trp Asn Ser Ser Gly Ser Glu Glu Asp Pro Glu Thr Glu
            20                  25                  30 tct ggg ccg cct gtg gag cgc tgc ggg gtc ctc agt aag tgg aca aac    144
Ser Gly Pro Pro Val Glu Arg Cys Gly Val Leu Ser Lys Trp Thr Asn
        35                  40                  45 tac att cat ggg tgg cag gat cgt tgg gta gtt ttg aaa aat aat gct    192
Tyr Ile His Gly Trp Gln Asp Arg Trp Val Val Leu Lys Asn Asn Ala
    50                  55                  60 ctg agt tac tac aaa tct gaa gat gaa aca gag tat ggc tgc aga gga    240
Leu Ser Tyr Tyr Lys Ser Glu Asp Glu Thr Glu Tyr Gly Cys Arg Gly
65                  70                  75                  80 tcc atc tgt ctt agc aag gct gtc atc aca cct cac gat ttt gat gaa    288
Ser Ile Cys Leu Ser Lys Ala Val Ile Thr Pro His Asp Phe Asp Glu
                85                  90                  95 tgt cga ttt gat att agt gta aat gat agt gtt tgg tat ctt cgt gct    336
Cys Arg Phe Asp Ile Ser Val Asn Asp Ser Val Trp Tyr Leu Arg Ala
            100                 105                 110 cag gat cca gat cat aga cag caa tgg ata gat gcc att gaa cag cac    384
Gln Asp Pro Asp His Arg Gln Gln Trp Ile Asp Ala Ile Glu Gln His
        115                 120                 125 aag act gaa tct gga tat gga tct gaa tcc agc ttg cgt cga cat ggc    432
Lys Thr Glu Ser Gly Tyr Gly Ser Glu Ser Ser Leu Arg Arg His Gly
    130                 135                 140 tca atg gtg tcc ctg gtg tct gga gca agt ggc tac tct gca aca tcc    480
Ser Met Val Ser Leu Val Ser Gly Ala Ser Gly Tyr Ser Ala Thr Ser
145                 150                 155                 160 acc tct tca ttc aag aaa ggc cac agt tta cgt gag aag ttg gct gaa    528
Thr Ser Ser Phe Lys Lys Gly His Ser Leu Arg Glu Lys Leu Ala Glu
                165                 170                 175 atg gaa aca ttt aga gac atc tta tgt aga caa gtt gac acg cta cag    576
Met Glu Thr Phe Arg Asp Ile Leu Cys Arg Gln Val Asp Thr Leu Gln
            180                 185                 190 aag tac ttt gat gcc tgt gct gat gct gtc tct aag gat gaa ctt caa    624
Lys Tyr Phe Asp Ala Cys Ala Asp Ala Val Ser Lys Asp Glu Leu Gln
        195                 200                 205 agg gat aaa gtg gta gaa gat gat gaa gat gac ttt cct aca acg cgt    672
Arg Asp Lys Val Val Glu Asp Asp Glu Asp Asp Phe Pro Thr Thr Arg
    210                 215                 220
```

-continued

```
tct gat ggt gac ttc ttg cat agt acc aac ggc aat aaa gaa aag tta      720
Ser Asp Gly Asp Phe Leu His Ser Thr Asn Gly Asn Lys Glu Lys Leu
225                 230                 235                 240 ttt cca cat gtg aca cca aaa gga att aat ggt ata gac ttt aaa ggg      768
Phe Pro His Val Thr Pro Lys Gly Ile Asn Gly Ile Asp Phe Lys Gly
                245                 250                 255 gaa gcg ata act ttt aaa gca act act gct gga atc ctt gca aca ctt      816
Glu Ala Ile Thr Phe Lys Ala Thr Thr Ala Gly Ile Leu Ala Thr Leu
            260                 265                 270 tct cat tgt att gaa cta atg gtt aaa cgt gag gac agc tgg cag aag      864
Ser His Cys Ile Glu Leu Met Val Lys Arg Glu Asp Ser Trp Gln Lys
        275                 280                 285 aga ctg gat aag gaa act gag aag aaa aga aga aca gag gaa gca tat      912
Arg Leu Asp Lys Glu Thr Glu Lys Lys Arg Arg Thr Glu Glu Ala Tyr
    290                 295                 300 aaa aat gca atg aca gaa ctt aag aaa aaa tcc cac ttt gga gga cca      960
Lys Asn Ala Met Thr Glu Leu Lys Lys Lys Ser His Phe Gly Gly Pro
305                 310                 315                 320 gat tat gaa gaa ggc cct aac agt ctg att aat gaa gaa gag ttc ttt     1008
Asp Tyr Glu Glu Gly Pro Asn Ser Leu Ile Asn Glu Glu Glu Phe Phe
                325                 330                 335 gat gct gtt gaa gct gct ctt gac aga caa gat aaa ata gaa gaa cag     1056
Asp Ala Val Glu Ala Ala Leu Asp Arg Gln Asp Lys Ile Glu Glu Gln
            340                 345                 350 tca cag agt gaa aag gtg aga tta cat tgg cct aca tcc ttg ccc tct     1104
Ser Gln Ser Glu Lys Val Arg Leu His Trp Pro Thr Ser Leu Pro Ser
        355                 360                 365 gga gat gcc ttt tct tct gtg ggg aca cat aga ttt gtc caa aag ccc     1152
Gly Asp Ala Phe Ser Ser Val Gly Thr His Arg Phe Val Gln Lys Pro
    370                 375                 380 tat agt cgc tct tcc tcc atg tct tcc att gat cta gtc agt gcc tct     1200
Tyr Ser Arg Ser Ser Ser Met Ser Ser Ile Asp Leu Val Ser Ala Ser
385                 390                 395                 400 gat gat gtt cac aga ttc agc tcc cag gtt gaa gag atg gtg cag aac     1248
Asp Asp Val His Arg Phe Ser Ser Gln Val Glu Glu Met Val Gln Asn
                405                 410                 415 cac atg act tac tca tta cag gat gta ggc gga gat gcc aat tgg cag     1296
His Met Thr Tyr Ser Leu Gln Asp Val Gly Gly Asp Ala Asn Trp Gln
            420                 425                 430 ttg gtt gta gaa gaa gga gaa atg aag gta tac aga aga gaa gta gaa     1344
Leu Val Val Glu Glu Gly Glu Met Lys Val Tyr Arg Arg Glu Val Glu
        435                 440                 445 gaa aat ggg att gtt ctg gat cct tta aaa gct acc cat gca gtt aaa     1392
Glu Asn Gly Ile Val Leu Asp Pro Leu Lys Ala Thr His Ala Val Lys
    450                 455                 460 ggc gtc aca gga cat gaa gtc tgc aat tat ttc tgg aat gtt gac gtt     1440
Gly Val Thr Gly His Glu Val Cys Asn Tyr Phe Trp Asn Val Asp Val
465                 470                 475                 480 cgc aat gac tgg gaa aca act ata gaa aac ttt cat gtg gtg gaa aca     1488
Arg Asn Asp Trp Glu Thr Thr Ile Glu Asn Phe His Val Val Glu Thr
                485                 490                 495 tta gct gat aat gca atc atc att tat caa aca cac aag agg gtg tgg     1536
Leu Ala Asp Asn Ala Ile Ile Ile Tyr Gln Thr His Lys Arg Val Trp
            500                 505                 510 cct gct tct cag cga gac gta tta tat ctt tct gtc att cga aag ata     1584
Pro Ala Ser Gln Arg Asp Val Leu Tyr Leu Ser Val Ile Arg Lys Ile
        515                 520                 525 cca gcc ttg act gaa aat gac cct gaa act tgg ata gtt tgt aat ttt     1632
Pro Ala Leu Thr Glu Asn Asp Pro Glu Thr Trp Ile Val Cys Asn Phe
```

-continued

```
        530                 535                 540
tct gtg gat cat gac agt gct cct cta aac aac cga tgt gtc cgt gcc      1680
Ser Val Asp His Asp Ser Ala Pro Leu Asn Asn Arg Cys Val Arg Ala
545                 550                 555                 560 aaa ata aat gtt gct atg att tgt caa acc ttg gta agc cca cca gag      1728
Lys Ile Asn Val Ala Met Ile Cys Gln Thr Leu Val Ser Pro Pro Glu
                565                 570                 575 gga aac cag gaa att agc agg gac aac att cta tgc aag att aca tat      1776
Gly Asn Gln Glu Ile Ser Arg Asp Asn Ile Leu Cys Lys Ile Thr Tyr
            580                 585                 590 gta gct aat gtg aac cct gga gga tgg gca cca gcc tca gtg tta agg      1824
Val Ala Asn Val Asn Pro Gly Gly Trp Ala Pro Ala Ser Val Leu Arg
        595                 600                 605 gca gtg gca aag cga gag tat cct aaa ttt cta aaa cgt ttt act tct      1872
Ala Val Ala Lys Arg Glu Tyr Pro Lys Phe Leu Lys Arg Phe Thr Ser
    610                 615                 620 tac gtc caa gaa aaa act gca gga aag cct att ttg ttc tag              1914
Tyr Val Gln Glu Lys Thr Ala Gly Lys Pro Ile Leu Phe
625                 630                 635

<210> SEQ ID NO 10
<211> LENGTH: 637
<212> TYPE: PRT
<213> ORGANISM: Artificial
<220> FEATURE:
<223> OTHER INFORMATION: Derived sequence

<400> SEQUENCE: 10

Gly Ala Gly Ala Gly Leu Leu Leu Gly Cys Arg Ala Ser Met Ser Asp
1               5                   10                  15

Asn Gln Ser Trp Asn Ser Ser Gly Ser Glu Glu Asp Pro Glu Thr Glu
            20                  25                  30

Ser Gly Pro Pro Val Glu Arg Cys Gly Val Leu Ser Lys Trp Thr Asn
        35                  40                  45

Tyr Ile His Gly Trp Gln Asp Arg Trp Val Val Leu Lys Asn Asn Ala
    50                  55                  60

Leu Ser Tyr Tyr Lys Ser Glu Asp Glu Thr Glu Tyr Gly Cys Arg Gly
65                  70                  75                  80

Ser Ile Cys Leu Ser Lys Ala Val Ile Thr Pro His Asp Phe Asp Glu
                85                  90                  95

Cys Arg Phe Asp Ile Ser Val Asn Asp Ser Val Trp Tyr Leu Arg Ala
            100                 105                 110

Gln Asp Pro Asp His Arg Gln Gln Trp Ile Asp Ala Ile Glu Gln His
        115                 120                 125

Lys Thr Glu Ser Gly Tyr Gly Ser Glu Ser Ser Leu Arg Arg His Gly
    130                 135                 140

Ser Met Val Ser Leu Val Ser Gly Ala Ser Gly Tyr Ser Ala Thr Ser
145                 150                 155                 160

Thr Ser Ser Phe Lys Lys Gly His Ser Leu Arg Glu Lys Leu Ala Glu
                165                 170                 175

Met Glu Thr Phe Arg Asp Ile Leu Cys Arg Gln Val Asp Thr Leu Gln
            180                 185                 190

Lys Tyr Phe Asp Ala Cys Ala Asp Ala Val Ser Lys Asp Glu Leu Gln
        195                 200                 205

Arg Asp Lys Val Val Glu Asp Asp Glu Asp Phe Pro Thr Thr Arg
    210                 215                 220

Ser Asp Gly Asp Phe Leu His Ser Thr Asn Gly Asn Lys Glu Lys Leu
```

```
            225                 230                 235                 240
        Phe Pro His Val Thr Pro Lys Gly Ile Asn Gly Ile Asp Phe Lys Gly
                        245                 250                 255
        Glu Ala Ile Thr Phe Lys Ala Thr Thr Ala Gly Ile Leu Ala Thr Leu
                        260                 265                 270
        Ser His Cys Ile Glu Leu Met Val Lys Arg Glu Asp Ser Trp Gln Lys
                        275                 280                 285
        Arg Leu Asp Lys Glu Thr Glu Lys Lys Arg Thr Glu Glu Ala Tyr
                        290                 295                 300
        Lys Asn Ala Met Thr Glu Leu Lys Lys Ser His Phe Gly Gly Pro
        305                 310                 315                 320
        Asp Tyr Glu Glu Gly Pro Asn Ser Leu Ile Asn Glu Glu Phe Phe
                        325                 330                 335
        Asp Ala Val Glu Ala Ala Leu Asp Arg Gln Asp Lys Ile Glu Glu Gln
                        340                 345                 350
        Ser Gln Ser Glu Lys Val Arg Leu His Trp Pro Thr Ser Leu Pro Ser
                        355                 360                 365
        Gly Asp Ala Phe Ser Ser Val Gly Thr His Arg Phe Val Gln Lys Pro
        370                 375                 380
        Tyr Ser Arg Ser Ser Ser Met Ser Ser Ile Asp Leu Val Ser Ala Ser
        385                 390                 395                 400
        Asp Asp Val His Arg Phe Ser Ser Gln Val Glu Met Val Gln Asn
                        405                 410                 415
        His Met Thr Tyr Ser Leu Gln Asp Val Gly Gly Asp Ala Asn Trp Gln
                        420                 425                 430
        Leu Val Val Glu Glu Gly Glu Met Lys Val Tyr Arg Arg Glu Val Glu
                        435                 440                 445
        Glu Asn Gly Ile Val Leu Asp Pro Leu Lys Ala Thr His Ala Val Lys
                        450                 455                 460
        Gly Val Thr Gly His Glu Val Cys Asn Tyr Phe Trp Asn Val Asp Val
        465                 470                 475                 480
        Arg Asn Asp Trp Glu Thr Thr Ile Glu Asn Phe His Val Val Glu Thr
                        485                 490                 495
        Leu Ala Asp Asn Ala Ile Ile Tyr Gln Thr His Lys Arg Val Trp
                        500                 505                 510
        Pro Ala Ser Gln Arg Asp Val Leu Tyr Leu Ser Val Ile Arg Lys Ile
                        515                 520                 525
        Pro Ala Leu Thr Glu Asn Asp Pro Glu Thr Trp Ile Val Cys Asn Phe
                        530                 535                 540
        Ser Val Asp His Asp Ser Ala Pro Leu Asn Asn Arg Cys Val Arg Ala
        545                 550                 555                 560
        Lys Ile Asn Val Ala Met Ile Cys Gln Thr Leu Val Ser Pro Pro Glu
                        565                 570                 575
        Gly Asn Gln Glu Ile Ser Arg Asp Asn Ile Leu Cys Lys Ile Thr Tyr
                        580                 585                 590
        Val Ala Asn Val Asn Pro Gly Gly Trp Ala Pro Ala Ser Val Leu Arg
                        595                 600                 605
        Ala Val Ala Lys Arg Glu Tyr Pro Lys Phe Leu Lys Arg Phe Thr Ser
                        610                 615                 620
        Tyr Val Gln Glu Lys Thr Ala Gly Lys Pro Ile Leu Phe
        625                 630                 635

<210> SEQ ID NO 11
```

<211> LENGTH: 1836
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1 )..(1836)
<223> OTHER INFORMATION:

<400> SEQUENCE: 11

| | | | | | | | | | | | | | | | | |
|---|---|---|---|---|---|---|---|---|---|---|---|---|---|---|---|---|
| gga | gcg | ggg | gcc | ggt | ctc | ctg | ctc | ggt | tgt | cga | gcc | tcc | atg | tcg | gat | 48 |
| Gly | Ala | Gly | Ala | Gly | Leu | Leu | Leu | Gly | Cys | Arg | Ala | Ser | Met | Ser | Asp | |
| 1 | | | | 5 | | | | | 10 | | | | | 15 | | |
| aat | cag | agc | tgg | aac | tcg | tcg | ggc | tcg | gag | gag | gat | cca | gag | acg | gag | 96 |
| Asn | Gln | Ser | Trp | Asn | Ser | Ser | Gly | Ser | Glu | Glu | Asp | Pro | Glu | Thr | Glu | |
| | | | | 20 | | | | | 25 | | | | | 30 | | |
| tct | ggg | ccg | cct | gtg | gag | cgc | tgc | ggg | gtc | ctc | agt | aag | tgg | aca | aac | 144 |
| Ser | Gly | Pro | Pro | Val | Glu | Arg | Cys | Gly | Val | Leu | Ser | Lys | Trp | Thr | Asn | |
| | | 35 | | | | | 40 | | | | | 45 | | | | |
| tac | att | cat | ggg | tgg | cag | gat | cgt | tgg | gta | gtt | ttg | aaa | aat | aat | gct | 192 |
| Tyr | Ile | His | Gly | Trp | Gln | Asp | Arg | Trp | Val | Val | Leu | Lys | Asn | Asn | Ala | |
| | 50 | | | | | 55 | | | | | 60 | | | | | |
| ctg | agt | tac | tac | aaa | tct | gaa | gat | gaa | aca | gag | tat | ggc | tgc | aga | gga | 240 |
| Leu | Ser | Tyr | Tyr | Lys | Ser | Glu | Asp | Glu | Thr | Glu | Tyr | Gly | Cys | Arg | Gly | |
| 65 | | | | | 70 | | | | | 75 | | | | | 80 | |
| tcc | atc | tgt | ctt | agc | aag | gct | gtc | atc | aca | cct | cac | gat | ttt | gat | gaa | 288 |
| Ser | Ile | Cys | Leu | Ser | Lys | Ala | Val | Ile | Thr | Pro | His | Asp | Phe | Asp | Glu | |
| | | | | 85 | | | | | 90 | | | | | 95 | | |
| tgt | cga | ttt | gat | att | agt | gta | aat | gat | agt | gtt | tgg | tat | ctt | cgt | gct | 336 |
| Cys | Arg | Phe | Asp | Ile | Ser | Val | Asn | Asp | Ser | Val | Trp | Tyr | Leu | Arg | Ala | |
| | | | | 100 | | | | | 105 | | | | | 110 | | |
| cag | gat | cca | gat | cat | aga | cag | caa | tgg | ata | gat | gcc | att | gaa | cag | cac | 384 |
| Gln | Asp | Pro | Asp | His | Arg | Gln | Gln | Trp | Ile | Asp | Ala | Ile | Glu | Gln | His | |
| | | 115 | | | | | 120 | | | | | 125 | | | | |
| aag | act | gaa | tct | gga | tat | gga | tct | gaa | tcc | agc | ttg | cgt | cga | cat | ggc | 432 |
| Lys | Thr | Glu | Ser | Gly | Tyr | Gly | Ser | Glu | Ser | Ser | Leu | Arg | Arg | His | Gly | |
| | 130 | | | | | 135 | | | | | 140 | | | | | |
| tca | atg | gtg | tcc | ctg | gtg | tct | gga | gca | agt | ggc | tac | tct | gca | aca | tcc | 480 |
| Ser | Met | Val | Ser | Leu | Val | Ser | Gly | Ala | Ser | Gly | Tyr | Ser | Ala | Thr | Ser | |
| 145 | | | | | 150 | | | | | 155 | | | | | 160 | |
| acc | tct | tca | ttc | aag | aaa | ggc | cac | agt | tta | cgt | gag | aag | ttg | gct | gaa | 528 |
| Thr | Ser | Ser | Phe | Lys | Lys | Gly | His | Ser | Leu | Arg | Glu | Lys | Leu | Ala | Glu | |
| | | | | 165 | | | | | 170 | | | | | 175 | | |
| atg | gaa | aca | ttt | aga | gac | atc | tta | tgt | aga | caa | gtt | gac | acg | cta | cag | 576 |
| Met | Glu | Thr | Phe | Arg | Asp | Ile | Leu | Cys | Arg | Gln | Val | Asp | Thr | Leu | Gln | |
| | | | | 180 | | | | | 185 | | | | | 190 | | |
| aag | tac | ttt | gat | gcc | tgt | gct | gat | gct | gtc | tct | aag | gat | gaa | ctt | caa | 624 |
| Lys | Tyr | Phe | Asp | Ala | Cys | Ala | Asp | Ala | Val | Ser | Lys | Asp | Glu | Leu | Gln | |
| | | | 195 | | | | | 200 | | | | | 205 | | | |
| agg | gat | aaa | gtg | gta | gaa | gat | gat | gaa | gat | gac | ttt | cct | aca | acg | cgt | 672 |
| Arg | Asp | Lys | Val | Val | Glu | Asp | Asp | Glu | Asp | Asp | Phe | Pro | Thr | Thr | Arg | |
| | 210 | | | | | 215 | | | | | 220 | | | | | |
| tct | gat | ggt | gac | ttc | ttg | cat | agt | acc | aac | ggc | aat | aaa | gaa | aag | tta | 720 |
| Ser | Asp | Gly | Asp | Phe | Leu | His | Ser | Thr | Asn | Gly | Asn | Lys | Glu | Lys | Leu | |
| 225 | | | | | 230 | | | | | 235 | | | | | 240 | |
| ttt | cca | cat | gtg | aca | cca | aaa | gga | att | aat | ggt | ata | gac | ttt | aaa | ggg | 768 |
| Phe | Pro | His | Val | Thr | Pro | Lys | Gly | Ile | Asn | Gly | Ile | Asp | Phe | Lys | Gly | |
| | | | | 245 | | | | | 250 | | | | | 255 | | |
| gaa | gcg | ata | act | ttt | aaa | gca | act | act | gct | gga | atc | ctt | gca | aca | ctt | 816 |
| Glu | Ala | Ile | Thr | Phe | Lys | Ala | Thr | Thr | Ala | Gly | Ile | Leu | Ala | Thr | Leu | |
| | | | 260 | | | | | 265 | | | | | 270 | | | |

-continued

```
tct cat tgt att gaa cta atg gtt aaa cgt gag gac agc tgg cag aag    864
Ser His Cys Ile Glu Leu Met Val Lys Arg Glu Asp Ser Trp Gln Lys
    275                 280                 285 aga ctg gat aag gaa act gag aag aaa aga aga aca gag gaa gca tat    912
Arg Leu Asp Lys Glu Thr Glu Lys Lys Arg Arg Thr Glu Glu Ala Tyr
290                 295                 300 aaa aat gca atg aca gaa ctt aag aaa aaa tcc cac ttt gga gga cca    960
Lys Asn Ala Met Thr Glu Leu Lys Lys Lys Ser His Phe Gly Gly Pro
305                 310                 315                 320 gat tat gaa gaa ggc cct aac agt ctg att aat gaa gaa gag ttc ttt   1008
Asp Tyr Glu Glu Gly Pro Asn Ser Leu Ile Asn Glu Glu Glu Phe Phe
                325                 330                 335 gat gct gtt gaa gct gct ctt gac aga caa gat aaa ata gaa gaa cag   1056
Asp Ala Val Glu Ala Ala Leu Asp Arg Gln Asp Lys Ile Glu Glu Gln
            340                 345                 350 tca cag agt gaa aag gtg aga tta cat tgg cct aca tcc ttg ccc tct   1104
Ser Gln Ser Glu Lys Val Arg Leu His Trp Pro Thr Ser Leu Pro Ser
        355                 360                 365 gga gat gcc ttt tct tct gtg ggg aca cat aga ttt gtc caa aag gtt   1152
Gly Asp Ala Phe Ser Ser Val Gly Thr His Arg Phe Val Gln Lys Val
370                 375                 380 gaa gag atg gtg cag aac cac atg act tac tca tta cag gat gta ggc   1200
Glu Glu Met Val Gln Asn His Met Thr Tyr Ser Leu Gln Asp Val Gly
385                 390                 395                 400 gga gat gcc aat tgg cag ttg gtt gta gaa gaa gga gaa atg aag gta   1248
Gly Asp Ala Asn Trp Gln Leu Val Val Glu Glu Gly Glu Met Lys Val
                405                 410                 415 tac aga aga gaa gta gaa gaa aat ggg att gtt ctg gat cct tta aaa   1296
Tyr Arg Arg Glu Val Glu Glu Asn Gly Ile Val Leu Asp Pro Leu Lys
            420                 425                 430 gct acc cat gca gtt aaa ggc gtc aca gga cat gaa gtc tgc aat tat   1344
Ala Thr His Ala Val Lys Gly Val Thr Gly His Glu Val Cys Asn Tyr
        435                 440                 445 ttc tgg aat gtt gac gtt cgc aat gac tgg gaa aca act ata gaa aac   1392
Phe Trp Asn Val Asp Val Arg Asn Asp Trp Glu Thr Thr Ile Glu Asn
450                 455                 460 ttt cat gtg gtg gaa aca tta gct gat aat gca atc atc att tat caa   1440
Phe His Val Val Glu Thr Leu Ala Asp Asn Ala Ile Ile Ile Tyr Gln
465                 470                 475                 480 aca cac aag agg gtg tgg cct gct tct cag cga gac gta tta tat ctt   1488
Thr His Lys Arg Val Trp Pro Ala Ser Gln Arg Asp Val Leu Tyr Leu
                485                 490                 495 tct gtc att cga aag ata cca gcc ttg act gaa aat gac cct gaa act   1536
Ser Val Ile Arg Lys Ile Pro Ala Leu Thr Glu Asn Asp Pro Glu Thr
            500                 505                 510 tgg ata gtt tgt aat ttt tct gtg gat cat gac agt gct cct cta aac   1584
Trp Ile Val Cys Asn Phe Ser Val Asp His Asp Ser Ala Pro Leu Asn
        515                 520                 525 aac cga tgt gtc cgt gcc aaa ata aat gtt gct atg att tgt caa acc   1632
Asn Arg Cys Val Arg Ala Lys Ile Asn Val Ala Met Ile Cys Gln Thr
530                 535                 540 ttg gta agc cca cca gag gga aac cag gaa att agc agg gac aac att   1680
Leu Val Ser Pro Pro Glu Gly Asn Gln Glu Ile Ser Arg Asp Asn Ile
545                 550                 555                 560 cta tgc aag att aca tat gta gct aat gtg aac cct gga gga tgg gca   1728
Leu Cys Lys Ile Thr Tyr Val Ala Asn Val Asn Pro Gly Gly Trp Ala
                565                 570                 575 cca gcc tca gtg tta agg gca gtg gca aag cga gag tat cct aaa ttt   1776
Pro Ala Ser Val Leu Arg Ala Val Ala Lys Arg Glu Tyr Pro Lys Phe
```

```
                                 580               585                 590
cta aaa cgt ttt act tct tac gtc caa gaa aaa act gca gga aag cct          1824
Leu Lys Arg Phe Thr Ser Tyr Val Gln Glu Lys Thr Ala Gly Lys Pro
        595                 600                 605 att ttg ttc tag                                                          1836
Ile Leu Phe
    610

<210> SEQ ID NO 12
<211> LENGTH: 611
<212> TYPE: PRT
<213> ORGANISM: artificial
<220> FEATURE:
<223> OTHER INFORMATION: Derived sequence

<400> SEQUENCE: 12

Gly Ala Gly Ala Gly Leu Leu Leu Gly Cys Arg Ala Ser Met Ser Asp
1               5                   10                  15

Asn Gln Ser Trp Asn Ser Ser Gly Ser Glu Glu Asp Pro Glu Thr Glu
            20                  25                  30

Ser Gly Pro Pro Val Glu Arg Cys Gly Val Leu Ser Lys Trp Thr Asn
        35                  40                  45

Tyr Ile His Gly Trp Gln Asp Arg Trp Val Val Leu Lys Asn Asn Ala
    50                  55                  60

Leu Ser Tyr Tyr Lys Ser Glu Asp Glu Thr Glu Tyr Gly Cys Arg Gly
65                  70                  75                  80

Ser Ile Cys Leu Ser Lys Ala Val Ile Thr Pro His Asp Phe Asp Glu
                85                  90                  95

Cys Arg Phe Asp Ile Ser Val Asn Asp Ser Val Trp Tyr Leu Arg Ala
            100                 105                 110

Gln Asp Pro Asp His Arg Gln Gln Trp Ile Asp Ala Ile Glu Gln His
        115                 120                 125

Lys Thr Glu Ser Gly Tyr Gly Ser Glu Ser Ser Leu Arg Arg His Gly
    130                 135                 140

Ser Met Val Ser Leu Val Ser Gly Ala Ser Gly Tyr Ser Ala Thr Ser
145                 150                 155                 160

Thr Ser Ser Phe Lys Lys Gly His Ser Leu Arg Glu Lys Leu Ala Glu
                165                 170                 175

Met Glu Thr Phe Arg Asp Ile Leu Cys Arg Gln Val Asp Thr Leu Gln
            180                 185                 190

Lys Tyr Phe Asp Ala Cys Ala Asp Ala Val Ser Lys Asp Glu Leu Gln
        195                 200                 205

Arg Asp Lys Val Val Glu Asp Glu Asp Phe Pro Thr Thr Arg
    210                 215                 220

Ser Asp Gly Asp Phe Leu His Ser Thr Asn Gly Asn Lys Glu Lys Leu
225                 230                 235                 240

Phe Pro His Val Thr Pro Lys Gly Ile Asn Gly Ile Asp Phe Lys Gly
                245                 250                 255

Glu Ala Ile Thr Phe Lys Ala Thr Thr Ala Gly Ile Leu Ala Thr Leu
            260                 265                 270

Ser His Cys Ile Glu Leu Met Val Lys Arg Glu Asp Ser Trp Gln Lys
        275                 280                 285

Arg Leu Asp Lys Glu Thr Glu Lys Lys Arg Arg Thr Glu Glu Ala Tyr
    290                 295                 300

Lys Asn Ala Met Thr Glu Leu Lys Lys Lys Ser His Phe Gly Gly Pro
305                 310                 315                 320
```

-continued

```
Asp Tyr Glu Glu Gly Pro Asn Ser Leu Ile Asn Glu Glu Phe Phe
            325                 330                 335

Asp Ala Val Glu Ala Ala Leu Asp Arg Gln Asp Lys Ile Glu Glu Gln
            340                 345                 350

Ser Gln Ser Glu Lys Val Arg Leu His Trp Pro Thr Ser Leu Pro Ser
        355                 360                 365

Gly Asp Ala Phe Ser Ser Val Gly Thr His Arg Phe Val Gln Lys Val
    370                 375                 380

Glu Glu Met Val Gln Asn His Met Thr Tyr Ser Leu Gln Asp Val Gly
385                 390                 395                 400

Gly Asp Ala Asn Trp Gln Leu Val Val Glu Glu Gly Glu Met Lys Val
                405                 410                 415

Tyr Arg Arg Glu Val Glu Asn Gly Ile Val Leu Asp Pro Leu Lys
            420                 425                 430

Ala Thr His Ala Val Lys Gly Val Thr Gly His Glu Val Cys Asn Tyr
        435                 440                 445

Phe Trp Asn Val Asp Val Arg Asn Asp Trp Glu Thr Thr Ile Glu Asn
    450                 455                 460

Phe His Val Val Glu Thr Leu Ala Asp Asn Ala Ile Ile Ile Tyr Gln
465                 470                 475                 480

Thr His Lys Arg Val Trp Pro Ala Ser Gln Arg Asp Val Leu Tyr Leu
                485                 490                 495

Ser Val Ile Arg Lys Ile Pro Ala Leu Thr Glu Asn Asp Pro Glu Thr
            500                 505                 510

Trp Ile Val Cys Asn Phe Ser Val Asp His Asp Ser Ala Pro Leu Asn
        515                 520                 525

Asn Arg Cys Val Arg Ala Lys Ile Asn Val Ala Met Ile Cys Gln Thr
    530                 535                 540

Leu Val Ser Pro Pro Glu Gly Asn Gln Glu Ile Ser Arg Asp Asn Ile
545                 550                 555                 560

Leu Cys Lys Ile Thr Tyr Val Ala Asn Val Asn Pro Gly Gly Trp Ala
                565                 570                 575

Pro Ala Ser Val Leu Arg Ala Val Ala Lys Arg Glu Tyr Pro Lys Phe
            580                 585                 590

Leu Lys Arg Phe Thr Ser Tyr Val Gln Glu Lys Thr Ala Gly Lys Pro
        595                 600                 605

Ile Leu Phe
    610
```

```
<210> SEQ ID NO 13
<211> LENGTH: 1968
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(1968)
<223> OTHER INFORMATION:

<400> SEQUENCE: 13 cca tcc ccc gac cct tca ccc cga gga ctg ggc gcc tcc tcc ggc gca       48
Pro Ser Pro Asp Pro Ser Pro Arg Gly Leu Gly Ala Ser Ser Gly Ala
1               5                   10                  15 gct gag gga gcg ggg gcc ggt ctc ctg ctc ggt tgt cga gcc tcc atg       96
Ala Glu Gly Ala Gly Ala Gly Leu Leu Leu Gly Cys Arg Ala Ser Met
            20                  25                  30
```

-continued

| | | |
|---|---|---|
| tcg gat aat cag agc tgg aac tcg tcg ggc tcg gag gag gat cca gag<br>Ser Asp Asn Gln Ser Trp Asn Ser Ser Gly Ser Glu Glu Asp Pro Glu<br>35 40 45 | | 144 |
| acg gag tct ggg ccg cct gtg gag cgc tgc ggg gtc ctc agt aag tgg<br>Thr Glu Ser Gly Pro Pro Val Glu Arg Cys Gly Val Leu Ser Lys Trp<br>50 55 60 | | 192 |
| aca aac tac att cat ggg tgg cag gat cgt tgg gta gtt ttg aaa aat<br>Thr Asn Tyr Ile His Gly Trp Gln Asp Arg Trp Val Val Leu Lys Asn<br>65 70 75 80 | | 240 |
| aat gct ctg agt tac tac aaa tct gaa gat gaa aca gag tat ggc tgc<br>Asn Ala Leu Ser Tyr Tyr Lys Ser Glu Asp Glu Thr Glu Tyr Gly Cys<br>85 90 95 | | 288 |
| aga gga tcc atc tgt ctt agc aag gct gtc atc aca cct cac gat ttt<br>Arg Gly Ser Ile Cys Leu Ser Lys Ala Val Ile Thr Pro His Asp Phe<br>100 105 110 | | 336 |
| gat gaa tgt cga ttt gat att agt gta aat gat agt gtt tgg tat ctt<br>Asp Glu Cys Arg Phe Asp Ile Ser Val Asn Asp Ser Val Trp Tyr Leu<br>115 120 125 | | 384 |
| cgt gct cag gat cca gat cat aga cag caa tgg ata gat gcc att gaa<br>Arg Ala Gln Asp Pro Asp His Arg Gln Gln Trp Ile Asp Ala Ile Glu<br>130 135 140 | | 432 |
| cag cac aag act gaa tct gga tat gga tct gaa tcc agc ttg cgt cga<br>Gln His Lys Thr Glu Ser Gly Tyr Gly Ser Glu Ser Ser Leu Arg Arg<br>145 150 155 160 | | 480 |
| cat ggc tca atg gtg tcc ctg gtg tct gga gca agt ggc tac tct gca<br>His Gly Ser Met Val Ser Leu Val Ser Gly Ala Ser Gly Tyr Ser Ala<br>165 170 175 | | 528 |
| aca tcc acc tct tca ttc aag aaa ggc cac agt tta cgt gag aag ttg<br>Thr Ser Thr Ser Ser Phe Lys Lys Gly His Ser Leu Arg Glu Lys Leu<br>180 185 190 | | 576 |
| gct gaa atg gaa aca ttt aga gac atc tta tgt aga caa gtt gac acg<br>Ala Glu Met Glu Thr Phe Arg Asp Ile Leu Cys Arg Gln Val Asp Thr<br>195 200 205 | | 624 |
| cta cag aag tac ttt gat gcc tgt gct gat gct gtc tct aag gat gaa<br>Leu Gln Lys Tyr Phe Asp Ala Cys Ala Asp Ala Val Ser Lys Asp Glu<br>210 215 220 | | 672 |
| ctt caa agg gat aaa gtg gta gaa gat gat gaa gat gac ttt cct aca<br>Leu Gln Arg Asp Lys Val Val Glu Asp Asp Glu Asp Asp Phe Pro Thr<br>225 230 235 240 | | 720 |
| acg cgt tct gat ggt gac ttc ttg cat agt acc aac ggc aat aaa gaa<br>Thr Arg Ser Asp Gly Asp Phe Leu His Ser Thr Asn Gly Asn Lys Glu<br>245 250 255 | | 768 |
| aag tta ttt cca cat gtg aca cca aaa gga att aat ggt ata gac ttt<br>Lys Leu Phe Pro His Val Thr Pro Lys Gly Ile Asn Gly Ile Asp Phe<br>260 265 270 | | 816 |
| aaa ggg gaa gcg ata act ttt aaa gca act act gct gga atc ctt gca<br>Lys Gly Glu Ala Ile Thr Phe Lys Ala Thr Thr Ala Gly Ile Leu Ala<br>275 280 285 | | 864 |
| aca ctt tct cat tgt att gaa cta atg gtt aaa cgt gag gac agc tgg<br>Thr Leu Ser His Cys Ile Glu Leu Met Val Lys Arg Glu Asp Ser Trp<br>290 295 300 | | 912 |
| cag aag aga ctg gat aag gaa act gag aag aaa aga aga aca gag gaa<br>Gln Lys Arg Leu Asp Lys Glu Thr Glu Lys Lys Arg Arg Thr Glu Glu<br>305 310 315 320 | | 960 |
| gca tat aaa aat gca atg aca gaa ctt aag aaa aaa tcc cac ttt gga<br>Ala Tyr Lys Asn Ala Met Thr Glu Leu Lys Lys Lys Ser His Phe Gly<br>325 330 335 | | 1008 |
| gga cca gat tat gaa gaa ggc cct aac agt ctg att aat gaa gaa gag<br>Gly Pro Asp Tyr Glu Glu Gly Pro Asn Ser Leu Ile Asn Glu Glu Glu | | 1056 |

```
                    340              345              350
ttc ttt gat gct gtt gaa gct gct ctt gac aga caa gat aaa ata gaa      1104
Phe Phe Asp Ala Val Glu Ala Ala Leu Asp Arg Gln Asp Lys Ile Glu
        355              360              365 gaa cag tca cag agt gaa aag gtg aga tta cat tgg cct aca tcc ttg      1152
Glu Gln Ser Gln Ser Glu Lys Val Arg Leu His Trp Pro Thr Ser Leu
    370              375              380 ccc tct gga gat gcc ttt tct tct gtg ggg aca cat aga ttt gtc caa      1200
Pro Ser Gly Asp Ala Phe Ser Ser Val Gly Thr His Arg Phe Val Gln
385              390              395              400 aag ccc tat agt cgc tct tcc tcc atg tct tcc att gat cta gtc agt      1248
Lys Pro Tyr Ser Arg Ser Ser Ser Met Ser Ser Ile Asp Leu Val Ser
            405              410              415 gcc tct gat gat gtt cac aga ttc agc tcc cag gtt gaa gag atg gtg      1296
Ala Ser Asp Asp Val His Arg Phe Ser Ser Gln Val Glu Glu Met Val
        420              425              430 cag aac cac atg act tac tca tta cag gat gta ggc gga gat gcc aat      1344
Gln Asn His Met Thr Tyr Ser Leu Gln Asp Val Gly Gly Asp Ala Asn
    435              440              445 tgg cag ttg gtt gta gaa gaa gga gaa atg aag gta tac aga aga gaa      1392
Trp Gln Leu Val Val Glu Glu Gly Glu Met Lys Val Tyr Arg Arg Glu
450              455              460 gta gaa gaa aat ggg att gtt ctg gat cct tta aaa gct acc cat gca      1440
Val Glu Glu Asn Gly Ile Val Leu Asp Pro Leu Lys Ala Thr His Ala
465              470              475              480 gtt aaa ggc gtc aca gga cat gaa gtc tgc aat tat ttc tgg aat gtt      1488
Val Lys Gly Val Thr Gly His Glu Val Cys Asn Tyr Phe Trp Asn Val
            485              490              495 gac gtt cgc aat gac tgg gaa aca act ata gaa aac ttt cat gtg gtg      1536
Asp Val Arg Asn Asp Trp Glu Thr Thr Ile Glu Asn Phe His Val Val
        500              505              510 gaa aca tta gct gat aat gca atc atc att tat caa aca cac aag agg      1584
Glu Thr Leu Ala Asp Asn Ala Ile Ile Ile Tyr Gln Thr His Lys Arg
    515              520              525 gtg tgg cct gct tct cag cga gac gta tta tat ctt tct gtc att cga      1632
Val Trp Pro Ala Ser Gln Arg Asp Val Leu Tyr Leu Ser Val Ile Arg
530              535              540 aag ata cca gcc ttg act gaa aat gac cct gaa act tgg ata gtt tgt      1680
Lys Ile Pro Ala Leu Thr Glu Asn Asp Pro Glu Thr Trp Ile Val Cys
545              550              555              560 aat ttt tct gtg gat cat gac agt gct cct cta aac aac cga tgt gtc      1728
Asn Phe Ser Val Asp His Asp Ser Ala Pro Leu Asn Asn Arg Cys Val
            565              570              575 cgt gcc aaa ata aat gtt gct atg att tgt caa acc ttg gta agc cca      1776
Arg Ala Lys Ile Asn Val Ala Met Ile Cys Gln Thr Leu Val Ser Pro
        580              585              590 cca gag gga aac cag gaa att agc agg gac aac att cta tgc aag att      1824
Pro Glu Gly Asn Gln Glu Ile Ser Arg Asp Asn Ile Leu Cys Lys Ile
    595              600              605 aca tat gta gct aat gtg aac cct gga gga tgg gca cca gcc tca gtg      1872
Thr Tyr Val Ala Asn Val Asn Pro Gly Gly Trp Ala Pro Ala Ser Val
610              615              620 tta agg gca gtg gca aag cga gag tat cct aaa ttt cta aaa cgt ttt      1920
Leu Arg Ala Val Ala Lys Arg Glu Tyr Pro Lys Phe Leu Lys Arg Phe
625              630              635              640 act tct tac gtc caa gaa aaa act gca gga aag cct att ttg ttc tag     1968
Thr Ser Tyr Val Gln Glu Lys Thr Ala Gly Lys Pro Ile Leu Phe
            645              650              655
```

```
<210> SEQ ID NO 14
<211> LENGTH: 655
<212> TYPE: PRT
<213> ORGANISM: artificial
<220> FEATURE:
<223> OTHER INFORMATION: Derived sequence

<400> SEQUENCE: 14
```

| | | | | | | | | | | | | | | | |
|---|---|---|---|---|---|---|---|---|---|---|---|---|---|---|---|
| Pro | Ser | Pro | Asp | Pro | Ser | Pro | Arg | Gly | Leu | Gly | Ala | Ser | Ser | Gly | Ala |
| 1 | | | | 5 | | | | | 10 | | | | | 15 | |
| Ala | Glu | Gly | Ala | Gly | Ala | Gly | Leu | Leu | Leu | Gly | Cys | Arg | Ala | Ser | Met |
| | | | 20 | | | | | 25 | | | | | 30 | | |
| Ser | Asp | Asn | Gln | Ser | Trp | Asn | Ser | Gly | Ser | Glu | Glu | Asp | Pro | Glu | |
| | | 35 | | | | | 40 | | | | | 45 | | | |
| Thr | Glu | Ser | Gly | Pro | Pro | Val | Glu | Arg | Cys | Gly | Val | Leu | Ser | Lys | Trp |
| | 50 | | | | | 55 | | | | | 60 | | | | |
| Thr | Asn | Tyr | Ile | His | Gly | Trp | Gln | Asp | Arg | Trp | Val | Val | Leu | Lys | Asn |
| 65 | | | | | 70 | | | | | 75 | | | | | 80 |
| Asn | Ala | Leu | Ser | Tyr | Tyr | Lys | Ser | Glu | Asp | Glu | Thr | Glu | Tyr | Gly | Cys |
| | | | | 85 | | | | | 90 | | | | | 95 | |
| Arg | Gly | Ser | Ile | Cys | Leu | Ser | Lys | Ala | Val | Ile | Thr | Pro | His | Asp | Phe |
| | | | 100 | | | | | 105 | | | | | 110 | | |
| Asp | Glu | Cys | Arg | Phe | Asp | Ile | Ser | Val | Asn | Asp | Ser | Val | Trp | Tyr | Leu |
| | | 115 | | | | | 120 | | | | | 125 | | | |
| Arg | Ala | Gln | Asp | Pro | Asp | His | Arg | Gln | Gln | Trp | Ile | Asp | Ala | Ile | Glu |
| | 130 | | | | | 135 | | | | | 140 | | | | |
| Gln | His | Lys | Thr | Glu | Ser | Gly | Tyr | Gly | Ser | Glu | Ser | Ser | Leu | Arg | Arg |
| 145 | | | | | 150 | | | | | 155 | | | | | 160 |
| His | Gly | Ser | Met | Val | Ser | Leu | Val | Ser | Gly | Ala | Ser | Gly | Tyr | Ser | Ala |
| | | | | 165 | | | | | 170 | | | | | 175 | |
| Thr | Ser | Thr | Ser | Ser | Phe | Lys | Lys | Gly | His | Ser | Leu | Arg | Glu | Lys | Leu |
| | | | | 180 | | | | | 185 | | | | | 190 | |
| Ala | Glu | Met | Glu | Thr | Phe | Arg | Asp | Ile | Leu | Cys | Arg | Gln | Val | Asp | Thr |
| | | | 195 | | | | | 200 | | | | | 205 | | |
| Leu | Gln | Lys | Tyr | Phe | Asp | Ala | Cys | Ala | Asp | Ala | Val | Ser | Lys | Asp | Glu |
| | 210 | | | | | 215 | | | | | 220 | | | | |
| Leu | Gln | Arg | Asp | Lys | Val | Val | Glu | Asp | Glu | Asp | Asp | Phe | Pro | Thr | |
| 225 | | | | | 230 | | | | | 235 | | | | | 240 |
| Thr | Arg | Ser | Asp | Gly | Asp | Phe | Leu | His | Ser | Thr | Asn | Gly | Asn | Lys | Glu |
| | | | | 245 | | | | | 250 | | | | | 255 | |
| Lys | Leu | Phe | Pro | His | Val | Thr | Pro | Lys | Gly | Ile | Asn | Gly | Ile | Asp | Phe |
| | | | 260 | | | | | 265 | | | | | 270 | | |
| Lys | Gly | Glu | Ala | Ile | Thr | Phe | Lys | Ala | Thr | Thr | Ala | Gly | Ile | Leu | Ala |
| | | 275 | | | | | 280 | | | | | 285 | | | |
| Thr | Leu | Ser | His | Cys | Ile | Glu | Leu | Met | Val | Lys | Arg | Glu | Asp | Ser | Trp |
| | 290 | | | | | 295 | | | | | 300 | | | | |
| Gln | Lys | Arg | Leu | Asp | Lys | Glu | Thr | Glu | Lys | Lys | Arg | Arg | Thr | Glu | Glu |
| 305 | | | | | 310 | | | | | 315 | | | | | 320 |
| Ala | Tyr | Lys | Asn | Ala | Met | Thr | Glu | Leu | Lys | Lys | Lys | Ser | His | Phe | Gly |
| | | | | 325 | | | | | 330 | | | | | 335 | |
| Gly | Pro | Asp | Tyr | Glu | Glu | Gly | Pro | Asn | Ser | Leu | Ile | Asn | Glu | Glu | Glu |
| | | | 340 | | | | | 345 | | | | | 350 | | |
| Phe | Phe | Asp | Ala | Val | Glu | Ala | Ala | Leu | Asp | Arg | Gln | Asp | Lys | Ile | Glu |
| | | 355 | | | | | 360 | | | | | 365 | | | |
| Glu | Gln | Ser | Gln | Ser | Glu | Lys | Val | Arg | Leu | His | Trp | Pro | Thr | Ser | Leu |

```
                370                 375                 380
Pro Ser Gly Asp Ala Phe Ser Val Gly Thr His Arg Phe Val Gln
385                 390                 395                 400

Lys Pro Tyr Ser Arg Ser Ser Met Ser Ser Ile Asp Leu Val Ser
                405                 410                 415

Ala Ser Asp Asp Val His Arg Phe Ser Ser Gln Val Glu Glu Met Val
                420                 425                 430

Gln Asn His Met Thr Tyr Ser Leu Gln Asp Val Gly Gly Asp Ala Asn
                435                 440                 445

Trp Gln Leu Val Val Glu Glu Gly Glu Met Lys Val Tyr Arg Arg Glu
450                 455                 460

Val Glu Glu Asn Gly Ile Val Leu Asp Pro Leu Lys Ala Thr His Ala
465                 470                 475                 480

Val Lys Gly Val Thr Gly His Glu Val Cys Asn Tyr Phe Trp Asn Val
                485                 490                 495

Asp Val Arg Asn Asp Trp Glu Thr Thr Ile Glu Asn Phe His Val Val
                500                 505                 510

Glu Thr Leu Ala Asp Asn Ala Ile Ile Ile Tyr Gln Thr His Lys Arg
                515                 520                 525

Val Trp Pro Ala Ser Gln Arg Asp Val Leu Tyr Leu Ser Val Ile Arg
530                 535                 540

Lys Ile Pro Ala Leu Thr Glu Asn Asp Pro Glu Thr Trp Ile Val Cys
545                 550                 555                 560

Asn Phe Ser Val Asp His Asp Ser Ala Pro Leu Asn Asn Arg Cys Val
                565                 570                 575

Arg Ala Lys Ile Asn Val Ala Met Ile Cys Gln Thr Leu Val Ser Pro
                580                 585                 590

Pro Glu Gly Asn Gln Glu Ile Ser Arg Asp Asn Ile Leu Cys Lys Ile
                595                 600                 605

Thr Tyr Val Ala Asn Val Asn Pro Gly Gly Trp Ala Pro Ala Ser Val
                610                 615                 620

Leu Arg Ala Val Ala Lys Arg Glu Tyr Pro Lys Phe Leu Lys Arg Phe
625                 630                 635                 640

Thr Ser Tyr Val Gln Glu Lys Thr Ala Gly Lys Pro Ile Leu Phe
                645                 650                 655

<210> SEQ ID NO 15
<211> LENGTH: 1890
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(1890)
<223> OTHER INFORMATION:

<400> SEQUENCE: 15 cca tcc ccc gac cct tca ccc cga gga ctg ggc gcc tcc tcc ggc gca    48
Pro Ser Pro Asp Pro Ser Pro Arg Gly Leu Gly Ala Ser Ser Gly Ala
1               5                   10                  15 gct gag gga gcg ggg gcc ggt ctc ctg ctc ggt tgt cga gcc tcc atg    96
Ala Glu Gly Ala Gly Ala Gly Leu Leu Leu Gly Cys Arg Ala Ser Met
                20                  25                  30 tcg gat aat cag agc tgg aac tcg tcg ggc tcg gag gag gat cca gag   144
Ser Asp Asn Gln Ser Trp Asn Ser Ser Gly Ser Glu Glu Asp Pro Glu
            35                  40                  45
```

```
acg gag tct ggg ccg cct gtg gag cgc tgc ggg gtc ctc agt aag tgg      192
Thr Glu Ser Gly Pro Pro Val Glu Arg Cys Gly Val Leu Ser Lys Trp
    50              55                  60 aca aac tac att cat ggg tgg cag gat cgt tgg gta gtt ttg aaa aat      240
Thr Asn Tyr Ile His Gly Trp Gln Asp Arg Trp Val Val Leu Lys Asn
65              70                  75                  80 aat gct ctg agt tac tac aaa tct gaa gat gaa aca gag tat ggc tgc      288
Asn Ala Leu Ser Tyr Tyr Lys Ser Glu Asp Glu Thr Glu Tyr Gly Cys
                85                  90                  95 aga gga tcc atc tgt ctt agc aag gct gtc atc aca cct cac gat ttt      336
Arg Gly Ser Ile Cys Leu Ser Lys Ala Val Ile Thr Pro His Asp Phe
            100                 105                 110 gat gaa tgt cga ttt gat att agt gta aat gat agt gtt tgg tat ctt      384
Asp Glu Cys Arg Phe Asp Ile Ser Val Asn Asp Ser Val Trp Tyr Leu
        115                 120                 125 cgt gct cag gat cca gat cat aga cag caa tgg ata gat gcc att gaa      432
Arg Ala Gln Asp Pro Asp His Arg Gln Gln Trp Ile Asp Ala Ile Glu
    130                 135                 140 cag cac aag act gaa tct gga tat gga tct gaa tcc agc ttg cgt cga      480
Gln His Lys Thr Glu Ser Gly Tyr Gly Ser Glu Ser Ser Leu Arg Arg
145                 150                 155                 160 cat ggc tca atg gtg tcc ctg gtg tct gga gca agt ggc tac tct gca      528
His Gly Ser Met Val Ser Leu Val Ser Gly Ala Ser Gly Tyr Ser Ala
                165                 170                 175 aca tcc acc tct tca ttc aag aaa ggc cac agt tta cgt gag aag ttg      576
Thr Ser Thr Ser Ser Phe Lys Lys Gly His Ser Leu Arg Glu Lys Leu
            180                 185                 190 gct gaa atg gaa aca ttt aga gac atc tta tgt aga caa gtt gac acg      624
Ala Glu Met Glu Thr Phe Arg Asp Ile Leu Cys Arg Gln Val Asp Thr
        195                 200                 205 cta cag aag tac ttt gat gcc tgt gct gat gct gtc tct aag gat gaa      672
Leu Gln Lys Tyr Phe Asp Ala Cys Ala Asp Ala Val Ser Lys Asp Glu
    210                 215                 220 ctt caa agg gat aaa gtg gta gaa gat gat gaa gat gac ttt cct aca      720
Leu Gln Arg Asp Lys Val Val Glu Asp Asp Glu Asp Asp Phe Pro Thr
225                 230                 235                 240 acg cgt tct gat ggt gac ttc ttg cat agt acc aac ggc aat aaa gaa      768
Thr Arg Ser Asp Gly Asp Phe Leu His Ser Thr Asn Gly Asn Lys Glu
                245                 250                 255 aag tta ttt cca cat gtg aca cca aaa gga att aat ggt ata gac ttt      816
Lys Leu Phe Pro His Val Thr Pro Lys Gly Ile Asn Gly Ile Asp Phe
            260                 265                 270 aaa ggg gaa gcg ata act ttt aaa gca act act gct gga atc ctt gca      864
Lys Gly Glu Ala Ile Thr Phe Lys Ala Thr Thr Ala Gly Ile Leu Ala
        275                 280                 285 aca ctt tct cat tgt att gaa cta atg gtt aaa cgt gag gac agc tgg      912
Thr Leu Ser His Cys Ile Glu Leu Met Val Lys Arg Glu Asp Ser Trp
    290                 295                 300 cag aag aga ctg gat aag gaa act gag aag aaa aga aga aca gag gaa      960
Gln Lys Arg Leu Asp Lys Glu Thr Glu Lys Lys Arg Arg Thr Glu Glu
305                 310                 315                 320 gca tat aaa aat gca atg aca gaa ctt aag aaa aaa tcc cac ttt gga     1008
Ala Tyr Lys Asn Ala Met Thr Glu Leu Lys Lys Lys Ser His Phe Gly
                325                 330                 335 gga cca gat tat gaa gaa ggc cct aac agt ctg att aat gaa gaa gag     1056
Gly Pro Asp Tyr Glu Glu Gly Pro Asn Ser Leu Ile Asn Glu Glu Glu
            340                 345                 350 ttc ttt gat gct gtt gaa gct gct ctt gac aga caa gat aaa ata gaa     1104
Phe Phe Asp Ala Val Glu Ala Ala Leu Asp Arg Gln Asp Lys Ile Glu
        355                 360                 365
```

```
gaa cag tca cag agt gaa aag gtg aga tta cat tgg cct aca tcc ttg      1152
Glu Gln Ser Gln Ser Glu Lys Val Arg Leu His Trp Pro Thr Ser Leu
370                 375                 380 ccc tct gga gat gcc ttt tct tct gtg ggg aca cat aga ttt gtc caa      1200
Pro Ser Gly Asp Ala Phe Ser Ser Val Gly Thr His Arg Phe Val Gln
385                 390                 395                 400 aag gtt gaa gag atg gtg cag aac cac atg act tac tca tta cag gat      1248
Lys Val Glu Glu Met Val Gln Asn His Met Thr Tyr Ser Leu Gln Asp
                405                 410                 415 gta ggc gga gat gcc aat tgg cag ttg gtt gta gaa gaa gga gaa atg      1296
Val Gly Gly Asp Ala Asn Trp Gln Leu Val Val Glu Glu Gly Glu Met
            420                 425                 430 aag gta tac aga aga gaa gta gaa gaa aat ggg att gtt ctg gat cct      1344
Lys Val Tyr Arg Arg Glu Val Glu Glu Asn Gly Ile Val Leu Asp Pro
        435                 440                 445 tta aaa gct acc cat gca gtt aaa ggc gtc aca gga cat gaa gtc tgc      1392
Leu Lys Ala Thr His Ala Val Lys Gly Val Thr Gly His Glu Val Cys
450                 455                 460 aat tat ttc tgg aat gtt gac gtt cgc aat gac tgg gaa aca act ata      1440
Asn Tyr Phe Trp Asn Val Asp Val Arg Asn Asp Trp Glu Thr Thr Ile
465                 470                 475                 480 gaa aac ttt cat gtg gtg gaa aca tta gct gat aat gca atc atc att      1488
Glu Asn Phe His Val Val Glu Thr Leu Ala Asp Asn Ala Ile Ile Ile
                485                 490                 495 tat caa aca cac aag agg gtg tgg cct gct tct cag cga gac gta tta      1536
Tyr Gln Thr His Lys Arg Val Trp Pro Ala Ser Gln Arg Asp Val Leu
            500                 505                 510 tat ctt tct gtc att cga aag ata cca gcc ttg act gaa aat gac cct      1584
Tyr Leu Ser Val Ile Arg Lys Ile Pro Ala Leu Thr Glu Asn Asp Pro
        515                 520                 525 gaa act tgg ata gtt tgt aat ttt tct gtg gat cat gac agt gct cct      1632
Glu Thr Trp Ile Val Cys Asn Phe Ser Val Asp His Asp Ser Ala Pro
530                 535                 540 cta aac aac cga tgt gtc cgt gcc aaa ata aat gtt gct atg att tgt      1680
Leu Asn Asn Arg Cys Val Arg Ala Lys Ile Asn Val Ala Met Ile Cys
545                 550                 555                 560 caa acc ttg gta agc cca cca gag gga aac cag gaa att agc agg gac      1728
Gln Thr Leu Val Ser Pro Pro Glu Gly Asn Gln Glu Ile Ser Arg Asp
                565                 570                 575 aac att cta tgc aag att aca tat gta gct aat gtg aac cct gga gga      1776
Asn Ile Leu Cys Lys Ile Thr Tyr Val Ala Asn Val Asn Pro Gly Gly
            580                 585                 590 tgg gca cca gcc tca gtg tta agg gca gtg gca aag cga gag tat cct      1824
Trp Ala Pro Ala Ser Val Leu Arg Ala Val Ala Lys Arg Glu Tyr Pro
        595                 600                 605 aaa ttt cta aaa cgt ttt act tct tac gtc caa gaa aaa act gca gga      1872
Lys Phe Leu Lys Arg Phe Thr Ser Tyr Val Gln Glu Lys Thr Ala Gly
610                 615                 620 aag cct att ttg ttc tag                                              1890
Lys Pro Ile Leu Phe
625

<210> SEQ ID NO 16
<211> LENGTH: 629
<212> TYPE: PRT
<213> ORGANISM: artificial
<220> FEATURE:
<223> OTHER INFORMATION: Derived sequence

<400> SEQUENCE: 16
```

-continued

```
Pro Ser Pro Asp Pro Ser Pro Arg Gly Leu Gly Ala Ser Gly Ala
1               5                   10                  15

Ala Glu Gly Ala Gly Ala Gly Leu Leu Leu Gly Cys Arg Ala Ser Met
            20                  25                  30

Ser Asp Asn Gln Ser Trp Asn Ser Gly Ser Glu Glu Asp Pro Glu
        35                  40                  45

Thr Glu Ser Gly Pro Pro Val Glu Arg Cys Gly Val Leu Ser Lys Trp
50                      55                      60

Thr Asn Tyr Ile His Gly Trp Gln Asp Arg Trp Val Val Leu Lys Asn
65                  70                  75                  80

Asn Ala Leu Ser Tyr Tyr Lys Ser Glu Asp Thr Glu Tyr Gly Cys
                85                  90                  95

Arg Gly Ser Ile Cys Leu Ser Lys Ala Val Ile Thr Pro His Asp Phe
                100                 105                 110

Asp Glu Cys Arg Phe Asp Ile Ser Val Asn Asp Ser Val Trp Tyr Leu
            115                 120                 125

Arg Ala Gln Asp Pro Asp His Arg Gln Gln Trp Ile Asp Ala Ile Glu
            130                 135                 140

Gln His Lys Thr Glu Ser Gly Tyr Gly Ser Ser Ser Leu Arg Arg
145                 150                 155                 160

His Gly Ser Met Val Ser Leu Val Ser Gly Ala Ser Gly Tyr Ser Ala
                165                 170                 175

Thr Ser Thr Ser Ser Phe Lys Lys Gly His Ser Leu Arg Glu Lys Leu
            180                 185                 190

Ala Glu Met Glu Thr Phe Arg Asp Ile Leu Cys Arg Gln Val Asp Thr
        195                 200                 205

Leu Gln Lys Tyr Phe Asp Ala Cys Ala Asp Ala Val Ser Lys Asp Glu
210                 215                 220

Leu Gln Arg Asp Lys Val Val Glu Asp Asp Glu Asp Phe Pro Thr
225                 230                 235                 240

Thr Arg Ser Asp Gly Asp Phe Leu His Ser Thr Asn Gly Asn Lys Glu
                245                 250                 255

Lys Leu Phe Pro His Val Thr Pro Lys Gly Ile Asn Gly Ile Asp Phe
            260                 265                 270

Lys Gly Glu Ala Ile Thr Phe Lys Ala Thr Thr Ala Gly Ile Leu Ala
        275                 280                 285

Thr Leu Ser His Cys Ile Glu Leu Met Val Lys Arg Glu Asp Ser Trp
290                 295                 300

Gln Lys Arg Leu Asp Lys Glu Thr Glu Lys Lys Arg Arg Thr Glu Glu
305                 310                 315                 320

Ala Tyr Lys Asn Ala Met Thr Glu Leu Lys Lys Ser His Phe Gly
                325                 330                 335

Gly Pro Asp Tyr Glu Glu Gly Pro Asn Ser Leu Ile Asn Glu Glu Glu
            340                 345                 350

Phe Phe Asp Ala Val Glu Ala Ala Leu Asp Arg Gln Asp Lys Ile Glu
            355                 360                 365

Glu Gln Ser Gln Ser Glu Lys Val Arg Leu His Trp Pro Thr Ser Leu
370                 375                 380

Pro Ser Gly Asp Ala Phe Ser Ser Val Gly Thr His Arg Phe Val Gln
385                 390                 395                 400

Lys Val Glu Glu Met Val Gln Asn His Met Thr Tyr Ser Leu Gln Asp
                405                 410                 415

Val Gly Gly Asp Ala Asn Trp Gln Leu Val Val Glu Glu Gly Glu Met
```

```
                    420                 425                 430
Lys Val Tyr Arg Arg Glu Val Glu Glu Asn Gly Ile Val Leu Asp Pro
            435                 440                 445

Leu Lys Ala Thr His Ala Val Lys Gly Val Thr Gly His Glu Val Cys
        450                 455                 460

Asn Tyr Phe Trp Asn Val Asp Val Arg Asn Asp Trp Glu Thr Thr Ile
465                 470                 475                 480

Glu Asn Phe His Val Val Glu Thr Leu Ala Asp Asn Ala Ile Ile Ile
                485                 490                 495

Tyr Gln Thr His Lys Arg Val Trp Pro Ala Ser Gln Arg Asp Val Leu
            500                 505                 510

Tyr Leu Ser Val Ile Arg Lys Ile Pro Ala Leu Thr Glu Asn Asp Pro
        515                 520                 525

Glu Thr Trp Ile Val Cys Asn Phe Ser Val Asp His Asp Ser Ala Pro
    530                 535                 540

Leu Asn Asn Arg Cys Val Arg Ala Lys Ile Asn Val Ala Met Ile Cys
545                 550                 555                 560

Gln Thr Leu Val Ser Pro Pro Glu Gly Asn Gln Glu Ile Ser Arg Asp
                565                 570                 575

Asn Ile Leu Cys Lys Ile Thr Tyr Val Ala Asn Val Asn Pro Gly Gly
            580                 585                 590

Trp Ala Pro Ala Ser Val Leu Arg Ala Val Ala Lys Arg Glu Tyr Pro
        595                 600                 605

Lys Phe Leu Lys Arg Phe Thr Ser Tyr Val Gln Glu Lys Thr Ala Gly
    610                 615                 620

Lys Pro Ile Leu Phe
625

<210> SEQ ID NO 17
<211> LENGTH: 2037
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(2037)
<223> OTHER INFORMATION:

<400> SEQUENCE: 17 cgg cgc ggc ggg cgg act tcg tcc ctc ctc ctg ctc ccc ccc aca ccg      48
Arg Arg Gly Gly Arg Thr Ser Ser Leu Leu Leu Leu Pro Pro Thr Pro
1               5                   10                  15 gag cgg gca ctc ttc gct tcg cca tcc ccc gac cct tca ccc cga gga      96
Glu Arg Ala Leu Phe Ala Ser Pro Ser Pro Asp Pro Ser Pro Arg Gly
            20                  25                  30 ctg ggc gcc tcc tcc ggc gca gct gag gga gcg ggc gcc ggt ctc ctg     144
Leu Gly Ala Ser Ser Gly Ala Ala Glu Gly Ala Gly Ala Gly Leu Leu
        35                  40                  45 ctc ggt tgt cga gcc tcc atg tcg gat aat cag agc tgg aac tcg tcg     192
Leu Gly Cys Arg Ala Ser Met Ser Asp Asn Gln Ser Trp Asn Ser Ser
    50                  55                  60 ggc tcg gag gag gat cca gag acg gag tct ggg ccg cct gtg gag cgc     240
Gly Ser Glu Glu Asp Pro Glu Thr Glu Ser Gly Pro Pro Val Glu Arg
65                  70                  75                  80 tgc ggg gtc ctc agt aag tgg aca aac tac att cat ggg tgg cag gat     288
Cys Gly Val Leu Ser Lys Trp Thr Asn Tyr Ile His Gly Trp Gln Asp
                85                  90                  95
```

```
cgt tgg gta gtt ttg aaa aat aat gct ctg agt tac tac aaa tct gaa       336
Arg Trp Val Val Leu Lys Asn Asn Ala Leu Ser Tyr Tyr Lys Ser Glu
            100                 105                 110 gat gaa aca gag tat ggc tgc aga gga tcc atc tgt ctt agc aag gct       384
Asp Glu Thr Glu Tyr Gly Cys Arg Gly Ser Ile Cys Leu Ser Lys Ala
        115                 120                 125 gtc atc aca cct cac gat ttt gat gaa tgt cga ttt gat att agt gta       432
Val Ile Thr Pro His Asp Phe Asp Glu Cys Arg Phe Asp Ile Ser Val
130                 135                 140 aat gat agt gtt tgg tat ctt cgt gct cag gat cca gat cat aga cag       480
Asn Asp Ser Val Trp Tyr Leu Arg Ala Gln Asp Pro Asp His Arg Gln
145                 150                 155                 160 caa tgg ata gat gcc att gaa cag cac aag act gaa tct gga tat gga       528
Gln Trp Ile Asp Ala Ile Glu Gln His Lys Thr Glu Ser Gly Tyr Gly
                165                 170                 175 tct gaa tcc agc ttg cgt cga cat ggc tca atg gtg tcc ctg gtg tct       576
Ser Glu Ser Ser Leu Arg Arg His Gly Ser Met Val Ser Leu Val Ser
            180                 185                 190 gga gca agt ggc tac tct gca aca tcc acc tct tca ttc aag aaa ggc       624
Gly Ala Ser Gly Tyr Ser Ala Thr Ser Thr Ser Ser Phe Lys Lys Gly
        195                 200                 205 cac agt tta cgt gag aag ttg gct gaa atg gaa aca ttt aga gac atc       672
His Ser Leu Arg Glu Lys Leu Ala Glu Met Glu Thr Phe Arg Asp Ile
    210                 215                 220 tta tgt aga caa gtt gac acg cta cag aag tac ttt gat gcc tgt gct       720
Leu Cys Arg Gln Val Asp Thr Leu Gln Lys Tyr Phe Asp Ala Cys Ala
225                 230                 235                 240 gat gct gtc tct aag gat gaa ctt caa agg gat aaa gtg gta gaa gat       768
Asp Ala Val Ser Lys Asp Glu Leu Gln Arg Asp Lys Val Val Glu Asp
                245                 250                 255 gat gaa gat gac ttt cct aca acg cgt tct gat ggt gac ttc ttg cat       816
Asp Glu Asp Asp Phe Pro Thr Thr Arg Ser Asp Gly Asp Phe Leu His
            260                 265                 270 agt acc aac ggc aat aaa gaa aag tta ttt cca cat gtg aca cca aaa       864
Ser Thr Asn Gly Asn Lys Glu Lys Leu Phe Pro His Val Thr Pro Lys
        275                 280                 285 gga att aat ggt ata gac ttt aaa ggg gaa gcg ata act ttt aaa gca       912
Gly Ile Asn Gly Ile Asp Phe Lys Gly Glu Ala Ile Thr Phe Lys Ala
    290                 295                 300 act act gct gga atc ctt gca aca ctt tct cat tgt att gaa cta atg       960
Thr Thr Ala Gly Ile Leu Ala Thr Leu Ser His Cys Ile Glu Leu Met
305                 310                 315                 320 gtt aaa cgt gag gac agc tgg cag aag aga ctg gat aag gaa act gag      1008
Val Lys Arg Glu Asp Ser Trp Gln Lys Arg Leu Asp Lys Glu Thr Glu
                325                 330                 335 aag aaa aga aga aca gag gaa gca tat aaa aat gca atg aca gaa ctt      1056
Lys Lys Arg Arg Thr Glu Glu Ala Tyr Lys Asn Ala Met Thr Glu Leu
            340                 345                 350 aag aaa aaa tcc cac ttt gga gga cca gat tat gaa gaa ggc cct aac      1104
Lys Lys Lys Ser His Phe Gly Gly Pro Asp Tyr Glu Glu Gly Pro Asn
        355                 360                 365 agt ctg att aat gaa gaa gag ttc ttt gat gct gtt gaa gct gct ctt      1152
Ser Leu Ile Asn Glu Glu Glu Phe Phe Asp Ala Val Glu Ala Ala Leu
    370                 375                 380 gac aga caa gat aaa ata gaa gaa cag tca cag agt gaa aag gtg aga      1200
Asp Arg Gln Asp Lys Ile Glu Glu Gln Ser Gln Ser Glu Lys Val Arg
385                 390                 395                 400 tta cat tgg cct aca tcc ttg ccc tct gga gat gcc ttt tct tct gtg      1248
Leu His Trp Pro Thr Ser Leu Pro Ser Gly Asp Ala Phe Ser Ser Val
                405                 410                 415
```

```
ggg aca cat aga ttt gtc caa aag ccc tat agt cgc tct tcc tcc atg      1296
Gly Thr His Arg Phe Val Gln Lys Pro Tyr Ser Arg Ser Ser Ser Met
        420                 425                 430 tct tcc att gat cta gtc agt gcc tct gat gat gtt cac aga ttc agc      1344
Ser Ser Ile Asp Leu Val Ser Ala Ser Asp Asp Val His Arg Phe Ser
            435                 440                 445 tcc cag gtt gaa gag atg gtg cag aac cac atg act tac tca tta cag      1392
Ser Gln Val Glu Glu Met Val Gln Asn His Met Thr Tyr Ser Leu Gln
450                 455                 460 gat gta ggc gga gat gcc aat tgg cag ttg gtt gta gaa gaa gga gaa      1440
Asp Val Gly Gly Asp Ala Asn Trp Gln Leu Val Val Glu Glu Gly Glu
465                 470                 475                 480 atg aag gta tac aga aga gaa gta gaa gaa aat ggg att gtt ctg gat      1488
Met Lys Val Tyr Arg Arg Glu Val Glu Glu Asn Gly Ile Val Leu Asp
                485                 490                 495 cct tta aaa gct acc cat gca gtt aaa ggc gtc aca gga cat gaa gtc      1536
Pro Leu Lys Ala Thr His Ala Val Lys Gly Val Thr Gly His Glu Val
            500                 505                 510 tgc aat tat ttc tgg aat gtt gac gtt cgc aat gac tgg gaa aca act      1584
Cys Asn Tyr Phe Trp Asn Val Asp Val Arg Asn Asp Trp Glu Thr Thr
        515                 520                 525 ata gaa aac ttt cat gtg gtg gaa aca tta gct gat aat gca atc atc      1632
Ile Glu Asn Phe His Val Val Glu Thr Leu Ala Asp Asn Ala Ile Ile
530                 535                 540 att tat caa aca cac aag agg gtg tgg cct gct tct cag cga gac gta      1680
Ile Tyr Gln Thr His Lys Arg Val Trp Pro Ala Ser Gln Arg Asp Val
545                 550                 555                 560 tta tat ctt tct gtc att cga aag ata cca gcc ttg act gaa aat gac      1728
Leu Tyr Leu Ser Val Ile Arg Lys Ile Pro Ala Leu Thr Glu Asn Asp
                565                 570                 575 cct gaa act tgg ata gtt tgt aat ttt tct gtg gat cat gac agt gct      1776
Pro Glu Thr Trp Ile Val Cys Asn Phe Ser Val Asp His Asp Ser Ala
            580                 585                 590 cct cta aac aac cga tgt gtc cgt gcc aaa ata aat gtt gct atg att      1824
Pro Leu Asn Asn Arg Cys Val Arg Ala Lys Ile Asn Val Ala Met Ile
        595                 600                 605 tgt caa acc ttg gta agc cca cca gag gga aac cag gaa att agc agg      1872
Cys Gln Thr Leu Val Ser Pro Pro Glu Gly Asn Gln Glu Ile Ser Arg
610                 615                 620 gac aac att cta tgc aag att aca tat gta gct aat gtg aac cct gga      1920
Asp Asn Ile Leu Cys Lys Ile Thr Tyr Val Ala Asn Val Asn Pro Gly
625                 630                 635                 640 gga tgg gca cca gcc tca gtg tta agg gca gtg gca aag cga gag tat      1968
Gly Trp Ala Pro Ala Ser Val Leu Arg Ala Val Ala Lys Arg Glu Tyr
                645                 650                 655 cct aaa ttt cta aaa cgt ttt act tct tac gtc caa gaa aaa act gca      2016
Pro Lys Phe Leu Lys Arg Phe Thr Ser Tyr Val Gln Glu Lys Thr Ala
            660                 665                 670 gga aag cct att ttg ttc tag                                          2037
Gly Lys Pro Ile Leu Phe
        675
```

<210> SEQ ID NO 18
<211> LENGTH: 678
<212> TYPE: PRT
<213> ORGANISM: artificial
<220> FEATURE:
<223> OTHER INFORMATION: Derived sequence

<400> SEQUENCE: 18

-continued

```
Arg Arg Gly Gly Arg Thr Ser Ser Leu Leu Leu Pro Pro Thr Pro
1               5                   10                  15

Glu Arg Ala Leu Phe Ala Ser Pro Ser Pro Asp Pro Ser Pro Arg Gly
            20                  25                  30

Leu Gly Ala Ser Ser Gly Ala Ala Glu Gly Ala Gly Ala Gly Leu Leu
            35                  40                  45

Leu Gly Cys Arg Ala Ser Met Ser Asp Asn Gln Ser Trp Asn Ser Ser
        50                  55                  60

Gly Ser Glu Glu Asp Pro Glu Thr Glu Ser Gly Pro Pro Val Glu Arg
65                  70                  75                  80

Cys Gly Val Leu Ser Lys Trp Thr Asn Tyr Ile His Gly Trp Gln Asp
                85                  90                  95

Arg Trp Val Val Leu Lys Asn Asn Ala Leu Ser Tyr Tyr Lys Ser Glu
            100                 105                 110

Asp Glu Thr Glu Tyr Gly Cys Arg Gly Ser Ile Cys Leu Ser Lys Ala
            115                 120                 125

Val Ile Thr Pro His Asp Phe Asp Glu Cys Arg Phe Asp Ile Ser Val
            130                 135                 140

Asn Asp Ser Val Trp Tyr Leu Arg Ala Gln Asp Pro Asp His Arg Gln
145                 150                 155                 160

Gln Trp Ile Asp Ala Ile Glu Gln His Lys Thr Glu Ser Gly Tyr Gly
                165                 170                 175

Ser Glu Ser Ser Leu Arg Arg His Gly Ser Met Val Ser Leu Val Ser
            180                 185                 190

Gly Ala Ser Gly Tyr Ser Ala Thr Ser Thr Ser Ser Phe Lys Lys Gly
            195                 200                 205

His Ser Leu Arg Glu Lys Leu Ala Glu Met Glu Thr Phe Arg Asp Ile
    210                 215                 220

Leu Cys Arg Gln Val Asp Thr Leu Gln Lys Tyr Phe Asp Ala Cys Ala
225                 230                 235                 240

Asp Ala Val Ser Lys Asp Glu Leu Gln Arg Asp Lys Val Val Glu Asp
            245                 250                 255

Asp Glu Asp Asp Phe Pro Thr Thr Arg Ser Asp Gly Asp Phe Leu His
            260                 265                 270

Ser Thr Asn Gly Asn Lys Glu Lys Leu Phe Pro His Val Thr Pro Lys
    275                 280                 285

Gly Ile Asn Gly Ile Asp Phe Lys Gly Glu Ala Ile Thr Phe Lys Ala
290                 295                 300

Thr Thr Ala Gly Ile Leu Ala Thr Leu Ser His Cys Ile Glu Leu Met
305                 310                 315                 320

Val Lys Arg Glu Asp Ser Trp Gln Lys Arg Leu Asp Lys Glu Thr Glu
            325                 330                 335

Lys Lys Arg Arg Thr Glu Glu Ala Tyr Lys Asn Ala Met Thr Glu Leu
            340                 345                 350

Lys Lys Lys Ser His Phe Gly Gly Pro Asp Tyr Glu Glu Gly Pro Asn
            355                 360                 365

Ser Leu Ile Asn Glu Glu Phe Phe Asp Ala Val Glu Ala Ala Leu
    370                 375                 380

Asp Arg Gln Asp Lys Ile Glu Glu Gln Ser Gln Ser Glu Lys Val Arg
385                 390                 395                 400

Leu His Trp Pro Thr Ser Leu Pro Ser Gly Asp Ala Phe Ser Ser Val
            405                 410                 415

Gly Thr His Arg Phe Val Gln Lys Pro Tyr Ser Arg Ser Ser Ser Met
```

```
                    420                 425                 430
    Ser Ser Ile Asp Leu Val Ser Ala Ser Asp Asp Val His Arg Phe Ser
            435                 440                 445

Ser Gln Val Glu Glu Met Val Gln Asn His Met Thr Tyr Ser Leu Gln
        450                 455                 460

Asp Val Gly Gly Asp Ala Asn Trp Gln Leu Val Val Glu Glu Gly Glu
    465                 470                 475                 480

Met Lys Val Tyr Arg Arg Glu Val Glu Glu Asn Gly Ile Val Leu Asp
                    485                 490                 495

Pro Leu Lys Ala Thr His Ala Val Lys Gly Val Thr Gly His Glu Val
                500                 505                 510

Cys Asn Tyr Phe Trp Asn Val Asp Val Arg Asn Asp Trp Glu Thr Thr
                515                 520                 525

Ile Glu Asn Phe His Val Val Glu Thr Leu Ala Asp Asn Ala Ile Ile
            530                 535                 540

Ile Tyr Gln Thr His Lys Arg Val Trp Pro Ala Ser Gln Arg Asp Val
    545                 550                 555                 560

Leu Tyr Leu Ser Val Ile Arg Lys Ile Pro Ala Leu Thr Glu Asn Asp
                    565                 570                 575

Pro Glu Thr Trp Ile Val Cys Asn Phe Ser Val Asp His Asp Ser Ala
                580                 585                 590

Pro Leu Asn Asn Arg Cys Val Arg Ala Lys Ile Asn Val Ala Met Ile
                595                 600                 605

Cys Gln Thr Leu Val Ser Pro Pro Glu Gly Asn Gln Glu Ile Ser Arg
        610                 615                 620

Asp Asn Ile Leu Cys Lys Ile Thr Tyr Val Ala Asn Val Asn Pro Gly
    625                 630                 635                 640

Gly Trp Ala Pro Ala Ser Val Leu Arg Ala Val Ala Lys Arg Glu Tyr
                    645                 650                 655

Pro Lys Phe Leu Lys Arg Phe Thr Ser Tyr Val Gln Glu Lys Thr Ala
                660                 665                 670

Gly Lys Pro Ile Leu Phe
            675

<210> SEQ ID NO 19
<211> LENGTH: 1959
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(1959)
<223> OTHER INFORMATION:

<400> SEQUENCE: 19 cgg cgc ggc ggg cgg act tcg tcc ctc ctc ctg ctc ccc ccc aca ccg      48
Arg Arg Gly Gly Arg Thr Ser Ser Leu Leu Leu Leu Pro Pro Thr Pro
1               5                   10                  15 gag cgg gca ctc ttc gct tcg cca tcc ccc gac cct tca ccc cga gga      96
Glu Arg Ala Leu Phe Ala Ser Pro Ser Pro Asp Pro Ser Pro Arg Gly
                20                  25                  30 ctg ggc gcc tcc tcc ggc gca gct gag gga gcg ggg gcc ggt ctc ctg     144
Leu Gly Ala Ser Ser Gly Ala Ala Glu Gly Ala Gly Ala Gly Leu Leu
            35                  40                  45 ctc ggt tgt cga gcc tcc atg tcg gat aat cag agc tgg aac tcg tcg     192
Leu Gly Cys Arg Ala Ser Met Ser Asp Asn Gln Ser Trp Asn Ser Ser
    50                  55                  60
```

| | | |
|---|---|---|
| ggc tcg gag gag gat cca gag acg gag tct ggg ccg cct gtg gag cgc<br>Gly Ser Glu Glu Asp Pro Glu Thr Glu Ser Gly Pro Pro Val Glu Arg<br>65                            70                     75                   80 | | 240 |
| tgc ggg gtc ctc agt aag tgg aca aac tac att cat ggg tgg cag gat<br>Cys Gly Val Leu Ser Lys Trp Thr Asn Tyr Ile His Gly Trp Gln Asp<br>                     85                     90                     95 | | 288 |
| cgt tgg gta gtt ttg aaa aat aat gct ctg agt tac tac aaa tct gaa<br>Arg Trp Val Val Leu Lys Asn Asn Ala Leu Ser Tyr Tyr Lys Ser Glu<br>                 100                  105                 110 | | 336 |
| gat gaa aca gag tat ggc tgc aga gga tcc atc tgt ctt agc aag gct<br>Asp Glu Thr Glu Tyr Gly Cys Arg Gly Ser Ile Cys Leu Ser Lys Ala<br>        115                  120                  125 | | 384 |
| gtc atc aca cct cac gat ttt gat gaa tgt cga ttt gat att agt gta<br>Val Ile Thr Pro His Asp Phe Asp Glu Cys Arg Phe Asp Ile Ser Val<br>130                           135                    140 | | 432 |
| aat gat agt gtt tgg tat ctt cgt gct cag gat cca gat cat aga cag<br>Asn Asp Ser Val Trp Tyr Leu Arg Ala Gln Asp Pro Asp His Arg Gln<br>145                          150                    155                 160 | | 480 |
| caa tgg ata gat gcc att gaa cag cac aag act gaa tct gga tat gga<br>Gln Trp Ile Asp Ala Ile Glu Gln His Lys Thr Glu Ser Gly Tyr Gly<br>                 165                  170                 175 | | 528 |
| tct gaa tcc agc ttg cgt cga cat ggc tca atg gtg tcc ctg gtg tct<br>Ser Glu Ser Ser Leu Arg Arg His Gly Ser Met Val Ser Leu Val Ser<br>        180                  185                  190 | | 576 |
| gga gca agt ggc tac tct gca aca tcc acc tct tca ttc aag aaa ggc<br>Gly Ala Ser Gly Tyr Ser Ala Thr Ser Thr Ser Ser Phe Lys Lys Gly<br>                 195                  200                 205 | | 624 |
| cac agt tta cgt gag aag ttg gct gaa atg gaa aca ttt aga gac atc<br>His Ser Leu Arg Glu Lys Leu Ala Glu Met Glu Thr Phe Arg Asp Ile<br>        210                  215                  220 | | 672 |
| tta tgt aga caa gtt gac acg cta cag aag tac ttt gat gcc tgt gct<br>Leu Cys Arg Gln Val Asp Thr Leu Gln Lys Tyr Phe Asp Ala Cys Ala<br>225                           230                    235                 240 | | 720 |
| gat gct gtc tct aag gat gaa ctt caa agg gat aaa gtg gta gaa gat<br>Asp Ala Val Ser Lys Asp Glu Leu Gln Arg Asp Lys Val Val Glu Asp<br>                 245                  250                 255 | | 768 |
| gat gaa gat gac ttt cct aca acg cgt tct gat ggt gac ttc ttg cat<br>Asp Glu Asp Asp Phe Pro Thr Thr Arg Ser Asp Gly Asp Phe Leu His<br>        260                  265                  270 | | 816 |
| agt acc aac ggc aat aaa gaa aag tta ttt cca cat gtg aca cca aaa<br>Ser Thr Asn Gly Asn Lys Glu Lys Leu Phe Pro His Val Thr Pro Lys<br>        275                  280                  285 | | 864 |
| gga att aat ggt ata gac ttt aaa ggg gaa gcg ata act ttt aaa gca<br>Gly Ile Asn Gly Ile Asp Phe Lys Gly Glu Ala Ile Thr Phe Lys Ala<br>290                           295                    300 | | 912 |
| act act gct gga atc ctt gca aca ctt tct cat tgt att gaa cta atg<br>Thr Thr Ala Gly Ile Leu Ala Thr Leu Ser His Cys Ile Glu Leu Met<br>305                           310                    315                 320 | | 960 |
| gtt aaa cgt gag gac agc tgg cag aag aga ctg gat aag gaa act gag<br>Val Lys Arg Glu Asp Ser Trp Gln Lys Arg Leu Asp Lys Glu Thr Glu<br>                 325                  330                 335 | | 1008 |
| aag aaa aga aga aca gag gaa gca tat aaa aat gca atg aca gaa ctt<br>Lys Lys Arg Arg Thr Glu Glu Ala Tyr Lys Asn Ala Met Thr Glu Leu<br>        340                  345                  350 | | 1056 |
| aag aaa aaa tcc cac ttt gga gga cca gat tat gaa gaa ggc cct aac<br>Lys Lys Lys Ser His Phe Gly Gly Pro Asp Tyr Glu Glu Gly Pro Asn<br>        355                  360                 365 | | 1104 |
| agt ctg att aat gaa gaa gag ttc ttt gat gct gtt gaa gct gct ctt<br>Ser Leu Ile Asn Glu Glu Glu Phe Phe Asp Ala Val Glu Ala Ala Leu | | 1152 |

```
                   370             375             380
gac aga caa gat aaa ata gaa gaa cag tca cag agt gaa aag gtg aga    1200
Asp Arg Gln Asp Lys Ile Glu Glu Gln Ser Gln Ser Glu Lys Val Arg
385                 390                 395                 400 tta cat tgg cct aca tcc ttg ccc tct gga gat gcc ttt tct tct gtg    1248
Leu His Trp Pro Thr Ser Leu Pro Ser Gly Asp Ala Phe Ser Ser Val
            405                 410                 415 ggg aca cat aga ttt gtc caa aag gtt gaa gag atg gtg cag aac cac    1296
Gly Thr His Arg Phe Val Gln Lys Val Glu Glu Met Val Gln Asn His
        420                 425                 430 atg act tac tca tta cag gat gta ggc gga gat gcc aat tgg cag ttg    1344
Met Thr Tyr Ser Leu Gln Asp Val Gly Gly Asp Ala Asn Trp Gln Leu
    435                 440                 445 gtt gta gaa gaa gga gaa atg aag gta tac aga aga gaa gta gaa gaa    1392
Val Val Glu Glu Gly Glu Met Lys Val Tyr Arg Arg Glu Val Glu Glu
450                 455                 460 aat ggg att gtt ctg gat cct tta aaa gct acc cat gca gtt aaa ggc    1440
Asn Gly Ile Val Leu Asp Pro Leu Lys Ala Thr His Ala Val Lys Gly
465                 470                 475                 480 gtc aca gga cat gaa gtc tgc aat tat ttc tgg aat gtt gac gtt cgc    1488
Val Thr Gly His Glu Val Cys Asn Tyr Phe Trp Asn Val Asp Val Arg
            485                 490                 495 aat gac tgg gaa aca act ata gaa aac ttt cat gtg gtg gaa aca tta    1536
Asn Asp Trp Glu Thr Thr Ile Glu Asn Phe His Val Val Glu Thr Leu
        500                 505                 510 gct gat aat gca atc atc att tat caa aca cac aag agg gtg tgg cct    1584
Ala Asp Asn Ala Ile Ile Ile Tyr Gln Thr His Lys Arg Val Trp Pro
    515                 520                 525 gct tct cag cga gac gta tta tat ctt tct gtc att cga aag ata cca    1632
Ala Ser Gln Arg Asp Val Leu Tyr Leu Ser Val Ile Arg Lys Ile Pro
530                 535                 540 gcc ttg act gaa aat gac cct gaa act tgg ata gtt tgt aat ttt tct    1680
Ala Leu Thr Glu Asn Asp Pro Glu Thr Trp Ile Val Cys Asn Phe Ser
545                 550                 555                 560 gtg gat cat gac agt gct cct cta aac aac cga tgt gtc cgt gcc aaa    1728
Val Asp His Asp Ser Ala Pro Leu Asn Asn Arg Cys Val Arg Ala Lys
            565                 570                 575 ata aat gtt gct atg att tgt caa acc ttg gta agc cca cca gag gga    1776
Ile Asn Val Ala Met Ile Cys Gln Thr Leu Val Ser Pro Pro Glu Gly
        580                 585                 590 aac cag gaa att agc agg gac aac att cta tgc aag att aca tat gta    1824
Asn Gln Glu Ile Ser Arg Asp Asn Ile Leu Cys Lys Ile Thr Tyr Val
    595                 600                 605 gct aat gtg aac cct gga gga tgg gca cca gcc tca gtg tta agg gca    1872
Ala Asn Val Asn Pro Gly Gly Trp Ala Pro Ala Ser Val Leu Arg Ala
610                 615                 620 gtg gca aag cga gag tat cct aaa ttt cta aaa cgt ttt act tct tac    1920
Val Ala Lys Arg Glu Tyr Pro Lys Phe Leu Lys Arg Phe Thr Ser Tyr
625                 630                 635                 640 gtc caa gaa aaa act gca gga aag cct att ttg ttc tag               1959
Val Gln Glu Lys Thr Ala Gly Lys Pro Ile Leu Phe
            645                 650
```

<210> SEQ ID NO 20
<211> LENGTH: 652
<212> TYPE: PRT
<213> ORGANISM: artificial
<220> FEATURE:
<223> OTHER INFORMATION: Derived sequence

<400> SEQUENCE: 20

```
Arg Arg Gly Gly Arg Thr Ser Ser Leu Leu Leu Pro Pro Thr Pro
  1               5                  10                 15

Glu Arg Ala Leu Phe Ala Ser Pro Ser Pro Asp Pro Ser Pro Arg Gly
                 20                  25                  30

Leu Gly Ala Ser Ser Gly Ala Ala Glu Gly Ala Gly Ala Gly Leu Leu
             35                  40                  45

Leu Gly Cys Arg Ala Ser Met Ser Asp Asn Gln Ser Trp Asn Ser Ser
 50                  55                  60

Gly Ser Glu Glu Asp Pro Glu Thr Glu Ser Gly Pro Pro Val Glu Arg
 65                  70                  75                  80

Cys Gly Val Leu Ser Lys Trp Thr Asn Tyr Ile His Gly Trp Gln Asp
                 85                  90                  95

Arg Trp Val Val Leu Lys Asn Asn Ala Leu Ser Tyr Tyr Lys Ser Glu
                100                 105                 110

Asp Glu Thr Glu Tyr Gly Cys Arg Gly Ser Ile Cys Leu Ser Lys Ala
                115                 120                 125

Val Ile Thr Pro His Asp Phe Asp Glu Cys Arg Phe Asp Ile Ser Val
130                 135                 140

Asn Asp Ser Val Trp Tyr Leu Arg Ala Gln Asp Pro Asp His Arg Gln
145                 150                 155                 160

Gln Trp Ile Asp Ala Ile Glu Gln His Lys Thr Glu Ser Gly Tyr Gly
                165                 170                 175

Ser Glu Ser Ser Leu Arg Arg His Gly Ser Met Val Ser Leu Val Ser
                180                 185                 190

Gly Ala Ser Gly Tyr Ser Ala Thr Ser Thr Ser Ser Phe Lys Lys Gly
                195                 200                 205

His Ser Leu Arg Glu Lys Leu Ala Glu Met Glu Thr Phe Arg Asp Ile
                210                 215                 220

Leu Cys Arg Gln Val Asp Thr Leu Gln Lys Tyr Phe Asp Ala Cys Ala
225                 230                 235                 240

Asp Ala Val Ser Lys Asp Glu Leu Gln Arg Asp Lys Val Val Glu Asp
                245                 250                 255

Asp Glu Asp Asp Phe Pro Thr Thr Arg Ser Asp Gly Asp Phe Leu His
                260                 265                 270

Ser Thr Asn Gly Asn Lys Glu Lys Leu Phe Pro His Val Thr Pro Lys
                275                 280                 285

Gly Ile Asn Gly Ile Asp Phe Lys Gly Glu Ala Ile Thr Phe Lys Ala
                290                 295                 300

Thr Thr Ala Gly Ile Leu Ala Thr Leu Ser His Cys Ile Glu Leu Met
305                 310                 315                 320

Val Lys Arg Glu Asp Ser Trp Gln Lys Arg Leu Asp Lys Glu Thr Glu
                325                 330                 335

Lys Lys Arg Arg Thr Glu Glu Ala Tyr Lys Asn Ala Met Thr Glu Leu
                340                 345                 350

Lys Lys Lys Ser His Phe Gly Gly Pro Asp Tyr Glu Glu Gly Pro Asn
                355                 360                 365

Ser Leu Ile Asn Glu Glu Phe Phe Asp Ala Val Glu Ala Ala Leu
370                 375                 380

Asp Arg Gln Asp Lys Ile Glu Glu Gln Ser Gln Ser Glu Lys Val Arg
385                 390                 395                 400

Leu His Trp Pro Thr Ser Leu Pro Ser Gly Asp Ala Phe Ser Ser Val
                405                 410                 415
```

-continued

```
Gly Thr His Arg Phe Val Gln Lys Val Glu Glu Met Val Gln Asn His
            420                 425                 430

Met Thr Tyr Ser Leu Gln Asp Val Gly Gly Asp Ala Asn Trp Gln Leu
            435                 440                 445

Val Val Glu Glu Gly Glu Met Lys Val Tyr Arg Arg Glu Val Glu Glu
        450                 455                 460

Asn Gly Ile Val Leu Asp Pro Leu Lys Ala Thr His Ala Val Lys Gly
465                 470                 475                 480

Val Thr Gly His Glu Val Cys Asn Tyr Phe Trp Asn Val Asp Val Arg
                485                 490                 495

Asn Asp Trp Glu Thr Thr Ile Glu Asn Phe His Val Val Glu Thr Leu
            500                 505                 510

Ala Asp Asn Ala Ile Ile Ile Tyr Gln Thr His Lys Arg Val Trp Pro
            515                 520                 525

Ala Ser Gln Arg Asp Val Leu Tyr Leu Ser Val Ile Arg Lys Ile Pro
        530                 535                 540

Ala Leu Thr Glu Asn Asp Pro Glu Thr Trp Ile Val Cys Asn Phe Ser
545                 550                 555                 560

Val Asp His Asp Ser Ala Pro Leu Asn Asn Arg Cys Val Arg Ala Lys
                565                 570                 575

Ile Asn Val Ala Met Ile Cys Gln Thr Leu Val Ser Pro Pro Glu Gly
            580                 585                 590

Asn Gln Glu Ile Ser Arg Asp Asn Ile Leu Cys Lys Ile Thr Tyr Val
            595                 600                 605

Ala Asn Val Asn Pro Gly Gly Trp Ala Pro Ala Ser Val Leu Arg Ala
        610                 615                 620

Val Ala Lys Arg Glu Tyr Pro Lys Phe Leu Lys Arg Phe Thr Ser Tyr
625                 630                 635                 640

Val Gln Glu Lys Thr Ala Gly Lys Pro Ile Leu Phe
                645                 650
```

<210> SEQ ID NO 21
<211> LENGTH: 2109
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(2109)
<223> OTHER INFORMATION:

<400> SEQUENCE: 21

```
gac ggc tgg aag ggt agg ctt cct tca ccg ctc gtc ctc ctt cct cgc      48
Asp Gly Trp Lys Gly Arg Leu Pro Ser Pro Leu Val Leu Leu Pro Arg
1               5                   10                  15 tcc gct cgg tgt cag gcg cgg cgg cgg cgc ggc ggg cgg act tcg tcc      96
Ser Ala Arg Cys Gln Ala Arg Arg Arg Arg Gly Gly Arg Thr Ser Ser
            20                  25                  30 ctc ctc ctg ctc ccc ccc aca ccg gag cgg gca ctc ttc gct tcg cca     144
Leu Leu Leu Leu Pro Pro Thr Pro Glu Arg Ala Leu Phe Ala Ser Pro
        35                  40                  45 tcc ccc gac cct tca ccc cga gga ctg ggc gcc tcc tcc ggc gca gct     192
Ser Pro Asp Pro Ser Pro Arg Gly Leu Gly Ala Ser Ser Gly Ala Ala
    50                  55                  60 gag gga gcg ggg gcc ggt ctc ctg ctc ggt tgt cga gcc tcc atg tcg     240
Glu Gly Ala Gly Ala Gly Leu Leu Leu Gly Cys Arg Ala Ser Met Ser
65                  70                  75                  80
```

```
gat aat cag agc tgg aac tcg tcg ggc tcg gag gag gat cca gag acg       288
Asp Asn Gln Ser Trp Asn Ser Ser Gly Ser Glu Glu Asp Pro Glu Thr
             85                  90                  95 gag tct ggg ccg cct gtg gag cgc tgc ggg gtc ctc agt aag tgg aca       336
Glu Ser Gly Pro Pro Val Glu Arg Cys Gly Val Leu Ser Lys Trp Thr
            100                 105                 110 aac tac att cat ggg tgg cag gat cgt tgg gta gtt ttg aaa aat aat       384
Asn Tyr Ile His Gly Trp Gln Asp Arg Trp Val Val Leu Lys Asn Asn
        115                 120                 125 gct ctg agt tac tac aaa tct gaa gat gaa aca gag tat ggc tgc aga       432
Ala Leu Ser Tyr Tyr Lys Ser Glu Asp Glu Thr Glu Tyr Gly Cys Arg
    130                 135                 140 gga tcc atc tgt ctt agc aag gct gtc atc aca cct cac gat ttt gat       480
Gly Ser Ile Cys Leu Ser Lys Ala Val Ile Thr Pro His Asp Phe Asp
145                 150                 155                 160 gaa tgt cga ttt gat att agt gta aat gat agt gtt tgg tat ctt cgt       528
Glu Cys Arg Phe Asp Ile Ser Val Asn Asp Ser Val Trp Tyr Leu Arg
                165                 170                 175 gct cag gat cca gat cat aga cag caa tgg ata gat gcc att gaa cag       576
Ala Gln Asp Pro Asp His Arg Gln Gln Trp Ile Asp Ala Ile Glu Gln
            180                 185                 190 cac aag act gaa tct gga tat gga tct gaa tcc agc ttg cgt cga cat       624
His Lys Thr Glu Ser Gly Tyr Gly Ser Glu Ser Ser Leu Arg Arg His
        195                 200                 205 ggc tca atg gtg tcc ctg gtg tct gga gca agt ggc tac tct gca aca       672
Gly Ser Met Val Ser Leu Val Ser Gly Ala Ser Gly Tyr Ser Ala Thr
    210                 215                 220 tcc acc tct tca ttc aag aaa ggc cac agt tta cgt gag aag ttg gct       720
Ser Thr Ser Ser Phe Lys Lys Gly His Ser Leu Arg Glu Lys Leu Ala
225                 230                 235                 240 gaa atg gaa aca ttt aga gac atc tta tgt aga caa gtt gac acg cta       768
Glu Met Glu Thr Phe Arg Asp Ile Leu Cys Arg Gln Val Asp Thr Leu
                245                 250                 255 cag aag tac ttt gat gcc tgt gct gat gct gtc tct aag gat gaa ctt       816
Gln Lys Tyr Phe Asp Ala Cys Ala Asp Ala Val Ser Lys Asp Glu Leu
            260                 265                 270 caa agg gat aaa gtg gta gaa gat gat gaa gat gac ttt cct aca acg       864
Gln Arg Asp Lys Val Val Glu Asp Asp Glu Asp Asp Phe Pro Thr Thr
        275                 280                 285 cgt tct gat ggt gac ttc ttg cat agt acc aac ggc aat aaa gaa aag       912
Arg Ser Asp Gly Asp Phe Leu His Ser Thr Asn Gly Asn Lys Glu Lys
    290                 295                 300 tta ttt cca cat gtg aca cca aaa gga att aat ggt ata gac ttt aaa       960
Leu Phe Pro His Val Thr Pro Lys Gly Ile Asn Gly Ile Asp Phe Lys
305                 310                 315                 320 ggg gaa gcg ata act ttt aaa gca act act gct gga atc ctt gca aca      1008
Gly Glu Ala Ile Thr Phe Lys Ala Thr Thr Ala Gly Ile Leu Ala Thr
                325                 330                 335 ctt tct cat tgt att gaa cta atg gtt aaa cgt gag gac agc tgg cag      1056
Leu Ser His Cys Ile Glu Leu Met Val Lys Arg Glu Asp Ser Trp Gln
            340                 345                 350 aag aga ctg gat aag gaa act gag aag aaa aga aga aca gag gaa gca      1104
Lys Arg Leu Asp Lys Glu Thr Glu Lys Lys Arg Arg Thr Glu Glu Ala
        355                 360                 365 tat aaa aat gca atg aca gaa ctt aag aaa aaa tcc cac ttt gga gga      1152
Tyr Lys Asn Ala Met Thr Glu Leu Lys Lys Lys Ser His Phe Gly Gly
    370                 375                 380 cca gat tat gaa gaa ggc cct aac agt ctg att aat gaa gaa gag ttc      1200
Pro Asp Tyr Glu Glu Gly Pro Asn Ser Leu Ile Asn Glu Glu Glu Phe
385                 390                 395                 400
```

-continued

| | |
|---|---|
| ttt gat gct gtt gaa gct gct ctt gac aga caa gat aaa ata gaa gaa<br>Phe Asp Ala Val Glu Ala Ala Leu Asp Arg Gln Asp Lys Ile Glu Glu<br>405 410 415 | 1248 |
| cag tca cag agt gaa aag gtg aga tta cat tgg cct aca tcc ttg ccc<br>Gln Ser Gln Ser Glu Lys Val Arg Leu His Trp Pro Thr Ser Leu Pro<br>420 425 430 | 1296 |
| tct gga gat gcc ttt tct tct gtg ggg aca cat aga ttt gtc caa aag<br>Ser Gly Asp Ala Phe Ser Ser Val Gly Thr His Arg Phe Val Gln Lys<br>435 440 445 | 1344 |
| ccc tat agt cgc tct tcc tcc atg tct tcc att gat cta gtc agt gcc<br>Pro Tyr Ser Arg Ser Ser Ser Met Ser Ser Ile Asp Leu Val Ser Ala<br>450 455 460 | 1392 |
| tct gat gat gtt cac aga ttc agc tcc cag gtt gaa gag atg gtg cag<br>Ser Asp Asp Val His Arg Phe Ser Ser Gln Val Glu Glu Met Val Gln<br>465 470 475 480 | 1440 |
| aac cac atg act tac tca tta cag gat gta ggc gga gat gcc aat tgg<br>Asn His Met Thr Tyr Ser Leu Gln Asp Val Gly Gly Asp Ala Asn Trp<br>485 490 495 | 1488 |
| cag ttg gtt gta gaa gaa gga gaa atg aag gta tac aga aga gaa gta<br>Gln Leu Val Val Glu Glu Gly Glu Met Lys Val Tyr Arg Arg Glu Val<br>500 505 510 | 1536 |
| gaa gaa aat ggg att gtt ctg gat cct tta aaa gct acc cat gca gtt<br>Glu Glu Asn Gly Ile Val Leu Asp Pro Leu Lys Ala Thr His Ala Val<br>515 520 525 | 1584 |
| aaa ggc gtc aca gga cat gaa gtc tgc aat tat ttc tgg aat gtt gac<br>Lys Gly Val Thr Gly His Glu Val Cys Asn Tyr Phe Trp Asn Val Asp<br>530 535 540 | 1632 |
| gtt cgc aat gac tgg gaa aca act ata gaa aac ttt cat gtg gtg gaa<br>Val Arg Asn Asp Trp Glu Thr Thr Ile Glu Asn Phe His Val Val Glu<br>545 550 555 560 | 1680 |
| aca tta gct gat aat gca atc atc att tat caa aca cac aag agg gtg<br>Thr Leu Ala Asp Asn Ala Ile Ile Ile Tyr Gln Thr His Lys Arg Val<br>565 570 575 | 1728 |
| tgg cct gct tct cag cga gac gta tta tat ctt tct gtc att cga aag<br>Trp Pro Ala Ser Gln Arg Asp Val Leu Tyr Leu Ser Val Ile Arg Lys<br>580 585 590 | 1776 |
| ata cca gcc ttg act gaa aat gac cct gaa act tgg ata gtt tgt aat<br>Ile Pro Ala Leu Thr Glu Asn Asp Pro Glu Thr Trp Ile Val Cys Asn<br>595 600 605 | 1824 |
| ttt tct gtg gat cat gac agt gct cct cta aac aac cga tgt gtc cgt<br>Phe Ser Val Asp His Asp Ser Ala Pro Leu Asn Asn Arg Cys Val Arg<br>610 615 620 | 1872 |
| gcc aaa ata aat gtt gct atg att tgt caa acc ttg gta agc cca cca<br>Ala Lys Ile Asn Val Ala Met Ile Cys Gln Thr Leu Val Ser Pro Pro<br>625 630 635 640 | 1920 |
| gag gga aac cag gaa att agc agg gac aac att cta tgc aag att aca<br>Glu Gly Asn Gln Glu Ile Ser Arg Asp Asn Ile Leu Cys Lys Ile Thr<br>645 650 655 | 1968 |
| tat gta gct aat gtg aac cct gga gga tgg gca cca gcc tca gtg tta<br>Tyr Val Ala Asn Val Asn Pro Gly Gly Trp Ala Pro Ala Ser Val Leu<br>660 665 670 | 2016 |
| agg gca gtg gca aag cga gag tat cct aaa ttt cta aaa cgt ttt act<br>Arg Ala Val Ala Lys Arg Glu Tyr Pro Lys Phe Leu Lys Arg Phe Thr<br>675 680 685 | 2064 |
| tct tac gtc caa gaa aaa act gca gga aag cct att ttg ttc tag<br>Ser Tyr Val Gln Glu Lys Thr Ala Gly Lys Pro Ile Leu Phe<br>690 695 700 | 2109 |

<210> SEQ ID NO 22

```
<211> LENGTH: 702
<212> TYPE: PRT
<213> ORGANISM: artificial
<220> FEATURE:
<223> OTHER INFORMATION: Derived sequence

<400> SEQUENCE: 22

Asp Gly Trp Lys Gly Arg Leu Pro Ser Pro Leu Val Leu Leu Pro Arg
1               5                   10                  15

Ser Ala Arg Cys Gln Ala Arg Arg Arg Gly Arg Thr Ser Ser
            20                  25                  30

Leu Leu Leu Leu Pro Pro Thr Pro Glu Arg Ala Leu Phe Ala Ser Pro
            35                  40                  45

Ser Pro Asp Pro Ser Pro Arg Gly Leu Gly Ala Ser Gly Ala Ala
        50                  55                  60

Glu Gly Ala Gly Ala Gly Leu Leu Leu Gly Cys Arg Ala Ser Met Ser
65                  70                  75                  80

Asp Asn Gln Ser Trp Asn Ser Gly Ser Glu Glu Asp Pro Glu Thr
                85                  90                  95

Glu Ser Gly Pro Pro Val Glu Arg Cys Gly Val Leu Ser Lys Trp Thr
            100                 105                 110

Asn Tyr Ile His Gly Trp Gln Asp Arg Trp Val Val Leu Lys Asn Asn
            115                 120                 125

Ala Leu Ser Tyr Tyr Lys Ser Glu Asp Glu Thr Glu Tyr Gly Cys Arg
        130                 135                 140

Gly Ser Ile Cys Leu Ser Lys Ala Val Ile Thr Pro His Asp Phe Asp
145                 150                 155                 160

Glu Cys Arg Phe Asp Ile Ser Val Asn Asp Ser Val Trp Tyr Leu Arg
                165                 170                 175

Ala Gln Asp Pro Asp His Arg Gln Gln Trp Ile Asp Ala Ile Glu Gln
            180                 185                 190

His Lys Thr Glu Ser Gly Tyr Gly Ser Glu Ser Ser Leu Arg Arg His
        195                 200                 205

Gly Ser Met Val Ser Leu Val Ser Gly Ala Ser Gly Tyr Ser Ala Thr
    210                 215                 220

Ser Thr Ser Ser Phe Lys Lys Gly His Ser Leu Arg Glu Lys Leu Ala
225                 230                 235                 240

Glu Met Glu Thr Phe Arg Asp Ile Leu Cys Arg Gln Val Asp Thr Leu
                245                 250                 255

Gln Lys Tyr Phe Asp Ala Cys Ala Asp Ala Val Ser Lys Asp Glu Leu
            260                 265                 270

Gln Arg Asp Lys Val Val Glu Asp Asp Glu Asp Asp Phe Pro Thr Thr
        275                 280                 285

Arg Ser Asp Gly Asp Phe Leu His Ser Thr Asn Gly Asn Lys Glu Lys
    290                 295                 300

Leu Phe Pro His Val Thr Pro Lys Gly Ile Asn Gly Ile Asp Phe Lys
305                 310                 315                 320

Gly Glu Ala Ile Thr Phe Lys Ala Thr Thr Ala Gly Ile Leu Ala Thr
                325                 330                 335

Leu Ser His Cys Ile Glu Leu Met Val Lys Arg Glu Asp Ser Trp Gln
            340                 345                 350

Lys Arg Leu Asp Lys Glu Thr Glu Lys Lys Arg Arg Thr Glu Glu Ala
        355                 360                 365

Tyr Lys Asn Ala Met Thr Glu Leu Lys Lys Lys Ser His Phe Gly Gly
    370                 375                 380
```

```
Pro Asp Tyr Glu Glu Gly Pro Asn Ser Leu Ile Asn Glu Glu Phe
385                 390                 395                 400

Phe Asp Ala Val Glu Ala Ala Leu Asp Arg Gln Asp Lys Ile Glu Glu
            405                 410                 415

Gln Ser Gln Ser Glu Lys Val Arg Leu His Trp Pro Thr Ser Leu Pro
        420                 425                 430

Ser Gly Asp Ala Phe Ser Ser Val Gly Thr His Arg Phe Val Gln Lys
        435                 440                 445

Pro Tyr Ser Arg Ser Ser Met Ser Ser Ile Asp Leu Val Ser Ala
    450                 455                 460

Ser Asp Val His Arg Phe Ser Ser Gln Val Glu Glu Met Val Gln
465                 470                 475                 480

Asn His Met Thr Tyr Ser Leu Gln Asp Val Gly Gly Asp Ala Asn Trp
                485                 490                 495

Gln Leu Val Val Glu Glu Gly Met Lys Val Tyr Arg Arg Glu Val
        500                 505                 510

Glu Glu Asn Gly Ile Val Leu Asp Pro Leu Lys Ala Thr His Ala Val
        515                 520                 525

Lys Gly Val Thr Gly His Glu Val Cys Asn Tyr Phe Trp Asn Val Asp
    530                 535                 540

Val Arg Asn Asp Trp Glu Thr Thr Ile Glu Asn Phe His Val Val Glu
545                 550                 555                 560

Thr Leu Ala Asp Asn Ala Ile Ile Ile Tyr Gln Thr His Lys Arg Val
                565                 570                 575

Trp Pro Ala Ser Gln Arg Asp Val Leu Tyr Leu Ser Val Ile Arg Lys
            580                 585                 590

Ile Pro Ala Leu Thr Glu Asn Asp Pro Glu Thr Trp Ile Val Cys Asn
        595                 600                 605

Phe Ser Val Asp His Asp Ser Ala Pro Leu Asn Arg Cys Val Arg
    610                 615                 620

Ala Lys Ile Asn Val Ala Met Ile Cys Gln Thr Leu Val Ser Pro Pro
625                 630                 635                 640

Glu Gly Asn Gln Glu Ile Ser Arg Asp Asn Ile Leu Cys Lys Ile Thr
                645                 650                 655

Tyr Val Ala Asn Val Asn Pro Gly Gly Trp Ala Pro Ala Ser Val Leu
            660                 665                 670

Arg Ala Val Ala Lys Arg Glu Tyr Pro Lys Phe Leu Lys Arg Phe Thr
        675                 680                 685

Ser Tyr Val Gln Glu Lys Thr Ala Gly Lys Pro Ile Leu Phe
    690                 695                 700
```

<210> SEQ ID NO 23
<211> LENGTH: 2031
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(2031)
<223> OTHER INFORMATION:

<400> SEQUENCE: 23

```
gac ggc tgg aag ggt agg ctt cct tca ccg ctc gtc ctc ctt cct cgc      48
Asp Gly Trp Lys Gly Arg Leu Pro Ser Pro Leu Val Leu Leu Pro Arg
1               5                   10                  15
```

-continued

| | | |
|---|---|---|
| tcc gct cgg tgt cag gcg cgg cgg cgc ggc ggg cgg act tcg tcc<br>Ser Ala Arg Cys Gln Ala Arg Arg Arg Gly Gly Arg Thr Ser Ser<br>20                        25                       30 | 96 |
| ctc ctc ctg ctc ccc ccc aca ccg gag cgg gca ctc ttc gct tcg cca<br>Leu Leu Leu Leu Pro Pro Thr Pro Glu Arg Ala Leu Phe Ala Ser Pro<br>35                       40                       45 | 144 |
| tcc ccc gac cct tca ccc cga gga ctg ggc gcc tcc tcc ggc gca gct<br>Ser Pro Asp Pro Ser Pro Arg Gly Leu Gly Ala Ser Ser Gly Ala Ala<br>50                       55                       60 | 192 |
| gag gga gcg ggg gcc ggt ctc ctg ctc ggt tgt cga gcc tcc atg tcg<br>Glu Gly Ala Gly Ala Gly Leu Leu Leu Gly Cys Arg Ala Ser Met Ser<br>65                       70                       75                 80 | 240 |
| gat aat cag agc tgg aac tcg tcg ggc tcg gag gag gat cca gag acg<br>Asp Asn Gln Ser Trp Asn Ser Ser Gly Ser Glu Glu Asp Pro Glu Thr<br>                   85                      90                       95 | 288 |
| gag tct ggg ccg cct gtg gag cgc tgc ggg gtc ctc agt aag tgg aca<br>Glu Ser Gly Pro Pro Val Glu Arg Cys Gly Val Leu Ser Lys Trp Thr<br>                 100                    105                 110 | 336 |
| aac tac att cat ggg tgg cag gat cgt tgg gta gtt ttg aaa aat aat<br>Asn Tyr Ile His Gly Trp Gln Asp Arg Trp Val Val Leu Lys Asn Asn<br>               115                    120                 125 | 384 |
| gct ctg agt tac tac aaa tct gaa gat gaa aca gag tat ggc tgc aga<br>Ala Leu Ser Tyr Tyr Lys Ser Glu Asp Glu Thr Glu Tyr Gly Cys Arg<br>130                      135                   140 | 432 |
| gga tcc atc tgt ctt agc aag gct gtc atc aca cct cac gat ttt gat<br>Gly Ser Ile Cys Leu Ser Lys Ala Val Ile Thr Pro His Asp Phe Asp<br>145                     150                   155                 160 | 480 |
| gaa tgt cga ttt gat att agt gta aat gat agt gtt tgg tat ctt cgt<br>Glu Cys Arg Phe Asp Ile Ser Val Asn Asp Ser Val Trp Tyr Leu Arg<br>                   165                  170                 175 | 528 |
| gct cag gat cca gat cat aga cag caa tgg ata gat gcc att gaa cag<br>Ala Gln Asp Pro Asp His Arg Gln Gln Trp Ile Asp Ala Ile Glu Gln<br>                   180                  185                 190 | 576 |
| cac aag act gaa tct gga tat gga tct gaa tcc agc ttg cgt cga cat<br>His Lys Thr Glu Ser Gly Tyr Gly Ser Glu Ser Ser Leu Arg Arg His<br>               195                    200                 205 | 624 |
| ggc tca atg gtg tcc ctg gtg tct gga gca agt ggc tac tct gca aca<br>Gly Ser Met Val Ser Leu Val Ser Gly Ala Ser Gly Tyr Ser Ala Thr<br>210                      215                   220 | 672 |
| tcc acc tct tca ttc aag aaa ggc cac agt tta cgt gag aag ttg gct<br>Ser Thr Ser Ser Phe Lys Lys Gly His Ser Leu Arg Glu Lys Leu Ala<br>225                     230                   235                 240 | 720 |
| gaa atg gaa aca ttt aga gac atc tta tgt aga caa gtt gac acg cta<br>Glu Met Glu Thr Phe Arg Asp Ile Leu Cys Arg Gln Val Asp Thr Leu<br>                   245                  250                 255 | 768 |
| cag aag tac ttt gat gcc tgt gct gat gct gtc tct aag gat gaa ctt<br>Gln Lys Tyr Phe Asp Ala Cys Ala Asp Ala Val Ser Lys Asp Glu Leu<br>                   260                  265                 270 | 816 |
| caa agg gat aaa gtg gta gaa gat gat gaa gat gac ttt cct aca acg<br>Gln Arg Asp Lys Val Val Glu Asp Asp Glu Asp Asp Phe Pro Thr Thr<br>               275                    280                 285 | 864 |
| cgt tct gat ggt gac ttc ttg cat agt acc aac ggc aat aaa gaa aag<br>Arg Ser Asp Gly Asp Phe Leu His Ser Thr Asn Gly Asn Lys Glu Lys<br>290                      295                   300 | 912 |
| tta ttt cca cat gtg aca cca aaa gga att aat ggt ata gac ttt aaa<br>Leu Phe Pro His Val Thr Pro Lys Gly Ile Asn Gly Ile Asp Phe Lys<br>305                     310                   315                 320 | 960 |
| ggg gaa gcg ata act ttt aaa gca act act gct gga atc ctt gca aca<br>Gly Glu Ala Ile Thr Phe Lys Ala Thr Thr Ala Gly Ile Leu Ala Thr<br>               325                    330                 335 | 1008 |

-continued

| | | |
|---|---|---|
| ctt tct cat tgt att gaa cta atg gtt aaa cgt gag gac agc tgg cag<br>Leu Ser His Cys Ile Glu Leu Met Val Lys Arg Glu Asp Ser Trp Gln<br>340                            345                      350 | 1056 | |
| aag aga ctg gat aag gaa act gag aag aaa aga aga aca gag gaa gca<br>Lys Arg Leu Asp Lys Glu Thr Glu Lys Lys Arg Arg Thr Glu Glu Ala<br>        355                          360                      365 | 1104 | |
| tat aaa aat gca atg aca gaa ctt aag aaa aaa tcc cac ttt gga gga<br>Tyr Lys Asn Ala Met Thr Glu Leu Lys Lys Lys Ser His Phe Gly Gly<br>370                          375                      380 | 1152 | |
| cca gat tat gaa gaa ggc cct aac agt ctg att aat gaa gaa gag ttc<br>Pro Asp Tyr Glu Glu Gly Pro Asn Ser Leu Ile Asn Glu Glu Glu Phe<br>385                          390                      395                    400 | 1200 | |
| ttt gat gct gtt gaa gct gct ctt gac aga caa gat aaa ata gaa gaa<br>Phe Asp Ala Val Glu Ala Ala Leu Asp Arg Gln Asp Lys Ile Glu Glu<br>                          405                      410                    415 | 1248 | |
| cag tca cag agt gaa aag gtg aga tta cat tgg cct aca tcc ttg ccc<br>Gln Ser Gln Ser Glu Lys Val Arg Leu His Trp Pro Thr Ser Leu Pro<br>        420                          425                      430 | 1296 | |
| tct gga gat gcc ttt tct tct gtg ggg aca cat aga ttt gtc caa aag<br>Ser Gly Asp Ala Phe Ser Ser Val Gly Thr His Arg Phe Val Gln Lys<br>435                          440                      445 | 1344 | |
| gtt gaa gag atg gtg cag aac cac atg act tac tca tta cag gat gta<br>Val Glu Glu Met Val Gln Asn His Met Thr Tyr Ser Leu Gln Asp Val<br>450                          455                      460 | 1392 | |
| ggc gga gat gcc aat tgg cag ttg gtt gta gaa gaa gga gaa atg aag<br>Gly Gly Asp Ala Asn Trp Gln Leu Val Val Glu Glu Gly Glu Met Lys<br>465                          470                      475                    480 | 1440 | |
| gta tac aga aga gaa gta gaa gaa aat ggg att gtt ctg gat cct tta<br>Val Tyr Arg Arg Glu Val Glu Glu Asn Gly Ile Val Leu Asp Pro Leu<br>                          485                      490                    495 | 1488 | |
| aaa gct acc cat gca gtt aaa ggc gtc aca gga cat gaa gtc tgc aat<br>Lys Ala Thr His Ala Val Lys Gly Val Thr Gly His Glu Val Cys Asn<br>        500                          505                      510 | 1536 | |
| tat ttc tgg aat gtt gac gtt cgc aat gac tgg gaa aca act ata gaa<br>Tyr Phe Trp Asn Val Asp Val Arg Asn Asp Trp Glu Thr Thr Ile Glu<br>515                          520                      525 | 1584 | |
| aac ttt cat gtg gtg gaa aca tta gct gat aat gca atc atc att tat<br>Asn Phe His Val Val Glu Thr Leu Ala Asp Asn Ala Ile Ile Ile Tyr<br>530                          535                      540 | 1632 | |
| caa aca cac aag agg gtg tgg cct gct tct cag cga gac gta tta tat<br>Gln Thr His Lys Arg Val Trp Pro Ala Ser Gln Arg Asp Val Leu Tyr<br>545                          550                      555                    560 | 1680 | |
| ctt tct gtc att cga aag ata cca gcc ttg act gaa aat gac cct gaa<br>Leu Ser Val Ile Arg Lys Ile Pro Ala Leu Thr Glu Asn Asp Pro Glu<br>                          565                      570                    575 | 1728 | |
| act tgg ata gtt tgt aat ttt tct gtg gat cat gac agt gct cct cta<br>Thr Trp Ile Val Cys Asn Phe Ser Val Asp His Asp Ser Ala Pro Leu<br>                      580                      585                    590 | 1776 | |
| aac aac cga tgt gtc cgt gcc aaa ata aat gtt gct atg att tgt caa<br>Asn Asn Arg Cys Val Arg Ala Lys Ile Asn Val Ala Met Ile Cys Gln<br>                595                      600                    605 | 1824 | |
| acc ttg gta agc cca cca gag gga aac cag gaa att agc agg gac aac<br>Thr Leu Val Ser Pro Pro Glu Gly Asn Gln Glu Ile Ser Arg Asp Asn<br>610                          615                      620 | 1872 | |
| att cta tgc aag att aca tat gta gct aat gtg aac cct gga gga tgg<br>Ile Leu Cys Lys Ile Thr Tyr Val Ala Asn Val Asn Pro Gly Gly Trp<br>625                          630                      635                    640 | 1920 | |
| gca cca gcc tca gtg tta agg gca gtg gca aag cga gag tat cct aaa<br>Ala Pro Ala Ser Val Leu Arg Ala Val Ala Lys Arg Glu Tyr Pro Lys | 1968 | |

```
                     645                 650                 655
ttt cta aaa cgt ttt act tct tac gtc caa gaa aaa act gca gga aag    2016
Phe Leu Lys Arg Phe Thr Ser Tyr Val Gln Glu Lys Thr Ala Gly Lys
            660                 665                 670 cct att ttg ttc tag                                                2031
Pro Ile Leu Phe
        675

<210> SEQ ID NO 24
<211> LENGTH: 676
<212> TYPE: PRT
<213> ORGANISM: artificial
<220> FEATURE:
<223> OTHER INFORMATION: Derived sequence

<400> SEQUENCE: 24

Asp Gly Trp Lys Gly Arg Leu Pro Ser Pro Leu Val Leu Leu Pro Arg
1               5                   10                  15

Ser Ala Arg Cys Gln Ala Arg Arg Arg Gly Gly Arg Thr Ser Ser
            20                  25                  30

Leu Leu Leu Leu Pro Pro Thr Pro Glu Arg Ala Leu Phe Ala Ser Pro
        35                  40                  45

Ser Pro Asp Pro Ser Pro Arg Gly Leu Gly Ala Ser Gly Ala Ala
    50                  55                  60

Glu Gly Ala Gly Ala Gly Leu Leu Leu Gly Cys Arg Ala Ser Met Ser
65                  70                  75                  80

Asp Asn Gln Ser Trp Asn Ser Gly Ser Glu Glu Asp Pro Glu Thr
                85                  90                  95

Glu Ser Gly Pro Pro Val Glu Arg Cys Gly Val Leu Ser Lys Trp Thr
            100                 105                 110

Asn Tyr Ile His Gly Trp Gln Asp Arg Trp Val Val Leu Lys Asn Asn
        115                 120                 125

Ala Leu Ser Tyr Tyr Lys Ser Glu Asp Glu Thr Glu Tyr Gly Cys Arg
    130                 135                 140

Gly Ser Ile Cys Leu Ser Lys Ala Val Ile Thr Pro His Asp Phe Asp
145                 150                 155                 160

Glu Cys Arg Phe Asp Ile Ser Val Asn Asp Ser Val Trp Tyr Leu Arg
                165                 170                 175

Ala Gln Asp Pro Asp His Arg Gln Gln Trp Ile Asp Ala Ile Glu Gln
            180                 185                 190

His Lys Thr Glu Ser Gly Tyr Gly Ser Glu Ser Ser Leu Arg Arg His
        195                 200                 205

Gly Ser Met Val Ser Leu Val Ser Gly Ala Ser Gly Tyr Ser Ala Thr
    210                 215                 220

Ser Thr Ser Ser Phe Lys Lys Gly His Ser Leu Arg Glu Lys Leu Ala
225                 230                 235                 240

Glu Met Glu Thr Phe Arg Asp Ile Leu Cys Arg Gln Val Asp Thr Leu
                245                 250                 255

Gln Lys Tyr Phe Asp Ala Cys Ala Asp Ala Val Ser Lys Asp Glu Leu
            260                 265                 270

Gln Arg Asp Lys Val Val Glu Asp Asp Glu Asp Phe Pro Thr Thr
        275                 280                 285

Arg Ser Asp Gly Asp Phe Leu His Ser Thr Asn Gly Asn Lys Glu Lys
    290                 295                 300

Leu Phe Pro His Val Thr Pro Lys Gly Ile Asn Gly Ile Asp Phe Lys
305                 310                 315                 320
```

```
Gly Glu Ala Ile Thr Phe Lys Ala Thr Thr Ala Gly Ile Leu Ala Thr
                325                 330                 335
Leu Ser His Cys Ile Glu Leu Met Val Lys Arg Glu Asp Ser Trp Gln
            340                 345                 350
Lys Arg Leu Asp Lys Glu Thr Glu Lys Lys Arg Arg Thr Glu Glu Ala
        355                 360                 365
Tyr Lys Asn Ala Met Thr Glu Leu Lys Lys Lys Ser His Phe Gly Gly
370                 375                 380
Pro Asp Tyr Glu Glu Gly Pro Asn Ser Leu Ile Asn Glu Glu Glu Phe
385                 390                 395                 400
Phe Asp Ala Val Glu Ala Ala Leu Asp Arg Gln Asp Lys Ile Glu Glu
                405                 410                 415
Gln Ser Gln Ser Glu Lys Val Arg Leu His Trp Pro Thr Ser Leu Pro
            420                 425                 430
Ser Gly Asp Ala Phe Ser Ser Val Gly Thr His Arg Phe Val Gln Lys
        435                 440                 445
Val Glu Glu Met Val Gln Asn His Met Thr Tyr Ser Leu Gln Asp Val
450                 455                 460
Gly Gly Asp Ala Asn Trp Gln Leu Val Val Glu Gly Glu Met Lys
465                 470                 475                 480
Val Tyr Arg Arg Glu Val Glu Glu Asn Gly Ile Val Leu Asp Pro Leu
                485                 490                 495
Lys Ala Thr His Ala Val Lys Gly Val Thr Gly His Glu Val Cys Asn
            500                 505                 510
Tyr Phe Trp Asn Val Asp Val Arg Asn Asp Trp Glu Thr Thr Ile Glu
        515                 520                 525
Asn Phe His Val Val Glu Thr Leu Ala Asp Asn Ala Ile Ile Ile Tyr
530                 535                 540
Gln Thr His Lys Arg Val Trp Pro Ala Ser Gln Arg Asp Val Leu Tyr
545                 550                 555                 560
Leu Ser Val Ile Arg Lys Ile Pro Ala Leu Thr Glu Asn Asp Pro Glu
                565                 570                 575
Thr Trp Ile Val Cys Asn Phe Ser Val Asp His Asp Ser Ala Pro Leu
            580                 585                 590
Asn Asn Arg Cys Val Arg Ala Lys Ile Asn Val Ala Met Ile Cys Gln
        595                 600                 605
Thr Leu Val Ser Pro Pro Glu Gly Asn Gln Glu Ile Ser Arg Asp Asn
610                 615                 620
Ile Leu Cys Lys Ile Thr Tyr Val Ala Asn Val Asn Pro Gly Gly Trp
625                 630                 635                 640
Ala Pro Ala Ser Val Leu Arg Ala Val Ala Lys Arg Glu Tyr Pro Lys
                645                 650                 655
Phe Leu Lys Arg Phe Thr Ser Tyr Val Gln Glu Lys Thr Ala Gly Lys
            660                 665                 670
Pro Ile Leu Phe
        675

<210> SEQ ID NO 25
<211> LENGTH: 2181
<212> TYPE: DNA
<213> ORGANISM: artificial
<220> FEATURE:
<223> OTHER INFORMATION: Derived sequence
<220> FEATURE:
<221> NAME/KEY: CDS
```

```
<222> LOCATION: (1)..(2181)
<223> OTHER INFORMATION:

<400> SEQUENCE: 25 gca tcg agg ggg cta agt tcg ggt ggc agc gcc ggg cgc aac gca ggg      48
Ala Ser Arg Gly Leu Ser Ser Gly Gly Ser Ala Gly Arg Asn Ala Gly
1               5                   10                  15 gtc acg gcg acg gcg gcg gcg gct gac ggc tgg aag ggt agg ctt cct      96
Val Thr Ala Thr Ala Ala Ala Ala Asp Gly Trp Lys Gly Arg Leu Pro
                20                  25                  30 tca ccg ctc gtc ctc ctt cct cgc tcc gct cgg tgt cag gcg cgg cgg     144
Ser Pro Leu Val Leu Leu Pro Arg Ser Ala Arg Cys Gln Ala Arg Arg
            35                  40                  45 cgg cgc ggc ggg cgg act tcg tcc ctc ctc ctg ctc ccc ccc aca ccg     192
Arg Arg Gly Gly Arg Thr Ser Ser Leu Leu Leu Leu Pro Pro Thr Pro
        50                  55                  60 gag cgg gca ctc ttc gct tcg cca tcc ccc gac cct tca ccc cga gga     240
Glu Arg Ala Leu Phe Ala Ser Pro Ser Pro Asp Pro Ser Pro Arg Gly
65                  70                  75                  80 ctg ggc gcc tcc tcc ggc gca gct gag gga gcg ggg gcc ggt ctc ctg     288
Leu Gly Ala Ser Ser Gly Ala Ala Glu Gly Ala Gly Ala Gly Leu Leu
                85                  90                  95 ctc ggt tgt cga gcc tcc atg tcg gat aat cag agc tgg aac tcg tcg     336
Leu Gly Cys Arg Ala Ser Met Ser Asp Asn Gln Ser Trp Asn Ser Ser
                100                 105                 110 ggc tcg gag gag gat cca gag acg gag tct ggg ccg cct gtg gag cgc     384
Gly Ser Glu Glu Asp Pro Glu Thr Glu Ser Gly Pro Pro Val Glu Arg
            115                 120                 125 tgc ggg gtc ctc agt aag tgg aca aac tac att cat ggg tgg cag gat     432
Cys Gly Val Leu Ser Lys Trp Thr Asn Tyr Ile His Gly Trp Gln Asp
        130                 135                 140 cgt tgg gta gtt ttg aaa aat aat gct ctg agt tac tac aaa tct gaa     480
Arg Trp Val Val Leu Lys Asn Asn Ala Leu Ser Tyr Tyr Lys Ser Glu
145                 150                 155                 160 gat gaa aca gag tat ggc tgc aga gga tcc atc tgt ctt agc aag gct     528
Asp Glu Thr Glu Tyr Gly Cys Arg Gly Ser Ile Cys Leu Ser Lys Ala
                165                 170                 175 gtc atc aca cct cac gat ttt gat gaa tgt cga ttt gat att agt gta     576
Val Ile Thr Pro His Asp Phe Asp Glu Cys Arg Phe Asp Ile Ser Val
                180                 185                 190 aat gat agt gtt tgg tat ctt cgt gct cag gat cca gat cat aga cag     624
Asn Asp Ser Val Trp Tyr Leu Arg Ala Gln Asp Pro Asp His Arg Gln
            195                 200                 205 caa tgg ata gat gcc att gaa cag cac aag act gaa tct gga tat gga     672
Gln Trp Ile Asp Ala Ile Glu Gln His Lys Thr Glu Ser Gly Tyr Gly
        210                 215                 220 tct gaa tcc agc ttg cgt cga cat ggc tca atg gtg tcc ctg gtg tct     720
Ser Glu Ser Ser Leu Arg Arg His Gly Ser Met Val Ser Leu Val Ser
225                 230                 235                 240 gga gca agt ggc tac tct gca aca tcc acc tct tca ttc aag aaa ggc     768
Gly Ala Ser Gly Tyr Ser Ala Thr Ser Thr Ser Ser Phe Lys Lys Gly
                245                 250                 255 cac agt tta cgt gag aag ttg gct gaa atg gaa aca ttt aga gac atc     816
His Ser Leu Arg Glu Lys Leu Ala Glu Met Glu Thr Phe Arg Asp Ile
                260                 265                 270 tta tgt aga caa gtt gac acg cta cag aag tac ttt gat gcc tgt gct     864
Leu Cys Arg Gln Val Asp Thr Leu Gln Lys Tyr Phe Asp Ala Cys Ala
            275                 280                 285 gat gct gtc tct aag gat gaa ctt caa agg gat aaa gtg gta gaa gat     912
Asp Ala Val Ser Lys Asp Glu Leu Gln Arg Asp Lys Val Val Glu Asp
```

```
              290                 295                 300
gat gaa gat gac ttt cct aca acg cgt tct gat ggt gac ttc ttg cat    960
Asp Glu Asp Asp Phe Pro Thr Thr Arg Ser Asp Gly Asp Phe Leu His
305                 310                 315                 320 agt acc aac ggc aat aaa gaa aag tta ttt cca cat gtg aca cca aaa   1008
Ser Thr Asn Gly Asn Lys Glu Lys Leu Phe Pro His Val Thr Pro Lys
                325                 330                 335 gga att aat ggt ata gac ttt aaa ggg gaa gcg ata act ttt aaa gca   1056
Gly Ile Asn Gly Ile Asp Phe Lys Gly Glu Ala Ile Thr Phe Lys Ala
        340                 345                 350 act act gct gga atc ctt gca aca ctt tct cat tgt att gaa cta atg   1104
Thr Thr Ala Gly Ile Leu Ala Thr Leu Ser His Cys Ile Glu Leu Met
            355                 360                 365 gtt aaa cgt gag gac agc tgg cag aag aga ctg gat aag gaa act gag   1152
Val Lys Arg Glu Asp Ser Trp Gln Lys Arg Leu Asp Lys Glu Thr Glu
370                 375                 380 aag aaa aga aga aca gag gaa gca tat aaa aat gca atg aca gaa ctt   1200
Lys Lys Arg Arg Thr Glu Glu Ala Tyr Lys Asn Ala Met Thr Glu Leu
385                 390                 395                 400 aag aaa aaa tcc cac ttt gga gga cca gat tat gaa gaa ggc cct aac   1248
Lys Lys Lys Ser His Phe Gly Gly Pro Asp Tyr Glu Glu Gly Pro Asn
                405                 410                 415 agt ctg att aat gaa gaa gag ttc ttt gat gct gtt gaa gct gct ctt   1296
Ser Leu Ile Asn Glu Glu Glu Phe Phe Asp Ala Val Glu Ala Ala Leu
        420                 425                 430 gac aga caa gat aaa ata gaa gaa cag tca cag agt gaa aag gtg aga   1344
Asp Arg Gln Asp Lys Ile Glu Glu Gln Ser Gln Ser Glu Lys Val Arg
            435                 440                 445 tta cat tgg cct aca tcc ttg ccc tct gga gat gcc ttt tct tct gtg   1392
Leu His Trp Pro Thr Ser Leu Pro Ser Gly Asp Ala Phe Ser Ser Val
450                 455                 460 ggg aca cat aga ttt gtc caa aag ccc tat agt cgc tct tcc tcc atg   1440
Gly Thr His Arg Phe Val Gln Lys Pro Tyr Ser Arg Ser Ser Ser Met
465                 470                 475                 480 tct tcc att gat cta gtc agt gcc tct gat gat gtt cac aga ttc agc   1488
Ser Ser Ile Asp Leu Val Ser Ala Ser Asp Asp Val His Arg Phe Ser
                485                 490                 495 tcc cag gtt gaa gag atg gtg cag aac cac atg act tac tca tta cag   1536
Ser Gln Val Glu Glu Met Val Gln Asn His Met Thr Tyr Ser Leu Gln
        500                 505                 510 gat gta ggc gga gat gcc aat tgg cag ttg gtt gta gaa gaa gga gaa   1584
Asp Val Gly Gly Asp Ala Asn Trp Gln Leu Val Val Glu Glu Gly Glu
            515                 520                 525 atg aag gta tac aga aga gaa gta gaa gaa aat ggg att gtt ctg gat   1632
Met Lys Val Tyr Arg Arg Glu Val Glu Glu Asn Gly Ile Val Leu Asp
530                 535                 540 cct tta aaa gct acc cat gca gtt aaa ggc gtc aca gga cat gaa gtc   1680
Pro Leu Lys Ala Thr His Ala Val Lys Gly Val Thr Gly His Glu Val
545                 550                 555                 560 tgc aat tat ttc tgg aat gtt gac gtt cgc aat gac tgg gaa aca act   1728
Cys Asn Tyr Phe Trp Asn Val Asp Val Arg Asn Asp Trp Glu Thr Thr
                565                 570                 575 ata gaa aac ttt cat gtg gtg gaa aca tta gct gat aat gca atc atc   1776
Ile Glu Asn Phe His Val Val Glu Thr Leu Ala Asp Asn Ala Ile Ile
        580                 585                 590 att tat caa aca cac aag agg gtg tgg cct gct tct cag cga gac gta   1824
Ile Tyr Gln Thr His Lys Arg Val Trp Pro Ala Ser Gln Arg Asp Val
            595                 600                 605 tta tat ctt tct gtc att cga aag ata cca gcc ttg act gaa aat gac   1872
```

```
Leu Tyr Leu Ser Val Ile Arg Lys Ile Pro Ala Leu Thr Glu Asn Asp
    610                 615                 620 cct gaa act tgg ata gtt tgt aat ttt tct gtg gat cat gac agt gct      1920
Pro Glu Thr Trp Ile Val Cys Asn Phe Ser Val Asp His Asp Ser Ala
625                 630                 635                 640 cct cta aac aac cga tgt gtc cgt gcc aaa ata aat gtt gct atg att      1968
Pro Leu Asn Asn Arg Cys Val Arg Ala Lys Ile Asn Val Ala Met Ile
                645                 650                 655 tgt caa acc ttg gta agc cca cca gag gga aac cag gaa att agc agg      2016
Cys Gln Thr Leu Val Ser Pro Pro Glu Gly Asn Gln Glu Ile Ser Arg
    660                 665                 670 gac aac att cta tgc aag att aca tat gta gct aat gtg aac cct gga      2064
Asp Asn Ile Leu Cys Lys Ile Thr Tyr Val Ala Asn Val Asn Pro Gly
        675                 680                 685 gga tgg gca cca gcc tca gtg tta agg gca gtg gca aag cga gag tat      2112
Gly Trp Ala Pro Ala Ser Val Leu Arg Ala Val Ala Lys Arg Glu Tyr
690                 695                 700 cct aaa ttt cta aaa cgt ttt act tct tac gtc caa gaa aaa act gca      2160
Pro Lys Phe Leu Lys Arg Phe Thr Ser Tyr Val Gln Glu Lys Thr Ala
705                 710                 715                 720 gga aag cct att ttg ttc tag                                           2181
Gly Lys Pro Ile Leu Phe
                725

<210> SEQ ID NO 26
<211> LENGTH: 726
<212> TYPE: PRT
<213> ORGANISM: artificial
<220> FEATURE:
<223> OTHER INFORMATION: Derived sequence

<400> SEQUENCE: 26

Ala Ser Arg Gly Leu Ser Ser Gly Ser Ala Gly Arg Asn Ala Gly
1               5                   10                  15

Val Thr Ala Thr Ala Ala Ala Asp Gly Trp Lys Gly Arg Leu Pro
                20                  25                  30

Ser Pro Leu Val Leu Pro Arg Ser Ala Arg Cys Gln Ala Arg Arg
            35                  40                  45

Arg Arg Gly Gly Arg Thr Ser Ser Leu Leu Leu Pro Pro Thr Pro
    50                  55                  60

Glu Arg Ala Leu Phe Ala Ser Pro Ser Pro Asp Pro Ser Pro Arg Gly
65                  70                  75                  80

Leu Gly Ala Ser Ser Gly Ala Ala Glu Gly Ala Gly Ala Gly Leu Leu
                85                  90                  95

Leu Gly Cys Arg Ala Ser Met Ser Asp Asn Gln Ser Trp Asn Ser Ser
                100                 105                 110

Gly Ser Glu Glu Asp Pro Glu Thr Glu Ser Gly Pro Pro Val Glu Arg
            115                 120                 125

Cys Gly Val Leu Ser Lys Trp Thr Asn Tyr Ile His Gly Trp Gln Asp
        130                 135                 140

Arg Trp Val Val Leu Lys Asn Asn Ala Leu Ser Tyr Tyr Lys Ser Glu
145                 150                 155                 160

Asp Glu Thr Glu Tyr Gly Cys Arg Gly Ser Ile Cys Leu Ser Lys Ala
                165                 170                 175

Val Ile Thr Pro His Asp Phe Asp Glu Cys Arg Phe Asp Ile Ser Val
                180                 185                 190

Asn Asp Ser Val Trp Tyr Leu Arg Ala Gln Asp Pro Asp His Arg Gln
            195                 200                 205
```

```
Gln Trp Ile Asp Ala Ile Glu Gln His Lys Thr Glu Ser Gly Tyr Gly
    210                 215                 220

Ser Glu Ser Ser Leu Arg Arg His Gly Ser Met Val Ser Leu Val Ser
225                 230                 235                 240

Gly Ala Ser Gly Tyr Ser Ala Thr Ser Thr Ser Ser Phe Lys Lys Gly
                245                 250                 255

His Ser Leu Arg Glu Lys Leu Ala Glu Met Glu Thr Phe Arg Asp Ile
            260                 265                 270

Leu Cys Arg Gln Val Asp Thr Leu Gln Lys Tyr Phe Asp Ala Cys Ala
        275                 280                 285

Asp Ala Val Ser Lys Asp Glu Leu Gln Arg Asp Lys Val Val Glu Asp
    290                 295                 300

Asp Glu Asp Asp Phe Pro Thr Thr Arg Ser Asp Gly Asp Phe Leu His
305                 310                 315                 320

Ser Thr Asn Gly Asn Lys Glu Lys Leu Phe Pro His Val Thr Pro Lys
                325                 330                 335

Gly Ile Asn Gly Ile Asp Phe Lys Gly Glu Ala Ile Thr Phe Lys Ala
            340                 345                 350

Thr Thr Ala Gly Ile Leu Ala Thr Leu Ser His Cys Ile Glu Leu Met
        355                 360                 365

Val Lys Arg Glu Asp Ser Trp Gln Lys Arg Leu Asp Lys Glu Thr Glu
    370                 375                 380

Lys Lys Arg Arg Thr Glu Glu Ala Tyr Lys Asn Ala Met Thr Glu Leu
385                 390                 395                 400

Lys Lys Lys Ser His Phe Gly Gly Pro Asp Tyr Glu Glu Gly Pro Asn
                405                 410                 415

Ser Leu Ile Asn Glu Glu Glu Phe Phe Asp Ala Val Glu Ala Ala Leu
            420                 425                 430

Asp Arg Gln Asp Lys Ile Glu Glu Gln Ser Gln Ser Glu Lys Val Arg
        435                 440                 445

Leu His Trp Pro Thr Ser Leu Pro Ser Gly Asp Ala Phe Ser Ser Val
    450                 455                 460

Gly Thr His Arg Phe Val Gln Lys Pro Tyr Ser Arg Ser Ser Ser Met
465                 470                 475                 480

Ser Ser Ile Asp Leu Val Ser Ala Ser Asp Asp Val His Arg Phe Ser
                485                 490                 495

Ser Gln Val Glu Glu Met Val Gln Asn His Met Thr Tyr Ser Leu Gln
            500                 505                 510

Asp Val Gly Gly Asp Ala Asn Trp Gln Leu Val Val Glu Glu Gly Glu
        515                 520                 525

Met Lys Val Tyr Arg Arg Glu Val Glu Glu Asn Gly Ile Val Leu Asp
    530                 535                 540

Pro Leu Lys Ala Thr His Ala Val Lys Gly Val Thr Gly His Glu Val
545                 550                 555                 560

Cys Asn Tyr Phe Trp Asn Val Asp Val Arg Asn Asp Trp Glu Thr Thr
                565                 570                 575

Ile Glu Asn Phe His Val Val Glu Thr Leu Ala Asp Asn Ala Ile Ile
            580                 585                 590

Ile Tyr Gln Thr His Lys Arg Val Trp Pro Ala Ser Gln Arg Asp Val
        595                 600                 605

Leu Tyr Leu Ser Val Ile Arg Lys Ile Pro Ala Leu Thr Glu Asn Asp
    610                 615                 620
```

-continued

| | | | | | | | | | | | |
|---|---|---|---|---|---|---|---|---|---|---|---|
| Pro | Glu | Thr | Trp | Ile | Val | Cys | Asn | Phe | Ser | Val | Asp | His | Asp | Ser | Ala |
| 625 | | | | 630 | | | | 635 | | | | 640 | | | |

Pro Leu Asn Asn Arg Cys Val Arg Ala Lys Ile Asn Val Ala Met Ile
                   645                    650                  655

Cys Gln Thr Leu Val Ser Pro Pro Glu Gly Asn Gln Glu Ile Ser Arg
        660                    665                    670

Asp Asn Ile Leu Cys Lys Ile Thr Tyr Val Ala Asn Val Asn Pro Gly
           675                  680                    685

Gly Trp Ala Pro Ala Ser Val Leu Arg Ala Val Ala Lys Arg Glu Tyr
     690                    695                700

Pro Lys Phe Leu Lys Arg Phe Thr Ser Tyr Val Gln Glu Lys Thr Ala
705                710                   715                 720

Gly Lys Pro Ile Leu Phe
           725

<210> SEQ ID NO 27
<211> LENGTH: 2103
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(2103)
<223> OTHER INFORMATION:

<400> SEQUENCE: 27

```
gca tcg agg ggg cta agt tcg ggt ggc agc gcc ggg cgc aac gca ggg       48
Ala Ser Arg Gly Leu Ser Ser Gly Gly Ser Ala Gly Arg Asn Ala Gly
1               5                   10                  15 gtc acg gcg acg gcg gcg gcg gct gac ggc tgg aag ggt agg ctt cct       96
Val Thr Ala Thr Ala Ala Ala Ala Asp Gly Trp Lys Gly Arg Leu Pro
                20                  25                  30 tca ccg ctc gtc ctc ctt cct cgc tcc gct cgg tgt cag gcg cgg cgg      144
Ser Pro Leu Val Leu Leu Pro Arg Ser Ala Arg Cys Gln Ala Arg Arg
            35                  40                  45 cgg cgc ggc ggg cgg act tcg tcc ctc ctc ctg ctc ccc ccc aca ccg      192
Arg Arg Gly Gly Arg Thr Ser Ser Leu Leu Leu Leu Pro Pro Thr Pro
        50                  55                  60 gag cgg gca ctc ttc gct tcg cca tcc ccc gac cct tca ccc cga gga      240
Glu Arg Ala Leu Phe Ala Ser Pro Ser Pro Asp Pro Ser Pro Arg Gly
65                  70                  75                  80 ctg ggc gcc tcc tcc ggc gca gct gag gga gcg ggg gcc ggt ctc ctg      288
Leu Gly Ala Ser Ser Gly Ala Ala Glu Gly Ala Gly Ala Gly Leu Leu
                85                  90                  95 ctc ggt tgt cga gcc tcc atg tcg gat aat cag agc tgg aac tcg tcg      336
Leu Gly Cys Arg Ala Ser Met Ser Asp Asn Gln Ser Trp Asn Ser Ser
            100                 105                 110 ggc tcg gag gag gat cca gag acg gag tct ggg ccg cct gtg gag cgc      384
Gly Ser Glu Glu Asp Pro Glu Thr Glu Ser Gly Pro Pro Val Glu Arg
        115                 120                 125 tgc ggg gtc ctc agt aag tgg aca aac tac att cat ggg tgg cag gat      432
Cys Gly Val Leu Ser Lys Trp Thr Asn Tyr Ile His Gly Trp Gln Asp
    130                 135                 140 cgt tgg gta gtt ttg aaa aat aat gct ctg agt tac tac aaa tct gaa      480
Arg Trp Val Val Leu Lys Asn Asn Ala Leu Ser Tyr Tyr Lys Ser Glu
145                 150                 155                 160 gat gaa aca gag tat ggc tgc aga gga tcc atc tgt ctt agc aag gct      528
Asp Glu Thr Glu Tyr Gly Cys Arg Gly Ser Ile Cys Leu Ser Lys Ala
                165                 170                 175
```

-continued

```
gtc atc aca cct cac gat ttt gat gaa tgt cga ttt gat att agt gta    576
Val Ile Thr Pro His Asp Phe Asp Glu Cys Arg Phe Asp Ile Ser Val
            180                 185                 190 aat gat agt gtt tgg tat ctt cgt gct cag gat cca gat cat aga cag    624
Asn Asp Ser Val Trp Tyr Leu Arg Ala Gln Asp Pro Asp His Arg Gln
            195                 200                 205 caa tgg ata gat gcc att gaa cag cac aag act gaa tct gga tat gga    672
Gln Trp Ile Asp Ala Ile Glu Gln His Lys Thr Glu Ser Gly Tyr Gly
            210                 215                 220 tct gaa tcc agc ttg cgt cga cat ggc tca atg gtg tcc ctg gtg tct    720
Ser Glu Ser Ser Leu Arg Arg His Gly Ser Met Val Ser Leu Val Ser
225                 230                 235                 240 gga gca agt ggc tac tct gca aca tcc acc tct tca ttc aag aaa ggc    768
Gly Ala Ser Gly Tyr Ser Ala Thr Ser Thr Ser Ser Phe Lys Lys Gly
                245                 250                 255 cac agt tta cgt gag aag ttg gct gaa atg gaa aca ttt aga gac atc    816
His Ser Leu Arg Glu Lys Leu Ala Glu Met Glu Thr Phe Arg Asp Ile
            260                 265                 270 tta tgt aga caa gtt gac acg cta cag aag tac ttt gat gcc tgt gct    864
Leu Cys Arg Gln Val Asp Thr Leu Gln Lys Tyr Phe Asp Ala Cys Ala
            275                 280                 285 gat gct gtc tct aag gat gaa ctt caa agg gat aaa gtg gta gaa gat    912
Asp Ala Val Ser Lys Asp Glu Leu Gln Arg Asp Lys Val Val Glu Asp
            290                 295                 300 gat gaa gat gac ttt cct aca acg cgt tct gat ggt gac ttc ttg cat    960
Asp Glu Asp Asp Phe Pro Thr Thr Arg Ser Asp Gly Asp Phe Leu His
305                 310                 315                 320 agt acc aac ggc aat aaa gaa aag tta ttt cca cat gtg aca cca aaa    1008
Ser Thr Asn Gly Asn Lys Glu Lys Leu Phe Pro His Val Thr Pro Lys
                325                 330                 335 gga att aat ggt ata gac ttt aaa ggg gaa gcg ata act ttt aaa gca    1056
Gly Ile Asn Gly Ile Asp Phe Lys Gly Glu Ala Ile Thr Phe Lys Ala
            340                 345                 350 act act gct gga atc ctt gca aca ctt tct cat tgt att gaa cta atg    1104
Thr Thr Ala Gly Ile Leu Ala Thr Leu Ser His Cys Ile Glu Leu Met
            355                 360                 365 gtt aaa cgt gag gac agc tgg cag aag aga ctg gat aag gaa act gag    1152
Val Lys Arg Glu Asp Ser Trp Gln Lys Arg Leu Asp Lys Glu Thr Glu
            370                 375                 380 aag aaa aga aga aca gag gaa gca tat aaa aat gca atg aca gaa ctt    1200
Lys Lys Arg Arg Thr Glu Glu Ala Tyr Lys Asn Ala Met Thr Glu Leu
385                 390                 395                 400 aag aaa aaa tcc cac ttt gga gga cca gat tat gaa gaa ggc cct aac    1248
Lys Lys Lys Ser His Phe Gly Gly Pro Asp Tyr Glu Glu Gly Pro Asn
                405                 410                 415 agt ctg att aat gaa gaa gag ttc ttt gat gct gtt gaa gct gct ctt    1296
Ser Leu Ile Asn Glu Glu Glu Phe Phe Asp Ala Val Glu Ala Ala Leu
            420                 425                 430 gac aga caa gat aaa ata gaa gaa cag tca cag agt gaa aag gtg aga    1344
Asp Arg Gln Asp Lys Ile Glu Glu Gln Ser Gln Ser Glu Lys Val Arg
            435                 440                 445 tta cat tgg cct aca tcc ttg ccc tct gga gat gcc ttt tct tct gtg    1392
Leu His Trp Pro Thr Ser Leu Pro Ser Gly Asp Ala Phe Ser Ser Val
            450                 455                 460 ggg aca cat aga ttt gtc caa aag gtt gaa gag atg gtg cag aac cac    1440
Gly Thr His Arg Phe Val Gln Lys Val Glu Glu Met Val Gln Asn His
465                 470                 475                 480 atg act tac tca tta cag gat gta ggc gga gat gcc aat tgg cag ttg    1488
Met Thr Tyr Ser Leu Gln Asp Val Gly Gly Asp Ala Asn Trp Gln Leu
                485                 490                 495
```

```
gtt gta gaa gaa gga gaa atg aag gta tac aga aga gaa gta gaa gaa    1536
Val Val Glu Glu Gly Glu Met Lys Val Tyr Arg Arg Glu Val Glu Glu
            500                 505                 510 aat ggg att gtt ctg gat cct tta aaa gct acc cat gca gtt aaa ggc    1584
Asn Gly Ile Val Leu Asp Pro Leu Lys Ala Thr His Ala Val Lys Gly
            515                 520                 525 gtc aca gga cat gaa gtc tgc aat tat ttc tgg aat gtt gac gtt cgc    1632
Val Thr Gly His Glu Val Cys Asn Tyr Phe Trp Asn Val Asp Val Arg
        530                 535                 540 aat gac tgg gaa aca act ata gaa aac ttt cat gtg gtg gaa aca tta    1680
Asn Asp Trp Glu Thr Thr Ile Glu Asn Phe His Val Val Glu Thr Leu
545                 550                 555                 560 gct gat aat gca atc atc att tat caa aca cac aag agg gtg tgg cct    1728
Ala Asp Asn Ala Ile Ile Ile Tyr Gln Thr His Lys Arg Val Trp Pro
                565                 570                 575 gct tct cag cga gac gta tta tat ctt tct gtc att cga aag ata cca    1776
Ala Ser Gln Arg Asp Val Leu Tyr Leu Ser Val Ile Arg Lys Ile Pro
            580                 585                 590 gcc ttg act gaa aat gac cct gaa act tgg ata gtt tgt aat ttt tct    1824
Ala Leu Thr Glu Asn Asp Pro Glu Thr Trp Ile Val Cys Asn Phe Ser
        595                 600                 605 gtg gat cat gac agt gct cct cta aac aac cga tgt gtc cgt gcc aaa    1872
Val Asp His Asp Ser Ala Pro Leu Asn Asn Arg Cys Val Arg Ala Lys
610                 615                 620 ata aat gtt gct atg att tgt caa acc ttg gta agc cca cca gag gga    1920
Ile Asn Val Ala Met Ile Cys Gln Thr Leu Val Ser Pro Pro Glu Gly
625                 630                 635                 640 aac cag gaa att agc agg gac aac att cta tgc aag att aca tat gta    1968
Asn Gln Glu Ile Ser Arg Asp Asn Ile Leu Cys Lys Ile Thr Tyr Val
                645                 650                 655 gct aat gtg aac cct gga gga tgg gca cca gcc tca gtg tta agg gca    2016
Ala Asn Val Asn Pro Gly Gly Trp Ala Pro Ala Ser Val Leu Arg Ala
            660                 665                 670 gtg gca aag cga gag tat cct aaa ttt cta aaa cgt ttt act tct tac    2064
Val Ala Lys Arg Glu Tyr Pro Lys Phe Leu Lys Arg Phe Thr Ser Tyr
        675                 680                 685 gtc caa gaa aaa act gca gga aag cct att ttg ttc tag               2103
Val Gln Glu Lys Thr Ala Gly Lys Pro Ile Leu Phe
690                 695                 700

<210> SEQ ID NO 28
<211> LENGTH: 700
<212> TYPE: PRT
<213> ORGANISM: artificial
<220> FEATURE:
<223> OTHER INFORMATION: Derived sequence

<400> SEQUENCE: 28

Ala Ser Arg Gly Leu Ser Ser Gly Gly Ser Ala Gly Arg Asn Ala Gly
1               5                   10                  15

Val Thr Ala Thr Ala Ala Ala Asp Gly Trp Lys Gly Arg Leu Pro
            20                  25                  30

Ser Pro Leu Val Leu Leu Pro Arg Ser Ala Arg Cys Gln Ala Arg Arg
        35                  40                  45

Arg Arg Gly Gly Arg Thr Ser Ser Leu Leu Leu Pro Pro Thr Pro
    50                  55                  60

Glu Arg Ala Leu Phe Ala Ser Pro Ser Pro Asp Pro Ser Pro Arg Gly
65                  70                  75                  80

Leu Gly Ala Ser Ser Gly Ala Ala Glu Gly Ala Gly Ala Gly Leu Leu
```

```
                    85                  90                  95
Leu Gly Cys Arg Ala Ser Met Ser Asp Asn Gln Ser Trp Asn Ser Ser
                100                 105                 110

Gly Ser Glu Glu Asp Pro Glu Thr Glu Ser Gly Pro Pro Val Glu Arg
            115                 120                 125

Cys Gly Val Leu Ser Lys Trp Thr Asn Tyr Ile His Gly Trp Gln Asp
        130                 135                 140

Arg Trp Val Val Leu Lys Asn Asn Ala Leu Ser Tyr Tyr Lys Ser Glu
145                 150                 155                 160

Asp Glu Thr Glu Tyr Gly Cys Arg Gly Ser Ile Cys Leu Ser Lys Ala
                165                 170                 175

Val Ile Thr Pro His Asp Phe Asp Glu Cys Arg Phe Asp Ile Ser Val
            180                 185                 190

Asn Asp Ser Val Trp Tyr Leu Arg Ala Gln Asp Pro Asp His Arg Gln
        195                 200                 205

Gln Trp Ile Asp Ala Ile Glu Gln His Lys Thr Glu Ser Gly Tyr Gly
    210                 215                 220

Ser Glu Ser Ser Leu Arg Arg His Gly Ser Met Val Ser Leu Val Ser
225                 230                 235                 240

Gly Ala Ser Gly Tyr Ser Ala Thr Ser Thr Ser Ser Phe Lys Lys Gly
                245                 250                 255

His Ser Leu Arg Glu Lys Leu Ala Glu Met Glu Thr Phe Arg Asp Ile
            260                 265                 270

Leu Cys Arg Gln Val Asp Thr Leu Gln Lys Tyr Phe Asp Ala Cys Ala
        275                 280                 285

Asp Ala Val Ser Lys Asp Glu Leu Gln Arg Asp Lys Val Val Glu Asp
290                 295                 300

Asp Glu Asp Asp Phe Pro Thr Thr Arg Ser Asp Gly Asp Phe Leu His
305                 310                 315                 320

Ser Thr Asn Gly Asn Lys Glu Lys Leu Phe Pro His Val Thr Pro Lys
                325                 330                 335

Gly Ile Asn Gly Ile Asp Phe Lys Gly Glu Ala Ile Thr Phe Lys Ala
            340                 345                 350

Thr Thr Ala Gly Ile Leu Ala Thr Leu Ser His Cys Ile Glu Leu Met
        355                 360                 365

Val Lys Arg Glu Asp Ser Trp Gln Lys Arg Leu Asp Lys Glu Thr Glu
    370                 375                 380

Lys Lys Arg Arg Thr Glu Glu Ala Tyr Lys Asn Ala Met Thr Glu Leu
385                 390                 395                 400

Lys Lys Lys Ser His Phe Gly Gly Pro Asp Tyr Glu Glu Gly Pro Asn
                405                 410                 415

Ser Leu Ile Asn Glu Glu Glu Phe Phe Asp Ala Val Glu Ala Ala Leu
            420                 425                 430

Asp Arg Gln Asp Lys Ile Glu Gln Ser Gln Ser Glu Lys Val Arg
        435                 440                 445

Leu His Trp Pro Thr Ser Leu Pro Ser Gly Asp Ala Phe Ser Ser Val
    450                 455                 460

Gly Thr His Arg Phe Val Gln Lys Val Glu Glu Met Val Gln Asn His
465                 470                 475                 480

Met Thr Tyr Ser Leu Gln Asp Val Gly Gly Asp Ala Asn Trp Gln Leu
                485                 490                 495

Val Val Glu Glu Gly Glu Met Lys Val Tyr Arg Arg Glu Val Glu Glu
            500                 505                 510
```

```
Asn Gly Ile Val Leu Asp Pro Leu Lys Ala Thr His Ala Val Lys Gly
            515                 520                 525

Val Thr Gly His Glu Val Cys Asn Tyr Phe Trp Asn Val Asp Val Arg
        530                 535                 540

Asn Asp Trp Glu Thr Thr Ile Glu Asn Phe His Val Val Glu Thr Leu
545                 550                 555                 560

Ala Asp Asn Ala Ile Ile Ile Tyr Gln Thr His Lys Arg Val Trp Pro
                565                 570                 575

Ala Ser Gln Arg Asp Val Leu Tyr Leu Ser Val Ile Arg Lys Ile Pro
            580                 585                 590

Ala Leu Thr Glu Asn Asp Pro Glu Thr Trp Ile Val Cys Asn Phe Ser
        595                 600                 605

Val Asp His Asp Ser Ala Pro Leu Asn Asn Arg Cys Val Arg Ala Lys
    610                 615                 620

Ile Asn Val Ala Met Ile Cys Gln Thr Leu Val Ser Pro Pro Glu Gly
625                 630                 635                 640

Asn Gln Glu Ile Ser Arg Asp Asn Ile Leu Cys Lys Ile Thr Tyr Val
                645                 650                 655

Ala Asn Val Asn Pro Gly Gly Trp Ala Pro Ala Ser Val Leu Arg Ala
            660                 665                 670

Val Ala Lys Arg Glu Tyr Pro Lys Phe Leu Lys Arg Phe Thr Ser Tyr
        675                 680                 685

Val Gln Glu Lys Thr Ala Gly Lys Pro Ile Leu Phe
    690                 695                 700

<210> SEQ ID NO 29
<211> LENGTH: 13
<212> TYPE: PRT
<213> ORGANISM: artificial
<220> FEATURE:
<223> OTHER INFORMATION: Derived sequence

<400> SEQUENCE: 29

Gly Ala Gly Ala Gly Leu Leu Leu Gly Cys Arg Ala Ser
1               5                   10

<210> SEQ ID NO 30
<211> LENGTH: 31
<212> TYPE: PRT
<213> ORGANISM: artificial
<220> FEATURE:
<223> OTHER INFORMATION: Derived sequence

<400> SEQUENCE: 30

Pro Ser Pro Asp Pro Ser Pro Arg Gly Leu Gly Ala Ser Ser Gly Ala
1               5                   10                  15

Ala Glu Gly Ala Gly Ala Gly Leu Leu Leu Gly Cys Arg Ala Ser
            20                  25                  30

<210> SEQ ID NO 31
<211> LENGTH: 54
<212> TYPE: PRT
<213> ORGANISM: artificial
<220> FEATURE:
<223> OTHER INFORMATION: Derived sequence

<400> SEQUENCE: 31

Arg Arg Gly Gly Arg Thr Ser Ser Leu Leu Leu Leu Pro Pro Thr Pro
1               5                   10                  15
```

-continued

Glu Arg Ala Leu Phe Ala Ser Pro Ser Pro Asp Pro Ser Pro Arg Gly
            20                  25                  30

Leu Gly Ala Ser Ser Gly Ala Ala Glu Gly Ala Gly Ala Gly Leu Leu
        35                  40                  45

Leu Gly Cys Arg Ala Ser
    50

<210> SEQ ID NO 32
<211> LENGTH: 78
<212> TYPE: PRT
<213> ORGANISM: artificial
<220> FEATURE:
<223> OTHER INFORMATION: Derived sequence

<400> SEQUENCE: 32

Asp Gly Trp Lys Gly Arg Leu Pro Ser Pro Leu Val Leu Leu Pro Arg
1               5                   10                  15

Ser Ala Arg Cys Gln Ala Arg Arg Arg Gly Gly Arg Thr Ser Ser
            20                  25                  30

Leu Leu Leu Leu Pro Pro Thr Pro Glu Arg Ala Leu Phe Ala Ser Pro
        35                  40                  45

Ser Pro Asp Pro Ser Pro Arg Gly Leu Gly Ala Ser Ser Gly Ala Ala
    50                  55                  60

Glu Gly Ala Gly Ala Gly Leu Leu Leu Gly Cys Arg Ala Ser
65                  70                  75

<210> SEQ ID NO 33
<211> LENGTH: 102
<212> TYPE: PRT
<213> ORGANISM: artificial
<220> FEATURE:
<223> OTHER INFORMATION: Derived sequence

<400> SEQUENCE: 33

Ala Ser Arg Gly Leu Ser Ser Gly Gly Ser Ala Gly Arg Asn Ala Gly
1               5                   10                  15

Val Thr Ala Thr Ala Ala Ala Ala Asp Gly Trp Lys Gly Arg Leu Pro
            20                  25                  30

Ser Pro Leu Val Leu Leu Pro Arg Ser Ala Arg Cys Gln Ala Arg Arg
        35                  40                  45

Arg Arg Gly Gly Arg Thr Ser Ser Leu Leu Leu Leu Pro Pro Thr Pro
    50                  55                  60

Glu Arg Ala Leu Phe Ala Ser Pro Ser Pro Asp Pro Ser Pro Arg Gly
65                  70                  75                  80

Leu Gly Ala Ser Ser Gly Ala Ala Glu Gly Ala Gly Ala Gly Leu Leu
                85                  90                  95

Leu Gly Cys Arg Ala Ser
            100

<210> SEQ ID NO 34
<211> LENGTH: 103
<212> TYPE: PRT
<213> ORGANISM: artificial
<220> FEATURE:
<223> OTHER INFORMATION: Derived sequence

<400> SEQUENCE: 34

Leu Ala Ser Arg Gly Leu Ser Ser Gly Gly Ser Ala Gly Arg Asn Ala
1               5                   10                  15

Gly Val Thr Ala Thr Ala Ala Ala Ala Asp Gly Trp Lys Gly Arg Leu

```
                    20                  25                  30
Pro Ser Pro Leu Val Leu Leu Pro Arg Ser Ala Arg Cys Gln Ala Arg
            35                  40                  45

Arg Arg Arg Gly Gly Arg Thr Ser Ser Leu Leu Leu Pro Pro Thr
    50                  55                  60

Pro Glu Arg Ala Leu Phe Ala Ser Pro Ser Pro Asp Pro Ser Pro Arg
65                  70                  75                  80

Gly Leu Gly Ala Ser Ser Gly Ala Ala Glu Gly Ala Gly Ala Gly Leu
                85                  90                  95

Leu Leu Gly Cys Arg Ala Ser
            100
```

<210> SEQ ID NO 35
<211> LENGTH: 90
<212> TYPE: PRT
<213> ORGANISM: artificial
<220> FEATURE:
<223> OTHER INFORMATION: Derived sequence

<400> SEQUENCE: 35

```
Leu Ala Ser Arg Gly Leu Ser Ser Gly Gly Ser Ala Gly Arg Asn Ala
1               5                   10                  15

Gly Val Thr Ala Thr Ala Ala Ala Asp Gly Trp Lys Gly Arg Leu
            20                  25                  30

Pro Ser Pro Leu Val Leu Leu Pro Arg Ser Ala Arg Cys Gln Ala Arg
            35                  40                  45

Arg Arg Arg Gly Gly Arg Thr Ser Ser Leu Leu Leu Pro Pro Thr
    50                  55                  60

Pro Glu Arg Ala Leu Phe Ala Ser Pro Ser Pro Asp Pro Ser Pro Arg
65                  70                  75                  80

Gly Leu Gly Ala Ser Ser Gly Ala Ala Glu
                85                  90
```

<210> SEQ ID NO 36
<211> LENGTH: 18
<212> TYPE: PRT
<213> ORGANISM: artificial
<220> FEATURE:
<223> OTHER INFORMATION: Derived sequence

<400> SEQUENCE: 36

```
Pro Arg Ser Ala Arg Cys Gln Ala Arg Arg Arg Arg Gly Gly Arg Thr
1               5                   10                  15

Ser Ser
```

<210> SEQ ID NO 37
<211> LENGTH: 897
<212> TYPE: DNA
<213> ORGANISM: artificial
<220> FEATURE:
<223> OTHER INFORMATION: Derived sequence
<220> FEATURE:
<221> NAME/KEY: CDS
<222> LOCATION: (1)..(897)
<223> OTHER INFORMATION:

<400> SEQUENCE: 37

```
atg tcg gat aat cag agc tgg aac tcg tcg ggc tcg gag gag gat cca       48
Met Ser Asp Asn Gln Ser Trp Asn Ser Ser Gly Ser Glu Glu Asp Pro
1               5                   10                  15 gag acg gag tct ggg ccg cct gtg gag cgc tgc ggg gtc ctc agt aag       96
```

```
                                              -continued

Glu Thr Glu Ser Gly Pro Pro Val Glu Arg Cys Gly Val Leu Ser Lys
         20                  25                  30 tgg aca aac tac att cat ggg tgg cag gat cgt tgg gta gtt ttg aaa           144
Trp Thr Asn Tyr Ile His Gly Trp Gln Asp Arg Trp Val Val Leu Lys
         35                  40                  45 aat gct ctg agt tac tac aaa tct gaa gat gaa aca gag tat ggc               192
Asn Ala Leu Ser Tyr Tyr Lys Ser Glu Asp Glu Thr Glu Tyr Gly
 50                  55                  60 tgc aga gga tcc atc tgt ctt agc aag gct gtc atc aca cct cac gat           240
Cys Arg Gly Ser Ile Cys Leu Ser Lys Ala Val Ile Thr Pro His Asp
65                  70                  75                  80 ttt gat gaa tgt cga ttt gat att agt gta aat gat agt gtt tgg tat           288
Phe Asp Glu Cys Arg Phe Asp Ile Ser Val Asn Asp Ser Val Trp Tyr
                 85                  90                  95 ctt cgt gct cag gat cca gat cat aga cag caa tgg ata gat gcc att           336
Leu Arg Ala Gln Asp Pro Asp His Arg Gln Gln Trp Ile Asp Ala Ile
                100                 105                 110 gaa cag cac aag act gaa tct gga tat gga tct gaa tcc agc ttg cgt           384
Glu Gln His Lys Thr Glu Ser Gly Tyr Gly Ser Glu Ser Ser Leu Arg
            115                 120                 125 cga cat ggc tca atg gtg tcc ctg gtg tct gga gca agt ggc tac tct           432
Arg His Gly Ser Met Val Ser Leu Val Ser Gly Ala Ser Gly Tyr Ser
        130                 135                 140 gca aca tcc acc tct tca ttc aag aaa ggc cac agt tta cgt gag aag           480
Ala Thr Ser Thr Ser Ser Phe Lys Lys Gly His Ser Leu Arg Glu Lys
145                 150                 155                 160 ttg gct gaa atg gaa aca ttt aga gac atc tta tgt aga caa gtt gac           528
Leu Ala Glu Met Glu Thr Phe Arg Asp Ile Leu Cys Arg Gln Val Asp
                165                 170                 175 acg cta cag aag tac ttt gat gcc tgt gct gat gct gtc tct aag gat           576
Thr Leu Gln Lys Tyr Phe Asp Ala Cys Ala Asp Ala Val Ser Lys Asp
            180                 185                 190 gaa ctt caa agg gat aaa gtg gta gaa gat gat gaa gat gac ttt cct           624
Glu Leu Gln Arg Asp Lys Val Val Glu Asp Asp Glu Asp Asp Phe Pro
        195                 200                 205 aca acg cgt tct gat ggt gac ttc ttg cat agt acc aac ggc aat aaa           672
Thr Thr Arg Ser Asp Gly Asp Phe Leu His Ser Thr Asn Gly Asn Lys
    210                 215                 220 gaa aag tta ttt cca cat gtg aca cca aaa gga att aat ggt ata gac           720
Glu Lys Leu Phe Pro His Val Thr Pro Lys Gly Ile Asn Gly Ile Asp
225                 230                 235                 240 ttt aaa ggg gaa gcg ata act ttt aaa gca act act gct gga atc ctt           768
Phe Lys Gly Glu Ala Ile Thr Phe Lys Ala Thr Thr Ala Gly Ile Leu
                245                 250                 255 gca aca ctt tct cat tgt att gaa cta atg gtt aaa cgt gag gac agc           816
Ala Thr Leu Ser His Cys Ile Glu Leu Met Val Lys Arg Glu Asp Ser
            260                 265                 270 tgg cag aag aga ctg gat aag gaa act gag aag aaa aga aga aca gag           864
Trp Gln Lys Arg Leu Asp Lys Glu Thr Glu Lys Lys Arg Arg Thr Glu
        275                 280                 285 gaa gca tat aaa aat gca atg aca gaa ctt aag                               897
Glu Ala Tyr Lys Asn Ala Met Thr Glu Leu Lys
    290                 295

<210> SEQ ID NO 38
<211> LENGTH: 299
<212> TYPE: PRT
<213> ORGANISM: artificial
<220> FEATURE:
<223> OTHER INFORMATION: Derived sequence
```

-continued

```
<400> SEQUENCE: 38

Met Ser Asp Asn Gln Ser Trp Asn Ser Ser Gly Ser Glu Glu Asp Pro
1               5                   10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
        35                  40                  45

Asn Asn Ala Leu Ser Tyr Tyr Lys Ser Glu Asp Glu Thr Glu Tyr Gly
50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205

Thr Thr Arg Ser Asp Gly Asp Phe Leu His Ser Thr Asn Gly Asn Lys
210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys
290                 295

<210> SEQ ID NO 39
<211> LENGTH: 5
<212> TYPE: PRT
<213> ORGANISM: artificial
<220> FEATURE:
<223> OTHER INFORMATION: Derived sequence

<400> SEQUENCE: 39

Ser His Cys Ile Glu
1               5

<210> SEQ ID NO 40
<211> LENGTH: 5
<212> TYPE: PRT
<213> ORGANISM: artificial
<220> FEATURE:
<223> OTHER INFORMATION: Derived sequence
```

```
<400> SEQUENCE: 40

Ser His Cys Ile Gln
1               5

<210> SEQ ID NO 41
<211> LENGTH: 10
<212> TYPE: PRT
<213> ORGANISM: artificial
<220> FEATURE:
<223> OTHER INFORMATION: Derived sequence

<400> SEQUENCE: 41

Ala Thr Thr Ala Gly Ile Leu Ala Thr Leu
1               5                   10

<210> SEQ ID NO 42
<211> LENGTH: 10
<212> TYPE: PRT
<213> ORGANISM: artificial
<220> FEATURE:
<223> OTHER INFORMATION: Derived sequence

<400> SEQUENCE: 42

Leu Met Val Lys Arg Glu Asp Ser Trp Gln
1               5                   10

<210> SEQ ID NO 43
<211> LENGTH: 15
<212> TYPE: PRT
<213> ORGANISM: artificial
<220> FEATURE:
<223> OTHER INFORMATION: Derived sequence

<400> SEQUENCE: 43

Ile Leu Ala Thr Leu Ser His Cys Ile Glu Leu Met Val Lys Arg
1               5                   10                  15

<210> SEQ ID NO 44
<211> LENGTH: 15
<212> TYPE: PRT
<213> ORGANISM: artificial
<220> FEATURE:
<223> OTHER INFORMATION: Derived sequence

<400> SEQUENCE: 44

Ile Leu Ala Thr Leu Ser His Cys Ile Gln Leu Met Val Lys Arg
1               5                   10                  15

<210> SEQ ID NO 45
<211> LENGTH: 10
<212> TYPE: PRT
<213> ORGANISM: artificial
<220> FEATURE:
<223> OTHER INFORMATION: Derived sequence

<400> SEQUENCE: 45

Glu Lys Thr Ala Gly Lys Pro Ile Leu Phe
1               5                   10

<210> SEQ ID NO 46
<211> LENGTH: 26
<212> TYPE: PRT
<213> ORGANISM: artificial
<220> FEATURE:
<223> OTHER INFORMATION: Derived sequence
```

```
<400> SEQUENCE: 46

Pro Tyr Ser Arg Ser Ser Ser Met Ser Ser Ile Asp Leu Val Ser Ala
1               5                   10                  15

Ser Asp Asp Val His Arg Phe Ser Ser Gln
            20                  25

<210> SEQ ID NO 47
<211> LENGTH: 21
<212> TYPE: RNA
<213> ORGANISM: artificial
<220> FEATURE:
<223> OTHER INFORMATION: Derived sequence

<400> SEQUENCE: 47
aaacuacauu caugguggc a                                          21

<210> SEQ ID NO 48
<211> LENGTH: 21
<212> TYPE: RNA
<213> ORGANISM: artificial
<220> FEATURE:
<223> OTHER INFORMATION: Derived sequence

<400> SEQUENCE: 48
aaacagagua uggcugcaga g                                         21

<210> SEQ ID NO 49
<211> LENGTH: 21
<212> TYPE: RNA
<213> ORGANISM: artificial
<220> FEATURE:
<223> OTHER INFORMATION: Derived sequence

<400> SEQUENCE: 49
aaguacuuug augccugugc u                                         21

<210> SEQ ID NO 50
<211> LENGTH: 21
<212> TYPE: RNA
<213> ORGANISM: artificial
<220> FEATURE:
<223> OTHER INFORMATION: Derived sequence

<400> SEQUENCE: 50
aaaggcguca caggacauga a                                         21

<210> SEQ ID NO 51
<211> LENGTH: 21
<212> TYPE: RNA
<213> ORGANISM: artificial
<220> FEATURE:
<223> OTHER INFORMATION: Derived sequence

<400> SEQUENCE: 51
aagcccuaua gucgcucuuc c                                         21

<210> SEQ ID NO 52
<211> LENGTH: 244
<212> TYPE: PRT
<213> ORGANISM: artificial
<220> FEATURE:
<223> OTHER INFORMATION: Derived sequence

<400> SEQUENCE: 52

Gly Leu Lys Gly Lys Arg Gly Asp Ser Gly Ser Pro Ala Thr Trp Thr
```

-continued

```
1               5                   10                  15
Thr Arg Gly Phe Val Phe Thr Arg His Ser Gln Thr Ala Ile Pro
                20                  25                  30
Ser Cys Pro Glu Gly Thr Val Pro Leu Tyr Ser Gly Phe Ser Phe Leu
                35                  40                  45
Phe Val Gln Gly Asn Gln Arg Ala His Gly Gln Asp Leu Gly Thr Leu
 50                  55                  60
Gly Ser Cys Leu Gln Arg Phe Thr Thr Met Pro Phe Leu Phe Cys Asn
 65                  70                  75                  80
Val Asn Asp Val Cys Asn Phe Ala Ser Arg Asn Asp Tyr Ser Tyr Trp
                85                  90                  95
Leu Ser Thr Pro Ala Leu Met Pro Met Asn Met Ala Pro Ile Thr Gly
                100                 105                 110
Arg Ala Leu Glu Pro Tyr Ile Ser Arg Cys Thr Val Cys Glu Gly Pro
                115                 120                 125
Ala Ile Ala Ile Ala Val His Ser Gln Thr Thr Asp Ile Pro Pro Cys
                130                 135                 140
Pro His Gly Trp Ile Ser Leu Trp Lys Gly Phe Ser Phe Ile Met Phe
145                 150                 155                 160
Thr Ser Ala Gly Ser Glu Gly Thr Gly Gln Ala Leu Ala Ser Pro Gly
                165                 170                 175
Ser Cys Leu Glu Glu Phe Arg Ala Ser Pro Phe Leu Glu Cys His Gly
                180                 185                 190
Arg Gly Thr Cys Asn Tyr Tyr Ser Asn Ser Tyr Ser Phe Trp Leu Ala
                195                 200                 205
Ser Leu Asn Pro Glu Arg Met Phe Arg Lys Pro Ile Pro Ser Thr Val
                210                 215                 220
Lys Ala Gly Glu Leu Glu Lys Ile Ile Ser Arg Cys Gln Val Cys Met
225                 230                 235                 240
Lys Lys Arg His
```

<210> SEQ ID NO 53
<211> LENGTH: 197
<212> TYPE: PRT
<213> ORGANISM: artificial
<220> FEATURE:
<223> OTHER INFORMATION: Derived sequence

<400> SEQUENCE: 53

```
Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
                20                  25                  30
His Arg Asp Thr Gly Ile Leu Asp Ser Ile Gly Arg Phe Phe Gly Gly
                35                  40                  45
Asp Arg Gly Ala Pro Lys Arg Gly Ser Gly Lys Val Pro Trp Leu Lys
 50                  55                  60
Pro Gly Arg Ser Pro Leu Pro Ser His Ala Arg Ser Gln Pro Gly Leu
 65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
                100                 105                 110
Val Val His Phe Phe Lys Asn Ile Val Thr Pro Arg Thr Pro Pro Pro
                115                 120                 125
```

```
Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 54
<211> LENGTH: 253
<212> TYPE: PRT
<213> ORGANISM: artificial
<220> FEATURE:
<223> OTHER INFORMATION: Derived sequence

<400> SEQUENCE: 54

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 55
<211> LENGTH: 42
<212> TYPE: PRT
<213> ORGANISM: artificial
```

```
<220> FEATURE:
<223> OTHER INFORMATION: Derived sequence

<400> SEQUENCE: 55

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 56
<211> LENGTH: 244
<212> TYPE: PRT
<213> ORGANISM: artificial
<220> FEATURE:
<223> OTHER INFORMATION: Derived sequence

<400> SEQUENCE: 56

Gly Leu Lys Gly Lys Arg Gly Asp Ala Gly Ser Pro Ala Thr Trp Thr
1               5                   10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175

Ser Cys Leu Glu Glu Phe Arg Ala Ser Pro Phe Leu Glu Cys His Gly
            180                 185                 190

Arg Gly Thr Cys Asn Tyr Tyr Ser Asn Ser Tyr Ser Phe Trp Leu Ala
        195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His

<210> SEQ ID NO 57
<211> LENGTH: 244
<212> TYPE: PRT
<213> ORGANISM: artificial
<220> FEATURE:
<223> OTHER INFORMATION: Derived sequence
```

```
<400> SEQUENCE: 57

Gly Leu Lys Gly Lys Arg Gly Asp Asp Gly Ser Pro Ala Thr Trp Thr
1               5                   10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175

Ser Cys Leu Glu Glu Phe Arg Ala Ser Pro Phe Leu Glu Cys His Gly
            180                 185                 190

Arg Gly Thr Cys Asn Tyr Tyr Ser Asn Ser Tyr Ser Phe Trp Leu Ala
        195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His

<210> SEQ ID NO 58
<211> LENGTH: 20
<212> TYPE: DNA
<213> ORGANISM: artificial
<220> FEATURE:
<223> OTHER INFORMATION: ON-hmbGPBP

<400> SEQUENCE: 58
cctccgagcc cgacgagttc                                              20

<210> SEQ ID NO 59
<211> LENGTH: 20
<212> TYPE: DNA
<213> ORGANISM: artificial
<220> FEATURE:
<223> OTHER INFORMATION: ON-dinb1

<400> SEQUENCE: 59
gaccgaaagg ggcacgcaac                                              20

<210> SEQ ID NO 60
<211> LENGTH: 33
<212> TYPE: DNA
<213> ORGANISM: artificial
<220> FEATURE:
```

<223> OTHER INFORMATION: ON-GPBP D102

<400> SEQUENCE: 60
aaaaagaatt cgcatcgagg gggctaagtt cgg                33

<210> SEQ ID NO 61
<211> LENGTH: 31
<212> TYPE: DNA
<213> ORGANISM: artificial
<220> FEATURE:
<223> OTHER INFORMATION: ON-GPBP D174

<400> SEQUENCE: 61
aaaaagaatt cgacggctgg aagggtaggc t                  31

<210> SEQ ID NO 62
<211> LENGTH: 32
<212> TYPE: DNA
<213> ORGANISM: artificial
<220> FEATURE:
<223> OTHER INFORMATION: ON-GPBP D246

<400> SEQUENCE: 62
aaaaagaatt ctgtcaggcg cggcggcggc gc                 32

<210> SEQ ID NO 63
<211> LENGTH: 30
<212> TYPE: DNA
<213> ORGANISM: artificial
<220> FEATURE:
<223> OTHER INFORMATION: ON-GPBP D315

<400> SEQUENCE: 63
gacgaattcc catcccccga cccttcaccc                    30

<210> SEQ ID NO 64
<211> LENGTH: 33
<212> TYPE: DNA
<213> ORGANISM: artificial
<220> FEATURE:
<223> OTHER INFORMATION: ON-GPBP D369

<400> SEQUENCE: 64
aaaaagaatt cggagcgggg gccggtctcc tgc                33

<210> SEQ ID NO 65
<211> LENGTH: 20
<212> TYPE: DNA
<213> ORGANISM: artificial
<220> FEATURE:
<223> OTHER INFORMATION: ON-pU1

<400> SEQUENCE: 65
acgactcact atagggagac                               20

<210> SEQ ID NO 66
<211> LENGTH: 20
<212> TYPE: DNA
<213> ORGANISM: artificial
<220> FEATURE:
<223> OTHER INFORMATION: ON-pcDNAc

<400> SEQUENCE: 66
ctctagcatt taggtgacac                               20

```
<210> SEQ ID NO 67
<211> LENGTH: 33
<212> TYPE: DNA
<213> ORGANISM: artificial
<220> FEATURE:
<223> OTHER INFORMATION: ON-GPBPMet (mutant)

<400> SEQUENCE: 67
ggttgtcgag cctccggatc ggataatcag agc                            33

<210> SEQ ID NO 68
<211> LENGTH: 30
<212> TYPE: DNA
<213> ORGANISM: artificial
<220> FEATURE:
<223> OTHER INFORMATION: ON-PrP-F3

<400> SEQUENCE: 68
gagaattcag cagtcattat ggcgaacctt                                30

<210> SEQ ID NO 69
<211> LENGTH: 31
<212> TYPE: DNA
<213> ORGANISM: artificial
<220> FEATURE:
<223> OTHER INFORMATION: ON- PrP-R1

<400> SEQUENCE: 69
gaactcgagc cttcctcatc ccactatcag g                              31

<210> SEQ ID NO 70
<211> LENGTH: 25
<212> TYPE: DNA
<213> ORGANISM: artificial
<220> FEATURE:
<223> OTHER INFORMATION: ON-E/K-PrP-F6

<400> SEQUENCE: 70
tatcacccag tacaagaggg aatct                                     25

<210> SEQ ID NO 71
<211> LENGTH: 25
<212> TYPE: DNA
<213> ORGANISM: artificial
<220> FEATURE:
<223> OTHER INFORMATION: ON-E/K-PrP-R6

<400> SEQUENCE: 71
agattccctc ttgtactggg tgata                                     25

<210> SEQ ID NO 72
<211> LENGTH: 22
<212> TYPE: DNA
<213> ORGANISM: artificial
<220> FEATURE:
<223> OTHER INFORMATION: ON-E168R-F1

<400> SEQUENCE: 72
cccatggata ggtacagcaa cc                                        22

<210> SEQ ID NO 73
<211> LENGTH: 22
<212> TYPE: DNA
<213> ORGANISM: artificial
<220> FEATURE:
<223> OTHER INFORMATION: ON-E168R-R1
```

<400> SEQUENCE: 73
ggttgctgta cctatccatg gg            22

<210> SEQ ID NO 74
<211> LENGTH: 25
<212> TYPE: DNA
<213> ORGANISM: artificial
<220> FEATURE:
<223> OTHER INFORMATION: ON-Q172R-F1

<400> SEQUENCE: 74
gagtacagca acaggaacaa ctttg            25

<210> SEQ ID NO 75
<211> LENGTH: 25
<212> TYPE: DNA
<213> ORGANISM: artificial
<220> FEATURE:
<223> OTHER INFORMATION: ON-Q172R-R1

<400> SEQUENCE: 75
caaagttgtt cctgttgctg tactc            25

<210> SEQ ID NO 76
<211> LENGTH: 22
<212> TYPE: DNA
<213> ORGANISM: artificial
<220> FEATURE:
<223> OTHER INFORMATION: ON-R220A-F1

<400> SEQUENCE: 76
cagtacgagg cggaatctca gg            22

<210> SEQ ID NO 77
<211> LENGTH: 22
<212> TYPE: DNA
<213> ORGANISM: artificial
<220> FEATURE:
<223> OTHER INFORMATION: ON-R220A-R1

<400> SEQUENCE: 77
cctgagattc cgcctcgtac tg            22

<210> SEQ ID NO 78
<211> LENGTH: 23
<212> TYPE: DNA
<213> ORGANISM: artificial
<220> FEATURE:
<223> OTHER INFORMATION: ON-R228A-F1

<400> SEQUENCE: 78
tattaccagg caggatcgag cat            23

<210> SEQ ID NO 79
<211> LENGTH: 23
<212> TYPE: DNA
<213> ORGANISM: artificial
<220> FEATURE:
<223> OTHER INFORMATION: ON-R228A-R1

<400> SEQUENCE: 79
atgctcgatc ctgcctggta ata            23

<210> SEQ ID NO 80
<211> LENGTH: 64

```
<212> TYPE: DNA
<213> ORGANISM: artificial
<220> FEATURE:
<223> OTHER INFORMATION: SiGPBP/D26-1

<400> SEQUENCE: 80
gatcccacta cattcatggg tggcattcaa gagatgccac ccatgaatgt agttttttg      60 gaaa                                                                  64

<210> SEQ ID NO 81
<211> LENGTH: 64
<212> TYPE: DNA
<213> ORGANISM: artificial
<220> FEATURE:
<223> OTHER INFORMATION: SiGPBP/D26-1

<400> SEQUENCE: 81
agcttttcca aaaaactac attcatgggt ggcatctctt gaatgccacc catgaatgta      60
gtgg                                                                  64

<210> SEQ ID NO 82
<211> LENGTH: 64
<212> TYPE: DNA
<213> ORGANISM: artificial
<220> FEATURE:
<223> OTHER INFORMATION: SiGPBP/D26-2

<400> SEQUENCE: 82
gatcccacag agtatggctg cagagttcaa gagactctgc agccatactc tgttttttg      60 gaaa                                                                  64

<210> SEQ ID NO 83
<211> LENGTH: 64
<212> TYPE: DNA
<213> ORGANISM: artificial
<220> FEATURE:
<223> OTHER INFORMATION: SiGPBP/D26-2

<400> SEQUENCE: 83
agcttttcca aaaaacaga gtatggctgc agagtctctt gaactctgca gccatactct      60
gtgg                                                                  64

<210> SEQ ID NO 84
<211> LENGTH: 64
<212> TYPE: DNA
<213> ORGANISM: artificial
<220> FEATURE:
<223> OTHER INFORMATION: SiGPBP/D26-3

<400> SEQUENCE: 84
gatcccgtac tttgatgcct gtgctttcaa gagaagcaca ggcatcaaag tactttttg      60 gaaa                                                                  64

<210> SEQ ID NO 85
<211> LENGTH: 64
<212> TYPE: DNA
<213> ORGANISM: artificial
<220> FEATURE:
<223> OTHER INFORMATION: SiGPBP/D26-3

<400> SEQUENCE: 85
agcttttcca aaaagtact ttgatgcctg tgcttctctt gaaagcacag gcatcaaagt      60
```

```
acgg                                                              64

<210> SEQ ID NO 86
<211> LENGTH: 64
<212> TYPE: DNA
<213> ORGANISM: artificial
<220> FEATURE:
<223> OTHER INFORMATION: SiGPBP/D26-4

<400> SEQUENCE: 86
gatcccaggc gtcacaggac atgaattcaa gagattcatg tcctgtgacg ccttttttg    60 gaaa                                                              64

<210> SEQ ID NO 87
<211> LENGTH: 64
<212> TYPE: DNA
<213> ORGANISM: artificial
<220> FEATURE:
<223> OTHER INFORMATION: SiGPBP/D26-4

<400> SEQUENCE: 87
agcttttcca aaaaaggcg tcacaggaca tgaatctctt gaattcatgt cctgtgacgc    60
ctgg                                                              64

<210> SEQ ID NO 88
<211> LENGTH: 64
<212> TYPE: DNA
<213> ORGANISM: artificial
<220> FEATURE:
<223> OTHER INFORMATION: SiGPBP

<400> SEQUENCE: 88
gatcccgccc tatagtcgct cttccttcaa gagaggaaga gcgactatag ggcttttttg    60
gaaa                                                              64

<210> SEQ ID NO 89
<211> LENGTH: 64
<212> TYPE: DNA
<213> ORGANISM: artificial
<220> FEATURE:
<223> OTHER INFORMATION: SiGPBP

<400> SEQUENCE: 89
agcttttcca aaaagccct atagtcgctc ttcctctctt gaaggaagag cgactatagg    60
gcgg                                                              64

<210> SEQ ID NO 90
<211> LENGTH: 14
<212> TYPE: PRT
<213> ORGANISM: artificial
<220> FEATURE:
<223> OTHER INFORMATION: Derived sequence

<400> SEQUENCE: 90

Leu Ala Thr Leu Ser His Cys Ile Glu Leu Met Val Lys Arg
1               5                   10

<210> SEQ ID NO 91
<211> LENGTH: 15
<212> TYPE: PRT
<213> ORGANISM: artificial
<220> FEATURE:
<223> OTHER INFORMATION: Derived sequence
```

-continued

```
<400> SEQUENCE: 91

Val Leu Met Ala Ser Leu Glu Thr Leu Cys Arg Ile His Lys Ile
1               5                   10                  15

<210> SEQ ID NO 92
<211> LENGTH: 22
<212> TYPE: PRT
<213> ORGANISM: artificial
<220> FEATURE:
<223> OTHER INFORMATION: Derived sequence

<400> SEQUENCE: 92

Lys Gly Lys Pro Gly Asp Thr Gly Pro Pro Ala Ala Gly Ala Val Met
1               5                   10                  15

Arg Gly Phe Val Phe Thr
            20

<210> SEQ ID NO 93
<211> LENGTH: 2760
<212> TYPE: DNA
<213> ORGANISM: Mus musculus
<220> FEATURE:
<221> NAME/KEY: CDS
<222> LOCATION: (138)..(2318)
<223> OTHER INFORMATION:

<400> SEQUENCE: 93
cgggccacca cgtgtaaata gtatcggacc cggcaggaag atggcggctg tagcggaggt      60
gtgagtgagt ggatctgggt ctctgccgtt ggcttggctc ttcccgtctt cctcccctcc    120
tccctccctg actgagg ttg gca tct agg ggg ccg agt tca ggt ggc ggc       170
                 Leu Ala Ser Arg Gly Pro Ser Ser Gly Gly Gly
                  1               5                   10 gcc ggg cgc agc gca ggg gtc acg gcc acg gcg gct gac ggc tgg aag      218
Ala Gly Arg Ser Ala Gly Val Thr Ala Thr Ala Ala Asp Gly Trp Lys
            15                  20                  25 ggc agg ctt tct tcg ccg ctc gtc ctc ctt ccc cgg tcc gct cgg tgt      266
Gly Arg Leu Ser Ser Pro Leu Val Leu Leu Pro Arg Ser Ala Arg Cys
        30                  35                  40 cag gcg cgg cgg cgg cgg cgc ggc ggg cgc gct tcg tcc ctc ttc ctg      314
Gln Ala Arg Arg Arg Arg Gly Gly Arg Ala Ser Ser Leu Phe Leu
    45                  50                  55 ttc cct cac tcc ccg gag cgg gct ctc ttg gcg gtg cca tcc ccc gac      362
Phe Pro His Ser Pro Glu Arg Ala Leu Leu Ala Val Pro Ser Pro Asp
60                  65                  70                  75 cct tca ccc cag gga cta ggc gcc tgc act ggc gca gct cgc gga gcg      410
Pro Ser Pro Gln Gly Leu Gly Ala Cys Thr Gly Ala Ala Arg Gly Ala
                80                  85                  90 ggg gcc ggt ctc ctg ctc ggc tgt cgc gtc tcc atg tcg gat aac cag      458
Gly Ala Gly Leu Leu Leu Gly Cys Arg Val Ser Met Ser Asp Asn Gln
            95                  100                 105 agc tgg aac tcg tcg ggc tcg gag gag gat ccg gag acg gag tcc ggg      506
Ser Trp Asn Ser Ser Gly Ser Glu Glu Asp Pro Glu Thr Glu Ser Gly
        110                 115                 120 ccg cct gtg gag cgc tgc ggg gtc ctc agc aag tgg aca aac tat att      554
Pro Pro Val Glu Arg Cys Gly Val Leu Ser Lys Trp Thr Asn Tyr Ile
    125                 130                 135 cat gga tgg cag gat cgt tgg gta gtt ttg aaa aat aat act ttg agt      602
His Gly Trp Gln Asp Arg Trp Val Val Leu Lys Asn Asn Thr Leu Ser
140                 145                 150                 155 tac tac aaa tct gaa gat gaa aca gaa tat ggc tgt agg gga tcc atc      650
Tyr Tyr Lys Ser Glu Asp Glu Thr Glu Tyr Gly Cys Arg Gly Ser Ile
```

-continued

```
                      160                 165                 170
tgt ctt agc aag gct gtg atc acg cct cac gat ttt gat gaa tgc cgg    698
Cys Leu Ser Lys Ala Val Ile Thr Pro His Asp Phe Asp Glu Cys Arg
            175                 180                 185 ttt gat atc agt gta aat gat agt gtt tgg tac ctt cga gct cag gac    746
Phe Asp Ile Ser Val Asn Asp Ser Val Trp Tyr Leu Arg Ala Gln Asp
            190                 195                 200 ccg gag cac aga cag caa tgg gta gac gcc att gaa cag cac aag act    794
Pro Glu His Arg Gln Gln Trp Val Asp Ala Ile Glu Gln His Lys Thr
        205                 210                 215 gaa tcg gga tat gga tct gag tcc agc ttg cgt aga cat ggc tca atg    842
Glu Ser Gly Tyr Gly Ser Glu Ser Ser Leu Arg Arg His Gly Ser Met
220                 225                 230                 235 gtg tca ctg gtg tct gga gcg agt ggc tat tct gct acg tcc acc tct    890
Val Ser Leu Val Ser Gly Ala Ser Gly Tyr Ser Ala Thr Ser Thr Ser
                240                 245                 250 tct ttc aag aaa ggc cac agt tta cgt gag aaa ctg gct gaa atg gag    938
Ser Phe Lys Lys Gly His Ser Leu Arg Glu Lys Leu Ala Glu Met Glu
            255                 260                 265 aca ttt cgg gac atc ctg tgc cgg cag gtt gat act ctc cag aag tac    986
Thr Phe Arg Asp Ile Leu Cys Arg Gln Val Asp Thr Leu Gln Lys Tyr
            270                 275                 280 ttt gat gtc tgt gct gac gct gtc tcc aag gat gag ctt cag agg gat   1034
Phe Asp Val Cys Ala Asp Ala Val Ser Lys Asp Glu Leu Gln Arg Asp
            285                 290                 295 aaa gtc gta gaa gat gat gaa gat gac ttc cct aca act cgt tct gat   1082
Lys Val Val Glu Asp Asp Glu Asp Asp Phe Pro Thr Thr Arg Ser Asp
300                 305                 310                 315 gga gac ttt ttg cac aat acc aat ggt aat aaa gaa aaa tta ttt cca   1130
Gly Asp Phe Leu His Asn Thr Asn Gly Asn Lys Glu Lys Leu Phe Pro
                320                 325                 330 cat gta aca cca aaa gga att aat ggc ata gac ttt aaa ggg gaa gca   1178
His Val Thr Pro Lys Gly Ile Asn Gly Ile Asp Phe Lys Gly Glu Ala
            335                 340                 345 ata act ttt aaa gca act act gct gga atc ctt gct aca ctt tct cat   1226
Ile Thr Phe Lys Ala Thr Thr Ala Gly Ile Leu Ala Thr Leu Ser His
            350                 355                 360 tgt att gaa tta atg gta aaa cgg gaa gag agc tgg caa aaa aga cac   1274
Cys Ile Glu Leu Met Val Lys Arg Glu Glu Ser Trp Gln Lys Arg His
365                 370                 375 gat agg gaa gtg gaa aag agg aga cga gtg gag gaa gcg tac aag aat   1322
Asp Arg Glu Val Glu Lys Arg Arg Arg Val Glu Glu Ala Tyr Lys Asn
380                 385                 390                 395 gtg atg gaa gaa ctt aag aag aaa ccc cgt ttc gga ggg ccg gat tat   1370
Val Met Glu Glu Leu Lys Lys Lys Pro Arg Phe Gly Gly Pro Asp Tyr
                400                 405                 410 gaa gaa ggt cca aac agt ctg att aat gag gaa gag ttc ttt gat gct   1418
Glu Glu Gly Pro Asn Ser Leu Ile Asn Glu Glu Glu Phe Phe Asp Ala
            415                 420                 425 gtt gaa gct gct ctt gac aga caa gat aaa ata gag gaa cag tca cag   1466
Val Glu Ala Ala Leu Asp Arg Gln Asp Lys Ile Glu Glu Gln Ser Gln
            430                 435                 440 agt gaa aag gtc agg tta cac tgg ccc aca tca ttg cca tct gga gac   1514
Ser Glu Lys Val Arg Leu His Trp Pro Thr Ser Leu Pro Ser Gly Asp
            445                 450                 455 acc ttt tct tct gtc ggg acg cat aga ttt gta caa aag ccc tat agt   1562
Thr Phe Ser Ser Val Gly Thr His Arg Phe Val Gln Lys Pro Tyr Ser
460                 465                 470                 475 cgc tct tcc tcc atg tct tcc att gat cta gtc agt gcc tct gac gat   1610
Arg Ser Ser Ser Met Ser Ser Ile Asp Leu Val Ser Ala Ser Asp Asp
```

```
                                                    -continued

Arg Ser Ser Ser Met Ser Ser Ile Asp Leu Val Ser Ala Ser Asp Asp
                480             485             490 gtt cac aga ttc agc tcc cag gtt gaa gaa atg gta cag aac cac atg    1658
Val His Arg Phe Ser Ser Gln Val Glu Glu Met Val Gln Asn His Met
            495                 500                 505 aat tat tca tta cag gat gta ggt ggt gat gca aat tgg caa ctg gtt    1706
Asn Tyr Ser Leu Gln Asp Val Gly Gly Asp Ala Asn Trp Gln Leu Val
        510                 515                 520 gtt gaa gaa gga gaa atg aag gta tac aga aga gaa gtg gaa gaa aat    1754
Val Glu Glu Gly Glu Met Lys Val Tyr Arg Arg Glu Val Glu Glu Asn
    525                 530                 535 gga att gtt ctg gat cct ttg aaa gct act cat gca gtt aaa ggt gtt    1802
Gly Ile Val Leu Asp Pro Leu Lys Ala Thr His Ala Val Lys Gly Val
540                 545                 550                 555 aca gga cat gag gtc tgc aat tac ttt tgg aat gtt gat gtt cgc aat    1850
Thr Gly His Glu Val Cys Asn Tyr Phe Trp Asn Val Asp Val Arg Asn
                560                 565                 570 gac tgg gaa act act ata gaa aac ttt cat gtg gtg gaa aca tta gct    1898
Asp Trp Glu Thr Thr Ile Glu Asn Phe His Val Val Glu Thr Leu Ala
            575                 580                 585 gat aat gca atc atc gtt tat caa acg cac aag aga gta tgg ccc gct    1946
Asp Asn Ala Ile Ile Val Tyr Gln Thr His Lys Arg Val Trp Pro Ala
        590                 595                 600 tct cag aga gac gta ctg tat ctt tct gct att cga aag atc cca gcc    1994
Ser Gln Arg Asp Val Leu Tyr Leu Ser Ala Ile Arg Lys Ile Pro Ala
    605                 610                 615 ttg act gaa aat gac cct gaa act tgg ata gtt tgt aat ttt tct gtg    2042
Leu Thr Glu Asn Asp Pro Glu Thr Trp Ile Val Cys Asn Phe Ser Val
620                 625                 630                 635 gat cat gat agt gct cct ctg aac aat cga tgt gtc cgt gcc aaa atc    2090
Asp His Asp Ser Ala Pro Leu Asn Asn Arg Cys Val Arg Ala Lys Ile
                640                 645                 650 aat att gct atg att tgt caa act tta gta agc cca cca gag gga gac    2138
Asn Ile Ala Met Ile Cys Gln Thr Leu Val Ser Pro Pro Glu Gly Asp
            655                 660                 665 cag gag ata agc aga gac aac att ctg tgc aag atc acg tat gta gct    2186
Gln Glu Ile Ser Arg Asp Asn Ile Leu Cys Lys Ile Thr Tyr Val Ala
        670                 675                 680 aat gtg aac cca gga gga tgg gcg cca gct tcg gtc tta aga gca gtg    2234
Asn Val Asn Pro Gly Gly Trp Ala Pro Ala Ser Val Leu Arg Ala Val
    685                 690                 695 gca aag cga gaa tac cct aag ttt cta aaa cgt ttt act tct tat gtc    2282
Ala Lys Arg Glu Tyr Pro Lys Phe Leu Lys Arg Phe Thr Ser Tyr Val
700                 705                 710                 715 caa gaa aaa act gca gga aaa cca att ttg ttt tag tattaacagt         2328
Gln Glu Lys Thr Ala Gly Lys Pro Ile Leu Phe
                720                 725 gactgaagca aggctgcgtg acgttccatg ttggagaaag gagggaaaaa ataaaaagaa   2388
tcctctaagc tggaacgtag gatctacagc cttgtctgtg gcccaagaag aaacattgca   2448
atcgtaaagc tgggtatcca gcactagcca tctcctgcta ggcctcctcg ctcagcgtgt   2508
aactataaat acatgtagaa tcacatggat atggctatat ttttatttgc ttgctccttg   2568
gagtgaaaac aaataacttt gaattacaac taggaattaa ccgatgcttt aattttgagg   2628 aacttttca gaattttta tttaccatgg tccagcctaa gatcctcagt tgtatcaggt     2688
tttgtgcaca aaagaaaagc acaaagttg aacgcacctg aggcatgtgc tctctgtgca   2748
ccaaatactc ag                                                       2760
```

```
<210> SEQ ID NO 94
<211> LENGTH: 726
<212> TYPE: PRT
<213> ORGANISM: Mus musculus

<400> SEQUENCE: 94
```

| | | | | | | | | | | | | | | | |
|---|---|---|---|---|---|---|---|---|---|---|---|---|---|---|---|
| Leu | Ala | Ser | Arg | Gly | Pro | Ser | Gly | Gly | Ala | Gly | Arg | Ser | Ala | | |
| 1 | | | | 5 | | | | | 10 | | | | | 15 | |
| Gly | Val | Thr | Ala | Thr | Ala | Ala | Asp | Gly | Trp | Lys | Gly | Arg | Leu | Ser | Ser |
| | | | 20 | | | | | 25 | | | | | 30 | | |
| Pro | Leu | Val | Leu | Leu | Pro | Arg | Ser | Ala | Arg | Cys | Gln | Ala | Arg | Arg | |
| | | 35 | | | | | 40 | | | | | 45 | | | |
| Arg | Arg | Gly | Gly | Arg | Ala | Ser | Ser | Leu | Phe | Leu | Phe | Pro | His | Ser | Pro |
| | 50 | | | | | 55 | | | | | 60 | | | | |
| Glu | Arg | Ala | Leu | Leu | Ala | Val | Pro | Ser | Pro | Asp | Pro | Ser | Pro | Gln | Gly |
| 65 | | | | | 70 | | | | | 75 | | | | | 80 |
| Leu | Gly | Ala | Cys | Thr | Gly | Ala | Ala | Arg | Gly | Ala | Gly | Ala | Gly | Leu | Leu |
| | | | | 85 | | | | | 90 | | | | | 95 | |
| Leu | Gly | Cys | Arg | Val | Ser | Met | Ser | Asp | Asn | Gln | Ser | Trp | Asn | Ser | Ser |
| | | | 100 | | | | | 105 | | | | | 110 | | |
| Gly | Ser | Glu | Glu | Asp | Pro | Glu | Thr | Glu | Ser | Gly | Pro | Pro | Val | Glu | Arg |
| | | 115 | | | | | 120 | | | | | 125 | | | |
| Cys | Gly | Val | Leu | Ser | Lys | Trp | Thr | Asn | Tyr | Ile | His | Gly | Trp | Gln | Asp |
| | 130 | | | | | 135 | | | | | 140 | | | | |
| Arg | Trp | Val | Val | Leu | Lys | Asn | Asn | Thr | Leu | Ser | Tyr | Tyr | Lys | Ser | Glu |
| 145 | | | | | 150 | | | | | 155 | | | | | 160 |
| Asp | Glu | Thr | Glu | Tyr | Gly | Cys | Arg | Gly | Ser | Ile | Cys | Leu | Ser | Lys | Ala |
| | | | | 165 | | | | | 170 | | | | | 175 | |
| Val | Ile | Thr | Pro | His | Asp | Phe | Asp | Glu | Cys | Arg | Phe | Asp | Ile | Ser | Val |
| | | | 180 | | | | | 185 | | | | | 190 | | |
| Asn | Asp | Ser | Val | Trp | Tyr | Leu | Arg | Ala | Gln | Asp | Pro | Glu | His | Arg | Gln |
| | | 195 | | | | | 200 | | | | | 205 | | | |
| Gln | Trp | Val | Asp | Ala | Ile | Glu | Gln | His | Lys | Thr | Glu | Ser | Gly | Tyr | Gly |
| | 210 | | | | | 215 | | | | | 220 | | | | |
| Ser | Glu | Ser | Ser | Leu | Arg | Arg | His | Gly | Ser | Met | Val | Ser | Leu | Val | Ser |
| 225 | | | | | 230 | | | | | 235 | | | | | 240 |
| Gly | Ala | Ser | Gly | Tyr | Ser | Ala | Thr | Ser | Thr | Ser | Ser | Phe | Lys | Lys | Gly |
| | | | | 245 | | | | | 250 | | | | | 255 | |
| His | Ser | Leu | Arg | Glu | Lys | Leu | Ala | Glu | Met | Glu | Thr | Phe | Arg | Asp | Ile |
| | | | 260 | | | | | 265 | | | | | 270 | | |
| Leu | Cys | Arg | Gln | Val | Asp | Thr | Leu | Gln | Lys | Tyr | Phe | Asp | Val | Cys | Ala |
| | | 275 | | | | | 280 | | | | | 285 | | | |
| Asp | Ala | Val | Ser | Lys | Asp | Glu | Leu | Gln | Arg | Asp | Lys | Val | Val | Glu | Asp |
| | 290 | | | | | 295 | | | | | 300 | | | | |
| Asp | Glu | Asp | Asp | Phe | Pro | Thr | Thr | Arg | Ser | Asp | Gly | Asp | Phe | Leu | His |
| 305 | | | | | 310 | | | | | 315 | | | | | 320 |
| Asn | Thr | Asn | Gly | Asn | Lys | Glu | Lys | Leu | Phe | Pro | His | Val | Thr | Pro | Lys |
| | | | | 325 | | | | | 330 | | | | | 335 | |
| Gly | Ile | Asn | Gly | Ile | Asp | Phe | Lys | Gly | Glu | Ala | Ile | Thr | Phe | Lys | Ala |
| | | | 340 | | | | | 345 | | | | | 350 | | |
| Thr | Thr | Ala | Gly | Ile | Leu | Ala | Thr | Leu | Ser | His | Cys | Ile | Glu | Leu | Met |
| | | 355 | | | | | 360 | | | | | 365 | | | |
| Val | Lys | Arg | Glu | Glu | Ser | Trp | Gln | Lys | Arg | His | Asp | Arg | Glu | Val | Glu |
| | 370 | | | | | 375 | | | | | 380 | | | | |

```
Lys Arg Arg Arg Val Glu Glu Ala Tyr Lys Asn Val Met Glu Glu Leu
385                 390                 395                 400

Lys Lys Lys Pro Arg Phe Gly Gly Pro Asp Tyr Glu Gly Pro Asn
            405                 410                 415

Ser Leu Ile Asn Glu Glu Glu Phe Phe Asp Ala Val Glu Ala Ala Leu
                420                 425                 430

Asp Arg Gln Asp Lys Ile Glu Glu Gln Ser Gln Ser Gly Lys Val Arg
            435                 440                 445

Leu His Trp Pro Thr Ser Leu Pro Ser Gly Asp Thr Phe Ser Ser Val
        450                 455                 460

Gly Thr His Arg Phe Val Gln Lys Pro Tyr Ser Arg Ser Ser Ser Met
465                 470                 475                 480

Ser Ser Ile Asp Leu Val Ser Ala Ser Asp Val His Arg Phe Ser
                485                 490                 495

Ser Gln Val Glu Glu Met Val Gln Asn His Met Asn Tyr Ser Leu Gln
            500                 505                 510

Asp Val Gly Gly Asp Ala Asn Trp Gln Leu Val Glu Glu Gly Glu
        515                 520                 525

Met Lys Val Tyr Arg Arg Glu Val Glu Glu Asn Gly Ile Val Leu Asp
530                 535                 540

Pro Leu Lys Ala Thr His Ala Val Lys Gly Val Thr Gly His Glu Val
545                 550                 555                 560

Cys Asn Tyr Phe Trp Asn Val Asp Val Arg Asn Asp Trp Glu Thr Thr
                565                 570                 575

Ile Glu Asn Phe His Val Val Glu Thr Leu Ala Asp Asn Ala Ile Ile
            580                 585                 590

Val Tyr Gln Thr His Lys Arg Val Trp Pro Ala Ser Gln Arg Asp Val
        595                 600                 605

Leu Tyr Leu Ser Ala Ile Arg Lys Ile Pro Ala Leu Thr Glu Asn Asp
610                 615                 620

Pro Glu Thr Trp Ile Val Cys Asn Phe Ser Val Asp His Asp Ser Ala
625                 630                 635                 640

Pro Leu Asn Asn Arg Cys Val Arg Ala Lys Ile Asn Ile Ala Met Ile
                645                 650                 655

Cys Gln Thr Leu Val Ser Pro Pro Glu Gly Asp Gln Glu Ile Ser Arg
            660                 665                 670

Asp Asn Ile Leu Cys Lys Ile Thr Tyr Val Ala Asn Val Asn Pro Gly
        675                 680                 685

Gly Trp Ala Pro Ala Ser Val Leu Arg Ala Val Ala Lys Arg Glu Tyr
690                 695                 700

Pro Lys Phe Leu Lys Arg Phe Thr Ser Tyr Val Gln Glu Lys Thr Ala
705                 710                 715                 720

Gly Lys Pro Ile Leu Phe
                725

<210> SEQ ID NO 95
<211> LENGTH: 2682
<212> TYPE: DNA
<213> ORGANISM: Mus musculus
<220> FEATURE:
<221> NAME/KEY: CDS
<222> LOCATION: (138)..(2240)
<223> OTHER INFORMATION:

<400> SEQUENCE: 95
```

-continued

| | |
|---|---|
| cgggccacca cgtgtaaata gtatcggacc cggcaggaag atggcggctg tagcggaggt | 60 |
| gtgagtgagt ggatctgggt ctctgccgtt ggcttggctc ttcccgtctt cctccctcc | 120 |

```
tccctccctg actgagg ttg gca tct agg ggg ccg agt tca ggt ggc ggc      170
                Leu Ala Ser Arg Gly Pro Ser Ser Gly Gly Gly
                 1               5                  10 gcc ggg cgc agc gca ggg gtc acg gcc acg gcg gct gac ggc tgg aag      218
Ala Gly Arg Ser Ala Gly Val Thr Ala Thr Ala Ala Asp Gly Trp Lys
             15                  20                  25 ggc agg ctt tct tcg ccg ctc gtc ctc ctt ccc cgg tcc gct cgg tgt      266
Gly Arg Leu Ser Ser Pro Leu Val Leu Leu Pro Arg Ser Ala Arg Cys
         30                  35                  40 cag gcg cgg cgg cgg cgg cgc ggc ggg cgc gct tcg tcc ctc ttc ctg      314
Gln Ala Arg Arg Arg Arg Arg Gly Gly Arg Ala Ser Ser Leu Phe Leu
     45                  50                  55 ttc cct cac tcc ccg gag cgg gct ctc ttg gcg gtg cca tcc ccc gac      362
Phe Pro His Ser Pro Glu Arg Ala Leu Leu Ala Val Pro Ser Pro Asp
 60                  65                  70                  75 cct tca ccc cag gga cta ggc gcc tgc act ggc gca gct cgc gga gcg      410
Pro Ser Pro Gln Gly Leu Gly Ala Cys Thr Gly Ala Ala Arg Gly Ala
                 80                  85                  90 ggg gcc ggt ctc ctg ctc ggc tgt cgc gtc tcc atg tcg gat aac cag      458
Gly Ala Gly Leu Leu Leu Gly Cys Arg Val Ser Met Ser Asp Asn Gln
             95                 100                 105 agc tgg aac tcg tcg ggc tcg gag gag gat ccg gag acg gag tcc ggg      506
Ser Trp Asn Ser Ser Gly Ser Glu Glu Asp Pro Glu Thr Glu Ser Gly
         110                 115                 120 ccg cct gtg gag cgc tgc ggg gtc ctc agc aag tgg aca aac tat att      554
Pro Pro Val Glu Arg Cys Gly Val Leu Ser Lys Trp Thr Asn Tyr Ile
     125                 130                 135 cat gga tgg cag gat cgt tgg gta gtt ttg aaa aat aat act ttg agt      602
His Gly Trp Gln Asp Arg Trp Val Val Leu Lys Asn Asn Thr Leu Ser
140                 145                 150                 155 tac tac aaa tct gaa gat gaa aca gaa tat ggc tgt agg gga tcc atc      650
Tyr Tyr Lys Ser Glu Asp Glu Thr Glu Tyr Gly Cys Arg Gly Ser Ile
                 160                 165                 170 tgt ctt agc aag gct gtg atc acg cct cac gat ttt gat gaa tgc cgg      698
Cys Leu Ser Lys Ala Val Ile Thr Pro His Asp Phe Asp Glu Cys Arg
             175                 180                 185 ttt gat atc agt gta aat gat agt gtt tgg tac ctt cga gct cag gac      746
Phe Asp Ile Ser Val Asn Asp Ser Val Trp Tyr Leu Arg Ala Gln Asp
         190                 195                 200 ccg gag cac aga cag caa tgg gta gac gcc att gaa cag cac aag act      794
Pro Glu His Arg Gln Gln Trp Val Asp Ala Ile Glu Gln His Lys Thr
     205                 210                 215 gaa tcg gga tat gga tct gag tcc agc ttg cgt aga cat ggc tca atg      842
Glu Ser Gly Tyr Gly Ser Glu Ser Ser Leu Arg Arg His Gly Ser Met
220                 225                 230                 235 gtg tca ctg gtg tct gga gcg agt ggc tat tct gct acg tcc acc tct      890
Val Ser Leu Val Ser Gly Ala Ser Gly Tyr Ser Ala Thr Ser Thr Ser
                 240                 245                 250 tct ttc aag aaa ggc cac agt tta cgt gag aaa ctg gct gaa atg gag      938
Ser Phe Lys Lys Gly His Ser Leu Arg Glu Lys Leu Ala Glu Met Glu
             255                 260                 265 aca ttt cgg gac atc ctg tgc cgg cag gtt gat act ctc cag aag tac      986
Thr Phe Arg Asp Ile Leu Cys Arg Gln Val Asp Thr Leu Gln Lys Tyr
         270                 275                 280 ttt gat gtc tgt gct gac gct gtc tcc aag gat gag ctt cag agg gat     1034
Phe Asp Val Cys Ala Asp Ala Val Ser Lys Asp Glu Leu Gln Arg Asp
     285                 290                 295
```

-continued

| | | | | | | | | | | | | | | | | |
|---|---|---|---|---|---|---|---|---|---|---|---|---|---|---|---|---|
| aaa | gtc | gta | gaa | gat | gat | gaa | gat | gac | ttc | cct | aca | act | cgt | tct | gat | 1082 |
| Lys | Val | Val | Glu | Asp | Asp | Glu | Asp | Asp | Phe | Pro | Thr | Thr | Arg | Ser | Asp | |
| 300 | | | | | 305 | | | | 310 | | | | | 315 | | |
| gga | gac | ttt | ttg | cac | aat | acc | aat | ggt | aat | aaa | gaa | aaa | tta | ttt | cca | 1130 |
| Gly | Asp | Phe | Leu | His | Asn | Thr | Asn | Gly | Asn | Lys | Glu | Lys | Leu | Phe | Pro | |
| | | | 320 | | | | | 325 | | | | | 330 | | | |
| cat | gta | aca | cca | aaa | gga | att | aat | ggc | ata | gac | ttt | aaa | ggg | gaa | gca | 1178 |
| His | Val | Thr | Pro | Lys | Gly | Ile | Asn | Gly | Ile | Asp | Phe | Lys | Gly | Glu | Ala | |
| | | | 335 | | | | | 340 | | | | | 345 | | | |
| ata | act | ttt | aaa | gca | act | act | gct | gga | atc | ctt | gct | aca | ctt | tct | cat | 1226 |
| Ile | Thr | Phe | Lys | Ala | Thr | Thr | Ala | Gly | Ile | Leu | Ala | Thr | Leu | Ser | His | |
| | | | 350 | | | | | 355 | | | | | 360 | | | |
| tgt | att | gaa | tta | atg | gta | aaa | cgg | gaa | gag | agc | tgg | caa | aaa | aga | cac | 1274 |
| Cys | Ile | Glu | Leu | Met | Val | Lys | Arg | Glu | Glu | Ser | Trp | Gln | Lys | Arg | His | |
| 365 | | | | | 370 | | | | 375 | | | | | | | |
| gat | agg | gaa | gtg | gaa | aag | agg | aga | cga | gtg | gag | gaa | gcg | tac | aag | aat | 1322 |
| Asp | Arg | Glu | Val | Glu | Lys | Arg | Arg | Arg | Val | Glu | Glu | Ala | Tyr | Lys | Asn | |
| 380 | | | | | 385 | | | | 390 | | | | | 395 | | |
| gtg | atg | gaa | gaa | ctt | aag | aag | aaa | ccc | cgt | ttc | gga | ggg | ccg | gat | tat | 1370 |
| Val | Met | Glu | Glu | Leu | Lys | Lys | Lys | Pro | Arg | Phe | Gly | Gly | Pro | Asp | Tyr | |
| | | | | 400 | | | | | 405 | | | | | 410 | | |
| gaa | gaa | ggt | cca | aac | agt | ctg | att | aat | gag | gaa | gag | ttc | ttt | gat | gct | 1418 |
| Glu | Glu | Gly | Pro | Asn | Ser | Leu | Ile | Asn | Glu | Glu | Glu | Phe | Phe | Asp | Ala | |
| | | | 415 | | | | | 420 | | | | | 425 | | | |
| gtt | gaa | gct | gct | ctt | gac | aga | caa | gat | aaa | ata | gag | gaa | cag | tca | cag | 1466 |
| Val | Glu | Ala | Ala | Leu | Asp | Arg | Gln | Asp | Lys | Ile | Glu | Glu | Gln | Ser | Gln | |
| | | 430 | | | | | 435 | | | | | 440 | | | | |
| agt | gaa | aag | gtc | agg | tta | cac | tgg | ccc | aca | tca | ttg | cca | tct | gga | gac | 1514 |
| Ser | Glu | Lys | Val | Arg | Leu | His | Trp | Pro | Thr | Ser | Leu | Pro | Ser | Gly | Asp | |
| | | 445 | | | | | 450 | | | | | 455 | | | | |
| acc | ttt | tct | tct | gtc | ggg | acg | cat | aga | ttt | gta | caa | aag | gtt | gaa | gaa | 1562 |
| Thr | Phe | Ser | Ser | Val | Gly | Thr | His | Arg | Phe | Val | Gln | Lys | Val | Glu | Glu | |
| 460 | | | | | 465 | | | | 470 | | | | | 475 | | |
| atg | gta | cag | aac | cac | atg | aat | tat | tca | tta | cag | gat | gta | ggt | ggt | gat | 1610 |
| Met | Val | Gln | Asn | His | Met | Asn | Tyr | Ser | Leu | Gln | Asp | Val | Gly | Gly | Asp | |
| | | | | 480 | | | | | 485 | | | | | 490 | | |
| gca | aat | tgg | caa | ctg | gtt | gtt | gaa | gaa | gga | gaa | atg | aag | gta | tac | aga | 1658 |
| Ala | Asn | Trp | Gln | Leu | Val | Val | Glu | Glu | Gly | Glu | Met | Lys | Val | Tyr | Arg | |
| | | | 495 | | | | | 500 | | | | | 505 | | | |
| aga | gaa | gtg | gaa | gaa | aat | gga | att | gtt | ctg | gat | cct | ttg | aaa | gct | act | 1706 |
| Arg | Glu | Val | Glu | Glu | Asn | Gly | Ile | Val | Leu | Asp | Pro | Leu | Lys | Ala | Thr | |
| | | 510 | | | | | 515 | | | | | 520 | | | | |
| cat | gca | gtt | aaa | ggt | gtt | aca | gga | cat | gag | gtc | tgc | aat | tac | ttt | tgg | 1754 |
| His | Ala | Val | Lys | Gly | Val | Thr | Gly | His | Glu | Val | Cys | Asn | Tyr | Phe | Trp | |
| | | 525 | | | | | 530 | | | | | 535 | | | | |
| aat | gtt | gat | gtt | cgc | aat | gac | tgg | gaa | act | act | ata | gaa | aac | ttt | cat | 1802 |
| Asn | Val | Asp | Val | Arg | Asn | Asp | Trp | Glu | Thr | Thr | Ile | Glu | Asn | Phe | His | |
| 540 | | | | | 545 | | | | 550 | | | | | 555 | | |
| gtg | gtg | gaa | aca | tta | gct | gat | aat | gca | atc | atc | gtt | tat | caa | acg | cac | 1850 |
| Val | Val | Glu | Thr | Leu | Ala | Asp | Asn | Ala | Ile | Ile | Val | Tyr | Gln | Thr | His | |
| | | | 560 | | | | | 565 | | | | | 570 | | | |
| aag | aga | gta | tgg | ccc | gct | tct | cag | aga | gac | gta | ctg | tat | ctt | tct | gct | 1898 |
| Lys | Arg | Val | Trp | Pro | Ala | Ser | Gln | Arg | Asp | Val | Leu | Tyr | Leu | Ser | Ala | |
| | | | 575 | | | | | 580 | | | | | 585 | | | |
| att | cga | aag | atc | cca | gcc | ttg | act | gaa | aat | gac | cct | gaa | act | tgg | ata | 1946 |
| Ile | Arg | Lys | Ile | Pro | Ala | Leu | Thr | Glu | Asn | Asp | Pro | Glu | Thr | Trp | Ile | |
| | | | 590 | | | | | 595 | | | | | 600 | | | |
| gtt | tgt | aat | ttt | tct | gtg | gat | cat | gat | agt | gct | cct | ctg | aac | aat | cga | 1994 |
| Val | Cys | Asn | Phe | Ser | Val | Asp | His | Asp | Ser | Ala | Pro | Leu | Asn | Asn | Arg | |

|  |  |  |  |  |  |  |  |  |  |  |  |  |  |  |
|---|---|---|---|---|---|---|---|---|---|---|---|---|---|---|
|  | 605 |  |  |  | 610 |  |  |  |  | 615 |  |  |  |  |
| tgt | gtc | cgt | gcc | aaa | atc | aat | att | gct | atg | att | tgt | caa | act | tta | gta | 2042 |
| Cys | Val | Arg | Ala | Lys | Ile | Asn | Ile | Ala | Met | Ile | Cys | Gln | Thr | Leu | Val |
| 620 |  |  |  |  | 625 |  |  |  |  | 630 |  |  |  |  | 635 |

| agc | cca | cca | gag | gga | gac | cag | gag | ata | agc | aga | gac | aac | att | ctg | tgc | 2090 |
|---|---|---|---|---|---|---|---|---|---|---|---|---|---|---|---|---|
| Ser | Pro | Pro | Glu | Gly | Asp | Gln | Glu | Ile | Ser | Arg | Asp | Asn | Ile | Leu | Cys |
|  |  |  |  | 640 |  |  |  |  | 645 |  |  |  |  | 650 |  |

| aag | atc | acg | tat | gta | gct | aat | gtg | aac | cca | gga | gga | tgg | gcg | cca | gct | 2138 |
|---|---|---|---|---|---|---|---|---|---|---|---|---|---|---|---|---|
| Lys | Ile | Thr | Tyr | Val | Ala | Asn | Val | Asn | Pro | Gly | Gly | Trp | Ala | Pro | Ala |
|  |  |  | 655 |  |  |  |  | 660 |  |  |  |  | 665 |  |  |

| tcg | gtc | tta | aga | gca | gtg | gca | aag | cga | gaa | tac | cct | aag | ttt | cta | aaa | 2186 |
|---|---|---|---|---|---|---|---|---|---|---|---|---|---|---|---|---|
| Ser | Val | Leu | Arg | Ala | Val | Ala | Lys | Arg | Glu | Tyr | Pro | Lys | Phe | Leu | Lys |
|  |  | 670 |  |  |  |  | 675 |  |  |  |  | 680 |  |  |  |

| cgt | ttt | act | tct | tat | gtc | caa | gaa | aaa | act | gca | gga | aaa | cca | att | ttg | 2234 |
|---|---|---|---|---|---|---|---|---|---|---|---|---|---|---|---|---|
| Arg | Phe | Thr | Ser | Tyr | Val | Gln | Glu | Lys | Thr | Ala | Gly | Lys | Pro | Ile | Leu |
|  | 685 |  |  |  |  | 690 |  |  |  |  | 695 |  |  |  |  |

| ttt | tag | tattaacagt | gactgaagca | aggctgcgtg | acgttccatg | ttggagaaag | 2290 |
|---|---|---|---|---|---|---|---|
| Phe |  |  |  |  |  |  |  |
| 700 |  |  |  |  |  |  |  |

| gagggaaaaa | ataaaaagaa | tcctctaagc | tggaacgtag | gatctacagc | cttgtctgtg | 2350 |
|---|---|---|---|---|---|---|
| gcccaagaag | aaacattgca | atcgtaaagc | tgggtatcca | gcactagcca | tctcctgcta | 2410 |
| ggcctcctcg | ctcagcgtgt | aactataaat | acatgtagaa | tcacatggat | atggctatat | 2470 |
| ttttatttgc | ttgctccttg | gagtgaaaac | aaataacttt | gaattacaac | taggaattaa | 2530 |
| ccgatgcttt | aattttgagg | aacttttca | gaattttta | tttaccatgg | tccagcctaa | 2590 |
| gatcctcagt | tgtatcaggt | tttgtgcaca | aagaaaagc | acaaagttg | aacgcacctg | 2650 |
| aggcatgtgc | tctctgtgca | ccaaatactc | ag |  |  | 2682 |

<210> SEQ ID NO 96
<211> LENGTH: 700
<212> TYPE: PRT
<213> ORGANISM: Mus musculus

<400> SEQUENCE: 96

| Leu | Ala | Ser | Arg | Gly | Pro | Ser | Ser | Gly | Gly | Ala | Gly | Arg | Ser | Ala |
|---|---|---|---|---|---|---|---|---|---|---|---|---|---|---|
| 1 |  |  |  | 5 |  |  |  |  | 10 |  |  |  |  | 15 |

| Gly | Val | Thr | Ala | Thr | Ala | Ala | Asp | Gly | Trp | Lys | Gly | Arg | Leu | Ser | Ser |
|---|---|---|---|---|---|---|---|---|---|---|---|---|---|---|---|
|  |  |  | 20 |  |  |  |  | 25 |  |  |  |  | 30 |  |  |

| Pro | Leu | Val | Leu | Leu | Pro | Arg | Ser | Ala | Arg | Cys | Gln | Ala | Arg | Arg |
|---|---|---|---|---|---|---|---|---|---|---|---|---|---|---|
|  |  |  | 35 |  |  |  |  | 40 |  |  |  | 45 |  |  |

| Arg | Arg | Gly | Gly | Arg | Ala | Ser | Ser | Leu | Phe | Leu | Phe | Pro | His | Ser | Pro |
|---|---|---|---|---|---|---|---|---|---|---|---|---|---|---|---|
|  | 50 |  |  |  |  | 55 |  |  |  |  | 60 |  |  |  |  |

| Glu | Arg | Ala | Leu | Leu | Ala | Val | Pro | Ser | Pro | Asp | Pro | Ser | Pro | Gln | Gly |
|---|---|---|---|---|---|---|---|---|---|---|---|---|---|---|---|
| 65 |  |  |  |  | 70 |  |  |  |  | 75 |  |  |  |  | 80 |

| Leu | Gly | Ala | Cys | Thr | Gly | Ala | Ala | Arg | Gly | Ala | Gly | Ala | Gly | Leu | Leu |
|---|---|---|---|---|---|---|---|---|---|---|---|---|---|---|---|
|  |  |  |  | 85 |  |  |  |  | 90 |  |  |  |  | 95 |  |

| Leu | Gly | Cys | Arg | Val | Ser | Met | Ser | Asp | Asn | Gln | Ser | Trp | Asn | Ser | Ser |
|---|---|---|---|---|---|---|---|---|---|---|---|---|---|---|---|
|  |  |  | 100 |  |  |  |  | 105 |  |  |  |  | 110 |  |  |

| Gly | Ser | Glu | Glu | Asp | Pro | Glu | Thr | Glu | Ser | Gly | Pro | Pro | Val | Glu | Arg |
|---|---|---|---|---|---|---|---|---|---|---|---|---|---|---|---|
|  |  | 115 |  |  |  |  | 120 |  |  |  |  | 125 |  |  |  |

| Cys | Gly | Val | Leu | Ser | Lys | Trp | Thr | Asn | Tyr | Ile | His | Gly | Trp | Gln | Asp |
|---|---|---|---|---|---|---|---|---|---|---|---|---|---|---|---|
|  | 130 |  |  |  |  | 135 |  |  |  |  | 140 |  |  |  |  |

| Arg | Trp | Val | Val | Leu | Lys | Asn | Asn | Thr | Leu | Ser | Tyr | Tyr | Lys | Ser | Glu |
|---|---|---|---|---|---|---|---|---|---|---|---|---|---|---|---|
| 145 |  |  |  |  | 150 |  |  |  |  | 155 |  |  |  |  | 160 |

| Asp | Glu | Thr | Glu | Tyr | Gly | Cys | Arg | Gly | Ser | Ile | Cys | Leu | Ser | Lys | Ala |
|---|---|---|---|---|---|---|---|---|---|---|---|---|---|---|---|

```
                            165                 170                 175
Val Ile Thr Pro His Asp Phe Asp Glu Cys Arg Phe Asp Ile Ser Val
                180                 185                 190

Asn Asp Ser Val Trp Tyr Leu Arg Ala Gln Asp Pro Glu His Arg Gln
            195                 200                 205

Gln Trp Val Asp Ala Ile Glu Gln His Lys Thr Glu Ser Gly Tyr Gly
        210                 215                 220

Ser Glu Ser Ser Leu Arg Arg His Gly Ser Met Val Ser Leu Val Ser
225                 230                 235                 240

Gly Ala Ser Gly Tyr Ser Ala Thr Ser Thr Ser Ser Phe Lys Lys Gly
                245                 250                 255

His Ser Leu Arg Glu Lys Leu Ala Glu Met Glu Thr Phe Arg Asp Ile
                260                 265                 270

Leu Cys Arg Gln Val Asp Thr Leu Gln Lys Tyr Phe Asp Val Cys Ala
            275                 280                 285

Asp Ala Val Ser Lys Asp Glu Leu Gln Arg Asp Lys Val Val Glu Asp
        290                 295                 300

Asp Glu Asp Asp Phe Pro Thr Thr Arg Ser Asp Gly Asp Phe Leu His
305                 310                 315                 320

Asn Thr Asn Gly Asn Lys Glu Lys Leu Phe Pro His Val Thr Pro Lys
                325                 330                 335

Gly Ile Asn Gly Ile Asp Phe Lys Gly Glu Ala Ile Thr Phe Lys Ala
                340                 345                 350

Thr Thr Ala Gly Ile Leu Ala Thr Leu Ser His Cys Ile Glu Leu Met
            355                 360                 365

Val Lys Arg Glu Glu Ser Trp Gln Lys Arg His Asp Arg Glu Val Glu
        370                 375                 380

Lys Arg Arg Arg Val Glu Glu Ala Tyr Lys Asn Val Met Glu Glu Leu
385                 390                 395                 400

Lys Lys Lys Pro Arg Phe Gly Gly Pro Asp Tyr Glu Glu Gly Pro Asn
                405                 410                 415

Ser Leu Ile Asn Glu Glu Glu Phe Phe Asp Ala Val Glu Ala Ala Leu
                420                 425                 430

Asp Arg Gln Asp Lys Ile Glu Glu Gln Ser Gln Ser Glu Lys Val Arg
            435                 440                 445

Leu His Trp Pro Thr Ser Leu Pro Ser Gly Asp Thr Phe Ser Ser Val
        450                 455                 460

Gly Thr His Arg Phe Val Gln Lys Val Glu Glu Met Val Gln Asn His
465                 470                 475                 480

Met Asn Tyr Ser Leu Gln Asp Val Gly Gly Asp Ala Asn Trp Gln Leu
                485                 490                 495

Val Val Glu Glu Gly Glu Met Lys Val Tyr Arg Arg Glu Val Glu Glu
                500                 505                 510

Asn Gly Ile Val Leu Asp Pro Leu Lys Ala Thr His Ala Val Lys Gly
            515                 520                 525

Val Thr Gly His Glu Val Cys Asn Tyr Phe Trp Asn Val Asp Val Arg
        530                 535                 540

Asn Asp Trp Glu Thr Thr Ile Glu Asn Phe His Val Val Glu Thr Leu
545                 550                 555                 560

Ala Asp Asn Ala Ile Ile Val Tyr Gln Thr His Lys Arg Val Trp Pro
                565                 570                 575

Ala Ser Gln Arg Asp Val Leu Tyr Leu Ser Ala Ile Arg Lys Ile Pro
                580                 585                 590
```

```
Ala Leu Thr Glu Asn Asp Pro Glu Thr Trp Ile Val Cys Asn Phe Ser
        595                 600                 605

Val Asp His Asp Ser Ala Pro Leu Asn Asn Arg Cys Val Arg Ala Lys
        610                 615                 620

Ile Asn Ile Ala Met Ile Cys Gln Thr Leu Val Ser Pro Pro Glu Gly
625                 630                 635                 640

Asp Gln Glu Ile Ser Arg Asp Asn Ile Leu Cys Lys Ile Thr Tyr Val
                645                 650                 655

Ala Asn Val Asn Pro Gly Gly Trp Ala Pro Ser Val Leu Arg Ala
                660                 665                 670

Val Ala Lys Arg Glu Tyr Pro Lys Phe Leu Lys Arg Phe Thr Ser Tyr
        675                 680                 685

Val Gln Glu Lys Thr Ala Gly Lys Pro Ile Leu Phe
        690                 695                 700

<210> SEQ ID NO 97
<211> LENGTH: 2361
<212> TYPE: DNA
<213> ORGANISM: Bos taurus
<220> FEATURE:
<221> NAME/KEY: CDS
<222> LOCATION: (103)..(2295)
<223> OTHER INFORMATION:

<400> SEQUENCE: 97
cggcaggaag atggcggcct agcggaggtg tgagtggacc tgggtctctg cagctgggtt      60
ttccctcttc ccgtctttct cctcttttcc tctccccga gg ttg gca tcg agg        114
                                              Leu Ala Ser Arg
                                                  1 ggg cca aat tcg ggc ggc ggc gcc ggg cgc agc gca ggg gtc aca acg       162
Gly Pro Asn Ser Gly Gly Gly Ala Gly Arg Ser Ala Gly Val Thr Thr
 5                  10                  15                  20 acg gcg acg gct gac ggt tgg aag ggc agg ctt cct tcg ccc ctc gac       210
Thr Ala Thr Ala Asp Gly Trp Lys Gly Arg Leu Pro Ser Pro Leu Asp
                 25                  30                  35 ctc ctt ccc cgg tcc gct tgg tgt cag gcg cgg cgg cgg cgg cgg           258
Leu Leu Pro Arg Ser Ala Trp Cys Gln Ala Arg Arg Arg Arg Arg
             40                  45                  50 cgg cgc ggc ggg cgg act cca tcc ctc ctc ccg ctc cct cct gca ccg       306
Arg Arg Gly Gly Arg Thr Pro Ser Leu Leu Pro Leu Pro Pro Ala Pro
         55                  60                  65 gag cgg gca ctc ctt cct tcg cca tcc ccc gac cct tca ccc cgg gga      354
Glu Arg Ala Leu Leu Pro Ser Pro Ser Pro Asp Pro Ser Pro Arg Gly
 70                  75                  80 ctg ggc gcc tcc acc ggc gca gct cag gga gcg ggg gcc ggt ctc ctg      402
Leu Gly Ala Ser Thr Gly Ala Ala Gln Gly Ala Gly Ala Gly Leu Leu
85                  90                  95                 100 ctc ggc tgt cgc gcc tcc atg tcg gat aac cag agc tgg aac tcg tcg      450
Leu Gly Cys Arg Ala Ser Met Ser Asp Asn Gln Ser Trp Asn Ser Ser
                105                 110                 115 ggc tcg gag gag gat ccg gag acg gag tcc ggg ccg ccg gtg gag cgc      498
Gly Ser Glu Glu Asp Pro Glu Thr Glu Ser Gly Pro Pro Val Glu Arg
            120                 125                 130 tgc gga gtc ctc agc aag tgg aca aac tat att cat ggg tgg cag gat      546
Cys Gly Val Leu Ser Lys Trp Thr Asn Tyr Ile His Gly Trp Gln Asp
        135                 140                 145 cgc tgg gta gtt ttg aaa aat aac act ctg agt tac tac aaa tct gaa      594
Arg Trp Val Val Leu Lys Asn Asn Thr Leu Ser Tyr Tyr Lys Ser Glu
    150                 155                 160
```

```
gat gag aca gag tat ggc tgc aga gga tcc atc tgt ctt agc aag gct    642
Asp Glu Thr Glu Tyr Gly Cys Arg Gly Ser Ile Cys Leu Ser Lys Ala
165                 170                 175                 180 gtc atc acg cct cat gat ttt gat gaa tgc cga ttt gat att agt gta    690
Val Ile Thr Pro His Asp Phe Asp Glu Cys Arg Phe Asp Ile Ser Val
                185                 190                 195 aat gat agt gtt tgg tat ctt cgt gct caa gat cca gat cac aga cag    738
Asn Asp Ser Val Trp Tyr Leu Arg Ala Gln Asp Pro Asp His Arg Gln
        200                 205                 210 cag tgg ata gat gcc att gaa cag cac aag act gaa tct gga tat gga    786
Gln Trp Ile Asp Ala Ile Glu Gln His Lys Thr Glu Ser Gly Tyr Gly
            215                 220                 225 tct gaa tcc agc ttg cgt cga cat ggc tcc atg gta tca ttg gta tcc    834
Ser Glu Ser Ser Leu Arg Arg His Gly Ser Met Val Ser Leu Val Ser
230                 235                 240 gga gca agt ggc tat tct gca aca tcc acc tcc tca ttc aag aag ggc    882
Gly Ala Ser Gly Tyr Ser Ala Thr Ser Thr Ser Ser Phe Lys Lys Gly
245                 250                 255                 260 cac agt tta cgt gag aaa ctg gct gaa atg gaa acc ttt aga gat ata    930
His Ser Leu Arg Glu Lys Leu Ala Glu Met Glu Thr Phe Arg Asp Ile
                265                 270                 275 ctg tgt aga caa gtt gat acc cta cag aag ttc ttt gat gcc tgt gct    978
Leu Cys Arg Gln Val Asp Thr Leu Gln Lys Phe Phe Asp Ala Cys Ala
        280                 285                 290 gat gct gtc tcc aag gat gaa ttt caa agg gat aaa gtg gta gaa gat   1026
Asp Ala Val Ser Lys Asp Glu Phe Gln Arg Asp Lys Val Val Glu Asp
            295                 300                 305 gat gaa gat gac ttt cct acg aca cgt tct gat gga gac ttc ttg cat   1074
Asp Glu Asp Asp Phe Pro Thr Thr Arg Ser Asp Gly Asp Phe Leu His
310                 315                 320 aat acc aat ggc aat aag gaa aag gta ttt cca cat gta aca cca aaa   1122
Asn Thr Asn Gly Asn Lys Glu Lys Val Phe Pro His Val Thr Pro Lys
325                 330                 335                 340 gga att aat ggt ata gac ttt aaa ggt gag gcg ata act ttt aaa gca   1170
Gly Ile Asn Gly Ile Asp Phe Lys Gly Glu Ala Ile Thr Phe Lys Ala
                345                 350                 355 act act gcc gga atc ctt gct aca ctt tct cat tgt att gag ctg atg   1218
Thr Thr Ala Gly Ile Leu Ala Thr Leu Ser His Cys Ile Glu Leu Met
        360                 365                 370 gta aaa cgt gag gac agc tgg caa aag aga atg gac aag gaa act gag   1266
Val Lys Arg Glu Asp Ser Trp Gln Lys Arg Met Asp Lys Glu Thr Glu
            375                 380                 385 aag aga aga aga gtg gag gaa gca tac aaa aat gcc atg aca gaa ctt   1314
Lys Arg Arg Arg Val Glu Glu Ala Tyr Lys Asn Ala Met Thr Glu Leu
390                 395                 400 aag aaa aaa tcc cac ttt gga gga cca gat tat gag gaa ggc cca aac   1362
Lys Lys Lys Ser His Phe Gly Gly Pro Asp Tyr Glu Glu Gly Pro Asn
405                 410                 415                 420 agt ttg att aat gaa gag gag ttc ttt gat gct gtt gaa gct gct ctt   1410
Ser Leu Ile Asn Glu Glu Glu Phe Phe Asp Ala Val Glu Ala Ala Leu
                425                 430                 435 gac aga caa gat aaa ata gaa gaa cag tcg cag agt gaa aag gtc agg   1458
Asp Arg Gln Asp Lys Ile Glu Glu Gln Ser Gln Ser Glu Lys Val Arg
        440                 445                 450 tta cat tgg tct act tca atg cca tct gga gat gcc ttt tct tct gtg   1506
Leu His Trp Ser Thr Ser Met Pro Ser Gly Asp Ala Phe Ser Ser Val
            455                 460                 465 ggg act cat aga ttt gtc caa aag ccc tat agt cgc tct tcc tcc atg   1554
Gly Thr His Arg Phe Val Gln Lys Pro Tyr Ser Arg Ser Ser Ser Met
```

```
                470             475             480
tct tcc att gat cta gtc agt gcc tct gac ggt gtt cac aga ttc agc     1602
Ser Ser Ile Asp Leu Val Ser Ala Ser Asp Gly Val His Arg Phe Ser
485                 490                 495                 500 tcc cag gtt gaa gag atg gtg cag aac cac atg acc tat tca ttg cag     1650
Ser Gln Val Glu Glu Met Val Gln Asn His Met Thr Tyr Ser Leu Gln
                505                 510                 515 gat gta ggt ggg gac gcc aac tgg cag ttg gtt gta gaa gaa ggg gag     1698
Asp Val Gly Gly Asp Ala Asn Trp Gln Leu Val Val Glu Glu Gly Glu
            520                 525                 530 atg aag gta tat aga aga gaa gta gaa gaa aat ggg att gtt ctg gat     1746
Met Lys Val Tyr Arg Arg Glu Val Glu Glu Asn Gly Ile Val Leu Asp
        535                 540                 545 cct ttg aaa gct acc cat gca gtt aaa ggc gtt aca gga cac gag gtc     1794
Pro Leu Lys Ala Thr His Ala Val Lys Gly Val Thr Gly His Glu Val
    550                 555                 560 tgc aat tac ttc tgg aat gtt gat gtt cgc aat gat tgg gaa aca act     1842
Cys Asn Tyr Phe Trp Asn Val Asp Val Arg Asn Asp Trp Glu Thr Thr
565                 570                 575                 580 ata gaa aac ttt cat gtg gtg gaa aca tta gct gat aat gca atc atc     1890
Ile Glu Asn Phe His Val Val Glu Thr Leu Ala Asp Asn Ala Ile Ile
                585                 590                 595 att tat caa acg cac aag aga gtg tgg cca gcc tct cag cgg gat gtc     1938
Ile Tyr Gln Thr His Lys Arg Val Trp Pro Ala Ser Gln Arg Asp Val
            600                 605                 610 tta tat ctg tct gcc att cga aag ata cca gct ttg aat gaa aat gac     1986
Leu Tyr Leu Ser Ala Ile Arg Lys Ile Pro Ala Leu Asn Glu Asn Asp
        615                 620                 625 ccg gag act tgg ata gtt tgt aat ttt tct gta gat cac agc agt gct     2034
Pro Glu Thr Trp Ile Val Cys Asn Phe Ser Val Asp His Ser Ser Ala
    630                 635                 640 cct cta aac aat cga tgt gtc cgt gcc aaa ata aac gtt gct atg att     2082
Pro Leu Asn Asn Arg Cys Val Arg Ala Lys Ile Asn Val Ala Met Ile
645                 650                 655                 660 tgt cag acc ttg gtg agc ccc cca gag gga aac cag gag att agc agg     2130
Cys Gln Thr Leu Val Ser Pro Pro Glu Gly Asn Gln Glu Ile Ser Arg
                665                 670                 675 gac aac att cta tgc aag att aca tac gtg gcc aat gta aac cct gga     2178
Asp Asn Ile Leu Cys Lys Ile Thr Tyr Val Ala Asn Val Asn Pro Gly
            680                 685                 690 gga tgg gcc cca gcc tca gtg tta cgg gca gtg gca aag cga gaa tat     2226
Gly Trp Ala Pro Ala Ser Val Leu Arg Ala Val Ala Lys Arg Glu Tyr
        695                 700                 705 cca aag ttt cta aag cgt ttt act tct tac gta caa gaa aaa act gca     2274
Pro Lys Phe Leu Lys Arg Phe Thr Ser Tyr Val Gln Glu Lys Thr Ala
    710                 715                 720 gga aaa cct att ttg ttc tag tattaacagt gactgaagca aggctgtgtg        2325
Gly Lys Pro Ile Leu Phe
725                 730 acattccatg ttggaggaaa aaaaaaaaaa aaaaaa                             2361

<210> SEQ ID NO 98
<211> LENGTH: 730
<212> TYPE: PRT
<213> ORGANISM: Bos taurus

<400> SEQUENCE: 98

Leu Ala Ser Arg Gly Pro Asn Ser Gly Gly Gly Ala Gly Arg Ser Ala
1               5                   10                  15
```

-continued

```
Gly Val Thr Thr Thr Ala Thr Ala Asp Gly Trp Lys Gly Arg Leu Pro
            20                  25                  30

Ser Pro Leu Asp Leu Leu Pro Arg Ser Ala Trp Cys Gln Ala Arg Arg
        35                  40                  45

Arg Arg Arg Arg Arg Gly Gly Arg Thr Pro Ser Leu Leu Pro Leu
50                      55                  60

Pro Pro Ala Pro Glu Arg Ala Leu Leu Pro Ser Pro Ser Pro Asp Pro
65              70                  75                      80

Ser Pro Arg Gly Leu Gly Ala Ser Thr Gly Ala Ala Gln Gly Ala Gly
            85                  90                  95

Ala Gly Leu Leu Leu Gly Cys Arg Ala Ser Met Ser Asp Asn Gln Ser
            100                 105                 110

Trp Asn Ser Ser Gly Ser Glu Glu Asp Pro Glu Thr Glu Ser Gly Pro
            115                 120                 125

Pro Val Glu Arg Cys Gly Val Leu Ser Lys Trp Thr Asn Tyr Ile His
            130                 135                 140

Gly Trp Gln Asp Arg Trp Val Val Leu Lys Asn Asn Thr Leu Ser Tyr
145                 150                 155                 160

Tyr Lys Ser Glu Asp Glu Thr Glu Tyr Gly Cys Arg Gly Ser Ile Cys
                165                 170                 175

Leu Ser Lys Ala Val Ile Thr Pro His Asp Phe Asp Glu Cys Arg Phe
            180                 185                 190

Asp Ile Ser Val Asn Asp Ser Val Trp Tyr Leu Arg Ala Gln Asp Pro
            195                 200                 205

Asp His Arg Gln Gln Trp Ile Asp Ala Ile Glu Gln His Lys Thr Glu
            210                 215                 220

Ser Gly Tyr Gly Ser Glu Ser Ser Leu Arg Arg His Gly Ser Met Val
225                 230                 235                 240

Ser Leu Val Ser Gly Ala Ser Gly Tyr Ser Ala Thr Ser Thr Ser Ser
            245                 250                 255

Phe Lys Lys Gly His Ser Leu Arg Glu Lys Leu Ala Glu Met Glu Thr
            260                 265                 270

Phe Arg Asp Ile Leu Cys Arg Gln Val Asp Thr Leu Gln Lys Phe Phe
            275                 280                 285

Asp Ala Cys Ala Asp Ala Val Ser Lys Asp Glu Phe Gln Arg Asp Lys
            290                 295                 300

Val Val Glu Asp Asp Glu Asp Asp Phe Pro Thr Thr Arg Ser Asp Gly
305                 310                 315                 320

Asp Phe Leu His Asn Thr Asn Gly Asn Lys Glu Lys Val Phe Pro His
                325                 330                 335

Val Thr Pro Lys Gly Ile Asn Gly Ile Asp Phe Lys Gly Glu Ala Ile
            340                 345                 350

Thr Phe Lys Ala Thr Thr Ala Gly Ile Leu Ala Thr Leu Ser His Cys
            355                 360                 365

Ile Glu Leu Met Val Lys Arg Glu Asp Ser Trp Gln Lys Arg Met Asp
            370                 375                 380

Lys Glu Thr Glu Lys Arg Arg Val Glu Ala Tyr Lys Asn Ala
385                 390                 395                 400

Met Thr Glu Leu Lys Lys Ser His Phe Gly Gly Pro Asp Tyr Glu
                405                 410                 415

Glu Gly Pro Asn Ser Leu Ile Asn Glu Glu Phe Phe Asp Ala Val
            420                 425                 430

Glu Ala Ala Leu Asp Arg Gln Asp Lys Ile Glu Glu Gln Ser Gln Ser
```

-continued

```
                  435                 440                 445
Glu Lys Val Arg Leu His Trp Ser Thr Ser Met Pro Ser Gly Asp Ala
    450                 455                 460

Phe Ser Ser Val Gly Thr His Arg Phe Val Gln Lys Pro Tyr Ser Arg
465                 470                 475                 480

Ser Ser Ser Met Ser Ser Ile Asp Leu Val Ser Ala Ser Asp Gly Val
                485                 490                 495

His Arg Phe Ser Ser Gln Val Glu Glu Met Val Gln Asn His Met Thr
            500                 505                 510

Tyr Ser Leu Gln Asp Val Gly Gly Asp Ala Asn Trp Gln Leu Val Val
        515                 520                 525

Glu Glu Gly Glu Met Lys Val Tyr Arg Arg Glu Val Glu Glu Asn Gly
    530                 535                 540

Ile Val Leu Asp Pro Leu Lys Ala Thr His Ala Val Lys Gly Val Thr
545                 550                 555                 560

Gly His Glu Val Cys Asn Tyr Phe Trp Asn Val Asp Val Arg Asn Asp
                565                 570                 575

Trp Glu Thr Thr Ile Glu Asn Phe His Val Val Glu Thr Leu Ala Asp
            580                 585                 590

Asn Ala Ile Ile Ile Tyr Gln Thr His Lys Arg Val Trp Pro Ala Ser
        595                 600                 605

Gln Arg Asp Val Leu Tyr Leu Ser Ala Ile Arg Lys Ile Pro Ala Leu
    610                 615                 620

Asn Glu Asn Asp Pro Glu Thr Trp Ile Val Cys Asn Phe Ser Val Asp
625                 630                 635                 640

His Ser Ser Ala Pro Leu Asn Asn Arg Cys Val Arg Ala Lys Ile Asn
                645                 650                 655

Val Ala Met Ile Cys Gln Thr Leu Val Ser Pro Pro Glu Gly Asn Gln
            660                 665                 670

Glu Ile Ser Arg Asp Asn Ile Leu Cys Lys Ile Thr Tyr Val Ala Asn
        675                 680                 685

Val Asn Pro Gly Gly Trp Ala Pro Ala Ser Val Leu Arg Ala Val Ala
    690                 695                 700

Lys Arg Glu Tyr Pro Lys Phe Leu Lys Arg Phe Thr Ser Tyr Val Gln
705                 710                 715                 720

Glu Lys Thr Ala Gly Lys Pro Ile Leu Phe
                725                 730
```

<210> SEQ ID NO 99
<211> LENGTH: 2283
<212> TYPE: DNA
<213> ORGANISM: Bos taurus
<220> FEATURE:
<221> NAME/KEY: CDS
<222> LOCATION: (103)..(2217)
<223> OTHER INFORMATION:

<400> SEQUENCE: 99

```
cggcaggaag atggcggcct agcggaggtg tgagtggacc tgggtctctg cagctgggtt     60
ttccctcttc ccgtctttct cctcttttcc tctccccga gg ttg gca tcg agg       114
                                              Leu Ala Ser Arg
                                                1 ggg cca aat tcg ggc ggc ggc gcc ggg cgc agc gca ggg gtc aca acg     162
Gly Pro Asn Ser Gly Gly Gly Ala Gly Arg Ser Ala Gly Val Thr Thr
 5                  10                  15                  20 acg gcg acg gct gac ggt tgg aag ggc agg ctt cct tcg ccc ctc gac     210
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | Thr | Ala | Thr | Ala | Asp | Gly | Trp | Lys | Gly | Arg | Leu | Pro | Ser | Pro | Leu | Asp  |
|     |     |     |     | 25  |     |     |     |     | 30  |     |     |     |     | 35  |     |      |
| ctc | ctt | ccc | cgg | tcc | gct | tgg | tgt | cag | gcg | cgg | cgg | cgg | cgg | cgg | cgg |  258 |
| Leu | Leu | Pro | Arg | Ser | Ala | Trp | Cys | Gln | Ala | Arg | Arg | Arg | Arg | Arg | Arg |      |
|     |     |     | 40  |     |     |     |     | 45  |     |     |     |     | 50  |     |     |      |
| cgg | cgc | ggc | ggg | cgg | act | cca | tcc | ctc | ctc | ccg | ctc | cct | cct | gca | ccg |  306 |
| Arg | Arg | Gly | Gly | Arg | Thr | Pro | Ser | Leu | Leu | Pro | Leu | Pro | Pro | Ala | Pro |      |
|     |     | 55  |     |     |     |     | 60  |     |     |     |     | 65  |     |     |     |      |
| gag | cgg | gca | ctc | ctt | cct | tcg | cca | tcc | ccc | gac | cct | tca | ccc | cgg | gga |  354 |
| Glu | Arg | Ala | Leu | Leu | Pro | Ser | Pro | Ser | Pro | Asp | Pro | Ser | Pro | Arg | Gly |      |
|     | 70  |     |     |     |     | 75  |     |     |     |     | 80  |     |     |     |     |      |
| ctg | ggc | gcc | tcc | acc | ggc | gca | gct | cag | gga | gcg | ggg | gcc | ggt | ctc | ctg |  402 |
| Leu | Gly | Ala | Ser | Thr | Gly | Ala | Ala | Gln | Gly | Ala | Gly | Ala | Gly | Leu | Leu |      |
| 85  |     |     |     |     | 90  |     |     |     |     | 95  |     |     |     |     | 100 |      |
| ctc | ggc | tgt | cgc | gcc | tcc | atg | tcg | gat | aac | cag | agc | tgg | aac | tcg | tcg |  450 |
| Leu | Gly | Cys | Arg | Ala | Ser | Met | Ser | Asp | Asn | Gln | Ser | Trp | Asn | Ser | Ser |      |
|     |     |     |     | 105 |     |     |     |     | 110 |     |     |     |     | 115 |     |      |
| ggc | tcg | gag | gag | gat | ccg | gag | acg | gag | tcc | ggg | ccg | ccg | gtg | gag | cgc |  498 |
| Gly | Ser | Glu | Glu | Asp | Pro | Glu | Thr | Glu | Ser | Gly | Pro | Pro | Val | Glu | Arg |      |
|     |     |     | 120 |     |     |     |     | 125 |     |     |     |     | 130 |     |     |      |
| tgc | gga | gtc | ctc | agc | aag | tgg | aca | aac | tat | att | cat | ggg | tgg | cag | gat |  546 |
| Cys | Gly | Val | Leu | Ser | Lys | Trp | Thr | Asn | Tyr | Ile | His | Gly | Trp | Gln | Asp |      |
|     |     | 135 |     |     |     |     | 140 |     |     |     |     | 145 |     |     |     |      |
| cgc | tgg | gta | gtt | ttg | aaa | aat | aac | act | ctg | agt | tac | tac | aaa | tct | gaa |  594 |
| Arg | Trp | Val | Val | Leu | Lys | Asn | Asn | Thr | Leu | Ser | Tyr | Tyr | Lys | Ser | Glu |      |
|     | 150 |     |     |     |     | 155 |     |     |     |     | 160 |     |     |     |     |      |
| gat | gag | aca | gag | tat | ggc | tgc | aga | gga | tcc | atc | tgt | ctt | agc | aag | gct |  642 |
| Asp | Glu | Thr | Glu | Tyr | Gly | Cys | Arg | Gly | Ser | Ile | Cys | Leu | Ser | Lys | Ala |      |
| 165 |     |     |     |     | 170 |     |     |     |     | 175 |     |     |     |     | 180 |      |
| gtc | atc | acg | cct | cat | gat | ttt | gat | gaa | tgc | cga | ttt | gat | att | agt | gta |  690 |
| Val | Ile | Thr | Pro | His | Asp | Phe | Asp | Glu | Cys | Arg | Phe | Asp | Ile | Ser | Val |      |
|     |     |     |     | 185 |     |     |     |     | 190 |     |     |     |     | 195 |     |      |
| aat | gat | agt | gtt | tgg | tat | ctt | cgt | gct | caa | gat | cca | gat | cac | aga | cag |  738 |
| Asn | Asp | Ser | Val | Trp | Tyr | Leu | Arg | Ala | Gln | Asp | Pro | Asp | His | Arg | Gln |      |
|     |     |     | 200 |     |     |     |     | 205 |     |     |     |     | 210 |     |     |      |
| cag | tgg | ata | gat | gcc | att | gaa | cag | cac | aag | act | gaa | tct | gga | tat | gga |  786 |
| Gln | Trp | Ile | Asp | Ala | Ile | Glu | Gln | His | Lys | Thr | Glu | Ser | Gly | Tyr | Gly |      |
|     |     | 215 |     |     |     |     | 220 |     |     |     |     | 225 |     |     |     |      |
| tct | gaa | tcc | agc | ttg | cgt | cga | cat | ggc | tcc | atg | gta | tca | ttg | gta | tcc |  834 |
| Ser | Glu | Ser | Ser | Leu | Arg | Arg | His | Gly | Ser | Met | Val | Ser | Leu | Val | Ser |      |
|     | 230 |     |     |     |     | 235 |     |     |     |     | 240 |     |     |     |     |      |
| gga | gca | agt | ggc | tat | tct | gca | aca | tcc | acc | tcc | tca | ttc | aag | aag | ggc |  882 |
| Gly | Ala | Ser | Gly | Tyr | Ser | Ala | Thr | Ser | Thr | Ser | Ser | Phe | Lys | Lys | Gly |      |
| 245 |     |     |     |     | 250 |     |     |     |     | 255 |     |     |     |     | 260 |      |
| cac | agt | tta | cgt | gag | aaa | ctg | gct | gaa | atg | gaa | acc | ttt | aga | gat | ata |  930 |
| His | Ser | Leu | Arg | Glu | Lys | Leu | Ala | Glu | Met | Glu | Thr | Phe | Arg | Asp | Ile |      |
|     |     |     |     | 265 |     |     |     |     | 270 |     |     |     |     | 275 |     |      |
| ctg | tgt | aga | caa | gtt | gat | acc | cta | cag | aag | ttc | ttt | gat | gcc | tgt | gct |  978 |
| Leu | Cys | Arg | Gln | Val | Asp | Thr | Leu | Gln | Lys | Phe | Phe | Asp | Ala | Cys | Ala |      |
|     |     |     | 280 |     |     |     |     | 285 |     |     |     |     | 290 |     |     |      |
| gat | gct | gtc | tcc | aag | gat | gaa | ttt | caa | agg | gat | aaa | gtg | gta | gaa | gat | 1026 |
| Asp | Ala | Val | Ser | Lys | Asp | Glu | Phe | Gln | Arg | Asp | Lys | Val | Val | Glu | Asp |      |
|     |     | 295 |     |     |     |     | 300 |     |     |     |     | 305 |     |     |     |      |
| gat | gaa | gat | gac | ttt | cct | acg | aca | cgt | tct | gat | gga | gac | ttc | ttg | cat | 1074 |
| Asp | Glu | Asp | Asp | Phe | Pro | Thr | Thr | Arg | Ser | Asp | Gly | Asp | Phe | Leu | His |      |
|     | 310 |     |     |     |     | 315 |     |     |     |     | 320 |     |     |     |     |      |
| aat | acc | aat | ggc | aat | aag | gaa | aag | gta | ttt | cca | cat | gta | aca | cca | aaa | 1122 |
| Asn | Thr | Asn | Gly | Asn | Lys | Glu | Lys | Val | Phe | Pro | His | Val | Thr | Pro | Lys |      |
| 325 |     |     |     |     | 330 |     |     |     |     | 335 |     |     |     |     | 340 |      |

-continued

```
gga att aat ggt ata gac ttt aaa ggt gag gcg ata act ttt aaa gca    1170
Gly Ile Asn Gly Ile Asp Phe Lys Gly Glu Ala Ile Thr Phe Lys Ala
            345                 350                 355 act act gcc gga atc ctt gct aca ctt tct cat tgt att gag ctg atg    1218
Thr Thr Ala Gly Ile Leu Ala Thr Leu Ser His Cys Ile Glu Leu Met
        360                 365                 370 gta aaa cgt gag gac agc tgg caa aag aga atg gac aag gaa act gag    1266
Val Lys Arg Glu Asp Ser Trp Gln Lys Arg Met Asp Lys Glu Thr Glu
    375                 380                 385 aag aga aga aga gtg gag gaa gca tac aaa aat gcc atg aca gaa ctt    1314
Lys Arg Arg Arg Val Glu Glu Ala Tyr Lys Asn Ala Met Thr Glu Leu
390                 395                 400 aag aaa aaa tcc cac ttt gga gga cca gat tat gag gaa ggc cca aac    1362
Lys Lys Lys Ser His Phe Gly Gly Pro Asp Tyr Glu Glu Gly Pro Asn
405                 410                 415                 420 agt ttg att aat gaa gag gag ttc ttt gat gct gtt gaa gct gct ctt    1410
Ser Leu Ile Asn Glu Glu Glu Phe Phe Asp Ala Val Glu Ala Ala Leu
                425                 430                 435 gac aga caa gat aaa ata gaa gaa cag tcg cag agt gaa aag gtc agg    1458
Asp Arg Gln Asp Lys Ile Glu Glu Gln Ser Gln Ser Glu Lys Val Arg
            440                 445                 450 tta cat tgg tct act tca atg cca tct gga gat gcc ttt tct tct gtg    1506
Leu His Trp Ser Thr Ser Met Pro Ser Gly Asp Ala Phe Ser Ser Val
        455                 460                 465 ggg act cat aga ttt gtc caa aag gtt gaa gag atg gtg cag aac cac    1554
Gly Thr His Arg Phe Val Gln Lys Val Glu Glu Met Val Gln Asn His
    470                 475                 480 atg acc tat tca ttg cag gat gta ggt ggg gac gcc aac tgg cag ttg    1602
Met Thr Tyr Ser Leu Gln Asp Val Gly Gly Asp Ala Asn Trp Gln Leu
485                 490                 495                 500 gtt gta gaa gaa ggg gag atg aag gta tat aga aga gaa gta gaa gaa    1650
Val Val Glu Glu Gly Glu Met Lys Val Tyr Arg Arg Glu Val Glu Glu
                505                 510                 515 aat ggg att gtt ctg gat cct ttg aaa gct acc cat gca gtt aaa ggc    1698
Asn Gly Ile Val Leu Asp Pro Leu Lys Ala Thr His Ala Val Lys Gly
            520                 525                 530 gtt aca gga cac gag gtc tgc aat tac ttc tgg aat gtt gat gtt cgc    1746
Val Thr Gly His Glu Val Cys Asn Tyr Phe Trp Asn Val Asp Val Arg
        535                 540                 545 aat gat tgg gaa aca act ata gaa aac ttt cat gtg gtg gaa aca tta    1794
Asn Asp Trp Glu Thr Thr Ile Glu Asn Phe His Val Val Glu Thr Leu
    550                 555                 560 gct gat aat gca atc atc att tat caa acg cac aag aga gtg tgg cca    1842
Ala Asp Asn Ala Ile Ile Ile Tyr Gln Thr His Lys Arg Val Trp Pro
565                 570                 575                 580 gcc tct cag cgg gat gtc tta tat ctg tct gcc att cga aag ata cca    1890
Ala Ser Gln Arg Asp Val Leu Tyr Leu Ser Ala Ile Arg Lys Ile Pro
                585                 590                 595 gct ttg aat gaa aat gac ccg gag act tgg ata gtt tgt aat ttt tct    1938
Ala Leu Asn Glu Asn Asp Pro Glu Thr Trp Ile Val Cys Asn Phe Ser
            600                 605                 610 gta gat cac agc agt gct cct cta aac aat cga tgt gtc cgt gcc aaa    1986
Val Asp His Ser Ser Ala Pro Leu Asn Asn Arg Cys Val Arg Ala Lys
        615                 620                 625 ata aac gtt gct atg att tgt cag acc ttg gtg agc ccc cca gag gga    2034
Ile Asn Val Ala Met Ile Cys Gln Thr Leu Val Ser Pro Pro Glu Gly
    630                 635                 640 aac cag gag att agc agg gac aac att cta tgc aag att aca tac gtg    2082
Asn Gln Glu Ile Ser Arg Asp Asn Ile Leu Cys Lys Ile Thr Tyr Val
645                 650                 655                 660
```

-continued

```
gcc aat gta aac cct gga gga tgg gcc cca gcc tca gtg tta cgg gca      2130
Ala Asn Val Asn Pro Gly Gly Trp Ala Pro Ala Ser Val Leu Arg Ala
            665                 670                 675 gtg gca aag cga gaa tat cca aag ttt cta aag cgt ttt act tct tac      2178
Val Ala Lys Arg Glu Tyr Pro Lys Phe Leu Lys Arg Phe Thr Ser Tyr
        680                 685                 690 gta caa gaa aaa act gca gga aaa cct att ttg ttc tag tattaacagt       2227
Val Gln Glu Lys Thr Ala Gly Lys Pro Ile Leu Phe
            695                 700 gactgaagca aggctgtgtg acattccatg ttggaggaaa aaaaaaaaaa aaaaaa        2283

<210> SEQ ID NO 100
<211> LENGTH: 704
<212> TYPE: PRT
<213> ORGANISM: Bos taurus

<400> SEQUENCE: 100

Leu Ala Ser Arg Gly Pro Asn Ser Gly Gly Ala Gly Arg Ser Ala
1               5                   10                  15

Gly Val Thr Thr Thr Ala Thr Ala Asp Gly Trp Lys Gly Arg Leu Pro
            20                  25                  30

Ser Pro Leu Asp Leu Leu Pro Arg Ser Ala Trp Cys Gln Ala Arg Arg
        35                  40                  45

Arg Arg Arg Arg Arg Gly Gly Arg Thr Pro Ser Leu Leu Pro Leu
    50                  55                  60

Pro Pro Ala Pro Glu Arg Ala Leu Leu Pro Ser Pro Ser Pro Asp Pro
65                  70                  75                  80

Ser Pro Arg Gly Leu Gly Ala Ser Thr Gly Ala Ala Gln Gly Ala Gly
                85                  90                  95

Ala Gly Leu Leu Leu Gly Cys Arg Ala Ser Met Ser Asp Asn Gln Ser
            100                 105                 110

Trp Asn Ser Ser Gly Ser Glu Asp Pro Glu Thr Glu Ser Gly Pro
        115                 120                 125

Pro Val Glu Arg Cys Gly Val Leu Ser Lys Trp Thr Asn Tyr Ile His
    130                 135                 140

Gly Trp Gln Asp Arg Trp Val Val Leu Lys Asn Asn Thr Leu Ser Tyr
145                 150                 155                 160

Tyr Lys Ser Glu Asp Glu Thr Glu Tyr Gly Cys Arg Gly Ser Ile Cys
                165                 170                 175

Leu Ser Lys Ala Val Ile Thr Pro His Asp Phe Asp Glu Cys Arg Phe
            180                 185                 190

Asp Ile Ser Val Asn Asp Ser Val Trp Tyr Leu Arg Ala Gln Asp Pro
        195                 200                 205

Asp His Arg Gln Gln Trp Ile Asp Ala Ile Glu Gln His Lys Thr Glu
    210                 215                 220

Ser Gly Tyr Gly Ser Glu Ser Ser Leu Arg Arg His Gly Ser Met Val
225                 230                 235                 240

Ser Leu Val Ser Gly Ala Ser Gly Tyr Ser Ala Thr Ser Thr Ser Ser
                245                 250                 255

Phe Lys Lys Gly His Ser Leu Arg Glu Lys Leu Ala Glu Met Glu Thr
            260                 265                 270

Phe Arg Asp Ile Leu Cys Arg Gln Val Asp Thr Leu Gln Lys Phe Phe
        275                 280                 285

Asp Ala Cys Ala Asp Ala Val Ser Lys Asp Glu Phe Gln Arg Asp Lys
    290                 295                 300
```

```
Val Val Glu Asp Asp Glu Asp Phe Pro Thr Thr Arg Ser Asp Gly
305                 310                 315                 320

Asp Phe Leu His Asn Thr Asn Gly Asn Lys Glu Lys Val Phe Pro His
            325                 330                 335

Val Thr Pro Lys Gly Ile Asn Gly Ile Asp Phe Lys Gly Glu Ala Ile
            340                 345                 350

Thr Phe Lys Ala Thr Thr Ala Gly Ile Leu Ala Thr Leu Ser His Cys
            355                 360                 365

Ile Glu Leu Met Val Lys Arg Glu Asp Ser Trp Gln Lys Arg Met Asp
370                 375                 380

Lys Glu Thr Glu Lys Arg Arg Val Glu Glu Ala Tyr Lys Asn Ala
385                 390                 395                 400

Met Thr Glu Leu Lys Lys Ser His Phe Gly Pro Asp Tyr Glu
                405                 410                 415

Glu Gly Pro Asn Ser Leu Ile Asn Glu Glu Phe Phe Asp Ala Val
            420                 425                 430

Glu Ala Ala Leu Asp Arg Gln Asp Lys Ile Glu Glu Gln Ser Gln Ser
            435                 440                 445

Glu Lys Val Arg Leu His Trp Ser Thr Ser Met Pro Ser Gly Asp Ala
            450                 455                 460

Phe Ser Ser Val Gly Thr His Arg Phe Val Gln Lys Val Glu Glu Met
465                 470                 475                 480

Val Gln Asn His Met Thr Tyr Ser Leu Gln Asp Val Gly Gly Asp Ala
            485                 490                 495

Asn Trp Gln Leu Val Val Glu Glu Gly Glu Met Lys Val Tyr Arg Arg
            500                 505                 510

Glu Val Glu Glu Asn Gly Ile Val Leu Asp Pro Leu Lys Ala Thr His
            515                 520                 525

Ala Val Lys Gly Val Thr Gly His Glu Val Cys Asn Tyr Phe Trp Asn
            530                 535                 540

Val Asp Val Arg Asn Asp Trp Glu Thr Thr Ile Glu Asn Phe His Val
545                 550                 555                 560

Val Glu Thr Leu Ala Asp Asn Ala Ile Ile Ile Tyr Gln Thr His Lys
            565                 570                 575

Arg Val Trp Pro Ala Ser Gln Arg Asp Val Leu Tyr Leu Ser Ala Ile
            580                 585                 590

Arg Lys Ile Pro Ala Leu Asn Glu Asn Asp Pro Glu Thr Trp Ile Val
            595                 600                 605

Cys Asn Phe Ser Val Asp His Ser Ser Ala Pro Leu Asn Asn Arg Cys
610                 615                 620

Val Arg Ala Lys Ile Asn Val Ala Met Ile Cys Gln Thr Leu Val Ser
625                 630                 635                 640

Pro Pro Glu Gly Asn Gln Glu Ile Ser Arg Asp Asn Ile Leu Cys Lys
            645                 650                 655

Ile Thr Tyr Val Ala Asn Val Asn Pro Gly Gly Trp Ala Pro Ala Ser
            660                 665                 670

Val Leu Arg Ala Val Ala Lys Arg Glu Tyr Pro Lys Phe Leu Lys Arg
            675                 680                 685

Phe Thr Ser Tyr Val Gln Glu Lys Thr Ala Gly Lys Pro Ile Leu Phe
            690                 695                 700

<210> SEQ ID NO 101
<211> LENGTH: 13
```

```
<212> TYPE: PRT
<213> ORGANISM: Mus musculus

<400> SEQUENCE: 101

Gly Ala Gly Ala Gly Leu Leu Leu Gly Arg Cys Val Ser
1               5                   10

<210> SEQ ID NO 102
<211> LENGTH: 171
<212> TYPE: PRT
<213> ORGANISM: artificial
<220> FEATURE:
<223> OTHER INFORMATION: Derived sequence

<400> SEQUENCE: 102

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 103
<211> LENGTH: 18
<212> TYPE: PRT
<213> ORGANISM: artificial
<220> FEATURE:
<223> OTHER INFORMATION: Derived sequence

<400> SEQUENCE: 103

Pro Arg Ser Ala Arg Cys Gln Ala Arg Arg Arg Gly Gly Arg Thr
1               5                   10                  15

Ser Ser
```

GOODPASTURE ANTIGEN-BINDING PROTEIN ISOFORMS AND PROTEIN MISFOLDED-MEDIATED DISORDERS

CROSS REFERENCE

This application claims priority to U.S. Provisional Patent Application Ser. Nos. 60/445,043 filed Feb. 5, 2003; 60/445,003 filed Feb. 5, 2003; and 60/445,004 filed Feb. 5, 2003, which are herewith incorporated by reference in their entirety.

BACKGROUND OF THE INVENTION

The conformation of the non-collagenous (NC1) domain of the α3 chain of the basement membrane collagen IV [α3(IV)NC1] depends in part on phosphorylation. Goodpasture Antigen Binding Protein (GPBP) (WO 00/50607; WO 02/061430) is a novel non-conventional protein kinase that catalyzes the conformational isomerization of the α3(IV) NC1 domain during its supramolecular assembly, resulting in the production and stabilization of multiple α3(IV)NC1 conformers in basement membranes. Elevated levels of GPBP have been associated with the production of non-tolerized α3(IV)NC1 conformers, which conduct the autoimmune response mediating Goodpasture ("GP") disease. In GP patients, autoantibodies against the non-collagenous C-terminal domain (NC1) of the type IV collagen α3 chain ("Goodpasture antigen" or "GP antigen") cause a rapidly progressive glomerulonephritis and often lung hemorrhage, the two cardinal clinical manifestations of the GP syndrome.

The identification of GPBP provided methods for identification of compounds for the treatment of autoimmune disorders, cancer, and aberrant apoptosis, and also provided potential therapeutics for these disorders. Thus, the identification of novel GPBP isoforms would be advantageous in at least these fields.

SUMMARY OF THE INVENTION

The present invention provides novel isoforms of the Goodpasture antigen binding protein (GPBP), and related reagents, and also provides methods for isolating and detecting such novel GPBP isoforms. The invention further provides methods identifying compounds to treat one or more of an autoimmune condition and a protein deposit-mediated disorder, as well as novel compounds and methods for treating such conditions and/or disorders.

DETAILED DESCRIPTION OF THE INVENTION

Figure 1:
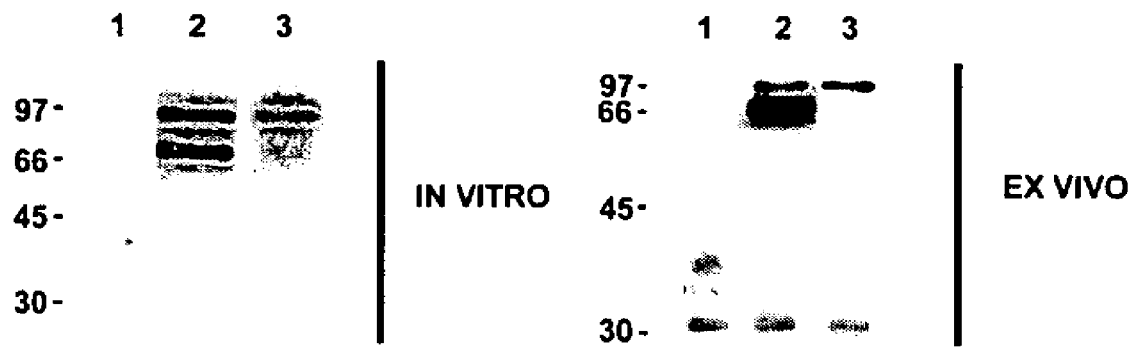
FIG. 1. 91-kDa GPBP represents a non-canonical translation product of the mRNA. The cDNAs present in pcDNA3 (1), pc-n4' (2) or pc-n4'-Met$_{mut}$ (3) were expressed in a cell-free system (in vitro) or in human 293 cells (ex vivo) and similar amounts of the corresponding mixtures or extracts were analyzed by fluorography (in vitro) or by Western blot using Mab6 antibodies (ex vivo), respectively. Unless otherwise indicated with numbers and bars we indicate in this and the following Figures the size in kDa and position of rainbow molecular weight markers from Amersham Bioscience.

All references cited are herein incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the term "GPBP" or "GPBP isoform" refers to Goodpasture antigen binding protein, and includes the various alternative GPBP isoforms disclosed herein, including GPBPΔ26 isoforms, and further includes both monomers and oligomers thereof. The various GPBP isoforms disclosed herein include 91 kDa GPBP, 77 kDa GPBP, 60 kDa GPBP, 44-47 kDa GPBP, and 32 kDa GPBP. Human, mouse, and bovine isoforms are provided herein.

As used herein, the term "GPBPΔ26" refers to Goodpasture antigen binding protein deleted for the 26 amino acid sequence shown in SEQ ID NO: 46, and the various alternative GPBP isoforms disclosed herein, and further includes both monomers and oligomers thereof. The various GPBPΔ26 isoforms disclosed herein include 91 kDa GPBPΔ26, and 77 kDa GPBPΔ26. Human, mouse, and bovine isoforms are provided herein.

As used herein, the singular forms "a", "an" and "the" include plural referents unless the context clearly dictates otherwise. For example, reference to a "GPBP isoform" means one or more GPBP isoforms.

As used herein the term "non-canonical" means that the GPBP being referred to is not expressed from the methionine initiation codon that yields 77 kDa GPBP or 77 kDa GPBPΔ26. For the sake of simplicity, recitations of "non-canonical GPBP" include both non-canonical GPBP isoforms and non-canonical GPBPΔ26 isoforms.

As used herein a "protein deposit-mediated disorder" means a disease mediated by abnormal deposition of a specific protein, including but not limited to Parkinson's disease, Alzheimer's disease, amyotrophic lateral sclerosis, prion diseases, type II diabetes, and autoimmune disorders. The protein deposit may be amyloid matter or para-amyloid matter.

As used herein an "autoimmune condition" is selected from the group consisting of Goodpasture Syndrome, multiple sclerosis, systemic lupus erythematosus, cutaneous lupus erythematosus, pemphigus, pemphigoid and lichen planus.

The amino acid sequence of 77 kDa GPBP and GPBPΔ26 was disclosed in U.S. Pat. No. 6,579,969 Issued Jun. 17, 2003 and corresponding PCT publication WO 00/50607, published Aug. 31, 2000. GPBP was identified therein as a 71 kDa protein that underwent post-translational modification to result in higher molecular weight polypeptides. It was also disclosed that the 71 kDa protein began at a methionine residue, but that in the 5' untranslated region upstream of the coding region encoding the amino-terminal methionine of the 71 kDa protein, the cDNA clone encoding 71 kDa GPBP contained an open reading frame without an initiation codon for translation. It was speculated that an mRNA editing process inserting a single base pair (U) might generate an operative in-frame start site and an ORF of 754-residues containing an export signal immediately downstream of the edited Met.

The present invention demonstrates that, rather than the mRNA editing process speculated on in WO 00/50607, the human GPBP mRNA undergoes non-canonical translation initiation to produce a 91-kDa isoform of GPBP (91 kDa GPBP). The resulting protein product is not the 753 amino acid residue protein speculated upon in WO 00/50607, but is believed to be a protein of approximately 727 amino acid residues comprising the amino acid sequence of SEQ ID NO:6. The corresponding predicted 91 kDa GPBPΔ26 amino acid sequence comprises the amino acid sequence of SEQ ID NO:8. The present invention also provides mouse and bovine homologs of the human 91 kDa polypeptide: mouse 91 kDa GPBP (SEQ ID NO:94), mouse 91 kD GPBPΔ26 (SEQ ID NO:96), bovine 91 kDa GPBP (SEQ ID NO:98), and bovine 91 kDa GPBPΔ26 (SEQ ID NO:100).

For the sake of simplicity, the different isoforms are referred to as being the same molecular weight, whether a GPBP isoform or a GPBPΔ26 isoform. It will be apparent to one of skill in the art that the GPBPΔ26 isoform will contain 26 fewer amino acid residues than the corresponding GPBP isoform, and thus will have a molecular weight approximately 2.6 kDa less than the corresponding GPBP isoform.

The present invention further demonstrates that various processed forms of these GPBP isoforms exist, and provides evidence for the dependency of their subcellular localization on the particular processing event that occurs. The invention further provides a series of truncation mutants of the GPBP cDNA that are predicted to encode the primary sequence signals to direct their differential subcellular localization patterns. The expression products of these truncation mutants are as follows (also, see FIG. 2):

| | |
|---|---|
| Δ102 GPBP | SEQ ID NO: 26 |
| Δ102 GPBPΔ26 | SEQ ID NO: 28 |
| Δ174 GPBP | SEQ ID NO: 22 |
| Δ174 GPBPΔ26 | SEQ ID NO: 24 |
| Δ246 GPBP | SEQ ID NO: 18 |
| Δ246 GPBPΔ26 | SEQ ID NO: 20 |
| Δ315 GPBP | SEQ ID NO: 14 |
| Δ315 GPBPΔ26 | SEQ ID NO: 16 |
| Δ369 GPBP | SEQ ID NO: 10 |
| Δ369 GPBPΔ26 | SEQ ID NO: 12 |

Thus, in one aspect, the present invention provides substantially purified polypeptide comprising or consisting of an amino acid sequence according to SEQ ID NO:29, which is the amino acid sequence present in Δ369 GPBP (or Δ369 GPBPΔ26) that is not present in GPBP (or GPBPΔ26). The amino acid sequence of SEQ ID NO:29 is GAGAGLLLGCRAS. In one embodiment of this aspect, the substantially purified polypeptides comprise or consist of the amino acid sequence of SEQ ID NO:30, which is the amino acid sequence present in Δ315 GPBP (or Δ315 GPBPΔ26) that is not present in GPBP (or GPBPΔ26).

In a further embodiment of this aspect, the substantially purified polypeptides comprise or consist of the amino acid sequence of SEQ ID NO:31, which is the amino acid sequence present in Δ246 GPBP (or Δ246 GPBPΔ26) that is not present in GPBP (or GPBPΔ26). In a further embodiment of this aspect, the substantially purified polypeptides comprise or consist of the amino acid sequence of SEQ ID NO:32, which is the amino acid sequence present in Δ174 GPBP (or Δ174 GPBPΔ26) that is not present in GPBP (or GPBPΔ26).

In a further embodiment of this aspect, the substantially purified polypeptides comprise or consist of the amino acid sequence of SEQ ID NO:33, which is the amino acid sequence present in Δ102 GPBP (or Δ102 GPBPΔ26) that is not present in GPBP (or GPBPΔ26). In a further embodiment of this aspect, the substantially purified polypeptides comprise or consist of the amino acid sequence of SEQ ID NO:34, which is the predicted amino acid sequence present in 91 kDa GPBP (or 91 kDa GPBPΔ26) that is not present in GPBP (or GPBPΔ26).

In various further embodiments of this aspect of the invention, the substantially purified polypeptides comprise or consist of an amino acid sequence selected from the group consisting of SEQ ID NO:6 (predicted 91 kDa GPBP), SEQ ID NO:8 (predicted 91 kDa GPBPΔ26), SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:SEQ ID NO:26, SEQ ID NO:28, SEQ ID NO:98 (bovine 91 kD GPBP homolog), and SEQ ID NO:100 (bovine 91 kD GPBPΔ26 homolog).

In a further aspect, the present invention provides substantially purified polypeptides comprising or consisting of an amino acid sequence according to SEQ ID NO:101 (GAGAGLLLGCRVS), which is present in mouse and rat GPBP isoforms, and which corrsponds to SEQ ID NO:29 from the human sequence but differs in a single amino acid residue (underlined). Sequence comparison of potential open reading frames in the mouse, bovine, and rat GPBP mRNA indicates that they encode sequences that are of great similarity to the human GPBP isoforms disclosed herein: at least 94% identity for the 91 kDa GPBP between human, mouse, and bovine homolgs and at least 81% identity between human, mouse, rat and bovine homolgs for the predicted amino acid sequences upstratem of canonical GPBP. Thus, in another embodiment of this aspect, the present invention provides substantially purified polypeptides comprising an amino acid sequence that are at least 80% identical to SEQ ID NO:34. Such sequence identity is as determined using the BLAST engine for local alignment. The stand-alone executable for blasting two sequences (bl2seq) can be retrieved from the NCBI internet site, and is also disclosed in FEMS Microbiol Lett. 174:247-250 (1999).

In another embodiment of this aspect, the present invention provides substantially purified polypeptides comprising or consisting of an amino acid sequence selected from the group consisting of SEQ ID NO:94 and SEQ ID NO:96. These polypeptides represent mouse homologs of human 91 kDa GPBP and 91 kDa GPBPΔ26, respectively.

In these various aspects and embodiments, the present invention provides novel polypeptides that can be used to generate antibodies to distinguish between different GPBP isoforms, and which can also be used, for example, as tools to identify candidate compounds for inhibiting various specific types of GPBP isoforms and also to identify candidate compounds for treating autoimmunity and amyloidosis disorders, as discussed in more detail below.

As used herein, the term "substantially purified" means that the protein has been separated from its in vivo cellular environments. Thus, the protein can either be purified from natural sources, or recombinant protein can be purified from the transfected host cells disclosed above. In a preferred embodiment, the proteins are produced by the transfected cells disclosed above, and purified using standard techniques. (See for example, *Molecular Cloning: A Laboratory Manual* (Sambrook, et al., 1989, Cold Spring Harbor Laboratory Press.)) The protein can thus be purified from prokaryotic or eukaryotic sources. In various further preferred embodiments, the protein is purified from bacterial, yeast, or mammalian cells. In a preferred embodiment, substantially purified means that the polypeptide is substantially free of gel agents, such as polyacrylamide and agarose. In a further preferred embodiment, "substantially purified" means that they are free of other GPBP isoforms. In a further preferred embodiment, the substantially purified proteins are present in solution. As used herein, the term "substantially free of other proteins" means that contaminating proteins make up no more than about 5% of the substantially purified sample, preferably no more than about 3%.

In another embodiment of this aspect of the invention, the substantially purified polypeptide comprises or consists of an amino acid sequence according to the genus R1-R2-R3, wherein
R1 is 0-90 amino acids of SEQ ID NO:35;
R2 is the amino acid sequence according to SEQ ID NO:29; and
R3 is an amino acid sequence selected from the group consisting of SEQ ID NO:2 and SEQ ID NO:4.

In this embodiment, the R1 position is variable, and can be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 amino acids of SEQ ID NO:35. If R1 is 90 amino acid residues of SEQ ID NO:35 the resulting polypeptide comprises the polypeptide of SEQ ID NO:6 or SEQ ID NO:8, depending on the identity of the R3 group. Based on the above teachings, the various polypeptides encompassed by this R1 embodiment will be apparent to one of skill in the art.

In another embodiment, the substantially purified polypeptide comprises or consists of a polypeptide of the genus X1-X2, wherein:
X1 is 0-90 amino acids of SEQ ID NO:35;
X2 is the amino acid sequence according to SEQ ID NO:29
wherein the polypeptide does not include the sequence of SEQ ID NO:2 or SEQ ID NO:4.

In this embodiment, the R1 position is variable, and can be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 amino acids of SEQ ID NO:35. If R1 is 90 amino acid residues of SEQ ID NO:35, the resulting polypeptide comprises the polypeptide of SEQ ID NO:34. Based on the above teachings, the various polypeptides encompassed by this R1 embodiment will be apparent to one of skill in the art.

In this embodiment, the substantially purified polypeptides provide tools to distinguish between the different isoforms of GPBP identified herein. For example, the substantially purified polypeptides according to this embodiment can be used to generate antibodies that selectively bind to the 91 kDa GPBP and that do not bind to the 77 kDa GPBP. Such antibodies will be of utility, for example, in immunodetection assays as described below.

The substantially purified polypeptides of the invention can be made by any method known to those of skill in the art, but are preferably made by recombinant means based on the teachings provided herein. For example, a coding region of interest as disclosed herein can be cloned into a recombinant expression vector, which can then be used to transfect a host cell for recombinant protein production by the host cells.

"Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.)

The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

As disclosed below, the inventors have further discovered that at least the 91-kDa GPBP enters into the cell secretory pathway, reaches the endosomal/lysosomal compartment and undergoes proteolysis to yield products of lower molecular mass. Thus, in another embodiment, the polypeptides of the present invention are substantially purified processed GPBP polypeptides derived from a precursor polypeptide comprising an amino acid sequence selected from the group consisting of SEQ ID NO:2, SEQ ID NO:4, SEQ ID NO:6, and/or SEQ ID NO:8 wherein the substantially purified polypeptide is reactive with an antibody selective for one or more epitopes within one or more of the GPBP isoforms disclosed herein, wherein the substantially purified processed GPBP polypeptide is selected from the group consisting of:

(a) a 60 kDa GPBP with a molecular weight of approximately 60 kDa in denaturing gel electrophoresis, wherein the 60 kDa GPBP is present in lysosomes, cytoplasm, microsomes, and mitochondria in liver tissue, wherein the 60 kDa GPBP is membrane-associated or soluble in the lysosomes in liver tissue;

(b) a 44-47 kDa GPBP with a molecular weight of approximately 44-47 kDa in denaturing gel electrophoresis, wherein the 44-47 kDa GPBP is present in lysosomes in liver tissue, wherein the 44-47 kDa GPBP is predominately formed through a leupeptin-sensitive proteolysis in liver tissue;

(c) a 32 kDa GPBP with a molecular weight of approximately 32 kDa in denaturing gel electrophoresis, wherein the 32 kDa GPBP is present in cytoplasm, mitochondria, microsomes, and lysosomes in liver tissue, and wherein the 32 kDa GPBP is formed through a leupeptin-insensitive proteolysis in liver lysosomes.

As used herein, being of an approximate molecular weight as determined by denaturing gel electrophoresis means that the polypeptide is within 0-10% of the recited molecular weight, more preferably within 0-5%, and even more preferably within 0-3% under the following gel conditions As used herein, determination of molecular weights is as would be determined under the following conditions: sodium dodecyl sulfate polyacrylamide gel electrophoresis (SDS-PAGE) performed on MiniProtean III (Bio-Rad) using polyacrylamide gels (29.2:0.8 acrylamide:bisacrylamide) at room temperature and constant voltage (200 volts); running buffer of 192 mM glycine, 24.7 mM Tris and 1% SDS; stacking gel of 3.65% acrylamide/bisacrylamide 122 mM HCl-Tris pH 6.8, 0.1% SDS, 0.146% ammonium persulfate, 0.146% Temed; running gel of 10% acrylamide/bisacrylamide, 373 mM HCl-Tris pH 8.8;0.1% SDS, 0.1% ammonium persulfate, 0.1% Temed; and samples were 31.25 mM HCl-Tris pH 6.8, 5.16% glycerol, 1% SDS and 2.5% β-mercaptoethanol.

This range represents a standard fluctuation for such molecular weight determinations based on differences in gel reagents, running time, temperature, and voltage, and other variables as would be recognized by those of skill in the art.

As used herein, the recitation of a processed GPBP being in a specific subcellular compartment in liver tissue means that the protein is present in detectable levels in the recited cellular compartment, and does not mean that it is not present in detectable levels in other cellular compartments.

As used herein, being "membrane-associated" means that, in extracts of the subcellular extract being analyzed, detectable levels of the polypeptide of interest are found in the membrane fraction in subcellular fractions isolated according to the methods disclosed below.

As used herein, "leupeptin-sensitive" means that, in the presence of sufficient quantities of leupeptin, production of the recited proteolytic product is reduced. As used herein, "leupeptin-insensitive" means that, in the presence of similar quantities of leupeptin as above, production of the recited proteolytic product is not reduced. Preferred embodiments for determining leupeptin-sensitivity are as described below in the experimental section.

The substantially purified processed GPBP polypeptides of this embodiment can be produced, for example, by a method comprising (a) providing cells that express one or more polypeptide comprising or consisting of an amino acid sequence selected from the group consisting of SEQ ID NO:2, SEQ ID NO:4, SEQ ID NO:6, and SEQ ID NO:8; (b) lysing the cells and isolating one or more fractions of the cells comprising fractions selected from the group consisting of cytoplasmic-containing fractions, mitochondrial-containing fractions, microsomal-containing fractions, and lysosomal-containing fractions; (c) contacting the isolated fractions with an immunoaffinity column comprising an antibody that selectively binds to a polypeptide comprising or consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:30, SEQ ID NO:31, SEQ ID NO:32, SEQ ID NO:33, SEQ ID NO:34, SEQ ID NO:35 under conditions that result in binding of one or more of the 60 kDa GPBP, the 44-47 kDa GPBP, and the 32 kDa GPBP to the immunoaffinity column; (d) washing the column under conditions that remove cellular contents that do not selectively bind to the immunoafinity column; (e) eluting the bound material from the immunoaffinity column to provide an eluate; and (f) size fractionating the eluate and isolating one or more of the fractions consisting of the approximately 60 kDa fraction, the approximately 44-47 kDa fraction, and the approximately 32 kDa fraction, wherein the approximately 60 kDa fraction contains the substantially purified 60 kDa GPBP; the approximately 44-47 kDa fraction contains the substantially purified 44-47 kDa GPBP, and the approximately 32 kDa fraction contains the substantially purified 32 kDa GPBP.

In a preferred embodiment of this method, the cells express at least one polypeptide comprising or consisting of an amino acid sequence selected from the group consisting of SEQ ID NO: 6 and SEQ ID NO:8, more preferably SEQ ID NO:6.

Antibodies for use in these methods include those described herein as well as in WO 00/50607 and WO 02/061430. Cell fractionation, immunoaffinity column chromatography, size fractionation, and suitable wash and elution conditions are known to those of skill in the art.

In another embodiment, the substantially purified processed GPBP polypeptides of this embodiment can be produced by a method comprising (a) providing cells that express one or more recombinant polypeptides comprising or consisting of an amino acid sequence selected from the group consisting of SEQ ID NO:2, SEQ ID NO:4, SEQ ID NO:6, and SEQ ID NO:8; (b) lysing the cells and obtaining a partially purified cell extract containing the recombinant polypeptides; (c) contacting the partially purified cell extract with liver lysosomal extracts under conditions that promote processing of the recombinant polypeptides to produce a processed extract; (d) contacting the processed extract with an immunoaffinity column comprising an antibody that selectively binds to an epitope within the recombinant polypeptides and/or their processed forms comprising or consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:30, SEQ ID NO:31, SEQ ID NO:32, SEQ ID NO:33, SEQ ID NO:34, SEQ ID NO:35 under conditions that result in binding of recombinant polypeptides and their processed forms to the immunoaffinity column; (e) washing the column under conditions that remove cellular contents that do not selectively bind to the immunoafinity column; (f) eluting the bound material from the immunoaffinity column to provide an eluate; and (g) size fractionating the eluate and isolating one or more of the fractions consisting of the approximately 60 kDa fraction, the approximately 44-47 kDa fraction, and the approximately 32 kDa fraction, wherein the approximately 60 kDa fraction contains the substantially purified 60 kDa GPBP; the approximately 44-47 kDa fraction contains the substantially purified 44-47 kDa GPBP, and the approximately 32 kDa fraction contains the substantially purified 32 kDa GPBP.

In a preferred embodiment of this method, the cells express at least one polypeptide comprising or consisting of an amino acid sequence selected from the group consisting of SEQ ID NO:6 and SEQ ID NO:8, more preferably SEQ ID NO:6.

For this embodiment, one of skill in the art can use the teachings of the invention to prepare recombinant expression vectors expressing the recited polypeptides. Preparing cell extracts and liver lysosomal extracts are known to those in the art, and are further described below.

In a further embodiment, the polypeptides of the present invention include an isolated polypeptide consisting of the amino acid sequence of SEQ ID NO:38 (AA 1-299 of SEQ ID NO:2). This polypeptide is a truncated version of the 77 kDa GPBP. As described below, this polypeptide is demonstrated to have a greater kinase activity under acidic conditions than GPBP, and thus may be functionally similar to the GPBP forms present in the lysosome.

In a further aspect, the present invention provides pharmaceutical compositions comprising one or more substantially purified polypeptide as described above and a pharmaceutically acceptable carrier. In a non-limiting example, the pharmaceutical compositions of this aspect of the invention can be used for immunization to prepare antibodies specific for non-canonical GPBP isoforms, which themselves can be used as therapeutics to modulate GPBP activity. Alternatively, the pharmaceutical compositions according to this aspect of the invention can themselves be used as therapeutics to inhibit GPBP activity in a subject in need thereof.

In another aspect, the present invention provides antibodies that selectively bind to the substantially purified polypeptides disclosed herein, but which do not selectively bind to the peptide sequence PRSARCQARRRRGGRTSS (SEQ ID NO:103).

In a preferred embodiment, the antibodies of the invention selectively bind to an epitope present within the GPBP isoforms disclosed herein and do not selectively bind to a polypeptide consisting of the amino acid sequence of SEQ ID NO:2 or SEQ ID NO:4. In this embodiment, it is further preferred that the antibodies selectively bind to one or more proteins comprising or consisting of a sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and/or to an epitope within one or more polypeptides selected from the group consisting of the 60 kDa GPBP, the 44-47 kDa GPBP, and the 32 kDa GPBP. Such antibodies can be produced by immunization of a host animal with either the complete GPBP isoforms disclosed herein or with antigenic peptides thereof, while selecting against those that selectively bind to SEQ ID NO:103, and/or to SEQ ID NO:2 and/or SEQ ID NO:4 (via, for example, adsorption of such antibodies on an affinity column comprising the polypeptide of SEQ ID NO:103, SEQ ID NO:2 and/or SEQ ID NO:4). In a preferred embodiment, the antibodies selectively bind to an epitope within an amino acid sequence selected from the group consisting of SEQ ID NO:29, SEQ ID NO:30, SEQ ID NO:31, SEQ ID NO:32, SEQ ID NO:33, SEQ ID NO:34, SEQ ID NO:35. These sequences are not included in the sequence of SEQ ID NO:2 or SEQ ID NO:4, and thus antibodies directed against epitopes within these sequences do not selectively bind to SEQ ID NO:2 or SEQ ID NO:4. Suitable antibodies include polyclonal, monoclonal, and humanized monoclonal antibodies.

In a further embodiment, the antibodies selectively bind to an isolated polypeptide consisting of the amino acid sequence of SEQ ID NO:38 (AA 1-299 of SEQ ID NO:2 or SEQ ID NO:4). This polypeptide is a truncated version of the 77 kDa GPBP or GPBPΔ26. As described below, this polypeptide is demonstrated to have a greater kinase activity under acidic conditions than GPBP, and thus may be functionally similar to the GPBP forms present in the lysosome.

As used herein, the term "selectively bind(s)" means that the antibodies preferentially bind to the polypeptide in question in a mixture of polypeptides.

In a further aspect, the present invention provides methods for making antibodies selective for one or more GPBP isoforms, comprising immunizing a host animal with an antigenic epitope derived from a polypeptide consisting of an amino sequence selected from the group consisting of SEQ ID NO:29, SEQ ID NO:30, SEQ ID NO:31, SEQ ID NO:32, SEQ ID NO:33, SEQ ID NO:34, SEQ ID NO:35, and SEQ ID NO:101 and isolating antibodies from the host animal that selectively bind to the polypeptide, wherein the isolated antibodies are selective for one or more Goodpasture antigen binding protein isoforms.

Antibodies can be made by well-known methods, such as described in Harlow and Lane, Antibodies; A Laboratory Manual, Cold Spring Harbor Laboratory, Cold Spring Harbor, N.Y., (1988). In one example, preimmune serum is collected prior to the first immunization. A substantially purified polypeptide of the invention, or antigenic fragments thereof, together with an appropriate adjuvant, are injected into an animal in an amount and at intervals sufficient to elicit an immune response. Animals are bled at regular intervals, preferably weekly, to determine antibody titer. The animals may or may not receive booster injections following the initial immunization. At about 7 days after each booster immunization, or about weekly after a single immunization, the animals are bled, the serum collected, and aliquots are stored at about −20° C. Polyclonal antibodies against the proteins and peptides of the invention can then be purified directly by passing serum collected from the animal through a column to which non-antigen-related proteins prepared from the same expression system without GPBP-related proteins bound.

Monoclonal antibodies can be produced by obtaining spleen cells from the animal. (See Kohler and Milstein, Nature 256, 495-497 (1975)). In one example, monoclonal antibodies (mAb) of interest are prepared by immunizing inbred mice with the proteins or peptides of the invention, or an antigenic fragment thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

"Humanized antibody" refers to antibodies derived from a non-human antibody, such as a mouse monoclonal antibody. Alternatively, humanized antibodies can be derived from chimeric antibodies that retains or substantially retains the antigen-binding properties of the parental, non-human, antibody but which exhibits diminished immunogenicity as compared to the parental antibody when administered to humans. For example, chimeric antibodies can comprise human and murine antibody fragments, generally human constant and mouse variable regions. Since humanized antibodies are far less immunogenic in humans than the non-human monoclonal antibodies, they are preferred for therapeutic antibody use.

Humanized antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991).

To generate an antibody response, the polypeptides of the present invention are typically formulated with a pharmaceutically acceptable carrier for parenteral administration. Such acceptable adjuvants include, but are not limited to, Freund's complete, Freund's incomplete, alum-precipitate, water in oil emulsion containing *Corynebacterium parvum* and tRNA. The formulation of such compositions, including the concentration of the polypeptide and the selection of the vehicle and other components, is within the skill of the art.

The term antibody as used herein is intended to include antibody fragments thereof which are selectively reactive with the polypeptides of the invention, or fragments thereof. Antibodies can be fragmented using conventional techniques, and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

In a further aspect, the invention provides methods for detecting the presence of one or more of the polypeptides of the invention in a protein sample, comprising providing a protein sample to be screened, contacting the protein sample to be screened with an antibody against one or more of the polypeptides of the invention, and detecting the formation of antibody-antigen complexes. In a preferred embodiment, methods for detecting the presence of a protein that is substantially similar to one or more polypeptides comprising or consisting of an amino acid sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and/or a protein that is substantially similar to one or more polypeptides selected from the group consisting of 60 kDa GPBP, 44-47 kDa GPBP, and 32 kDa GPBP comprise a) providing a protein sample to be screened;
b) contacting the protein sample to be screened with an antibody selective for one or more of the GPBP isoforms disclosed herein under conditions that promote antibody-antigen complex formation; and c) detecting the formation of antibody-antigen complexes, wherein the presence of the antibody-antigen complex indicates the presence of a protein comprising or consisting of a sequence that is substantially similar to a sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and/or a protein that is substantially similar to one or more polypeptides selected from the group consisting of 60 kDa GPBP, 44-47 kDa GPBP, and 32 kDa GPBP.

As used herein, the term "substantially similar" means that the polypeptides share at least 70% amino acid identity along their co-linear portions, and more preferably 75%, 80%, 85%, 90%, or 95% identity.

The antibody can be polyclonal, monoclonal, or humanized monoclonal as described above, although monoclonal antibodies are preferred. As used herein, the term "protein sample" refers to any sample that may contain the polypeptides of the invention, and fragments thereof, including but not limited to tissues and portions thereof, tissue sections, intact cells, cell extracts, purified or partially purified protein samples, bodily fluids, and nucleic acid expression libraries. Accordingly, this aspect of the present invention may be used to test for the presence of the non-canonical GPBP isoforms disclosed herein in these various protein samples by standard techniques including, but not limited to, immunolocalization, immunofluorescence analysis, Western blot analysis, ELISAs, and nucleic acid expression library screening, (See for example, Sambrook et al, 1989.) In one embodiment, the techniques may determine only the presence or absence of the protein or peptide of interest. Alternatively, the techniques may be quantitative, and provide information about the relative amount of the protein or peptide of interest in the sample. For quantitative purposes, ELISAs are preferred.

Detection of immunocomplex formation between the polypeptides of the invention, and their antibodies or fragments thereof, can be accomplished by standard detection techniques. For example, detection of immunocomplexes can be accomplished by using labeled antibodies or secondary antibodies. Such methods, including the choice of label are known to those ordinarily skilled in the art. (Harlow and Lane, Supra). Alternatively, the antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic-group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of suitable radioactive material include $^{125}$I, $^{131}$I, $^{35}$S or $^{3}$H.

Such methods of detection are useful for a variety of purposes, including but not limited to detecting an autoimmune condition, identifying cells targeted for or undergoing apoptosis, immunolocalization of the proteins of interest in a tissue sample, Western blot analysis, and screening of expression libraries to find related proteins.

In another aspect, the present invention provides isolated nucleic acids that encode the truncated GPBP polypeptides of the invention. In one embodiment, the isolated nucleic acids consist of sequences selected from the group consisting of SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27.

The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In another aspect, the present invention provides recombinant expression vectors comprising isolated nucleic acids consisting of a sequence selected from the group consisting of SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27. Recombinant expression vectors are vectors that operatively link a nucleic acid coding region or gene to any promoter capable of effecting expression of the gene product that are operably linked to a promoter, and are discussed in more detail above.

In a further aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2$^{nd}$ Ed. (R. I. Freshney. 1987. Liss, Inc. New York, N.Y.).

Methods for Identifying and Making Candidate Compounds to Treat Autoimmune Conditions and/or Protein Deposit-mediated Disorders GPBP displays a number of biological features to be considered a good candidate as a pivotal component of the cellular machinery catalyzing conformational isomerization and supramolecular assembly of autoantigens and inducing immune response during autoimmune pathogenesis (See below, as well as WO 00/50607; WO 02/061430). The results disclosed herein suggest that GPBP is an integral component of the endosomal-lysosomal pathway which activity is regulated in part by a catepsin-dependent processing, a biological strategy described for other enzymes (Pham, C. T., & T. J. Ley, (1999). Proc Natl Acad Sci USA 96(15): 8627-8632). These proteases are critical in processing proteins entering endosomal pathway and producing peptides that are presented through MHC class II (Chapman, H. A., (1998) Curr Opin Immunol 10(1): 93-102). Disturbance of lysosomal environment in a more general manner such as modifying the pH using compounds as chloroquine or in a more specific manner using catepsin inhibitors such as leupeptin has been shown to alter peptide presentation by MHC class II (Demotz, S., P. M. Matricardi, C. Irle, P. Panina, A. Lanzavecchia, & G. Corradin, (1989) J Immunol 143(12): 3881-3886; Turk, V., B. Turk, & D. Turk, (2001) EMBO J 20(17): 4629-4633). We have shown herein that leupeptin treatment substantially alters lysosomal processing of GPBP and therefore also likely induces an alteration in GPBP activity, which in turn suggests that altered peptide presentation and altered GPBP activity may be related and perhaps critical in autoimmune pathogenesis, which necessarily requires aberrant peptide presentation to be effective.

A feature common to many degenerative diseases is the formation of deposits of specific polypeptides. Where and how these deposits appear is highly specific and tightly related with pathogenesis. The deposits can be nuclear inclusion bodies, as in cerebellar ataxia, or be at the ER lumen, such as in some degenerative disease affecting liver and neurons, or be cytoplasmic inclusion bodies, as in Parkinson's disease, Alzheimer's disease, and amyotrophic lateral sclerosis; or endosomal-lysosomal, as in Alzheimer's disease, prion diseases, and type II diabetes. GPBP is an ubiquitous protein that has been independently related to conformational catalysis of substrate proteins (WO 00/50607; WO 02/061430) and in the formation of protein deposits in animal models that develop a degenerative nephropaty associated to an autoimmune response. Consequently the finding disclosed herein that GPBP interacts with PrP and Aβ$_{1-42}$ two polypeptides that undergo conformational alteration and form amyloid deposits in prion diseases and Alzheimer's disease, respectively, represents strong evidence for GPBP being involved in the pathogenesis of these degenerative diseases. More specifically, a protein resident in the endosomal-lysosomal pathway named Protein X has been proposed to bind to PrP and catalyze the conformational transition from PrP$^C$ to Prp$^{Sc}$ (Prusiner, S. B., (1998). "Prions." Proc Natl Acad Sci USA 95(23): 13363-13383.). Herein we present evidence demonstrating that GPBP binds to PrP in a Protein X fashion, phosphorylates PrP, forms aggregates with it and, as a consequence of this interaction, PrP undergoes conformational changes that renders PrP highly insoluble and precipitable. To our knowledge, GPBP represents the best molecular candidate to be Protein X in prion diseases as well as to perform a similar role in other protein deposit-mediated human disease.

Thus, in another aspect, the present invention provides methods for identifying compounds to treat an autoimmune disorder, wherein the method comprises identifying compounds that inhibit activity of one or more GPBP isoforms of the present invention. In a preferred embodiment, the one or more GPBP isoform comprises or consists of a sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or one or more GPBP isoforms selected from the group consisting of 60 kDa GPBP, 44-47 kDa GPBP, and 32 kDa GPBP, wherein such compounds are candidate compounds for treating an autoimmune condition and/or protein deposit-mediated disorders.

In another aspect, the present invention provides methods for identifying compounds to treat a protein deposit-mediated condition, wherein the method comprises identifying compounds that inhibit activity of one or more GPBP isoforms of the present invention. In a preferred embodiment, the one or more GPBP isoforms comprises or consists of a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or are selected from the group consisting of 60 kDa GPBP, 44-47 kDa GPBP, and 32 kDa GPBP, wherein such compounds are candidate compounds for treating an autoimmune condition and/or protein deposit-mediated disorders.

In a further embodiment of these methods, the method further comprises making the compounds identifed as candidate compounds for treating an autoimmune condition and/or protein deposit-mediated disorders. In one example, such compounds are organic molecules that are made using standard chemical methods. In another example, such compounds are polypeptides, which are made by methods disclosed herein for making polypeptides.

In one embodiment of these aspects, the method comprises identifying compounds that inhibit GPBP kinase activity. Such inhibition can be inhibition of GPBP autophosphorylation and/or inhibition of GPBP phosphorylation of target polypeptide, such as α3(IV) NC1 domain, myelin basic protein, and prion protein. Examples of such target polypeptides comprise those provided as SEQ ID NO:52 (α3(IV)NC1); SEQ ID NO:53 (MBP); and SEQ ID NO:54 (PrP), or functional equivalents. In a further embodiment, the method comprises identifying compounds that inhibit GPBP catalysis of conformational isomerization of a target polypeptide, such as α3(IV) NC1 domain, myelin basic protein, prion protein, and $A\beta_{1-42}$. Examples of such polypeptides are as described above, also polypeptides comprising SEQ ID NO:55 ($A\beta_{1-42}$), and functional equivalents thereof. Those of skill in the art will be able to identify other target polypeptides that can be used in the methods of the invention, such as SEQ ID NO:102, a functional equivalent for MBP.

In a further embodiment of these aspects, the method comprises identifying compounds that inhibit both GPBP kinase activity and GPBP catalysis of conformational isomerization of a target polypeptide.

The phosphorylation assays can be conducted in vitro on isolated targets, or can comprise analyzing the effects of the one or more test compounds on phosphorylation in cultured cells, although in vitro assays are preferred. A preferred method for identifying compounds that reduce in vitro phosphorylation of the target polypeptide comprises incubating a target polypeptide and ATP in vitro in the presence or absence of one or more test compounds under conditions that promote phosphorylation of the target polypeptide in the absence of the one or more test compounds; detecting phosphorylation of the target polypeptide; and identifying test compounds that reduce phosphorylation of the target polypeptide relative to phosphorylation of the target polypeptide in the absence of the one or more test compounds.

One of skill in the art is capable of determining suitable phosphorylation conditions for conducting the phosphorylation assay, and thus the present method is not limited by the details of the particular phosphorylation conditions employed. A non-limiting example of such suitable conditions for assaying phosphorylation of the first target comprises the use of 25 mM β-glycerol phosphate pH 7, 0.5 mM EGTA, 8 mM Mg Cl$_2$, 5 mM MnCl$_2$, 1 mM DTT, y 0.132 µM [$\gamma^{32}$P]-ATP using 100-200 ng of enzyme and 1 µg of substrate at variable time at 30° C.

In one embodiment of these aspects, the target polypeptide is GPBP, and the assay comprises analyzing the effect(s) of the one or more test compounds on GPBP autophosphorylation. In such an embodiment, an exemplary amount of GPBP for use in the assay is between 50 to 200 ng. In an alternative embodiment, the target polypeptide is selected from the group consisting of an α3 type IV collagen NC1 domain polypeptide comprising the amino acid sequence of SEQ ID NO:52, an MBP polypeptide comprising the amino acid sequence of SEQ ID NO:53, and a prion protein, such as that in SEQ ID NO:54 and the assay is conducted in the presence of a GPBP isoform as recited above, to test for transphosphorylation of the target polypeptide by the protein kinase. In this embodiment, the target polypeptide can comprise a full length α3 type IV collagen NC1 domain polypeptide (including α3(IV)NC1Asp$^9$ SEQ ID NO:57 or α3(IV)NC1Ala$^9$ SEQ ID NO:56), full length MBP, and prion protein, or portions thereof that contain sequences sufficient for phosphorylation by GPBP.

For in vitro phosphorylation assays, detection of phosphorylation can be accomplished by any number of means, including but not limited to using $^{32}$P labeled ATP and carrying out autoradiography of a Western blot of the resulting protein products on a reducing or non-reducing gel, or by scintillation counting after a step to separate incorporated from unincorporated label.

Analysis of in vitro phosphorylation may further include identifying the effect of the one or more test compounds on phosphorylation of individual conformational isomers of the target polypeptide. Such identification can be accomplished, for example, by carrying out SDS-PAGE on the reaction products of the phosphorylation reaction, followed by Western blotting, autoradiography and immunodetection of the target protein, as disclosed in WO 02/061430.

Analysis of in vitro phosphorylation may further include identifying the effect of the one or more test compounds on Ser$^9$ phosphorylation of the α3 type IV collagen NC1 domain, as disclosed in WO 02/061430. Such identification can be accomplished, for example, by comparing the immunoreactive patterns of antibodies specifically reacting with the N terminus of the α3(IV)NC1 (including but not limited to antibodies disclosed in WO 02/061430) and antibodies specifically reacting with Ser(P), such as those commercially available from Sigma Chemical Co. (St. Louis, Mo.).

The data presented in WO 02/061430 suggest that phosphorylation at Ser$^9$ exerts a positive control over conformational isomerization of α3(IV)NC1, and efficiently changes the cohort of α3(IV)NC1 conformers produced by a cell. These findings suggest that Ser$^9$ is one of the structural features that renders the α3(IV)NC1 domain potentially immunogenic, and suggest that, during pathogenesis, an aberrant phosphorylation event on this serine can lead the formation of conformers for which the immune system has not established a tolerance. Thus, determining the effect of test compounds on phosphorylation of the Ser$^9$ residue of α3 type IV collagen NC1 domain may be important in identifying especially useful candidate compounds for treating autoimmune disorders. Ser$^8$ in MBP has been shown to be functionally similar to Ser$^9$ in α3(IV)NC1 conformation and therefore similar tests can be conducted to identify compounds affecting MBP Ser$^8$ phosphorylation. (See WO 00/50507 and WO 02/061430)

Alternatively, the effects of test compounds on phosphorylation of the target polypeptide can be analyzed in cultured cells. Such a method involves contacting cells that express a target polypeptide selected from the group consisting of an α3 type IV collagen NC1 domain polypeptide, MBP, and prion protein under conditions to promote phosphorylation, detecting phosphorylation of the target polypeptide; and identifying test compounds that reduce phosphorylation of the target polypeptide relative to phosphorylation of the target polypeptide in the absence of the one or more test compounds. Appropriate cells for use are eukaryotic cells that express the appropriate target protein. Methods of detecting phosphorylation are as described above.

As used herein, the phrase "reduce/reducing phosphorylation" means to lessen the phosphorylation of the target polypeptide relative to phosphorylation of the target polypeptide in the absence of the one or more test compounds. Such "reducing" does not require elimination of phosphorylation, and includes any detectable reduction in phosphorylation. Thus, a test compound that inhibits phosphorylation of the target by, for example, as little as 10-20% would be considered a test compound that reduced phosphorylation. Such a compound may, for example, affect phosphorylation of $Ser^9$ of the α3(IV) NC1 polypeptide or $Ser^8$ in MBP, which is shown to exert a powerful control on conformational diversification, and thus to be a strong candidate for an inhibitor of autoimmunity. Alternatively, a test compound may inhibit phosphorylation of target polypeptide by 90%, but have little inhibitory effect on conformational isomerization of the target polypeptide, because reduction affects phosphorylation at sites other than $Ser^9$ or $Ser^8$. By performing assays both for phosphorylation inhibition of the target polypeptide, and conformer inhibition of the target polypeptide, it is possible to identify those compounds with the best potential for use as therapeutics for autoimmune disorders.

The above methods can be performed in whole cells or cell extracts expressing recombinant or naturally occurring forms of the polypeptides, in the absence of cells using proteins isolated via any of the methods disclosed herein and optionally including lysosomal extracts, or via any other methods known in the art.

Similarly, inhibition of conformational isomerization of the target polypeptide can be carried out in vitro using isolated components, or can be carried out in cultured cells, although the use of cultured cells is preferred. In a preferred embodiment using cultured cells, identifying compounds that reduce formation of conformational isomers of the target polypeptide comprises:

(a) providing cells that express a target polypeptide selected from the group consisting of α3(IV)NC1 domain, MBP, prion protein, Aβ1-42 and functional equivalents thereof (b) contacting the cells with one or more GPBP isoforms comprising or consisting of an amino acid sequence selected from the group consisting of SEQ ID NO:2 (for identifying compounds for treating a protein dposit-mediated disorder), SEQ ID NO:4 (for identifying compounds for treating a protein dposit-mediated disorder), SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or one or more GPBP isoforms selected from the group consisting of 60 kDa GPBP, 44-47 kDa GPBP, and 32 kDa GPBP;

(c) contacting the cells in the presence or absence of one or more test compounds, under conditions that promote conformational isomerization of the target polypeptide catalyzed by the one or more GPBP isoforms in the absence of the one or more test compounds, wherein the contacting of the cells with the one or more test compounds can occur prior to, simultaneous with, or subsequent to contacting the cells with the one or more GPBP isoforms;

(d) detecting conformational isomerization of the target polypeptide; and iv) identifying test compounds that reduce conformational isomerization of the target polypeptide relative to conformational isomerization of the target polypeptide in the absence of the one or more test compounds.

Appropriate cells for use are eukaryotic cells that express the appropriate target polypeptide. In a preferred embodiment, cell lines stably transfected to express the target polypeptide are used.

In this embodiment, detection of conformational isomers of the target polypeptide, and the effects of the test compounds thereon, generally involve immunodetection using Western blots of non-reducing SDS-PAGE gels containing the polypeptides from the cells. The target polypeptide can be purified via standard techniques (such as using cells transfected with a recombinant target polypeptide that is linked to an epitope tag or other tag to facilitate purification), or cell extracts can be analyzed. In a most preferred embodiment, stable cell lines (such as those disclosed in WO 02/061430) expressing recombinant target polypeptide are used. In some cases, such as for the α3 type IV collagen NC1 domain polypeptide, the target polypeptide is secreted into the medium in a monomeric form, permitting running of serum-free media samples on SDS-PAGE gels and subsequent Western blot analysis and immunodetection. Alternatively, protein extracts from the cells can be made by standard techniques. In a further alternatively, serum free media or otherwise isolated proteins can be used to coat ELISA plates, followed by similar immunodetection using antibodies that selectively bind to native conformers and either aberrant conformers or all conformers, respectively, and analysis using plate readers.

In a further embodiment, a reduction in conformational isomerization is determined by first subjecting the samples (in vitro reactions or cultured cells) to centrifugation and using the supernatant for limited proteolysis and further analysis of products by either Western blot or mass spectrometry. Alternatively, supernatants can be analyzed by ELISA using monoclonal antibodies that recognize conformational epitopes of the target protein. In this embodiment, it is possible to distinguish between a reduction in conformational isomerization and reduction of random aggregation, since the supernatant is used to analyze conformational isomerization, while the precipitate is used to analyze random aggregation, as described below.

In a preferred embodiment of an in vitro assay for inhibitors of conformational isomerization of the target polypeptide, the method comprises incubating (a) a target polypeptide selected from the group consisting of α3(IV)NC1 domain, MBP, and prion protein, and functional equivalents thereof (b) a GPBP isoform comprising an amino acid sequence selected from the group consisting of SEQ ID NO:2 (for identifying compounds for treating a protein dposit-mediated disorder), SEQ ID NO:4 (for identifying compounds for treating a protein dposit-mediated disorder), SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28; or a GPBP isoform selected from the group consisting of 60 kDa GPBP, 44-47 kDa GPBP, and 32 kDa GPBP; in the presence or absence of one or more test compounds, under conditions that promote conformational isomerization of the target polypeptide catalyzed by the GPBP isoform in the absence of the one or more test compounds, detecting conformational isomerization of the target polypeptide; and identifying test compounds that reduce conformational isomerization of the target polypeptide relative to conformational isomerization of the target polypeptide in the absence of the one or more test compounds, wherein such compounds are candidate compounds to treat one or more of an autoimmune condition and a protein deposit-mediated disorder.

As used herein, the phrase "reduce/reducing conformational isomerization" means to lessen the formation of conformers of the target polypeptide relative to conformer production under control conditions. Such "reducing" does not require elimination of conformer formation, and includes any detectable reduction in conformer formation. Furthermore, such "reduction in conformer formation" may entail a reduction in only one, or fewer than all conformational isomers; one can envision that such a reduction in production of specific conformers may be accompanied by an increase in the formation of other conformers. For example, we present evidence in WO 02/061430 that, for the α3(IV) NC1 domain polypeptide, a 27 kDa conformer is the primary product from which the remaining conformers derive. Thus, in a further preferred embodiment, the method comprises identifying those compounds that do not alter the formation of the 27-kDa conformer, but reduce formation of one or more of the other conformers. A preferred method for monitoring this inhibition of specific conformers is to use Mab3 antibody (described in WO 02/061430), which only reacts with the 27-kDa conformer, in parallel with Mab175, which is equally reactive with all α3 type IV collagen NC1 domain conformers.

In a further preferred embodiment of the assays to identify inhibitors of conformational isomerization of the target polypeptide, the target polypeptide is an α3(IV)NC1 domain polypeptide, and analysis of test compound effect on conformer formation of each of wild type α3(IV)NC1 and α3(IV)NC1Asp$^9$ (SEQ ID NO:57) is carried out in parallel. α3(IV)NC1Asp$^9$ is modified to replace Ser$^9$ with Asp$^9$, an amino acid residue that mimics a permanently phosphorylated residue, which is used herein as an example of an aberrant phosphorylation of α3(IV)NC1, that leads to the production of aberrant conformers. In WO 02/061430, we show that α3(IV)NC1Asp$^9$ expressing cells produce a larger number of conformers than cells expressing α3(IV) NC1Ser$^9$. Furthermore α3(IV)NC1Asp$^9$ cells express a 27-kDa conformer that reacts more strongly with Mab3, as well as with Goodpasture patient autoantibodies, than the 27-kDa conformer produced by α3(IV)NC1Ser$^9$ expressing cells. It is most preferred to identify compounds that abolish these differences in conformer production between α3(IV) NC1Asp$^9$ and α3(IV)NC1Ser$^9$, because this will indicate that the compound inhibits the production of an aberrant 27-kDa conformer from α3(IV)NC1Asp$^9$, while maintaining appropriate conformer production for α3(IV)NC1Ser$^9$.

In a further preferred embodiment, identifying compounds for treating an autoimmune disorder further comprises identifying compounds that reduce random aggregation of the target protein. As used herein, "random aggregation" is defined as non-physiological protein aggregation, as opposed to non-random, physiological protein oligomerization. GPBP catalyzes in vitro oligomerization and prevents random aggregation of protein substrates such as α3(IV)NC 1.

While not being limited by a specific mechanism, we propose that the ideal drug candidate for treating autoimmune disorders and/or protein deposit-mediated disorders would inhibit the kinase and chaperonine activity of GPBP, but would not inhibit its chaperone (ie: random aggregate-disrupting) activity (See WO 02/061430), in order to minimize the possibility that inhibition of GPBP activity would lead to increased random aggregate formation. Even more preferably, the ideal drug candidate would, in fact, enhance the chaperone activity of GPBP, to minimize secondary effects derived from undesirable aggregation of conformers.

Both in vitro assays and assays utilizing cultured cells can be used for identifying compounds that reduce random aggregation of the target polypeptide, although in vitro methods are preferred. One embodiment of an in vitro assay comprises:

i) incubating in vitro a target polypeptide selected from the group consisting of α3(IV)NC1, MBP, prion protein, Aβ$_{1-42}$, and functional equivalents thereof, with a GPBP isoform comprising an amino acid sequence selected from the group consisting of SEQ ID NO:2 (for identifying compounds for treating a protein-deposit-mediated disorder), SEQ ID NO:4 (for identifying compounds for treating a protein-deposit-mediated disorder), SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28; or a GPBP isoform selected from the group consisting of 60 kDa GPBP, 44-47 kDa GPBP, and 32 kDa GPBP in the presence or absence of one or more test compounds, under conditions to promote random aggregation of the target polypeptide by the GPBP isoform in the absence of the one or more test compounds; and ii) identifying test compounds that reduce random aggregation of the target polypeptide by the GPBP isoform relative random aggregation of the target polypeptide by the GPBP isoform in the absence of the one or more test compounds.

Detection of random aggregates, and the effect of test compounds thereon, is preferably carried out by Western blotting of a non-reducing SDS-PAGE gel of the isolated target polypeptide after incubation, and probing with antibodies that recognize the target polypeptide. Preferably, immunodetection is carried out using, in parallel, an antibody that detects a native conformation of the target polypeptide (such as Mab3 which selectively binds to an α3 type IV collagen NC1 domain polypeptide conformer (WO 02/061430)), and an antibody that detects all target polypeptide conformational isomers (such as Mab175 disclosed in WO 02/061430).

In a further embodiment, detection of random aggregation either in vitro or in cultured cells comprises centrifuging the samples and using the precipitates for direct Western blot analysis or for specific limited proteolysis followed by analysis of proteolytic products by either Western blot analysis or mass spectrometry. In many cases this is a preferred embodiment, as random aggregates of the target protein are generally precipitable, and therefore centrifugation separates random from non-random aggregates.

In a preferred embodiment of the random aggregation assay using cultured cells, cells that express the α3(IV)NC1 domain alone, the entire α3(IV) chain or or type IV collagen containing α3(IV) chain are contacted with the one or more test compounds, and the α3(IV)NC1 domain or collagenase digested α3(IV) chain or type IV collagen produced and secreted by the cells analyzed for α3(IV)NC1 oligomers by Western blot analysis as described in WO 02/061430.

As used herein the phrase "reduce/reducing GPBP induced random aggregation of the target polypeptide" means to decrease the amount of GPBP induced random aggregates of the target polypeptide relative to random aggregation under control conditions. Such "reducing" does not require elimination of random aggregation formation, and includes any detectable reduction in random aggregation formation, including reduction in only a single species of random aggregation in the presence of increased in other species of random aggregates.

In a further embodiment, the method for identifying candidate compounds to treat an autoimmune condition and/or a protein deposit-mediated disorder comprises contacting: (a) a GPBP isoform comprising or consisting of an amino acid sequence selected from the group consisting of SEQ ID NO:2 (for identifying compounds for treating protein deposit-mediated disorders), SEQ ID NO:4 (for identifying compounds for treating protein deposit-mediated disorders), SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28; or a GPBP isoform selected from the group consisting of 60 kDa GPBP, 44-47 kDa GPBP, and 32 kDa GPBP with (b) a target polypeptide selected from the group consisting of α3(IV) NC1 domain, MBP, prion protein, Aβ$_{1-42}$, and functional equivalents thereof, in the presence of one or more test compounds, under conditions that promote formation of an interaction between the GPBP isoform and the target polypeptide in the absence of test compounds and identifying test compounds that inhibit the interaction, wherein such compounds are candidate compounds to treat an autoimmune condition and/or a protein deposit-mediated disorder.

Such methods can be performed in whole cells or cell extracts (such as mammalian brain extracts) expressing recombinant or naturally occurring forms of the GPBP isoform and/or the target polypeptide, in the absence of cells using proteins isolated via any of the methods disclosed herein and optionally including lysosomal extracts, or via any other methods known in the art. The interaction between the GPBP isoform and the target polypeptide can be monitored by a variety of methods, including co-immunoprecipitation assays using antibodies directed against the GPBP isoform, the target polypeptide, and/or antibodies directed against expression tags added to recombinant versions of the GPBP isoform and/or the target polypeptide. Alternatively interactions can be monitored by analyzing aggregation kinetics as discussed below.

It should be noted that in each of the above embodiments of methods for detecting candidate compounds for treating an autoimmune condition and/or protein deposit-mediated disorders, conditions can be modified to reduce the pH of the reactions to approximate conditions in cellular compartments to which various GPBP isoforms have been localized. Such reaction conditions may better approximate physiological conditions. For example, a pH in the range of 5 to 5.5 could be used to simulate conditions in the lysosome or 6-6.5 to simulate conditions in the ER/Golgi.

As used herein a "protein deposit-mediated disorder" means a disease mediated by abnormal deposition of a specific protein, including but not limited to Parkinson's disease, Alzheimer's disease, amyotrophic lateral sclerosis, prion diseases, and type II diabetes, and autoimmune disorders. The protein deposit may be amyloid matter or para-amyloid matter.

As used herein an "autoimmune condition" is selected from the group consisting of Goodpasture Syndrome, multiple sclerosis, systemic lupus erythematosus, cutaneous lupus erythematosus, pemphigus, pemphigoid and lichen planus.

Modulators of GPBP Activity

In another aspect, the present invention provides a method for treating an autoimmune disorder, a tumor, a protein deposit-mediated disorder, and/or for preventing cell apoptosis comprising modification of the expression or activity of a GPBP isoform comprising or consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:SEQ ID NO:26, SEQ ID NO:28; or a GPBP isoform selected from the group consisting of 60 kDa GPBP, 44-47 kDa GPBP, and 32 kDa GPBP. Modifying the expression or activity of these polypeptides can be accomplished by using inducers or inhibitors of GPBP expression or activity, such as GPBP antibodies, antisense oligonucleotides complimentary to the transcription product of the GPBP gene, small interfering RNAs targeting the transcription product of the GPBP gene, gene or protein therapy using GP or myelin basic protein alternative products, cell therapy using host cells expressing GP or myelin basic protein alternative products, or other techniques known in the art. As used herein, "modification of expression or activity" refers to modifying expression or activity of either the RNA or protein product. Examples of such inducers or inhibitors are discussed below.

As part of the present invention, the inventors have identified further inhibitors of GPBP activity. Thus, in another aspect, the present invention provides an isolated polypeptide consisting of an amino acid sequence according to the general formula X1-SHCIX2-X3, wherein:

X1 is 0-10 amino acids of the sequence ATTAGILATL (SEQ ID NO:41);

X2 is E or Q; and

X2 is 0-10 amino acids of the sequence LMVKREDSWQ (SEQ ID NO:42).

As described below, the inventors have identified the peptide "SHCIE" (SEQ ID NO:39), which is derived from the GPBP sequence disclosed in WO 00/50607, as a key site for self-interaction of GPBP. As such, use of peptides comprising this sequence has been shown to inhibit GPBP kinase activity which makes them useful as therapeutics for a number of indications, as discussed below. A similar sequence (SHCIQ (SEQ ID NO:40)) is present in aggregatable CaM kinase II subunits α, β and δ, whereas it is not present in non-aggregatable CaM kinases I and IV (see below).

X1 and X3 provide optional amino acid sequences from GPBP immediately flanking the core sequence, to provide appropriate secondary structural characteristics to the polypeptide for optimal inhibitory activity.

In a preferred embodiment of this aspect of the invention, the polypeptide consists of a sequence selected from the group consisting of SHCIE (SEQ ID NO:39), SHCIQ (SEQ ID NO:40), ILATLSHCIELMVKR (SEQ ID NO:43), and ILATLSHCIQLMVKR (SEQ ID NO:44).

As described below, the inventors have further identified the peptide EKTAGKPILF (SEQ ID NO:45), present at the carboxy terminus of GPBP, as being a key site for GPBP self-interaction. As such, peptides of 6 or more amino acids derived from this sequence are useful as therapeutics for a number of indications, as discussed below. Thus, in another embodiment, the present invention provides isolated polypeptides consisting of at least 6 amino acids of the sequence EKTAGKPILF (SEQ ID NO:45). In a preferred embodiment, the isolated polypeptide consists of the sequence EKTAGKPILF (SEQ ID NO:45).

The polypeptides according of this aspect of the invention can further be derivatized to provide enhanced half-life, such as by the addition of polyethylene glycol (PEG) or as otherwise known in the art. The polypeptides of the invention may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare polypeptides with novel properties. For example, a polypeptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

The term "polypeptide" is used in its broadest sense to refer to a sequence of subunit amino acids, amino acid analogs, or peptidomimetics. The subunits are linked by peptide bonds, although the polypeptide can comprise further moieties that are not necessarily linked to the polypeptide by a peptide bond. For example, as discussed above, the polypeptide can further comprise a non-amino acid molecule that contains an aromatic ring.

The polypeptides described herein may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic.

Preferably, the polypeptides for use in the methods of the present invention are chemically synthesized. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, such as by using automated synthesizers.

In a further aspect, the present invention provides silencers of GPBP and/or GPBPΔ26 expression, selected from the group consisting of siGPBPΔ26-1 (SEQ ID NO:47), siG-PBPΔ26-2 (SEQ ID NO:48), siGPBPΔ26-3 (SEQ ID NO:49), siGPBPΔ26-4 (SEQ ID NO:50), and siGPBP (SEQ ID NO:51). These nucleic acids may be DNA or RNA, and may be single stranded or double stranded (in which case they also include the nucleic acid sequence complementary to the recited sequence, as well be recognized by those of skill in the art), although they are preferably RNA and double stranded. When used as DNA they are delivered into the cell in an appropriate vector for intracellular transcription and double stranded RNA synthesis, as is known in the art. As discussed below, each of these silencers was shown to diminish GPBP and/or GPBPΔ26 expression, and thus they are useful for the therapeutic methods of the invention, as discussed below. The silencers can be made by standard methods, such as those disclosed herein.

In a preferred embodiment, the nucleic acids are used in the methods for the invention as double stranded RNAs. Methods for using such double stranded RNAs are as described, for example in U.S. Pat. No. 6,506,559. For example, RNA may be synthesized in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

In another aspect, the present invention provides pharmaceutical compositions comprising the polypeptide or GPBP silencers of this aspect of the invention or pharmaceutically acceptable salts thereof, and a pharmaceutically acceptable carrier.

These peptides, or pharmaceutical compositions thereof, can be used in methods for treating one or more of autoimmune conditions and a protein deposit-mediated disorder, which comprise providing an amount effective of the polypeptides or GPBP silencers to a patient in need thereof to treat the autoimmune condition and/or a protein deposit-mediated disorder. The terms "autoimmune condition" and "protein deposit-mediated disorder" are as defined above.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

In a further embodiment, the present invention provides methods for inhibiting GPBP activity, comprising administering to a patient in need thereof an amount effective to inhibit GPBP activity of one or more novel polypeptides or silencers according to this aspect of the invention. As used herein, the term "inhibiting" or "inhibit" means to decrease GPBP expression or activity, such as decreasing GPBP kinase activity.

The present invention further provides methods for treating one or more of an autoimmune disorder and a protein deposit-mediated disorder comprising administering to a subject in need thereof an amount effective to treat the disorder of a compound selected from the group consisting of staurosporine, $Ca^{2+}$CaM, 1-[N,O-bis-(5-Isoquinolinesulfonyl)-N-methyl-L-tyrosyl]-4-phenylpiperazine (KN62), and 2-[N-(2-hydroxyethyl)-N-(4-methoxybenzenesulfonyl)] amino-N-(4-chlorocinnamyl)-N-methylbenzylamine (KN-93), or pharmaceutically acceptable salts thereof. The experimental results below demonstrate that each of these compounds is, either alone or in combination with other compounds, an inhibitor of GPBP activity.

For administration, the polypeptides, nucleic acids, or other compounds disclosed above (hereinafter referred to collectively as "compounds") are ordinarily combined with one or more adjuvants appropriate for the indicated route of administration. The compounds may be mixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The compounds of the invention can be administered as the sole active pharmaceutical agent, or they can be used in combination with one or more other compounds useful for carrying out the methods of the invention. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

The compounds of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds and pharmaceutical compositions of the present invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds and pharmaceutical compositions of the present invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.01 mg to about 50 mg per kilogram of body weight per day, and more preferably between 0.1 mg to about 50 mg per kilogram of body weight per day, are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions containing the compounds described herein are administered to an individual in need thereof. In a preferred embodiment, the subject is a mammal; in a more preferred embodiment, the subject is a human. In therapeutic applications, compositions are administered in an amount sufficient to carry out the methods of the invention. Amounts effective for these uses depend on factors including, but not limited to, the nature of the compound (specific activity, etc.), the route of administration, the stage and severity of the disorder, the weight and general state of health of the subject, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the invention in any way.

The present invention may be better understood with reference to the accompanying examples that are intended for purposes of illustration only and should not be construed to limit the scope of the invention, as defined by the claims appended hereto.

EXAMPLES

Synthetic oligonucleotides. The following oligonucleotides and others used for cDNA sequencing were synthesized by Amershan Biosiences o Roche:

| | | |
|---|---|---|
| ON-hmbGPBP-5c, | 5'-CCTCCGAGCCCGACGAGTTC-3' | (SEQ ID NO: 58) |
| ON-dinb1, | 5'-GACCGAAAGGGGCACGCAAC-3'; | (SEQ ID NO: 59) |
| ON-GPBPΔ102, | 5'-AAAAAGAATTCGCATCGAGGGGGCTAAGTTCGG-3'; | (SEQ ID NO: 60) |
| ON-GPBPΔ174, | 5'-AAAAAGAATTCGACGGCTGGAAGGGTAGGCT-3'; | (SEQ ID NO: 61) |
| ON-GPBPΔ246, | 5'-AAAAAGAATTCTGTCAGGCGCGGCGGCGGCGC-3'; | (SEQ ID NO: 62) |
| ON-GPBPΔ315, | 5'-GACGAATTCCCATCCCCCGACCCTTCACCC-3'; | (SEQ ID NO: 63) |
| ON-GPBPΔ369, | 5'-AAAAAGAATTCGGAGCGGGGCCGGTCTCCTGC-3'; | (SEQ ID NO: 64) |
| ON-pU1, | 5'-ACGACTCACTATAGGGAGAC-3'; | (SEQ ID NO: 65) |
| ON-pcDNAc, | 5'-CTCTAGCATTTAGGTGACAC-3'; | (SEQ ID NO: 66) |
| ON-GPBPMet$_{mut}$ | 5'-GGTTGTCGAGCCTCCGGATCGGATAATCAGAGC-3'; | (SEQ ID NO: 67) |
| ON-PrP-F3, | 5'-GAGAATTCAGCAGTCATTATGGCGAACCTT-3'; | (SEQ ID NO: 68) |
| ON-PrP-R1, | 5'-GAACTCGAGCCTTCCTCATCCCACTATCAGG-3'; | (SEQ ID NO: 69) |
| ON-E/K-PrP-F6, | 5'-TATCACCCAGTACAAGAGGGAATCT-3'; | (SEQ ID NO: 70) |
| ON-E/K-PrP-R6, | 5'-AGATTCCCTCTTGTACTGGGTGATA-3'; | (SEQ ID NO: 71) |
| ON-E168R-F1, | 5'-CCCATGGATAGGTACAGCAACC-3'; | (SEQ ID NO: 72) |

-continued

```
ON-E168R-R1,    5'-GGTTGCTGTACCTATCCATGGG-3';           (SEQ ID NO: 73)

ON-Q172R-F1,    5'-GAGTACAGCAACAGGAACAACTTTG-3';        (SEQ ID NO: 74)

ON-Q172R-R1,    5'-CAAAGTTGTTCCTGTTGCTGTACTC-3';        (SEQ ID NO: 75)

ON-R220A-F1,    5'-CAGTACGAGGCGGAATCTCAGG-3';           (SEQ ID NO: 76)

ON-R220A-R1,    5'-CCTGAGATTCCGCCTCGTACTG-3';           (SEQ ID NO: 77)

ON-R228A-F1,    5'-TATTACCAGGCAGGATCGAGCAT-3';          (SEQ ID NO: 78)

ON-R228A-R1,    5'-ATGCTCGATCCTGCCTGGTAATA             (SEQ ID NO: 79)
``` cDNA cloning and plasmid constructs for deletion mutants. To generate the cDNA for the different GPBP deletion mutants, we performed PCR on pc-n4' using one of the following synthetic oligonucleotides ON-GPBPΔ102, ON-GPBPΔ174, ON-GPBPΔ246, ON-GPBPΔ315, ON-GPBPΔ369 and ON-pcDNAc. The resulting cDNAs were individually cloned in EcoRI of pc-DNA3 (Invitrogen) to generate the pc-n4'Δ series. To obtain YFP-Flag-n4' and YFP-n4'Δ102, the cDNAs in pc-Flag-n4' and pc-n4'Δ102 were EcoRI excised and cloned in-frame into pEYFP-C1 (Clontech).

The cloning identification and characterization of cDNA for bovine and mouse GPBP and GPBPΔ26 has been reported (WO 00/50607 and WO 02/061430). The 5' UTR region for rat GPBP mRNA was obtained by standard reverse transcriptase-coupled-PCR using ON-hmbGPBP-5c and ON-dinb1 and total RNA was extracted from cultured rat astrocytes provided by C. Guerri at FVIB, and subsequent nucleotide sequencing of PCR product.

The pc-n4'Met$_{mut}$ construct was obtained by Transformer™Site-Directed Mutagenesis (Clontech) using pc-n4' and ON-GPBPMet$_{mut}$ following manufacturer's instructions.

We used human DNA extracted from blood and ON-PrP-F3 and ON-PrP-R1 to obtain a DNA that was subsequently cloned in EcoRI and XhoI of pc-DNA3 (Invitrogen) to produce pc-PrP. To produce the derived mutants we used a double-PCR approach using complementary oligonucleotides (ON-E/K-PrP-F6/ON-E/K-PrP-R6; ON-E168R-F1/ON-E168R-R1; ON-Q172R-F1/ON-Q172R-R1; ON-R220A-F1/ON-R220A-R1; ON-R228A-F1/ON-R228A-R1) that introduce the desired mutation and ON-pcDNAc or ON-pU1, and pc-PrP as a template. The resulting DNAs were similarly cloned in pc-DNA3.

SimRNA production. Silencers were generated using pSilencer 2.1-U6 hygro plasmid (Ambion) following manufacturers recommendations. The oligonucleotide pairs used were:

```
SiGPBP/Δ26-1:
5'GATCCCACTACATTCATGGGTGGCATTCAAGAGATGCCACCCATGAATGTAGTTTT    (SEQ ID NO: 80)

TTTGGAAA-3' and

5'AGCTTTTCCAAAAAAACTACATTCATGGGTGGCATCTCTTGAATGCCACCCATGAA    (SEQ ID NO: 81)

TGTAGTGG-3'.

SiGPBP/Δ26-2:
5'GATCCCACAGAGTATGGCTGCAGAGTTCAAGAGACTCTGCAGCCATACTCTGTTTT    (SEQ ID NO: 82)

TTTGGAAA-3' and

5'AGCTTTTCCAAAAAAACAGAGTATGGCTGCAGAGTCTCTTGAACTCTGCAGCCATA    (SEQ ID NO: 83)

CTCTGTGG-3';

SiGPBP/Δ26-3:
5'GATCCCGTACTTTGATGCCTGTGCTTTCAAGAGAAGCACAGGCATCAAAGTACTTT    (SEQ ID NO: 84)

TTTGGAAA-3' and

5'AGCTTTTCCAAAAAAGTACTTTGATGCCTGTGCTTCTCTTGAAAGCACAGGCATCA    (SEQ ID NO: 85)

AAGTACGG-3';

SiGPBP/Δ26-4:
5'GATCCCAGGCGTCACAGGACATGAATTCAAGAGATTCATGTCCTGTGACGCCTTTT    (SEQ ID NO: 86)

TTTGGAAA-3'
```

-continued and

5'AGCTTTTCCAAAAAAAGGCGTCACAGGACATGAATCTCTTGAATTCATGTCCTGTG    (SEQ ID NO: 87)

ACGCCTGG-3';

SiGPBP:
5'GATCCCGCCCTATAGTCGCTCTTCCTTCAAGAGAGGAAGAGCGACTATAGGGCTTT    (SEQ ID NO: 88)

TTTGGAAA-3' and

5'AGCTTTTCCAAAAAAGCCCTATAGTCGCTCTTCCTCTCTTGAAGGAAGAGCGACTA    (SEQ ID NO: 89)
TAGGGCGG-3'.

GPBP Expression in yeast and purification of recombinant protein. Recombinant FLAG-tagged human GPBP was essentially prepared as indicated in Raya, A., Revert, F., Navarro, S., and Saus J (1999) J. Biol. Chem. 274, 12642-12649. For light scattering purposes FLAG-affinity purified GPBP was further purified by FPLC on a Resource-Q column (Amersham Bioscience) equilibrated with 20 mM Tris HCl pH 8 and eluted in a linear gradient of NaCl 0-1M established in the same buffer and the peak containing the material which eluted at ~0.6 M NaCl was aliquot and stored at −80° C. until use.

Recombinant protein expression in cultured cells. The pcDNA3-based contructs containing the cDNA encoding the different human proteins of interest were used to transfect human 293 cells using standard calcium phosphate procedures in ProFection Mammalian Transfection System (Promega). 24-48 h after transfection cell lysates were used for Western blot, precipitation or immunoprecipitation studies. Cells expressing GPBP or derived deletion mutants were collected on ice with 50 mM Tris HCl pH 7.4, 0.05% Triton X-100, 1 mM PMSF and 5 μg/ml leupeptin, disrupted by vortex and insoluble material discarded by centrifugation at 14.000 rpm in Eppendorf at 4° C. for 10 min and supernatant used for Western blot analysis.

For other purposes after transfection and prior analysis cells were incubated with GPBP modulators or lysosomal inhibitors.

Recombinant protein expression in a cell-free system. Approximately 1 μg of the pcDNA3-based construct was expressed in a coupled transcription-translation system (Promega) following manufacturer's recommendation and using $^{35}$S-Methionine. The mixtures were analyzed by SDS-PAGE and a standard procedure for fluorography.

Subcellular fractioning and related studies. Rat liver subcellular fractionation was essentially performed as indicated in Aniento, F., Roche, E., Cuervo, A. M., Knecht, E. (1993). J. Biol. Chem. 268, 10463-10470. For some purposes lysosomal fractions (freshly prepared entire lysosomes) were dispersed in pure water and subjected to ten consecutive cycles of freezing and thawing to alter lysosomal membrane integrity (broken lysosomes). For other purposes, lysosomal fractions were similarly disrupted in the presence of protease inhibitors (PMSF 2 mM, leupeptin 0.2 mM and EDTA 2 mM) and subsequently centrifuged 130,000×g for 10 min at room temp to separate the soluble lysosomal fraction (also called here lysosomal extract) from the non-soluble fraction which, after rinse with 0.3 M saccharose in 10 mM MOPS pH 7.2, was used as the lysosomal membrane fraction.

To determine whether the GPBP immunoreactive polypeptides in lysosomal, microsomal and mitochondrial fractions represented cytoplasmic components non-specifically bound to these organelles we subjected each individual fraction to five consecutive washes with 0.3 M saccharose in 10 mM MOPS pH 7.2. Similar amounts of individual fractions representing each wash were analyzed by Western blot using Mab6. For similar purposes, mitochondrial and lysosomal fractions were treated with trypsine at different concentrations for 1 h at room temperature, digestion stopped by adding soybean trypsin inhibitor and samples similarly analyzed. In these cases, Western blot was performed in parallel with Mab6 and either anti-catepsin D antibodies for lysosomal samples or anti-carbamyl phosphate synthetase for mitochondrial fractions as degradation control of an integral component.

For still other purposes, entire or broken lysosomes (50 μg) were incubated at 30° C. with 25 mM β-glycerol phosphate pH 7, 0.5 mM EGTA, 8 mM Mg Cl$_2$, 5 mM MnCl$_2$, 1 mM DTT, y 0.132 μM [γ$^{32}$P]-ATP, maintaining saccharose concentration to 0.25 M in a final volume of 50 μl. The time of incubation was between 0 and 60 min and the phosphate transfer reactions stopped by adding SDS-PAGE sample buffer and heating at 95° C.

Fluorescence microscopy studies. In a typical assay 20.000 cells were seeded on glass slides and after 12 h the cells were rinsed with PBS (phosphate buffered saline) and fixed with methanol/acetone (50:50) for 5 min at −20° C. Cells were brought to room temperature by rinsing with PBS and used for indirect immunofluorescence. Briefly, cells were blocked for 45 min with PBS 3% BSA and then subsequently incubated for periods of 45 min with the corresponding primary and secondary antibodies. Finally, the slides were mounted for observation. A Zeiss Axioskop 2 microscope was used for standard fluorescence microscopy and an ACAS 570 interactive laser cytometer using a pinhole size of 225 mm corresponding to a 0.99 mm slice for confocal microscopy.

For other purposes, Cos-1 and HeLa cells were grown in 22 mm glass coverslips and transient transfections were performed 24-36 hours after seeding using SuperFect (Qiagen) or Fugene (Roche) transfection reagents. 24-48 hours after transfection, cells were washed with HBSS (Hanks buffered salt solution) containing 5 mM glucose and 10 mM Hepes, pH 7.4. Coverslips were transferred to a microscopy chamber (Attofluor, Molecular Probes, The Netherlands) and cell fluorescence was imaged with an epifluorescence inverted microscope (DMIRE-2, Leica Microsystems, Germany) equipped with an oil immersion 40× objective (NA 1.25). Fluorescence was excited at 475 nm (YFP) using a monocromator (Hamamatsu Photonics, Japan) and emitted light collected by a CCD camera (Orca- ER, Hamamatsu Photonics, Japan). The emission filter (Omega Optical, Brattleboro, Vt., USA) was 535±13 nm and the beam splitter was 445DRLP. Images were acquired and analyzed using the Aquacosmos software (Hamamatsu Photonics, Japan).

Animal studies. NZW, male or female, 4-6 month-old were injected intraperitoneally either with 1 µg/g of body weight of DAB-Am-4 and/or with 20 µg/g of body weight of the $Q_{2L}$ or $Q_{2D}$ peptide. These products were administered in a volume of 500 µl of steril saline solution 3 times per week, at alternate days, during 12 consecutive weeks. Age-matched uninjected mice were used as controls. At the end of the experiment, mice were sacrificed and kidneys were fixed in 10% paraformaldehide and processed for pathological studies. Similar DAB-Am-4 treatment studies were performed on C57BL/6 animals for genetic background control.

Light-scattering studies. A 0.7 µM solution of bovine recombinant $PrP^C$ (Prionics) in 20 mM Mes pH 6.5 buffer supplemented with 20 mM NaCl and 1 mM sodium citrate was placed in the measurement cell. After 10 min FPLC-purified human recombinant GPBP was added from a stock solution in TBS (Tris-buffered saline, 50 mM Tris-HCl pH 8, 150 mM NaCl) to rich a final concentration of 0.19 µM. In a second type of experiment the protein initially placed in the measurement cell was GPBP and $PrP^C$ was the added protein. For other purposes, GPBP solution was placed in the measurement cell and 10 min after inhibitory $Q_{2L}$ or non-active $Q_{2L}$ (100 µM) or $Q_{2D}$ (20 µM) were added, incubation continued for an additional 5-10 min period and $PrP^C$ added. Light scattering at 90° was recorded on a JASCO FP6500 spectrofluorimeter at 500 nm as a function of time.

SDS-PAGE, Western and far Western studies. These studies were essentially performed as indicated in Raya, A., Revert, F., Navarro, S., and Saus J (1999) J. Biol. Chem. 274, 12642-12649 and Raya, A. et al., (2000) J. Biol. Chem. 275, 40392-40399.

Yeast two-hybrid studies. Yeast two hybrid-studies to map interactive motifs for GPBP self-aggregation were performed essentially as described in Raya, A. et al., (2000) J. Biol. Chem. 275, 40392-40399 using different deletion mutants for GPBP obtained by standard DNA recombinant techniques.

Precipitation and immunoprecipitation studies. After transfection or modulator treatment, cells were washed once with ice-cold PBS, lysed with 100-300 µl of lysis buffer (20 mM Tris-HCl pH 8, 100 mM NaCl, 0.5% NP-40 0.5%, sodium deoxycholate, 1 mM PMSF and leupeptin 10 µg/ml) and protein concentration estimated using Bio-Rad protein assay and bovine serum albumin as standard. For precipitation studies, equal amounts of protein were brought to 50 µl with lysis buffer and centrifuged at 16.000×g for 15 min at 4° C. Supernatants and pellets were analyzed by Western blot. For immunoprecipitation studies lystes were pre-cleared at 500×g for 5 min at 4° C. before protein quantification and equal amounts of protein were brought to 250 µl with lysis buffer. 5 volumes were diluted with TBS and incubated with anti-FLAG M2-Agarose Affinity Gel (Sigma) for 1 h at 4° C. with gentle agitation; beds were washed three times with TBS and used for Western blot analysis using biotin-labeled antibodies.

Cell cultures with GPBP modulators. One day after transfection (for PrP-expressing cells) or after seeding (for α3(IV)NC1-expressing cells), culture media were replaced with media (PrP-expressing cells) or serum-free media (α3(IV)NC1-expressing cells) containing GPBP modulators and cultures were extended for an additional 24 h (PrP-expressing cells) or 24-48 h (α3(IV)NC1-expressing cells). Cell lysates from PrP expressing cells were used for Western blot, precipitation and immunoprecipitation studies, and culture media from α3(IV)NC1 expressing cells for Western blot analysis. For α3(IV)NC1-expressing cells, synthetic peptides were used at 100-200 µM and organic compounds at 5-50 µM. For PrP-expressing cells, $Q_{2D}$ was used at 1-10 µM, DAB-Am-4 at 1-5 µM and DAB-Am-32 at 0.25-1 µM.

In vitro phosphorylation. These studies were essentially performed as described in Raya, A., Revert, F., Navarro, S., and Saus J (1999) J. Biol. Chem. 274, 12642-12649. Where indicated GPBP modulators were used at 200 µM in a 10 min autophosphorylation reaction. Further autophosphorylation studies were performed using DAB-Am4 and $Q_{2D}$ and we have determined that similar activation and inhibition effects were obtained using decreasing concentrations up to 10 µM.

Histochemical and immunohistochemical on paraffin-embedded tissues. Immunohistochemical studies were essentially performed as indicated in Raya, A., Revert, F., Navarro, S., and Saus J (1999) J. Biol. Chem. 274, 12642-12649 and Raya, A. et al., (2000) J. Biol. Chem. 275, 40392-40399. Hematoxylin/eosin and trichromic Mason staining on mice kidney samples were performed following standard procedures.

Antibody production. The production of chicken polyclonal antibodies against GPBPpep1 recognizing GPBP and monoclonal antibodies against GST-GPBP recognizing GPBP/GPBPΔ26 (Mab14) have been previously described in Raya, A., Revert, F., Navarro, S., and Saus J (1999) J. Biol. Chem. 274, 12642-12649 and Raya, A. et al., (2000) J. Biol. Chem. 275, 40392-40399. Similar procedures were used for production of chicken polyclonal antibodies against GPBPpep2 recognizing non-canonical sequence of GPBP/GPBPΔ26 and monoclonal antibodies against GPBPpep1 only reacting GPBP (Mab6). For immunofluorescence and immunohistochemistry studies we used polyclonal antibodies whereas monoclonals were used for Western and far Western blot studies. The production and characterization of monoclonal antibodies against α3(IV)NC1 domain was previously reported (WO 02/061430). For some purposes antibody biotinylation was performed as described in AntibodyArray™ Instruction Manual from Hypromatrix.

Cell lines. The human cells lines used were HEK293 (ATCC), hTERT-RPE1 and hTERTBJ1 (Clontech). The cell line used for α3(IV)NC1 expression was obtained by stably transfecting HEK293 cells and its production has been previously reported (WO 02/061430).

Other products: Synthetic peptides GPBPpep1, Ac-PYSRSSSMSSIDLVSASDDVHRFSSQ-NH2 (SEQ ID NO:46) and GPBPpep2, Ac-PRSARCQARRRRGGRTSS-NH2 (SEQ ID NO:36) were from Genosys. Synthetic peptides $Q_4$ (Ac-EKTAGKPILF-OH) (SEQ ID NO:45), $Q_{2LI}$ (Ac-ILATLSHCIELMVKR-NH2) (SEQ ID NO:43), $Q_{2L}$ (Ac-LATLSHCIELMVKR-NH2) (SEQ ID NO:90) $Q_{2L}$, (Ac-VLMASLETLCRIHKI-NH2) (SEQ ID NO:92), $Q_{2DI}$ (Ac-ILATLSHCIELMVKR-NH2) (SEQ ID NO:43) and $Q_{2D}$ (Ac-LATLSHCIELMVKR-NH2) (SEQ ID NO:90) were synthesized at the FVIB. Initial in vitro and ex vivo studies were performed using $Q_{2LI}$ and $Q_{2DI}$ however further synthesis and uses were performed in absence of first isoleucine and we synthesized $Q_{2L}$ and $Q_{2D}$ peptides that show similar activity both in vitro and ex vivo but were more soluble and used for animal studies. Antibodies for co-localization were anti-catepsin D from Santa Cruz Biotechnology; anti-Golgin-91 (CDF4) and anti-human E2 subunit of pyruvate dehydrogenase from Molecular Probes. Anti-GAPDH and anti-carbamoyl phosphate synthetase were kindly provided by E. Knecht and J. Cervera at FVIB. GPpep1bov (Ac- KGKPGDTGPPAAGAVMRGFVFT-NH2) (SEQ ID NO:93) was synthesized by DiverDrugs and antibodies specific provided by Billy G. Hudson. $A\beta_{1-42}$ and FLAG peptides and the corresponding specific antibodies were from Sigma. All the conjugates used except anti-mouse Ig peroxidase (Promega) were from Sigma. Recombinant bovine PrP was from Prionics. PrP-specific antibodies were from Chemicon (clone 3F4) or from Santa Cruz Biotechnology (C-20). Rat cerebellar neuronal extracts were prepared essentially as described in Miñana MD, Montoliu C, Llansola M, Grisolía S, Felipo V. (1998) Neuropharmacology 137; 847-857 were provided by V. Felipo at FVIB. SiGFP, an mRNA silencer for green fluorescence protein was from Ambion.

Results

Identification of a 91-kDa isoform of GPBP (91 kDa GPBP) as non canonical mRNA translation start site product. We have made the observation that the 5' untranslatable region (5'UTR) of the mRNA of human GPBP contains an upstream open reading frame (ORF) of 130 residues with an in-frame stop codon at the beginning (See WO 00/50607). In vitro or ex vivo translation of the n4' mRNA (n4') resulted in the expression of two molecular species, one consistent with canonical translation at iMet displaying a molecular mass of ~77-kDa (77 kDa GPBP) and other with an apparent higher molecular mass (~91-kDa). To investigate the nature of the 91-kDa molecular species (91 kDa GPBP), a cDNA representing an mRNA with no 5'UTR was obtained and similarly expressed. The expression of this mRNA mutant resulted in a single protein of ~77-kDa (77 kDa GPBP), indicating that the existence of 91-kDa GPBP depends on non-canonical translation of the ORF at the 5'UTR. A cDNA representing a Met to Gly mRNA mutant for translation initiation expressed only the 91-kDa molecular species (FIG. 1), indicating that the 91-kDa GPBP is expressed from a non-canonical translation start site located 5' from the codon encoding the canonical Met initiation codon. Similar 91 kDa GPBP isoforms were shown to be present in mouse and rat cells, and are predicted to be expressed from GPBP mRNA in bovine cells.

Figure 2:
FIG. 2. The 91-kDa GPBP represent a non-canonical translation of the ORF existing in 5'UTR of the mRNA. In A, the ORF of the 5'-UTR of human GPBP mRNA is written in capitals and one-letter code. The 5' end and the translation direction of the indicated pcDNA3-based constructs are marked with bent arrows. The sequence of the synthetic peptide (GPBPpep2) is highlighted. In B, the cDNAs in the indicated constructs were expressed in a cell-free system (in vitro) or in human 293 cells (ex vivo) and analyzed as in FIG. 1.
Figure 2:
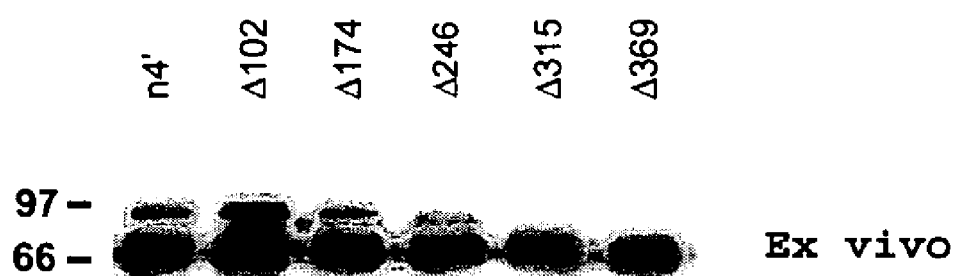

The 91-kDa GPBP isoform results from previously unrecognized mRNA translation mechanism. To explore the mechanism underlying expression of 91-kDa GPBP, we generated mutants representing truncated versions of the mRNA at the 5'UTR and performed recombinant expression in a cell-free system (in vitro) or in cultured human cells (ex vivo) (FIG. 2).

Whereas all the deletion mutants expressed the canonical polypeptide of 77-kDa GPBP, 91-kDa GPBP was only expressed from the complete mRNA (n4') and from a mutant which is devoid of the 5' 102 nucleotides (Δ102). Additional 5' deletions failed to abolish non-canonical translation initiation and caused a gradual reduction in the size of the non-canonical product (FIG. 2), suggesting that there are multiple non-canonical translation start sites displaying 5' to 3' hierarchy.

The relative expression of the two polypeptides in cell-free system (in vitro) sharply contrasted with the levels of these two polypeptides when the mRNA was expressed inside the cell, in which case 77-kDa GPBP isoform was significantly more abundant.

Figure 3:
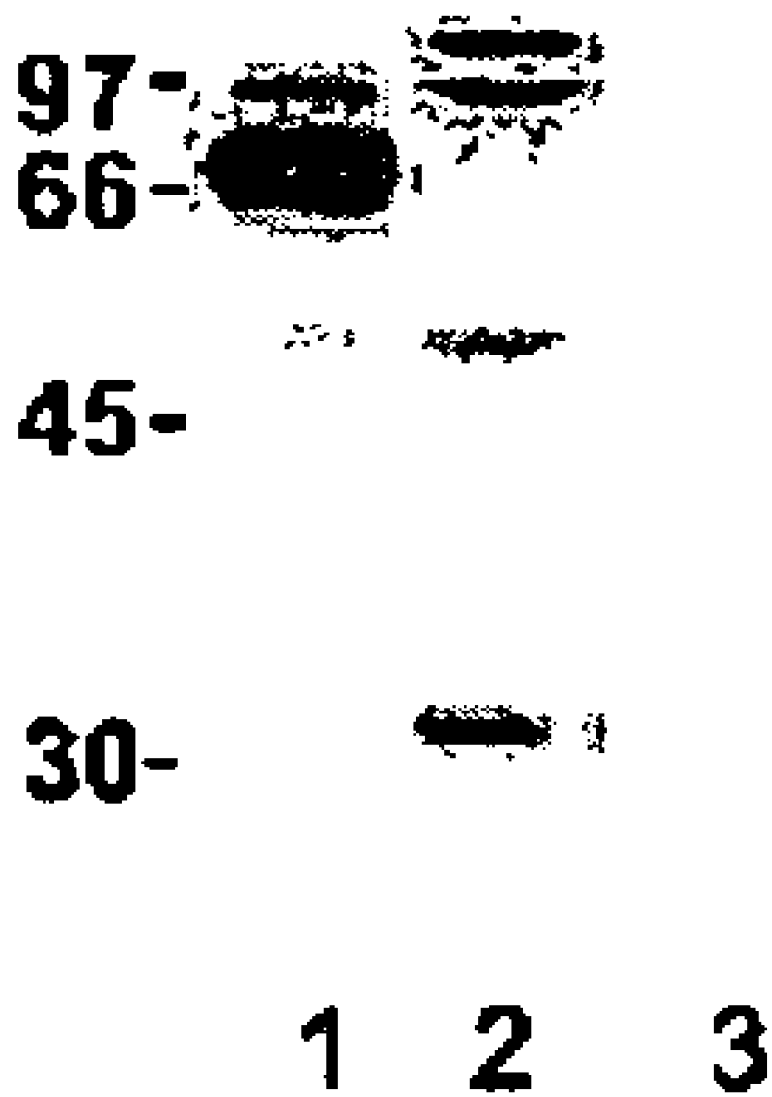
FIG. 3. In the cell the non-canonical 91-kDa GPBP isoform is more abundant than canonical 77-kDa. Lysates from pc-n4' (1) or from non-transfected (2,3) 293 cells were analyzed by Western blot with Mab6 (1,2) or with Mab6 and GPBPpep1 (3).

In cells and tissues, the expression of GPBP mainly depends on the non-conventional translation of the corresponding mRNA. In a first attempt to investigate the significance of our findings we compared recombinant and endogenous expression of GPBP in cultured human 293 cells (FIG. 3). As expected monoclonal antibodies specifically recognizing GPBP (Mab6) reacted with the two recombinant molecular species being expressed from cDNA in cell extracts deriving from transfected cells (91 kDa GPBP and 77 kDa GPBP) (lane 1). Cell extracts derived from non-transfected cells expressed several reactive polypeptides (lane 2), one co-migrating with recombinant 91-kDa GPBP and other polypeptides of higher and lower molecular mass (120-, 47- and 32-kDa), none of which displayed the molecular mass of the canonical recombinant polypeptide (compare lanes 1 and 2). In some studies the presence of an additional 60-kDa polypeptide also was evident. The specificity of the multiple reactivity displayed by Mab6 was confirmed by full inhibiting antibody binding in the presence of GPBPpep1, a synthetic peptide representing the GPBP exclusive 26-residues used in Mab6 production (lane 3). These findings suggest that at the steady state of the cell canonical translation product is virtually absent whereas non-canonical 91-kDa GPBP product is comparatively more abundant. Furthermore, we identified an additional major GPBP isoforms of 120-kDa along with minor lower molecular mass GPBP isoforms of 60-kDa, 47-kDa and 32-kDa.

Figure 4:
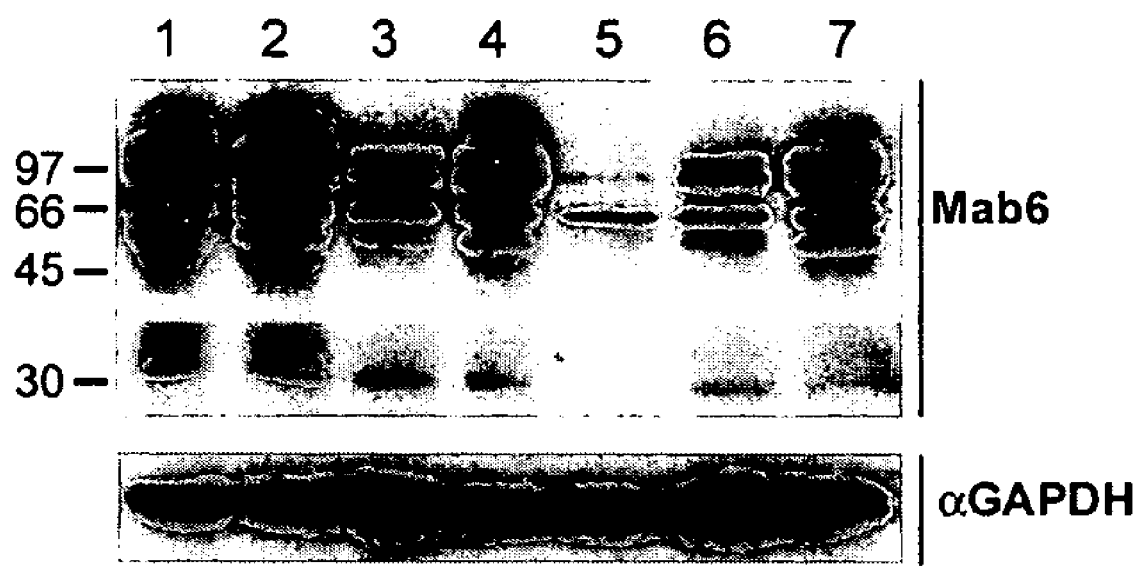
FIG. 4. Cellular 91- and 120-kDa GPBP-related polypeptides are translation products of GPBP mRNA. Similar amounts (~50 μg) of lysates from non-transfected 293 cells (1) or from 293 cells transfected with a plasmid encoding for SiGFP (2), SiGPBP (3), SiGPBP/Δ26-1 (4) SiGPBP/Δ26-2 (5), SiGPBP/Δ26-3 (6), SiGPBP/Δ26-4 (7) were analyzed by Western blot using the indicated antibodies.

To further investigate the nature of the immunoreactive polypeptides, we generated a number of GPBP mRNA silencers and assayed their capacity to inhibit endogenous expression of GPBP related polypeptides (FIG. 4). All individual mRNA silencers displaying the capacity to inhibit recombinant GPBP expression (not shown) also negatively impacted endogenous expression of 91 kDa GPBP and 120-kDa GPBP. The consequences on expression of GPBP polypeptides of lower molecular mass varied substantially between silencers. Thus, silencers that were more efficient reducing 91 kDa GPBP and 120-kDa GPBP promoted the expression of 60 kDa GPBP and reduced in an opposite but coordinated manner the expression of 47-kDa GPBP. All these data suggest that the expression of 91 kDa GPBP and 120-kDa GPBP depends more on mRNA translation than the expression of GPBP isoforms of lower molecular mass, which depend on a complex degradation program operating on the primary products and involving a positive feedback of the primary products in the proteolytic step from 60- to 47-kDa. Our findings support that all the polypeptides reactive with Mab6 indeed are GPBP related products, and suggest that at the cellular steady state GPBP expression depends more on non-canonical translation than on canonical translation of the mRNA.

We have extensively studied the expression of GPBP in multiple human tissue extracts and found an expression pattern that in general was similar to that found with cultured cells with the exception of a human striated muscle sample in which case we identified aminor reactive polypeptide of 77-kDa. In this case it remained unclear whether the 77-kDa polypeptide represented a canonical translation event or represented a proteolytical intermediate deriving from non-canonical 91-kDa GPBP (see below). Although the structural relationship between the 91-kDa and polypeptides of higher and lower molecular mass remains to be determined, the evidence suggest that non-canonical translation is more relevant in vivo than canonical. Immunochemical studies performed on paraffin embedded human tissues revealed that the immunostaining patterns obtained using antibodies that recognize canonical and non-canonical GPBP isoforms are virtually identical to those obtained with antibodies only reacting with non-canonical GPBP products.

In cultured cells, GPBP shows multiple subcellular localization including a prominent presence at the endosomal/lysosomal compartment. Immunohistochemical studies support that non-canonical GPBP isoforms display a broad subcellular localization including extracellular matrix, plasma membrane, cytosol (homogenous, fibillar and granular) and nucleus (WO 00/50607). An analysis for prediction of subcellular localization supports the multiple localization for non-canonical versus canonical products (see below), despite the fact that many of these destinies are non-compatible using conventional protein sorting routes. Consequently, we have explored GPBP subcellular localization using conventional immunofluorescence and confocal microscopy in cultured human cells. Indirect immunofluorescence studies on human RPE and BJ1 cells respectively representing epithelial and fibroblastic type of cells immortalized by telomerase (Clontech) revealed two principal cellular expression patterns for GPBP. Most of the cells express GPBP at the cytosol in a diffuse and fibrillar manner, with a remarkable expression of the protein at the nuclear membrane and perhaps presence of the protein in the nuclear environment. A limited number of cells show abundant GPBP expression at granular structures that distribute in the perinuclear region. The percentage of cells expressing the intense granular pattern varied between 10-30% and was more abundant in BJ1 than in RPE cells.

We have explored the cells in which GPBP is over expressed at defined granules to identify their subcellular nature. We performed conventional double indirect immunofluorescence and confocal microscopy using validated immunological probes for secondary lysosomes, Golgi apparatus or mitochondria. These studies revealed that GPBP shows a preferential localization at the lysosomes and a more limited but significant presence in Golgi apparatus and mitochondria. We have also performed fluorescence studies directed to address the intracellular distribution of proteins representing canonical or non-canonical GPBP primary products fused to yellow fluorescence protein. These studies revealed a major granular distribution for the non-canonical GPBP whereas the canonical GPBP appeared to be mainly diffuse cytosolic.

All these results suggest that the endosomal/lysosomal compartment is a principal subcellular destiny for non-canonical GPBP.

Figure 5:
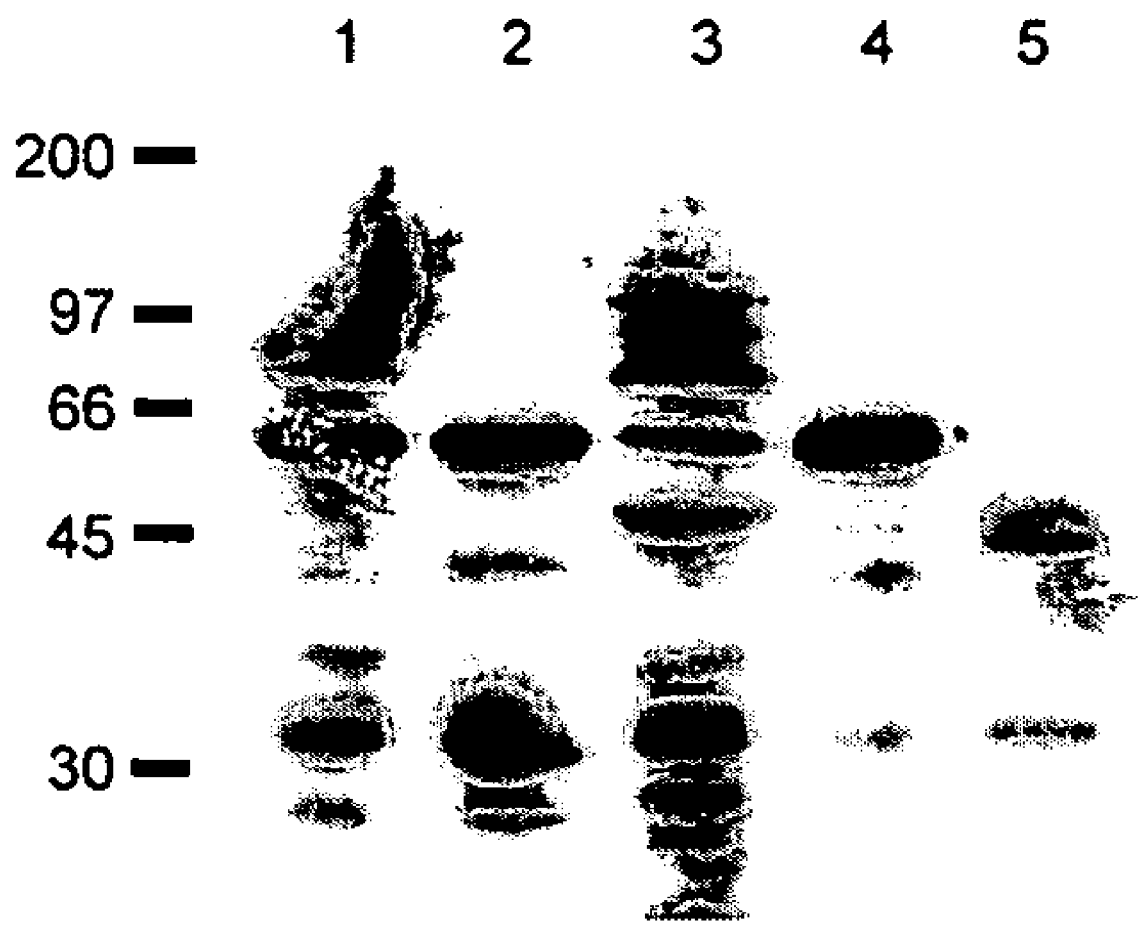
FIG. 5. Localization of GPBP by subcellular fractioning of rat hepatocytes. Similar amounts (~50 μg) of homogenate (1), cytosol (2), microsomes (3), mitochondria (4) and lysosomes (5) isolated from rat liver were analyzed by Western blot using Mab6 antibodies. Parallel studies performed in the absence of Mab6 revealed no immunoreactive polypeptides in any of the fractions analyzed.

The 91-kDa GPBP is the precursor of multiple related polypeptides including lysosomal 44-47-kDa isoforms. To investigate subcellular localization of GPBP in tissues we have used rat liver, a validated and reliable model for cell subfractioning. From the corresponding homogenates we prepared cytosolic, mitochondrial, microsomal and lysosomal fractions and assessed the presence of GPBP by Western blot (FIG. 5). The antibodies reacted with multiple polypeptides, which displayed 120-, 91-, 77-, 60-, 44-47, and 32-kDa. The distribution of reactive polypeptides among cellular fractions greatly varied. The polypeptides of higher molecular mass, (120-, 91-, and 77-kDa) were found preferentially in microsomes, the polypeptide of 60-kDa was mainly found in cytosol and mitochondria with traces in microsomes, whereas 44-47-kDa polypeptides were essentially lysosomal. Finally, the 32-kDa polypeptide was the most widely distributed being found in every fraction, followed by the 60-kDa polypeptide that was found in all fractions except in lysosomes. Extensive washing or trypsin treatment of either mitochondrial or lysosomal fractions resulted in no significant reduction in the content of immunoreactive peptides, suggesting that these polypeptides are integral components of these cell compartments.

Figure 6:
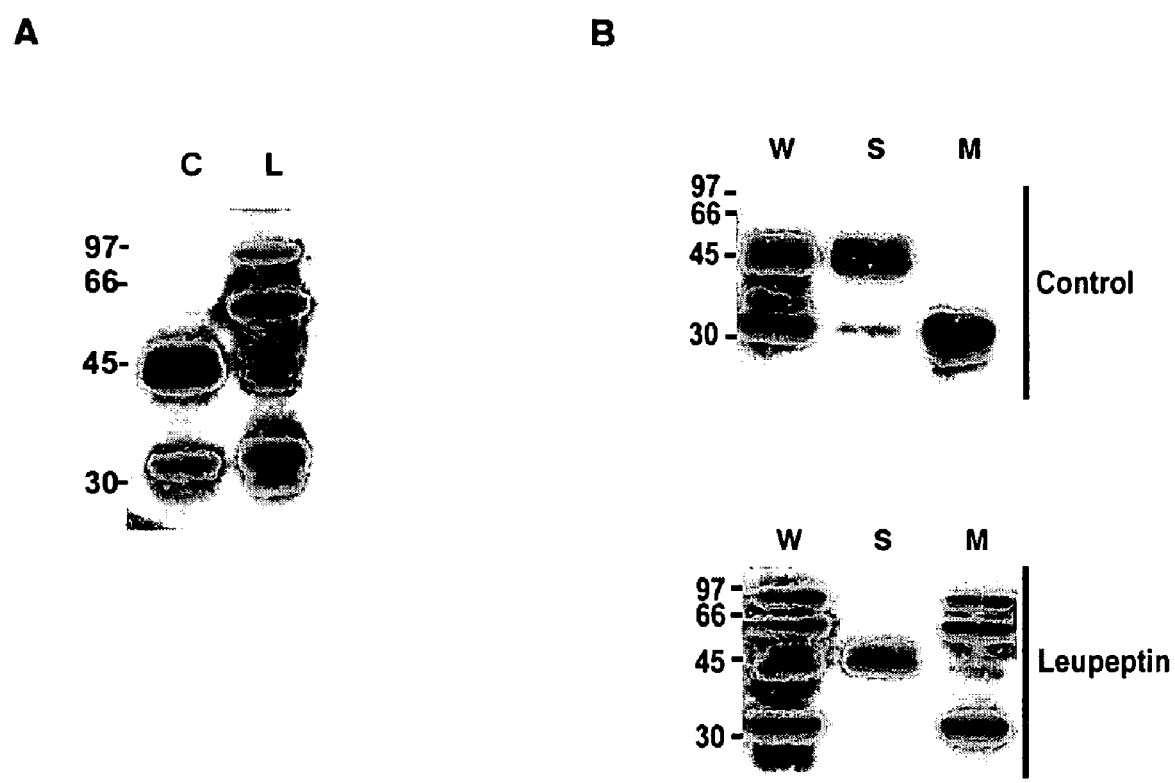
FIG. 6. Identification of 91-kDa GPBP isoform in rat liver lysosomes and evidence for processing to 44-47-kDa isoforms. In A, similar amounts (~50 μg) of lysosomal fractions from liver of untreated (C) or leupeptin-treated (L) rats were analyzed by Western blot using Mab6 antibodies. In B, lysosomal fractions as in A were further fractioned and whole (W), soluble (S) or non-soluble (M) fractions were similarly analyzed.

All our findings suggest that the primary products of GPBP mRNA translation are subjected to a complex intracellular processing coupled to subcellular localization. Immunofluorescence studies suggest that the endosomal/lysosomal compartment is among the most prominent destinations for GPBP. This compartment is also of major interest in antibody-mediated autoimmune pathogenesis and in tissue degeneration, since is actively implicated in the production of both non-tolerized peptides and in protein deposition. To investigate the presence of GPBP in this compartment, we isolated lysosomes from the liver of untreated or leupeptin-treated rats, and the presence of GPBP was investigated by Western blot analysis using specific monoclonal antibodies (FIG. 6). Lysosomes from untreated animals contained major reactive polypeptides of 44-47-kDa and aminor polypeptide of 32-kDa. Treatment with leupeptin substantially changed the immunoreactive pattern and thus polypeptides of higher molecular mass (91- and 60-kDa), virtually undetectable in untreated lysosomes were the most abundant whereas the 44-47-kDa polypeptides significantly diminished. Although in most of the cases leupeptin treatment did not change the level of 32-kDa there were examples in which we found increased levels of this polypeptide, and in some other cases treatment was associated with detection of 77-kDa and 120-kDa polypeptides. These data suggest that the 44-47-kDa polypeptides are integral components of the lysosome that derive from limited leupeptin-sensitive proteolysis of a 91-kDa precursor through a major intermediate of 60-kDa. Furthermore, the non-reduced or moderated augmented expression of 32-kDa polypeptide associated with leupeptin treatment, suggests that the 91-kDa polypeptide is also subjected to a second degradation process which is leupeptin-insensitive.

To further localize and to investigate the relationship among the different GPBP-related polypeptides, we isolated matrix and membranes from lysosomes of treated or untreated rats and the corresponding extracts were similarly analyzed. Western blot studies on untreated lysosomal fractions revealed that the major 44-47-kDa polypeptides are located at the lumen and with the exception of the 60-kDa polypeptide, which appeared in some preparations equally distributed between matrix and membrane fractions, the polypeptides other than the 44-47 kDa were found to be membrane-associated components. These findings, in addition to further confirming that the 44-47-kDa GPBP-related polypeptides are integral components of the lysosomes provide some insights on the mechanism of their production. Without being limited to a specific mechanism, we propose that the 91-kDa form exists exclusively attached to the inner face of the lysosomal membrane where it undergoes limited leupeptin-sensitive or leupeptin-insensitive proteolysis to yield the 44-47-kDa or the 32-kDa polypeptides respectively. Leupeptin-sensitive processing is predicted to occur in two principal steps, one with the polypeptide being attached to the membrane yielding a 60-kDa product, and the other requiring release of the 60-kDa intermediate from the membrane and yielding a final products of soluble 44-47-kDa polypeptides. Leupeptin-insensitive processing appears to occur however only on a membrane-bound 91-kDa polypeptide to generate a final product of 32-kDa still bound to the membrane. It remains to be determined whether the 77-kDa polypeptide found in some leupeptin-treated lysosomes represents a proteolytic intermediate or the canonical translation primary product that also enters into this compartment.

Figure 7:
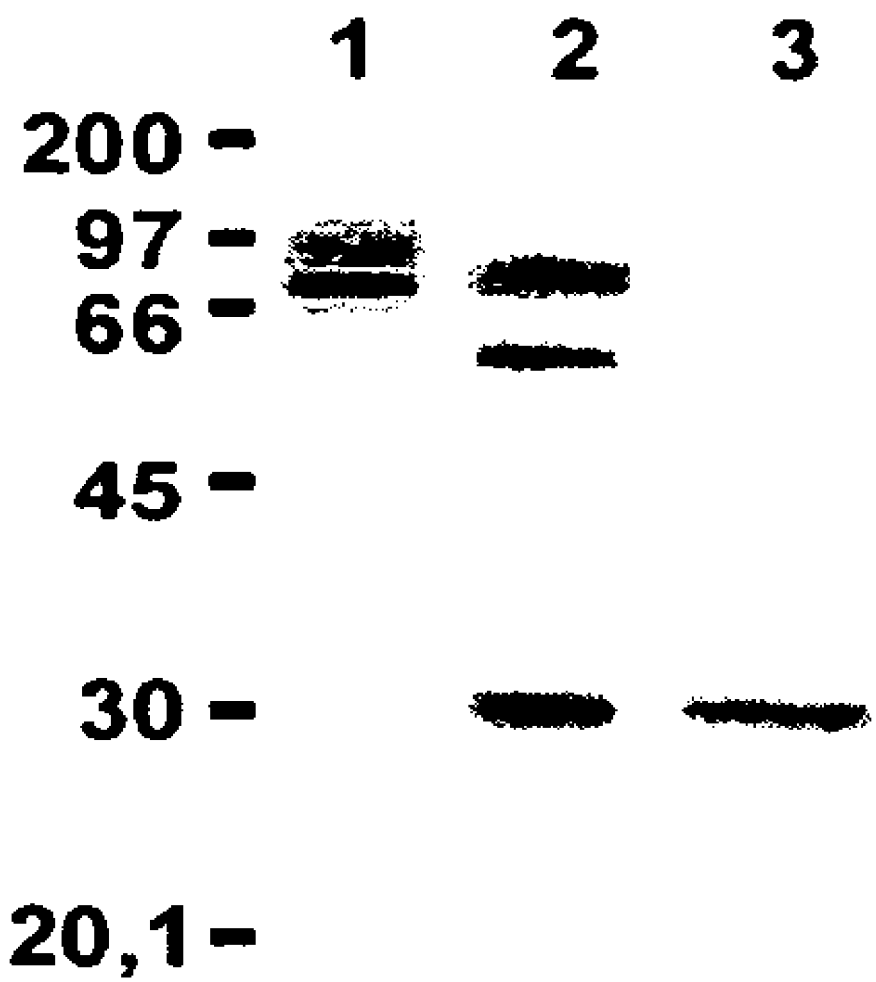
FIG. 7. Lysosomal proteolysis of in vitro expressed GPBP generates polypeptides of similar molecular mass than endogenous GPBP-related polypeptides. The cDNA in pc-n4' was expressed in a cell-free system and similar amounts of the mixtures were incubated in the absence of lysosomal extract for 20 min (1) or in the presence of lysosomal extract for 5 (2) or 20 (3) min and analyzed by SDS-PAGE and fluorography.

All our findings suggest that the 44-47-kDa polypeptides are lysosomal isoforms of GPBP, which mainly derive from non-canonical 91-kDa GPBP. These studies also reveal that, with the exception of the 120-kDa polypeptide, lysosomes contain the enzymatic resources to generate all the GPBP isoforms found in tissue and cell homogenates. This was specifically confirmed by coupling recombinant expression of the mRNA in a cell-free system coupled to limited proteolysis using rat liver lysosomal extracts (FIG. 7). Recombinant expression of mRNA coupled to limited proteolysis produced polypeptides of 77-, 60-, 47-, 44- and 32-kDa revealed that lysosomal proteolysis of primary translation products accounts for all the related polypeptides of lower molecular mass. Similar results were obtained when the proteolytic assays were performed using individual recombinant product (91- or 77-kDa).

Figure 8:
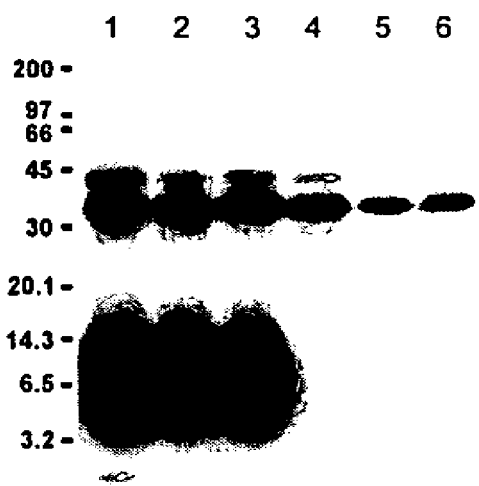
FIG. 8. Phosphate transfer activity in isolated rat liver lysosomes. In A, entire (1,2,3) or broken (4,5,6) rat liver lysosomes were incubated for 0 (1,4), 10 (2,5) or 20 (3,6) min with a phosphorylation mixture containing [γ$^{32}$P]ATP and further analyzed by SDS-PAGE and autoradiography. In B, entire lysosomes from liver of untreated (Control) or leupeptin-treated (Leupeptin) rats were similarly incubated for 0 (1), 15 (2), 30 (3) or 60 (4) min and further analyzed by Western blot using Mab6 (Western) and autoradiography ($^{32}$P). Here and in the following Figures the autoradiographic study was performed first to avoid labeling leakage during Western blot processing. With numbers and bars we indicate the size in kDa and position of Mab6 reactive polypeptides on either study. The arrows denote the autoradiographic bands whose intensity increased during time of incubation.
Figure 8:
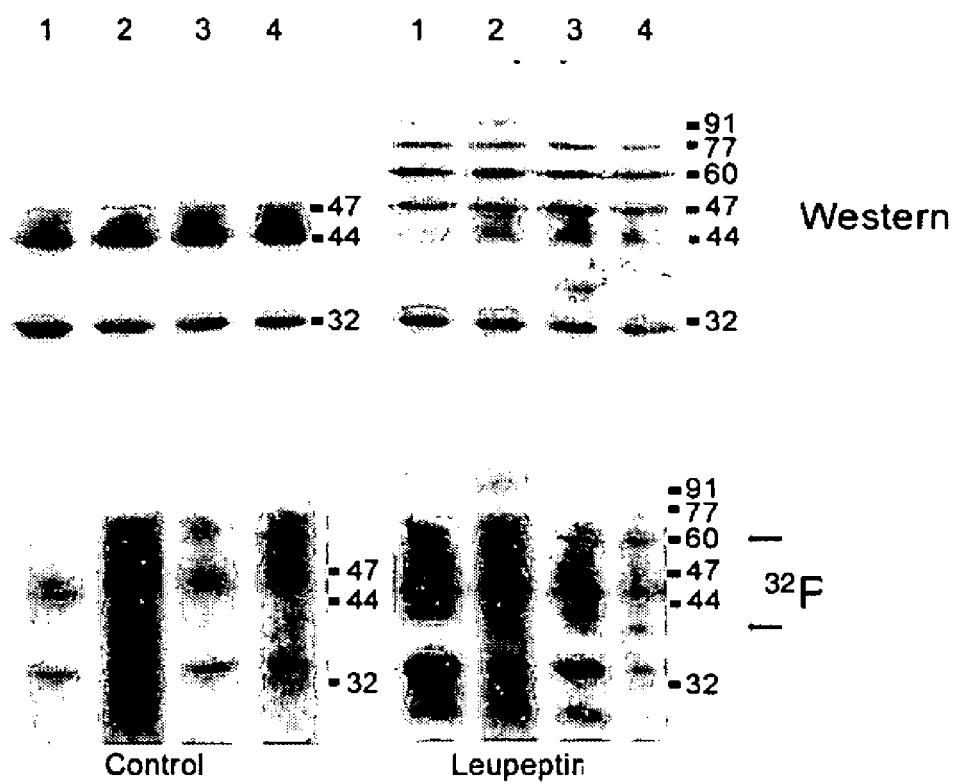

Identification of phosphate transfer activity in isolated intact lysosomes and phosphorylation of the 44-kDa GPBP form. The above data suggest that the 44-47 kDa polypeptides are the isoforms of GPBP in the lysosome. We assessed the ability of these polypeptides to transfer phosphates by incubating intact or broken lysosomes with $[\gamma^{32}P]$-ATP and further analyzing the mixtures by SDS-PAGE and autoradiography (FIG. 8A). Untreated, intact lysosomes incubated with isotonic buffer at pH 7 efficiently incorporated $^{32}P$ at components of 44-47-, 34- and 3.2 to 15-kDa, whereas lysosomal disruption greatly impaired labeling of these materials. To determine the relationship between molecular species that incorporated $^{32}P$ and GPBP, a protein kinase with a prominent capacity to undergo autophosphorylation, we combined Western blot and autoradiography of SDS-PAGE analysis of phosphorylation mixtures representing control or leupeptin-treated lysosomes (FIG. 8B). These studies revealed the presence of labeled components co-migrating with 44-47-kDa polypeptides in control lysosomes in addition to a labeled component of lower molecular mass (~34-kDa) not associated to any immunoreactive species. In general, we observed a fast initial labeling and a gradual reduction in $^{32}P$-labeling with the time of incubation. The studies on leupeptin-treated lysosomes revealed a more efficient initial $^{32}P$ labeling of virtually all the components previously identified in control lysosomes. However, in treated lysosomes the gradual reduction in $^{32}P$-labeling of the 44-47-kDa components was accompanied by a gradual labeling of a component that co-migrated with 60-kDa GPBP isoform. Similarly, labeling reduction of non-immunoreactive 34-kDa material was accompanied by increased labeling of a component with higher molecular mass (~38-kDa) that was also not detectable by monoclonal antibodies. These findings suggest that lysosomal GPBP isoforms are either the target of an unknown protein kinase therein or, more likely, the labeling of the GPBP isoforms is the result of an autophosphorylation event. Accordingly, a C-terminal deletion mutant of GPBP with approximately 44-kDa molecular mass (residues 1-299 of GPBP) displayed greater auto-phosphorylation activity at pH 5 than full sized GPBP, suggesting that lysosomal 44-47-kDa are GPBP isoforms more efficient than 91- and 77-kDa primary products to operate inside the lysosome. In any event, the demonstration of $^{32}P$ incorporation at the 60- and t44-47-kDa polypeptides provides, to our knowledge, the first evidence for an intrinsic protein kinase activity in lysosomes and points to 44-47-kDa GPBP as the first protein kinase operating inside this cell compartment.

Figure 9:
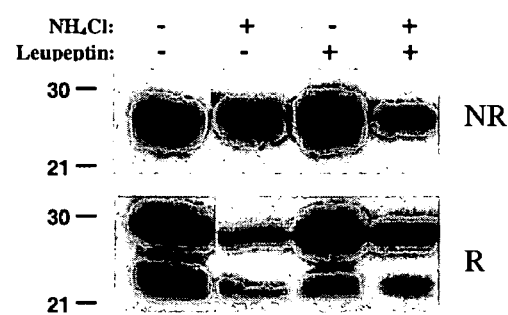
FIG. 9. Conformational diversification of the α3(IV)NC1 domain occurs at the endosomal-lysosomal compartment and depends on GPBP. In A, 293 cells expressing recombinant α3(IV)NC1 domain were treated with 20 mM NH$_4$Cl and/or 100 μM leupeptin. Similar amounts of serum-free media were analyzed by SDS-PAGE under reducing (R) or non-reducing (NR) conditions and Western-blot using α3(IV)NC1-specific antibodies (Mab175). In B, similar amounts of recombinant GPBP or α3(IV)NC1-expressing cells were incubated or cultured respectively in the absence (Con) or in the presence of the indicated GPBP modulator. Phosphorylation mixtures were analyzed as in FIG. 8 ($^{32}$P) using Mab14 in the Western blot staining to determine that were not differences in the amount of recombinant protein among lanes (not shown). Culture media were analyzed as in A (Western).
Figure 9:
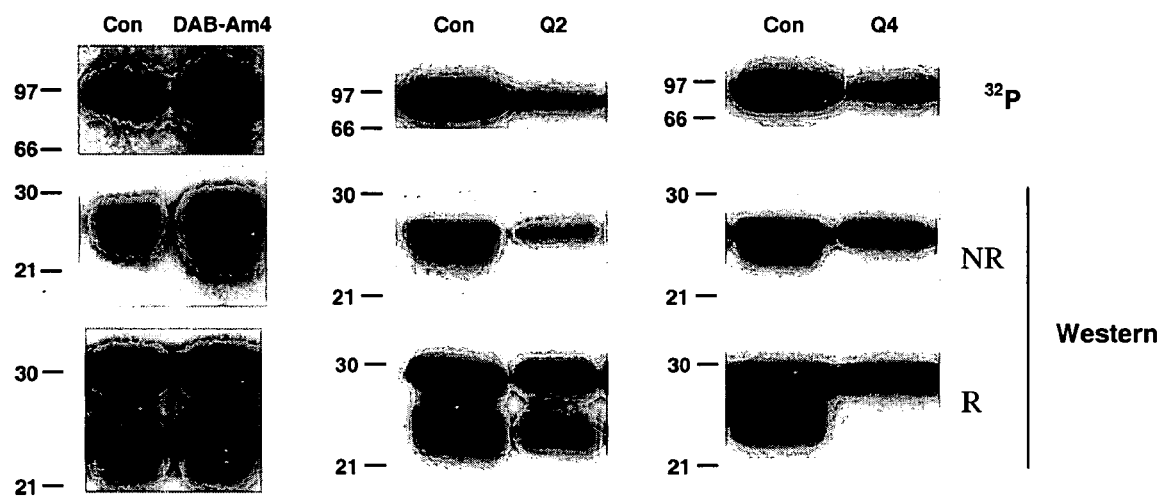

The conformational isomerization of the α3(IV)NC1 domain mainly occurs at the endosomal/lysosomal compartment and depends on GPBP. Recombinant expression of the α3(IV)NC1 domain in human 293 cells results in the synthesis and secretion of multiple polypeptides ranging in size between 22-27-kDa (WO 00/50607 and WO 02/061430). Reduction of disulfide bonds results in a major single molecular species of 29-kDa and multiple derived proteolytic products of lower molecular mass, suggesting that the multiple polypeptides are conformational isoforms (conformers) maintained and stabilized by disulfide bonds that undergo limited proteolysis (FIG. 9A). To explore the cell compartment at which the conformational diversification of the α3(IV)NC1 domain occurs, the cells were cultured in the presence of $NH_4Cl$ or leupeptin, lysosomotropic agents that increase the pH and inhibit cysteine proteases respectively. The presence of $NH_4Cl$ reduced conformer production whereas leupeptin inhibited the presence of proteolytic products, suggesting that conformational diversification of the α3(IV)NC1 domain mainly occurs at the endosomal/lysosomal compartment. To explore the role of GPBP in α3(IV)NC1 conformer production, compounds with the capacity to modulate GPBP kinase activity in vitro (see below) were used to regulate the corresponding cellular conformer production (FIG. 9B). When a positive GPBP modulator (DAB-Am4) was added to the culture medium an efficient increase in conformer production occurred. In contrast, when the compound added was a negative GPBP modulator ($Q_2$ or $Q_4$), a reduction in conformer production occurred. All these findings suggest that lysosomal GPBP isoforms are actively involved in the conformational isomerization of the α3(IV)NC1 domain and consequently, the assembly of aberrant α3(IV)NC1 conformers mediating Goodpasture autoantibody production is expected to be a lysosomal event. DAB-Am-4 is a branched polyamine and these compounds have been shown to accumulate in secondary lysosomes (Supattapone S et al. J. Virol (2001) 75, 3453-3461). Fluorescein-labeled $Q_2$ showed a granular cell distribution with broad co-localization with GPBP as determined by indirect immunofluorescence approaches on cultured cells. D-amino acid version of $Q_2$, known to be more refractory to degradation, was significantly more effective inhibiting GPBP cell conformer production.

GPBP, autoimmunity and tissue degeneration. Several lines of evidence support the idea that GPBP is involved in the pathogenesis of other autoimmune diseases: 1) GPBP is preferentially expressed in cells and tissues that are targets of common autoimmune responses; 2) GPBP binds to and phosphorylates other human autoantigens; and 3) Biochemical and immunohistochemical studies show increased levels of GPBP expression in tissues undergoing an autoimmune attack, including cutaneous lupus erythematosus (WO 00/50607) and more recently in cutaneous lesions of patients undergoing systemic lupus erythematosus (SLE).

The autoimmunity response in SLE is due to the involvement of both genetic and environmental factors. New Zealand White (NZW) mice, which do not develop autoimmunity, carry a genetic background that promotes SLE when bred with other mice strains, such as New Zealand Black (NZB). The genetic predisposition of NZW to undergo SLE, and more specifically renal lupus (autoimmune glomerulonephritis), has not been associated with any specific gene(s). In an attempt to relate GPBP with this genetic background, we have performed histological and immunohistochemical studies to address the expression of GPBP in the renal glomerulus of NZW. Our studies suggest that these mice do not undergo a frank autoimmune response. However, 7-9 months after birth they develop a degenerative glomerulopathy that cause glomerulosclerosis and end-stage renal disease (ESRD) with a premature death at 13-14 month of age. Morphologically, this nephropathy presents an evolution with several histological stages. Stage 1, characterized by minimal changes consisting of slight cell proliferation (endothelial and/or mesangial) and light thickening of mesangium. Stage 2, the cell proliferation is moderate and there are collagenous-like deposits at the mesangium which stain with aniline blue, and other deposits of hyaline nature in the subendothelial space that stain with acid fuchsin. Stage 3, characterized by an intense cell proliferation predominantly mesangial with extensive protein deposits that invade subendothelial space (Stage 3a), or endothelial with extensive nodular deposits that invade the mesangium (Stage 3b). At this stage the more characteristic histochemical image is the presence of fuchsinophilic hyaline deposits surrounded by protein deposits of collagenous-like nature. Stage 4, in this stage the glomeruli undergo sclerosis likely as a consequence of scar organization of the collagenous deposits. When sclerosis results from deposits primarily mesangial this is more diffuse and homogeneous (Stage 4a) than when scar results from reactive fibrosis against subendothelial deposits, in which case this is more nodular and laminated (Stage 4b).

Immunochemical studies performed to address the presence of GPBP revealed that, in contrast to what has been previously described for control mice kidneys (BALB/c and C57BL/6) (WO 00/50607), the NZW kidneys show from moderate to abundant expression of GPBP in tubules and in the interstitial spaces, without significant expression in the glomeruli. However, as glomerular degeneration starts and develops, we detected GPBP expression at the subendothelial space in intimate association with the fuchsinophilic subendothelial material. As the disease progress through Stages 3b and 4b, the expression of GPBP increases substantially.

Furthermore, in an attempt to relate the degenerative process and the production of autoantibodies, we have performed studies to address the presence of immunoglobulin associated with material deposited in the glomerulus of NZW. These studies revealed the presence of linear deposits of immunoglobulins in peripheral capillary loops in a number of glomeruli that varied among individuals (focal and segmentary distribution). As the degenerative process evolved, the number of glomeruli showing linear deposits of immunoglobulins decreases, suggesting that these deposits are a marker of the glomerular structures which are going to undergo degeneration. Consistently, the subendothelial deposits with nodular pattern characteristic of the Stages 3b and 4b showed a high immunoglobulin content.

Finally, in an attempt to determine the nature of the proteinaceous material deposited, we performed histochemical studies using Congo red and thioflavin T, compounds that become adsorbed to the protein deposits of amyloid nature and induce birefringence yellow-green of the polarized light or emit fluorescence, respectively. These studies revealed that the material, which is deposited in the subendothelial space as well as the collagenous material at the mesangium adsorbed these two compounds. However, whereas thioflavin T was excitable and emitted fluorescence, the adsorbed Congo red was unable to induce birefringence to the polarized light. These results indicate that the material deposited shares some structural features with amyloid matter (para-amyloid or amyloid-like).

Our studies suggest that the glomerular degeneration of NZW is primarily caused by an alteration in the folding of certain proteins, which cause aggregation and deposit formation at the subendothelial space (fuchsinophilic deposits), and at the mesangium (aniline blue stained material). A reactive fibrosis against these deposits is likely the cause of glomerular sclerosis (end-stage renal disease, ESRD). The protein deposits although different than amyloid matter, share with it some structural features. As previously described, we have not found a frank autoimmune response in NZW. However, the presence of immunoglobulins intimately associated with the subendothelial deposits suggest that, as in Goodpasture disease, aberrant conformers induce autoantibody production.

In light of all these findings, we suggest that an aberrant expression of GPBP is part of the genetic background which predispose NZW mice to undergo tissue degeneration (deposition of proteins) and autoantibody production (autoimmune response). Furthermore, the coordinated increase of protein deposits, GPBP, and immunoglobulins at the subendothelial space suggest that the three processes are related.

GPBP is a molecular target for treating diseases mediated by amyloid-like matter.

In an attempt to establish the causal relationship between GPBP activity and the formation of protein deposits in NZW, we have identified modulators of the activity of GPBP and we administered them to these mice.

Branched polyamines (dendrimers) are chemical structures with a large number of peripheral reactive amines which are commonly used to be substituted by one or more chemical groups to increase their presence at the molecular surface and thus enhance their biological/therapeutic activity. We have found that branched polyamine of first generation [Sigma product numbers 46,069-9: polypropylenimine tetraamine dendrimer (DAB-Am-4)] is a potent activator of GPBP kinase activity in vitro and α3(IV)NC1 conformer production in cultured cells (see above). After performing toxicity assays in mice, we administered non-toxic doses of DAB-Am-4 to 4-6 month-old NZW mice, and we studied its consequences in the progression of the glomerulopathy. These studies revealed that DAB-Am-4 caused an acceleration of the degenerative process, resulting in premature glomerulosclerosis at 7-9 month of age. Whereas in the natural progression of the disease, the morphological pattern more frequently found was that through Stages 3a and 4a, the treatment induces almost constantly a progression through Stages 3b and 4b with abundant presence of GPBP intimately associated with protein deposits. These data suggest that an augmented activity of GPBP is causally related with the progression of the degenerative process towards sclerosis and ESRD. In trials on control mice (C57BL/6) we have not observed histological changes of relevance due to administration of DAB-Am-4, suggesting that the capacity for DAB-Am-4 to induce glomerular sclerosis depends mainly on the NZW genetic background which possibly involves aberrant activation/expression of GPBP.

To verify that an induction of GPBP in the genetic context of NZW is responsible for the degenerative process, NZW mice were treated with DAB-Am-4 or with DAB-Am-4 and $Q_2$, a synthetic peptide (LATLSHCIELMVKR) (SEQ ID NO:90) that encompasses a motif of GPBP for self-interaction in two-hybrid studies, and thus suspected to be critical for GPBP aggregation, that efficiently inhibits GPBP kinase activity in vitro and α3(IV)NC1 conformer production in cultured cells (see above and below sections). The treatment with $Q_2$ sharply reduced the material deposited in the glomerulus of NZW of suspected collagenous nature although it was shown to be unable to reduce the presence of fuchsinophilic material at the subendothelial space. A D-amino acid version of $Q_2$ was significantly more effective than the L-amino acid version consistent with its more potent inhibitory activity on GPBP kinase activity in vitro and on cellular conformer production.

One way to interpret these findings is that $Q_2$ efficiently blocks progression from Stage 3b to 4b during disease induction by DAB-Am-4. In other words, the presence of abundant fuchsinophilic material in $Q_2$ treated mice is suspected to be caused by the lack of fibrotic reaction which substitutes or masks fuchsinophilic material during disease progression. This results in glomeruli virtually devoid of fibrotic reaction that causes ESRD.

When we assessed thioflavin T or Congo red staining, we found that the material which stains with acid fuchsin, contrary to the homologous material at Stage 3b in natural disease or in DAB-Am-4 induced disease, did not adsorb either compound, suggesting that by inhibiting GPBP, $Q_2$ efficiently inhibited amyloid-like matter formation in NZW. Finally, this specific effect on protein deposit structure could be responsible for an attenuated fibrotic reaction, and the lack of progression towards glomerular sclerosis and ESRD.

Identification of multiple compounds that modulate GPBP kinase activity in vitro and α3(IV)NC1 conformer production in culture cells. To determine the role of GPBP in the conformational diversification of the α3(IV)NC1 domain, we have first identified and characterized different modulators of kinase activity of GPBP in vitro, and later we have used them to modulate conformer production in cultured cells.

We have reported that GPBP self-interacts and that aggregation regulates kinase activity (WO 00/50607). By combining a yeast two-hybrid system and cDNA deletion mutants of GPBP, we have identified a five-residue (SHCIE) (SEQ ID NO:39) and a ten residue (EKTAGKPILF) (SEQ ID NO:45) motifs in the GPBP amino acid sequence that are critical for self-interaction. A synthetic peptide representing the five-residue motif and flanking regions (LATLSHCIELMVKR, called here $Q_2$) (SEQ ID NO:90) efficiently inhibited GPBP autophosphorylation, whereas a synthetic peptide representing the ten-residue motif (EKTAGKPILF, called here $Q_4$) (SEQ ID NO:45) inhibited GPBP autophosphorylation in a more limited manner. Furthermore, when these peptides where separately added to the culture media of cells expressing α3(IV)NC1, $Q_2$ was more effective inhibiting cell conformer production than $Q_4$ which had a more limited inhibitory effect (see above). A D-amino acid version of $Q_2$ ($Q_{2D}$) was more efficient inhibiting GPBP autophosphorylation and conformer cell production than the corresponding L-amino acid version ($Q_{2L}$).

We have also assayed a number of protein kinase inhibitors (Calbiochem Cat No 539572) and found that staurosporine (a broad range Ser/Thr kinase inhibitor) and KN93, 2-[N-(2-hydroxyethyl)-N-(4-methoxybenzenesulfonyl)]amino-N-(4-chlorocinnamyl)-N-methylbenzylamine [an inhibitor highly specific for $Ca^{2+}$ Calmodulin-dependent protein kinase II (CaM kinase II)], efficiently impaired GPBP kinase activity in vitro. KN62, 1-[N,O-bis-(5-Isoquinolinesulfonyl)-N-methyl-L-tyrosyl]-4-phenylpiperazine [another specific inhibitor for CaM kinase II (Sigma Cat No I2142)], inhibited GPBP kinase activity in vitro to a larger extent than KN93, which in contrast is known to be a more potent inhibitor than KN62 for CaM kinase II. These organic compounds are thought to inhibit CaM kinase II by interfering with the binding of the $Ca^{2+}$ Calmodulin activator complex to the kinase. In vitro studies consistently revealed that calmodulin inhibited GPBP kinase activity in a $Ca^{2+}$ dependent manner, suggesting that GPBP contains a binding site for $Ca^{2+}$Calmodulin similar to that of CaM kinase II, although the consequences of binding on kinase activity were different in each case. Finally, when KN62 and KN93 were separately added to the culture media of α3(IV)NC1-secreting cells, we found that these compounds reduced cell conformer production. These findings, in addition to identify potential compounds for modulating GPBP kinase activity and α3(IV)NC1 cell conformer production, uncover important features of allosteric regulation of GPBP, and reveal that GPBP has catalytic features that are similar to CaM kinase II. CaM kinase II also requires self-aggregation to be functional, and $Q_2$ efficiently inhibited CaM kinase II, suggesting that the interacting motifs of these two kinases are structurally related. Consistent with this idea aggregatable CaM kinase II contains a highly homologous five-residues motif, SHCIQ (SEQ ID NO:40), not present in non-aggregatable CaM kinases.

Although $Q_4$ appeared to be a poor inhibitor under experimental conditions in which $Q_2$ efficiently inhibited GPBP kinase activity, this peptide showed synergistic inhibitory effect on GPBP kinase activity with KN62 (+++), $Ca^{2+}$CaM (++) and $Q_2$ (+). Similarly we found inhibitory synergism on GPBP kinase activity when combining KN62 and $Ca^{2+}$CaM (+++), whereas no cooperative inhibitory effect was observable when combining $Q_2$ and $Ca^{2+}$ CaM or $Q_2$ and KN62.

In contrast to the positive regulatory effect of DAB-Am-4, fourth generation of branched polyamines (DAB-Am-32) (Sigma Chemical Co. product number 46,908-4) efficiently inhibited GPBP protein kinase activity. This compound has been shown to accumulate in the lysosomes and exert a curative effect on prion infected cultured cells (Supattapone S. et al. J. Virol (2001) 75, 3453-3461).

These data, in addition to provide experimental evidence for the role of GPBP in the conformational isomerization of the α3(IV)NC1 domain in vitro and ex vivo, report the first repertoire of lead compounds to be use for treatment of autoimmune diseases and protein deposit-mediated disorders.

GPBP is a potential molecular target for treating amyloidosis. GPBP represents the first example of a molecular enzyme showing kinase and polypeptide conformation isomerase activity (WO 00/50607 and WO 02/061430). We have shown that a 91-kDa isoform of GPBP resulting from non-canonical mRNA translation enters the lysosome and undergoes processing to yield a 44-47-kDa product, which in turn represents a GPBP isoforms that are integral components of this cell compartment. The evidence suggests that in this acidic environment, GPBP can transfer phosphate and therefore conceivably could also catalyze conformational isomerization reactions.

An important number of human degenerative diseases, including Alzheimer's and prion diseases, are mediated by the presence of aggregates (amyloid matter) made of non-soluble conformational versions of specific cellular components ($Aβ_{1-42}$ and $PrP^{Sc}$, respectively). The conformational isomerization of prion protein, PrP, which represents the best known process involving conformational shift of a polypeptide ($PrP^{C}$ to $PrP^{Sc}$), occurs after anchorage of the $PrP^{C}$ to the plasma membrane during internalization through the endosomal pathway, and is suspected to be assisted by a chaperone-like protein (Protein X). N terminal trimming of $PrP^{Sc}$ to produce PrP 27-30, the material found in amyloid deposits of infected cultured cells, occurs in secondary lysosomes, suggesting that this cell compartment is critically involved in the pathogenesis prion diseases (Prusiner, S. B. (2001) N England J Med 344, 1516-1526).

Our data suggest that the α3(IV)NC1 conformers are secreted and undergo proteolysis via endosomal/lysosomal pathways, and that specific modulators of GPBP regulate α3(IV)NC1 conformer production in cultured cells. All of the above suggests that α3(IV)NC1 and PrP share secretory and degradation pathways, and, therefore GPBP may catalyze similar conformational isomerization reactions on PrP.

Fourth generation branched polyamines DAB-Am-32 have been reported to accumulate in lysosomes and to cure prion infected cells. DAB-Am-32 strongly inhibited GPBP in vitro at concentrations at which DAB-Am-4 caused induction. This suggests that, as for para-amyloid matter formation, amyloid matter deposition requires GPBP action and also suggests that one of the mechanisms by which DAB-Am-32 eliminates amyloid matter in prion infected cells involves inhibition of GPBP at the lysosomal compartment. This results point to GPBP as a potential candidate for Protein X activity.

The results above suggest that the reported curative effect of branched polyamines on prion infected cells may be due in part to inhibition of otherwise active lysosomal GPBP, thus implicating GPBP as a therapeutic target in prion-mediated disorders.

Figure 10:
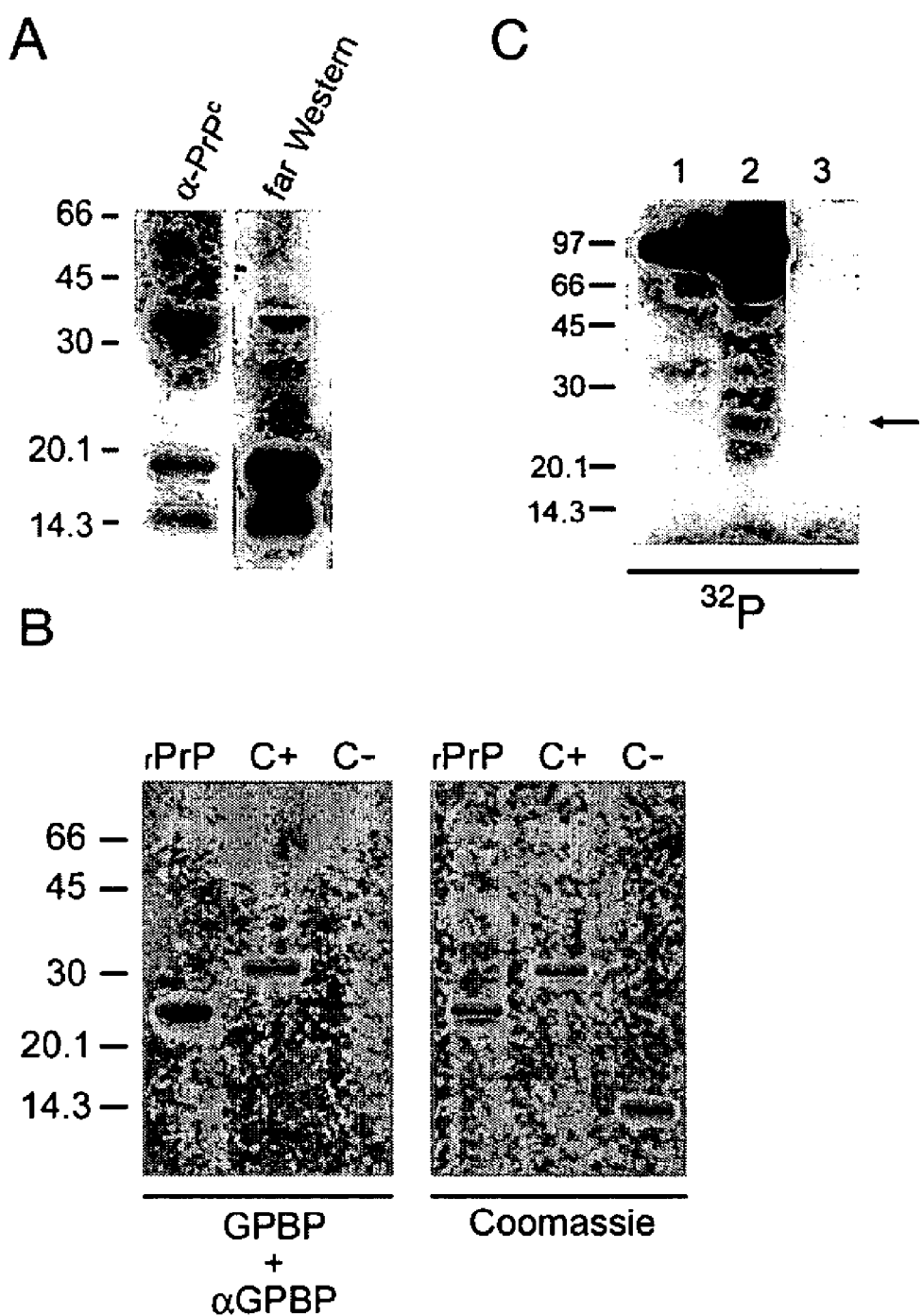
FIG. 10. GPBP interacts and phosphorylates PrP$^C$. In A, cellular extracts of cultured rat cerebellar neurons were analyzed by SDS-PAGE and Western blot using PrP (C-20) antibodies (α-PrP$^C$) or by far Western blot using recombinant GPBP and Mab14 (far Western). In B, 1 μg of bovine recombinant PrP (Prionics), human recombinant α3(IV) NC1 (C+) or horse heart cytochrome c from Sigma (C−) were analyzed by SDS-PAGE and Coomassie blue stained (Coomassie) or by far Western blot as in A (GPBP+α-GPBP). In C, 100 ng of human recombinant GPBP (1), same amount of GPBP with 1 μg of bovine recombinant PrP (2) or the same amount of bovine recombinant PrP (3) were separately subjected to in vitro phosphorylation and the corresponding mixtures analyzed by Western blot using PrP specific antibodies in A (not shown) and autoradiography ($^{32}$P). With an arrow we note the position of recombinant PrP.

GPBP binds to PrP$^C$ in vitro. To show the biological relationship between GPBP and proteins that promote amyloid matter formation when they undergo conformational degeneration, the interaction between GPBP and PrP$^C$ was assessed in far Western assays using cellular extracts of primary cultures of rat cerebelar neurons and recombinant human GPBP. GPBP bound to a limited number of polypeptides of different sizes all of which were recognized by specific antibodies against PrP$^C$ (Santa Cruz Biotech Ca# SC7693) (FIG. 10). The presence of GPBP in these cells was further demonstrated by Western blot analysis of the corresponding cell extracts using specific antibodies. Furthermore, we used recombinant material representing human GPBP and bovine PrP$^C$ in specific far Western and phosphorylation studies and found that GPBP interacts with PrP$^C$ and when incubated in the presence of [γ$^{32}$P]-ATP transferred phosphates to PrP as a result of this interaction (FIG. 10).

Human GPBP aggregates with bovine PrP$^C$. To explore further the pathway of complex formation between PrP$^C$ and GPBP, we used spectroscopy methods. Light scattering at 90° was measured for the aggregation kinetic assays. Upon addition of GPBP at a PrP$^C$ solution, aggregation occurred and could be monitored by light scattering. The complex formation is independent of the time course of protein addition since the same increase in the light scattering signal is obtained when a PrP$^C$ solution is added to a GPBP solution initially placed in the measurement cell. To ascertain whether the different versions of inhibitory Q$_2$ peptide (L-amino acid and D-amino acid versions of Q$_2$ peptide-Q$_{2L}$, Q$_{2D}$ respectively- and Q$_{2Lr}$, an inactive scrambled peptide with the same amino acid composition than Q$_{2L}$) could affect GPBP-PrP$^C$ complex formation in a similar manner than they affected kinase activity, we monitored aggregation in the presence of each individual peptide. Upon addition of GPBP to a PrP$^C$ solution containing 100 μM of Q$_{2L}$, GPBP-PrP$^C$ complex formation was efficiently inhibited. The inactive peptide Q$_{2Lr}$ had no effect on complex formation at these concentrations, whereas the more potent Q$_{2D}$ peptide at 20 μM fully inhibited GPBP-PrP$^C$ complex formation.

Figure 11:
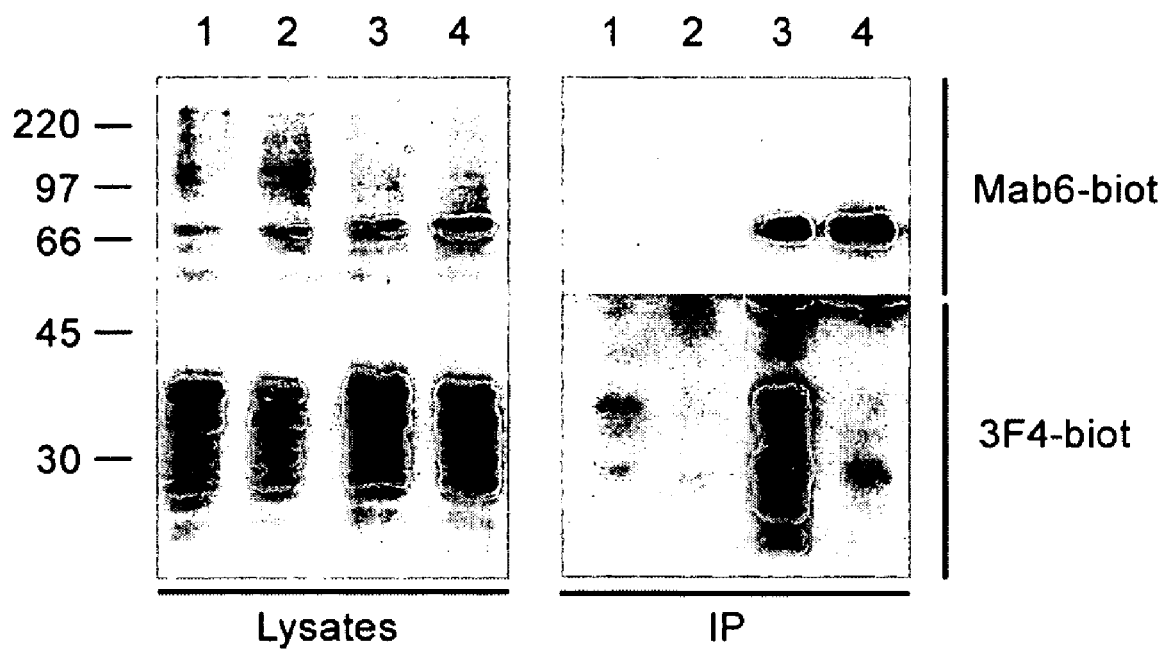
FIG. 11. PrP and GPBP interact in cells lysates. Cultured 293 cells were transfected with pc-DNA3 and pc-PrP (1), pc-DNA3 and pc-PrP$^{E168R}$ (2), pc-Flag-n4' and pc-PrP (3) or with pc-Flag-n4' and pcPrP$^{E168R}$ (4), lysed and subjected to anti-FLAG immunoprecipitation. Lysates and immunoprecipitated (IP) materials were analyzed by Western blot using the indicated biotin-labeled antibodies.

Aggregation of GPBP and PrP$^C$ depends on structural requirements for Protein X interaction. Interaction of PrP$^C$ and Protein X is expected to occur through a defined number of residues at the C terminal region of PrP which comprises the Protein X binding site (Kaneko, K, et al., (1997) Proc. Natl. Acad. Sci. USA 94, 10069-10074). We have performed recombinant expression and immunoprecipitation studies in an attempt to first assess whether GPBP-PrP complex formation is mediated by a Protein X-type interaction. We have used specific antibodies recognizing FLAG-tag sequence only present in recombinant GPBP to precipitate co-expressed recombinant human PrP. FLAG-specific antibodies efficiently precipitated FLAG-GPBP along with PrP, suggesting that FLAG antibodies-GPBP-PrP form a precipitable ternary complex and that GPBP and PrP interact in the cellular environment. When immunoprecipitations were done on cell extracts expressing GPBP and individual PrP mutants we observed that mutants expected to alter Protein X binding site were precipitated by FLAG-antibodies in a much less efficiency than mutants not involving these residues, which showed a similar capacity to undergo precipitation than PrP representing wild type sequence. In FIG. 11 we illustrate a comparative study between PrP and PrP$^{E168R}$, a human PrP mutant in which a residue proposed to be part of Protein X epitope, E$^{168}$, has been replaced by R to generate a PrP$^C$ mutant non-susceptible for PrP$^{Sc}$ conversion (Kaneko, K, et al., (1997) Proc. Natl. Acad. Sci. USA 94, 10069-10074). Similar results were obtained with functionally homologous PrP$^{Q172R}$ and PrP$^{E219K}$ mutants but not with two independent non-functionally related PrP$^{R220A}$ and PrP$^{R228A}$ mutants.

Figure 12:
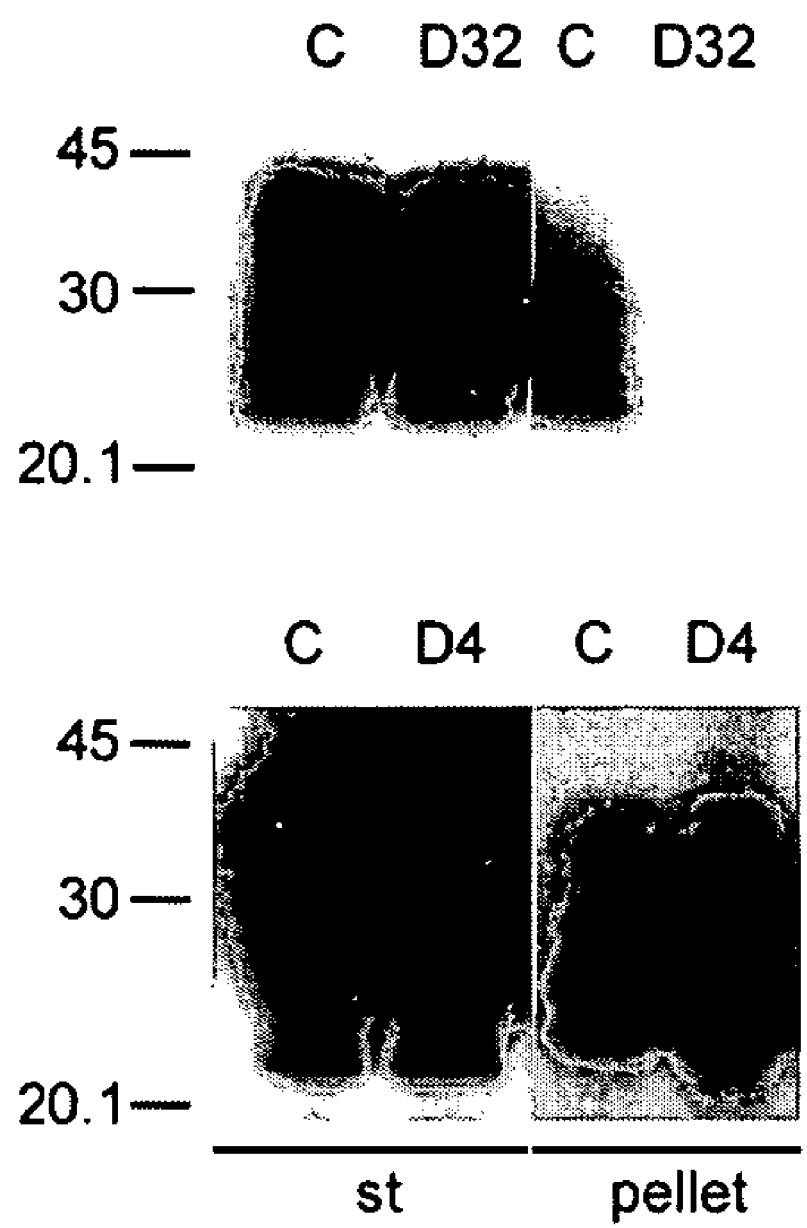
FIG. 12. Evidence for GPBP modulators regulating human recombinant PrP conformation in 293 cells. Human 293 cells were transfected with pc-PrP, cultured in the absence (C) or in the presence of DAB-Am-32 (D32) or DAB-Am4 (D4) and further lysed and centrifuged. The corresponding supernatants (st) and pellets were analyzed by Western blot using 3F4 anti-PrP antibodies. Similar results to those obtained with DAB-Am-32 were also observed with Q$_{2D}$ (not shown).
Figure 13:
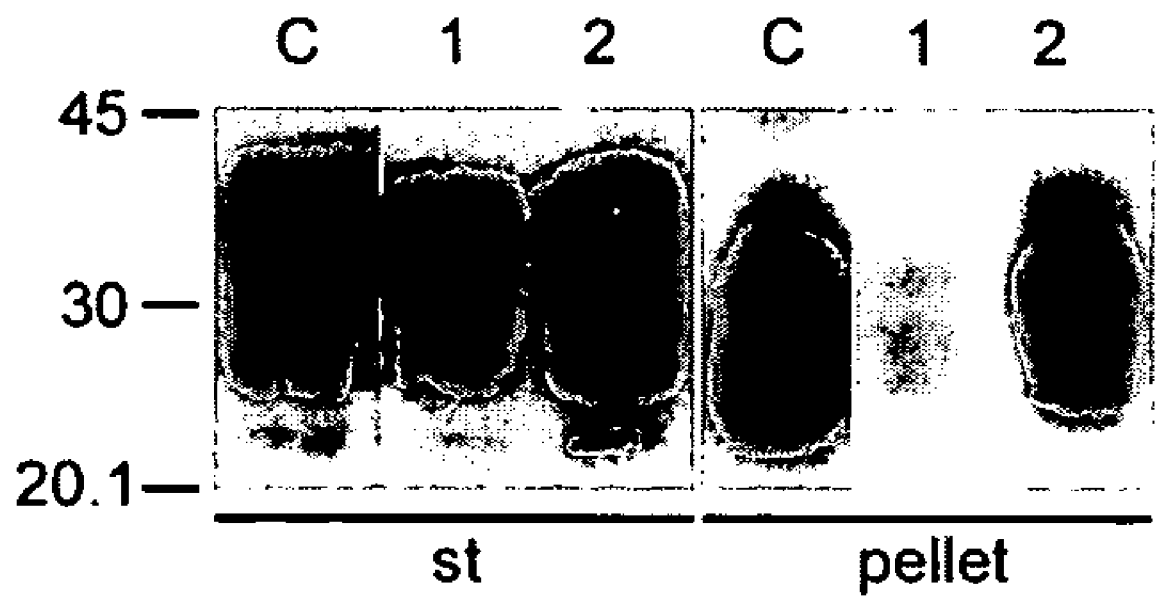
FIG. 13. Evidence for GPBP mRNA silencers regulating recombinant PrP conformation in 293 cells. Human 293 cells were transfected with pc-PrP and either SiGFP (C), SiGPBP/Δ26-2 (1) or SiGPBP/Δ26-4 (2) cultured for 48 h and further lysed and centrifuged. The corresponding supernatants (st) and pellets were analyzed by Western blot using 3F4 anti-PrP antibodies. Western blot analysis on the cell lysates confirmed that SiGPBP/Δ26-2 silenced endogenous GPBP more efficiently than SiGPBP/Δ26-4 (not shown).

GPBP promotes conformational changes in PrP. A widely used method to monitor conformational alterations in PrP$^C$ relevant to pathogenesis comprises determination of the number of related polypeptides being expressed by the cell and their soluble or precipitable condition. In general, PrP$^C$ is expressed inside the cell as a highly soluble single polypeptide and an increased number of polypeptides with poor solubility is characteristic of PrP$^{Sc}$ and other non-physiological conformational forms of PrP such as PrP$^{Res}$ or PrP$^{Sc-like}$, and more recent data suggest that inside the cell insoluble conformers of PrP are continuously being produced and cleared and that the levels of these conformers at the steady state reflects the dynamics of these two opposite processes (Ma, J. and Lindquist (2002) Science 298, 1785-1788). We have used inhibitors and activators of GPBP to regulate the levels of precipitable recombinant human PrP polypeptides in cultured cells (FIG. 12). The presence of DAB-Am-4 in the culture media of cell expressing recombinant PrP efficiently induced the expression of non-soluble precipitable PrP polypeptides, whereas the presence of DAB-Am-32 efficiently inhibited expression of non-soluble precipitable PrP polypeptides. Similarly, we have generated and used a number of mRNA silencers to regulate the level of expression of non-soluble PrP polypeptides and found that individual mRNA silencers down-regulated non-soluble PrP expression to an extent consistent with the capacity displayed by each individual mRNA silencer to impair endogenous non-canonical expression of GPBP. In FIG. 13 we illustrate a comparative study using a non-relevant silencer (C) and two specific silencers (1,2) with higher (1) or lower (2) capacity to reduce 91- and 120-kDa GPBP expression (see FIG. 4, lanes 5 and 7, respectively).

GPBP Bind to Aβ$_{1-42}$

Figure 14:
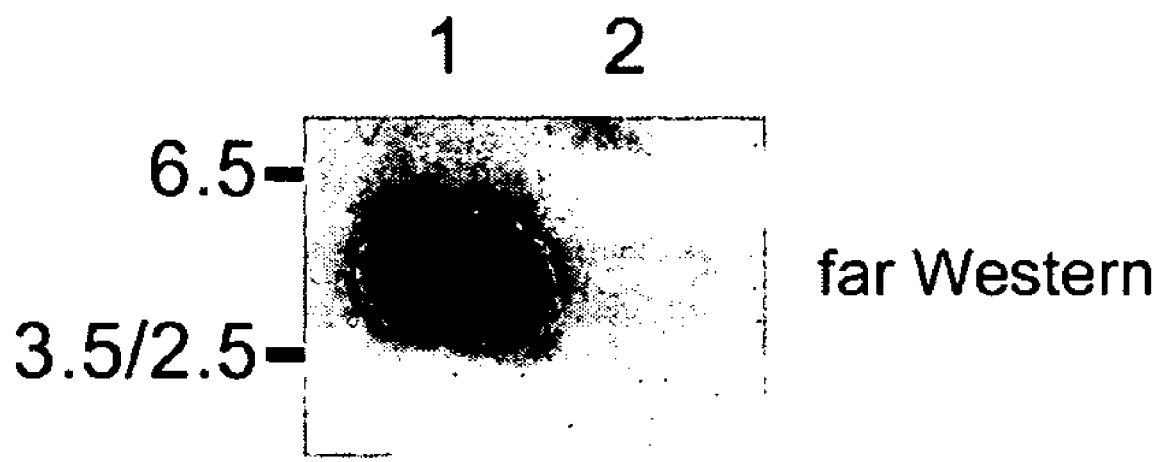
FIG. 14. Evidences for GPBP interacting with Aβ$_{1-42}$. Similar amounts (1 μg) of Aβ$_{1-42}$ (1) or GPpep1bov (2) were analyzed by far Western blot as in previous Figures. The presence of similar amounts of each of the two polypeptides in the Immobilon P membrane was determined either with specific antibodies reacting with each polypeptide or by Ponceau S staining (not shown).

Several lines of evidence suggest that senile plaques in Alzheimer's disease derive from neurons that have undergone degeneration primarily caused by amyloid deposition of Aβ$_{1-42}$ at secondary lysosomes (Nixon, et al., (2000) Neurochem Res 25, 1161-1172; Andrea, M R, et al (2001) 38, 120-134). Conceivably, a similar mechanism to that proposed above to be mediating amyloid matter formation in prion diseases could be mediating amyloid matter deposition in Alzheimer's disease. To assess this possibility the capacity of GPBP to bind to Aβ$_{1-42}$ was assessed in specific far Western studies (FIG. 14). Recombinant human GPBP displayed high affinity for a synthetic polypeptide representing Aβ$_{1-42}$, whereas in the same assay conditions GPBP did not display binding capacity towards a synthetic peptide representing the non-phosphorylable N terminal region of bovine α3(IV)NC1. Incubation of GPBP with Aβ$_{1-42}$ in the presence of [γ$^{32}$P]ATP did not result in $^{32}$P-labeling of synthetic polypeptide, suggesting that although Aβ$_{1-42}$ contains sites for GPBP molecular recognition, it does not harbor GPBP phosphorylation sites. Consequently, Aβ$_{1-42}$ perhaps represents a substrate of GPBP for a conformational catalysis in which phosphate transfer of protein substrate is not required. The latter suggests that GPBP-mediated conformational catalysis on protein substrates can occur in a phosphorylation-dependent or independent manner, or that conformational catalysis can be performed on phosphorylated or non-phosphorylated substrates. Consistently, GPBP bound with more affinity to recombinant proteins representing phosphorylated version of human autoantigens (Goodpasture antigen and myelin basic protein) at specific Ser that conform phosphorylation sites for GPBP (Ser$^9$ and Ser$^8$, respectively), suggesting that the phosphorylated products are not the end product of GPBP catalysis, but they are the substrate for a conformational isomerization and supramolecular assembly catalysis.

In full our data provide the first experimental support for GPBP being the chaperone-like molecular enzyme suspected to be involved in PrP$^C$ to PrP$^{Sc}$ conformational isomerization in the pathogenesis of prion diseases, and also represents the first molecular link between two previously unrelated processes, tissue degeneration mediated by amyloid and para-amyloid matter deposition and autoimmunity.

Discussion

Autoimmune diseases comprise a large number of disorders mediated by an immune attack against self-components (autoantigens) as a result of a failure in the mechanisms of immune tolerance. When autoantigens are administered to animal models they have the peculiar capacity to engage the immune system in a response that mimics the natural disease revealing that these components display biological features of immunological relevance. Consequently, certain alterations in autoantigen biology could have an important impact in their immunological recognition, thus triggering an immune response. For these reasons, understanding autoantigen biology is necessary to design an appropriate molecular model for autoimmune disorders.

By studying Goodpasture (GP) disease we have provided new insights into the molecular mechanism of autoimmune disorders. GP disease is characterized by the coexistence of glomerulonephritis and lung hemorrhage caused by an immune attack that is mediated by circulating autoantibodies, which deposit in a linear manner in the glomerular and alveolar basement membranes. The autoantibodies are directed against the C terminal non-collagenous domain (NC1) of the $\alpha$3 chain of collagen IV, $\alpha$3(IV)NC1 domain, also called the Goodpasture antigen. Collagen IV is composed of six $\alpha$-chains that exhibit a high degree of homology which is more evident at the NC1 domain. However, only the $\alpha$3(IV)NC1 domain has been shown to induce Goodpasture syndrome in animals models, and only the human $\alpha$3(IV)NC1 domain has been implicated in a common natural autoimmune response. Comparative structural studies identified a highly divergent region at the N terminus of the $\alpha$3(IV)NC1 domain which undergoes phosphorylation by cAMP-dependent protein kinase and also by GPBP. $\alpha$3(IV)NC1 domain is purified from natural sources as a set of conformational isomers (conformers) with differential phosphoserine content. The more abundant $\alpha$3(IV)NC1 conformer, which likely represents the native conformation, is virtually devoid of phosphoserine, whereas the less abundant $\alpha$3(IV)NC1 conformers, likely representing derived alternative conformations, display the highest degree of phosphoserine content. These data suggested that phosphorylation is part of the strategy used by cells to generated alternative protein conformations (WO 00/50607; WO 02/061430).

Other biological consequences associated with phosphorylation of the $\alpha$3(IV)NC1 domain include regulation of $\alpha$3(IV)NC1 domain aggregation. In the absence of ATP, GPBP displays the capacity to catalyze a physiological aggregation of the $\alpha$3(IV)NC1 domain (disulfide-dependent oligomerization) by a process involving conformational isomerization (WO 02/061430). This data indicate that GPBP possesses a conformational isomerase activity independent of its kinase activity that is critical for a broader enzymatic catalysis, resulting in assembly of a protein substrate into a quaternary structure.

The relationship between GPBP and autoimmune pathogenesis was initially established by showing (a) elevated levels of GPBP in Goodpasture patients; (b) In vitro, GPBP catalyzes the production of $\alpha$3(IV)NC1 conformers that are found in patient kidneys but not control kidneys; and (c) The presence of aberrant $\alpha$3(IV)NC1 conformers in patient kidneys that are specifically recognized by pathogenic autoantibodies. (WO 02/061430) These results led to a new model of autoimmune disease, wherein the autoimmune response is considered a legitimate reaction of the immune system against aberrant conformations of an autoantigen (such as the $\alpha$3(IV)NC1 in GP disease), which assemble and for which the immune system has not established a tolerance (WO 00/50607; WO 02/061430).

These observations identify critical and exclusive biological features in a human autoantigen (the $\alpha$3(IV)NC1) that do not have a counterpart in homologous domains (the other type IV collagen NC1 domains) which are not autoantigens, and represent a new strategy to study the molecular basis of a human exclusive disease. Recent studies performed in our laboratory have identified the presence of a serine residue in the N terminal region of myelin basic protein ("MBP") that is structurally and functionally similar to that found in the $\alpha$3(IV)NC1 (WO 02/061430). Myelin basic protein is a major autoantigen in an autoimmune response mediating multiple sclerosis, which, like Goodpasture disease, is an exclusively human autoimmune disease. Recent studies further demonstrated that phosphorylation of MBP plays a critical role in regulating its conformation and have identified conformational-dependent differences in the proteolytical susceptibility of myelin basic protein from control and patients affected by multiple sclerosis (data not shown). These data represent a strong validation of our model of autoimmune disease, based on the biology of two unrelated human autoantigens and autoimmune disorders, and suggest that a common autoimmune pathogenic mechanism is emerging in which GPBP plays a central role. In this mechanism, human autoantigens are polypeptides with the capacity to bind to GPBP and, as a consequence of such a binding, undergo phosphorylation and conformational isomerization, which makes these polypeptides vulnerable to an aberrant catalysis and production of non-tolerized conformers (WO 00/50607; WO 02/061430).

The high phosphorylability of myelin basic protein in vitro contrasts with its low content in Ser(P) residues, suggesting that (a) endogenous phosphorylation of this autoantigen is highly regulated; and (b) there are multiple MBP species with different degree of phosphorylation [Eichberg, J., & S. Iyer Neurochem Res 21, 527-535 (1996)]. Conceivably, the sequential phosphorylation and dephosphorylation of specific sites on autoantigens, such as those identified at the N terminus in myelin basic protein and in the human α3(IV)NC1 domain, could generate a heterogenous population of molecules or conformers for supramolecular assembly, and an alteration in the homeostasis of phosphorylation events could result in the assembly of aberrant non-tolerized conformers in the corresponding quaternary structure of the autoantigens.

GPBP displays a number of biological features to be considered a good candidate as a pivotal component of the cellular machinery catalyzing the supramolecular assembly of autoantigens and inducing immune response during autoimmune pathogenesis. For example: (1) GPBP phosphorylates homologous sites in two different human autoantigens and targets other human autoantigens; (2) The GPBP phosphorylation sites in myelin basic protein and Goodpasture antigen play a conformational regulatory role; (3) GPBP binds preferentially to recombinant species representing the phosphorylated versions at these sites, suggesting that the phosphorylated versions are not only the product of a phosphate transfer reaction, but are also the substrate of an additional catalysis that includes conformational isomerization and supramolecular assembly; (4) Immunochemical studies show that GPBP is present in tissue, cellular and subcellular localizations that are common targets of autoimmune responses; (5) Increased levels of GPBP relative to its alternatively spliced isoform, GPBPΔ26, are found in several autoimmune conditions (WO 00/50607; WO 02/061430 and data not shown).

To further establish the role of GPBP in autoimmune pathogenesis, a major issue is to determine the mechanism by which GPBP is delivered to such a broad number of subcellular localizations. Proteins can be synthesized at free ribosomes (proteins to be resident at the cytosol or to be further transported to, for example, nucleus, mitochondria or peroxisome) or at ribosomes associated with ER (proteins that enter into the secretory pathway and end up being either ER, Golgi apparatus, lysosomes and plasma membrane resident, or secreted to the extracellular matrix). There are proteases present in all these locations, and there are many examples in which primary translation products undergo proteolysis to render shorter biologically active polypeptides.

In the cell, protein sorting is accomplished via a number of signal sequences, many of which have been characterized. However, there are increasing examples of non-canonical mechanisms for cellular protein sorting.

By studying the cellular expression of GPBP, we have established that the cell expresses at least seven GPBP-related polypeptides of 120-, 91-, 77-, 60-, 44-47-, 32-kDa. With the exception of 120-kDa GPBP, whose origin is not certain, the rest can be generated by limited proteolysis of the 91-kDa polypeptide, as shown herein. We present evidence suggesting that the 91 kDa GPBP is a non-canonical translation product of GPBP mRNA. The evidence presented herein also suggests that 91 kDa GPBP enters into the secretory pathway and undergoes processing to produce GPBP isoforms of lower molecular mass that can be found in the ER, Golgi apparatus, lysosomes and plasma membrane.

Confocal studies performed in our laboratory show a major co-localization of GPBP and Goodpasture antigen in human glomerulus suggesting the presence of GPBP in basement membranes. In contrast, our evidence from recombinant expression studies suggests that canonical 77-kDa polypeptide is essentially cytosolic (data not shown). However, subfractioning studies show that at the cellular steady state the levels of canonical primary product are negligible and only a major derived product of 60-kDa can be detected, suggesting that the 77-kDa primary product, if it is expressed, undergoes an efficient processing to a lower molecular mass isoform. The mechanisms for GPBP transport to the nucleus and mitochondria (WO 00/50607; WO 02/061430) remain to be verified, although our data suggests that certain non-canonical translation products may provide the requisite targeting signals for such localization.

Recombinant expression shows that the 5'-UTR contains multiple non-canonical sites for translation initiation that display a 5' to 3' hierarchy. Based on sequence analysis and using programs that predict subcellular localization, the ORF in Δ102 contains a canonical signal peptide sequence to entry into the secretory pathway (residues 1-46). This signal peptide is immediately followed by a signal for nuclear localization (residues 47-50) and another for mitochondrial destination (residues 52-56), in turn, suggesting that by varying transcription initiation site the cell may regulate the expression of non-canonical polypeptides that are destined for the secretory pathway (ER/Golgi apparatus/lysosomes/plasma membrane/extracellular matrix), nuclear o mitochondrial whereas only canonical translation would generate a genuine cytosolic polypeptide. Furthermore, GPBP also displays two other potential mechanism to reach nuclear environment: (a) GPBP contains a bipartite nuclear localization signal; and (b) GPBP binds to a family of transcription factors that could shuttle the protein into the nucleus (WO 03/048193).

The cellular expression of GPBPΔ26 was also explored using Mab14, a monoclonal antibody recognizing both GPBP and GPBPΔ26 recombinant counterparts. Mab14 reacted with a single 77-kDa cytosolic polypeptide and did not show significant reactivity towards polypeptides reacting with Mab6. The specificity of these Mab14 antibodies was confirmed by demonstrating that GPBP/GPBPΔ26 silencers reduced the expression of 77-kDa polypeptide to similar extent than 91- and 120-kDa polypeptides that only reacted with Mab6. These results suggest that the 77-kDa polypeptide is primarily GPBPΔ26 and cytosolic, whereas non-canonical polypeptides are mainly GPBP, and virtually ubiquitous.

In summary, our data suggest that for native cellular expression Mab14 is an immunological probe for GPBPΔ26 whereas Mab6 is an immunological probe for GPBP-related polypeptides.

Our findings suggest that GPBP is an integral component of the endosomal-lysosomal pathway which activity is regulated in part by a catepsin-dependent processing, a biological strategy described for other enzymes (Pham, C. T., & T. J. Ley, (1999). Proc Natl Acad Sci USA 96(15): 8627-8632). These proteases are critical in processing proteins entering the endosomal pathway, and for producing peptides that are presented through MHC class II (Chapman, H. A., (1998) Curr Opin Immunol 10(1): 93-102). Disturbances of lysosomal environment in a general manner, such as modifying the pH using compounds as chloroquine, or in a specific manner using catepsin inhibitors such as leupeptin, have been shown to alter peptide presentation by MHC class II (Demotz, S., P. M. Matricardi, C. Irle, P. Panina, A. Lanzavecchia, & G. Corradin, (1989) J Immunol 143(12): 3881-3886; Turk, V., B. Turk, & D. Turk, (2001) EMBO J 20(17): 4629-4633). We have shown herein that leupeptin treatment substantially alters lysosomal processing of GPBP and therefore also likely induces an alteration in GPBP activity, which in turn suggests that altered peptide presentation and altered GPBP activity may be related and perhaps critical in autoimmune pathogenesis, which necessarily requires aberrant peptide presentation to be effective.

A feature common to many degenerative diseases is the formation of deposits of specific polypeptides. Where and how these deposits appear is highly specific and tightly related with pathogenesis. The deposits can be nuclear inclusion bodies, as in cerebelar ataxia, or be at the ER lumen, such as in some degenerative disease affecting liver and neurons, or be cytoplasmic inclusion bodies, as in Parkinson's disease, Alzheimer's disease, and amyotrophic lateral sclerosis; and endosomal-lysosomal, as in Alzheimer's disease, prion diseases, and type II diabetes. GPBP is an ubiquitous protein that has been independently related to conformational catalysis of substrate proteins (WO 00/50607; WO 02/061430) and in the formation of protein deposits in animal models that develop a degenerative nephropaty associated to an autoimmune response. Consequently the finding that GPBP interacts with PrP and $A\beta_{1-42}$ two polypeptides that undergo conformational alteration and form amyloid deposits in prion and Alzheimer's disease, respectively, represents strong evidence for GPBP being involved in the pathogenesis of these degenerative disorders. More specifically a protein resident in the endosomal-lysosomal pathway named Protein X has been proposed to bind to PrP and catalyze the conformational transition from $PrP^C$ to $Prp^{Sc}$ (Prusiner, S. B., (1998). "Prions." Proc Natl Acad Sci USA 95(23): 13363-13383.). Here we present evidence indicating that GPBP binds to PrP in a Protein X fashion, phosphorylates PrP, forms aggregates with it and, as a consequence of this interaction, PrP undergoes conformational changes that renders PrP highly insoluble and precipitable. To our knowledge, GPBP represents the best molecular candidate to be Protein X in prion diseases as well as to perform a similar catalytical role in other protein deposit-mediated human disease.

A major obstacle when studying the molecular basis of degenerative or autoimmune diseases is the almost general consensus that any protein can be an autoantigen or to conformationally degenerate and form deposits. According to this view, the establishment of an autoimmune response represents a non-legitimate immune reaction, while conformational degeneration is thought to represent a stage that any polypeptide chain can achieve if the environment is appropriately altered. However, this view cannot explain the principal fact that only a very limited number of cellular components can be autoantigenic or can form deposits that cause tissue degeneration, indicating that autoantigens and deposit-forming polypeptides share biological features. Our studies suggest that a common biological feature of autoantigens is being a substrate of an enzymatic strategy to form quaternary structures in which GPBP plays a central role and the protein substrate undergoes conformational isomerization. Our results regarding polypeptides that, like PrP and $A\beta_{1-42}$, conformationally degenerate and form deposits, suggest that they are also substrates of GPBP and its catalytic action is required for deposit formation. While the present invention is not limited to a specific mechanism, we propose that GPBP is a novel molecular enzyme that binds to and phosphorylates protein substrates as part of an enzymatic strategy in which conformational catalysis of protein substrates occur during their supramolecular assembly (quaternary structure). Alterations in its performance produce aberrant conformers that are soluble and induce autoimmunity, or are insoluble and form deposits of amyloid or para-amyloid nature that cause tissue degeneration.

We claim:

1. An isolated polypeptide consisting of X1-SHCIX2-X3 (SEQ ID NO: 104)
   wherein X1 is 0-10 contiguous amino acids of the sequence ATTAGILATL (SEQ ID NO:41), wherein X1 is contiguous with SHCIX2 from the X1 C-terminus;
   X2 is E or Q; and
   X3 is 0-10 continuous amino acids of the sequence LMVKREDSWQ (SEQ ID) NO:42), wherein X3 is contiguous with SHCIX2 from the X3 N-terminus.

2. A composition comprising the polypeptide of claim 1 and a pharmaceutically acceptable carrier.

3. The isolated polypeptide of claim 1 wherein X2 is E.

4. The isolated polypeptide of claim 1 wherein X2 is Q.

5. The isolated polypeptide of claim 1 wherein the polypeptide consists of ILATLSHCIELMVKR (SEO ID NO: 43).

6. The isolated polypeptide of claim 1 wherein the polypeptide consists of ILATLSHCIQLMVKR (SEQ ID NO: 44).

7. A pharmaceutically composition comprising the polypeptide of claim 3 and a pharmaceutically acceptable carrier.

8. A composition comprising the polypeptide of claim 4 and a pharmaceutically acceptable carrier.

9. A composition comprising the polypeptide of claim 5 and a pharmaceutically acceptable carrier.

10. A pharmaceutically composition comprising the polypeptide of claim 6 and a pharmaceutically acceptable carrier.

* * * * *